United States Patent
Kleiner et al.

(10) Patent No.: US 12,053,393 B2
(45) Date of Patent: *Aug. 6, 2024

(54) BONE GRAFT DELIVERY SYSTEM AND METHOD FOR USE

(71) Applicant: Spinal Surgical Strategies, Inc., Incline Village, NV (US)

(72) Inventors: Jeffrey B. Kleiner, Denver, CO (US); Edward John Grimberg, Denver, CO (US)

(73) Assignee: Spinal Surgical Strategies, Inc., Incline Village, NV (US)

(*) Notice: Subject to any disclaimer, the term of this patent is extended or adjusted under 35 U.S.C. 154(b) by 151 days.

This patent is subject to a terminal disclaimer.

(21) Appl. No.: 17/719,295

(22) Filed: Apr. 12, 2022

(65) Prior Publication Data

US 2022/0233331 A1 Jul. 28, 2022

Related U.S. Application Data

(63) Continuation of application No. 17/203,655, filed on Mar. 16, 2021, now Pat. No. 11,660,208, which is a
(Continued)

(51) Int. Cl.
*A61F 2/46* (2006.01)
*A61F 2/44* (2006.01)
(Continued)

(52) U.S. Cl.
CPC .......... *A61F 2/4601* (2013.01); *A61F 2/4455* (2013.01); *A61F 2/447* (2013.01);
(Continued)

(58) Field of Classification Search
CPC .................................................... A61F 2/4601
See application file for complete search history.

(56) References Cited

U.S. PATENT DOCUMENTS

D30,951 S    6/1899  Saint, Jr.
1,867,624 A  7/1932  Hoffman
(Continued)

FOREIGN PATENT DOCUMENTS

AU    765774      10/2003
AU    2004100977  12/2004
(Continued)

OTHER PUBLICATIONS

"BAK® /Proximity™ (BP®) Cage", Zimmer Website, as early as Oct. 23, 2007, available at www.zimmer.com/z/ctl/op/global/action/1/id/7930/template/MP/prcat/M6/prod/y, printed on Jun. 8, 2009, 1 page.
(Continued)

*Primary Examiner* — Christian A Sevilla
(74) *Attorney, Agent, or Firm* — Corner Counsel, LLC

(57) ABSTRACT

A bone graft delivery system for delivering graft material into a surgical site. The delivery system includes an elongate hollow tube constructed to receive the bone graft material and having a hollow interior and indicia formed on an exterior surface of the elongate hollow tube. The delivery system also includes a plunger adapted to extend in the elongate hollow tube and to form a substantially congruent fit with the hollow interior of the elongate hollow tube such that the plunger is precluded from rotating within the elongate hollow tube. The plunger is adapted to urge bone graft material through the elongate hollow tube to deliver bone graft material through an opening thereof.

20 Claims, 75 Drawing Sheets

Related U.S. Application Data continuation of application No. 16/373,410, filed on Apr. 2, 2019, now Pat. No. 10,973,656, which is a continuation-in-part of application No. 16/198,754, filed on Nov. 21, 2018, now Pat. No. 10,245,159, which is a continuation-in-part of application No. 15/486,511, filed on Apr. 13, 2017, now Pat. No. 10,195,053, which is a continuation of application No. 14/887,598, filed on Oct. 20, 2015, now Pat. No. 9,629,729, which is a continuation-in-part of application No. 14/263,963, filed on Apr. 28, 2014, now Pat. No. 9,186,193, which is a continuation-in-part of application No. 14/088,148, filed on Nov. 22, 2013, now Pat. No. 8,709,088, which is a continuation of application No. 13/947,255, filed on Jul. 22, 2013, now Pat. No. 8,685,031, which is a continuation-in-part of application No. 13/714,971, filed on Dec. 14, 2012, now Pat. No. 9,173,694, which is a continuation-in-part of application No. 13/367,295, filed on Feb. 6, 2012, now Pat. No. 9,060,877, which is a continuation-in-part of application No. 12/886,452, filed on Sep. 20, 2010, now Pat. No. 8,906,028.

(60) Provisional application No. 62/696,093, filed on Jul. 10, 2018, provisional application No. 61/243,664, filed on Sep. 18, 2009.

(51) Int. Cl.
 A61F 2/28 (2006.01)
 A61F 2/30 (2006.01)

(52) U.S. Cl.
 CPC ..... *A61F 2/4611* (2013.01); *A61F 2002/2817* (2013.01); *A61F 2002/2835* (2013.01); *A61F 2002/30011* (2013.01); *A61F 2002/30153* (2013.01); *A61F 2002/30224* (2013.01); *A61F 2002/30235* (2013.01); *A61F 2002/30525* (2013.01); *A61F 2002/30579* (2013.01); *A61F 2002/30593* (2013.01); *A61F 2002/30601* (2013.01); *A61F 2002/3071* (2013.01); *A61F 2/30767* (2013.01); *A61F 2002/30784* (2013.01); *A61F 2002/30785* (2013.01); *A61F 2002/30787* (2013.01); *A61F 2002/30828* (2013.01); *A61F 2002/30878* (2013.01); *A61F 2002/30904* (2013.01); *A61F 2002/3093* (2013.01); *A61F 2002/4627* (2013.01); *A61F 2002/4628* (2013.01); *A61F 2002/4635* (2013.01); *A61F 2002/469* (2013.01); *A61F 2002/4693* (2013.01); *A61F 2002/4694* (2013.01); *A61F 2310/00017* (2013.01); *A61F 2310/00023* (2013.01); *A61F 2310/00029* (2013.01); *A61F 2310/00047* (2013.01); *A61F 2310/00059* (2013.01)

(56) References Cited

U.S. PATENT DOCUMENTS

| | | |
|---|---|---|
| 2,520,464 A | 8/1950 | Hubner |
| 3,697,011 A | 10/1972 | Christensen et al. |
| 3,741,496 A | 6/1973 | Beller |
| 3,836,092 A | 9/1974 | Hull |
| 3,855,638 A | 12/1974 | Pilliar |
| 4,039,156 A | 8/1977 | Abraham |
| 4,041,939 A | 8/1977 | Hall |
| 4,047,524 A | 9/1977 | Hall |
| 4,206,516 A | 6/1980 | Pilliar |
| 4,277,184 A | 7/1981 | Solomon |
| 4,338,925 A | 7/1982 | Miller |
| 4,430,062 A | 2/1984 | Henrichsen et al. |
| 4,462,402 A | 7/1984 | Burgio et al. |
| 4,467,478 A | 8/1984 | Jurgutis |
| 4,501,269 A | 2/1985 | Bagby |
| 4,522,270 A | 6/1985 | Kishi |
| 4,570,623 A | 2/1986 | Ellison et al. |
| 4,580,978 A | 4/1986 | Motola et al. |
| 4,592,346 A | 6/1986 | Jurgutis |
| 4,743,256 A | 5/1988 | Brantigan |
| 4,759,769 A | 7/1988 | Hedman et al. |
| 4,863,476 A | 9/1989 | Shepperd |
| 4,877,020 A | 10/1989 | Vich |
| 4,877,399 A | 10/1989 | Frank et al. |
| 4,925,924 A | 5/1990 | Silver et al. |
| D309,499 S | 7/1990 | Bowman et al. |
| D312,309 S | 11/1990 | Michelson |
| 4,991,570 A | 2/1991 | Bullard |
| 5,037,422 A | 8/1991 | Hayhurst |
| 5,053,038 A | 10/1991 | Sheehan |
| 5,055,104 A | 10/1991 | Ray |
| 5,058,823 A | 10/1991 | Emura et al. |
| 5,122,130 A | 6/1992 | Keller |
| 5,282,744 A | 2/1994 | Meyer |
| 5,290,295 A | 3/1994 | Querals et al. |
| 5,311,640 A | 5/1994 | Holland |
| 5,312,407 A | 5/1994 | Carter |
| 5,312,417 A | 5/1994 | Wilk |
| 5,324,307 A | 6/1994 | Jarrett et al. |
| 5,329,834 A | 7/1994 | Wong |
| 5,333,812 A | 8/1994 | Sato |
| D351,022 S | 9/1994 | Saito |
| 5,354,292 A | 10/1994 | Braeuer et al. |
| 5,395,372 A | 3/1995 | Holt et al. |
| 5,425,772 A | 6/1995 | Brantigan |
| D360,689 S | 7/1995 | Giampapa |
| 5,431,658 A | 7/1995 | Moskovich |
| 5,443,514 A | 8/1995 | Steffee |
| D364,462 S | 11/1995 | Michelson |
| 5,520,611 A | 5/1996 | Rao et al. |
| D370,531 S | 6/1996 | Ash et al. |
| 5,527,312 A | 6/1996 | Ray |
| D372,311 S | 7/1996 | Koros et al. |
| 5,531,749 A | 7/1996 | Michelson |
| D372,781 S | 8/1996 | Reif |
| 5,549,607 A | 8/1996 | Olson et al. |
| 5,558,674 A | 9/1996 | Heggeness et al. |
| 5,564,191 A | 9/1996 | Lahille et al. |
| D374,283 S | 10/1996 | Michelson |
| 5,562,661 A | 10/1996 | Yoshimi et al. |
| 5,569,246 A | 10/1996 | Ojima et al. |
| 5,586,989 A | 12/1996 | Bray |
| 5,595,563 A | 1/1997 | Moisdon |
| 5,601,557 A | 2/1997 | Hayhurst |
| D378,409 S | 3/1997 | Michelson |
| 5,611,800 A | 3/1997 | Davis et al. |
| 5,634,925 A | 6/1997 | Urbanski |
| 5,653,763 A | 8/1997 | Errico et al. |
| 5,658,335 A | 8/1997 | Allen |
| 5,662,655 A | 9/1997 | Laboureau et al. |
| 5,665,122 A | 9/1997 | Kambin |
| 5,669,909 A | 9/1997 | Zdeblick et al. |
| 5,683,464 A | 11/1997 | Wagner et al. |
| 5,688,285 A | 11/1997 | Yamada |
| 5,697,932 A | 12/1997 | Smith et al. |
| 5,702,449 A | 12/1997 | McKay |
| 5,704,892 A | 1/1998 | Adair |
| D390,592 S | 2/1998 | Agata |
| 5,741,253 A | 4/1998 | Michelson |
| 5,752,969 A | 5/1998 | Cunci et al. |
| 5,762,629 A | 6/1998 | Kambin |
| 5,776,199 A | 7/1998 | Michelson |
| 5,779,642 A | 7/1998 | Nightengale |
| 5,782,832 A | 7/1998 | Larsen et al. |
| 5,782,919 A | 7/1998 | Zdeblick et al. |
| D397,439 S | 8/1998 | Koros et al. |
| 5,797,918 A | 8/1998 | McGuire et al. |
| 5,836,948 A | 11/1998 | Zucherman et al. |
| 5,836,958 A | 11/1998 | Ralph |
| 5,860,973 A | 1/1999 | Michelson |

(56) References Cited

U.S. PATENT DOCUMENTS

| | | | |
|---|---|---|---|
| 5,860,977 A | 1/1999 | Zucherman et al. |
| 5,865,746 A | 2/1999 | Murugesan et al. |
| 5,865,846 A | 2/1999 | Bryan et al. |
| 5,865,848 A | 2/1999 | Baker |
| 5,871,462 A | 2/1999 | Yoder et al. |
| 5,888,228 A | 3/1999 | Knothe et al. |
| 5,893,889 A | 4/1999 | Harrington |
| 5,904,689 A | 5/1999 | Jonjic |
| 5,904,718 A | 5/1999 | Jefferies |
| 5,906,616 A | 5/1999 | Pavlov et al. |
| 5,925,051 A | 7/1999 | Mikhail |
| 5,925,056 A | 7/1999 | Thomas et al. |
| 5,935,129 A | 8/1999 | McDevitt et al. |
| 5,944,658 A | 8/1999 | Koros et al. |
| 5,944,686 A | 8/1999 | Patterson et al. |
| 5,947,972 A | 9/1999 | Gage et al. |
| 5,976,146 A | 11/1999 | Ogawa et al. |
| 5,980,522 A | 11/1999 | Koros et al. |
| 5,989,257 A | 11/1999 | Tidwell et al. |
| 5,989,289 A | 11/1999 | Coates et al. |
| 5,997,895 A | 12/1999 | Narotam et al. |
| 6,004,191 A | 12/1999 | Schur et al. |
| 6,004,326 A | 12/1999 | Castro et al. |
| 6,008,433 A | 12/1999 | Stone |
| 6,013,028 A | 1/2000 | Jho et al. |
| 6,019,765 A * | 2/2000 | Thornhill ............ A61F 2/4601 606/93 |
| 6,030,356 A | 2/2000 | Carlson et al. |
| 6,030,388 A | 2/2000 | Yoshimi et al. |
| 6,030,390 A | 2/2000 | Mehdizadeh |
| 6,030,401 A | 2/2000 | Marino |
| 6,033,408 A | 3/2000 | Gage et al. |
| 6,033,438 A | 3/2000 | Bianchi et al. |
| 6,045,555 A | 4/2000 | Smith et al. |
| 6,045,579 A | 4/2000 | Hochshuler et al. |
| 6,059,829 A | 5/2000 | Schlapfer et al. |
| 6,080,193 A | 6/2000 | Hochshuler et al. |
| 6,090,143 A | 7/2000 | Meriwether et al. |
| 6,096,080 A | 8/2000 | Nicholson et al. |
| 6,102,950 A | 8/2000 | Vaccaro |
| 6,117,174 A | 9/2000 | Nolan |
| 6,120,503 A | 9/2000 | Michelson |
| 6,123,705 A | 9/2000 | Michelson |
| 6,129,763 A | 10/2000 | Chauvin et al. |
| 6,136,001 A | 10/2000 | Michelson |
| 6,142,998 A | 11/2000 | Smith et al. |
| 6,145,998 A | 11/2000 | Lynch et al. |
| 6,146,420 A | 11/2000 | McKay |
| 6,149,096 A | 11/2000 | Hartley |
| 6,152,871 A | 11/2000 | Foley et al. |
| 6,159,211 A | 12/2000 | Boriani et al. |
| 6,159,245 A | 12/2000 | Meriwether et al. |
| 6,176,882 B1 | 1/2001 | Biedermann et al. |
| 6,179,873 B1 | 1/2001 | Zientek |
| 6,180,085 B1 | 1/2001 | Achilefu |
| 6,190,414 B1 | 2/2001 | Young et al. |
| 6,200,322 B1 | 3/2001 | Branch et al. |
| 6,209,886 B1 | 4/2001 | Estes et al. |
| 6,214,050 B1 | 4/2001 | Huene |
| 6,216,573 B1 | 4/2001 | Moutafis et al. |
| 6,217,579 B1 | 4/2001 | Koros |
| 6,224,599 B1 | 5/2001 | Baynham et al. |
| 6,224,607 B1 | 5/2001 | Michelson |
| 6,235,805 B1 | 5/2001 | Chang et al. |
| 6,238,397 B1 | 5/2001 | Zucherman et al. |
| 6,241,733 B1 | 6/2001 | Nicholson et al. |
| 6,241,769 B1 | 6/2001 | Nicholson et al. |
| 6,245,108 B1 | 6/2001 | Bisoup |
| D444,878 S | 7/2001 | Walter |
| D445,188 S | 7/2001 | Walter |
| 6,258,094 B1 | 7/2001 | Nicholson et al. |
| 6,261,293 B1 | 7/2001 | Nicholson et al. |
| 6,261,295 B1 | 7/2001 | Nicholson et al. |
| 6,261,296 B1 | 7/2001 | Aebi et al. |
| 6,268,125 B1 | 7/2001 | Paul et al. |
| 6,290,724 B1 | 9/2001 | Marino |
| 6,299,613 B1 | 10/2001 | Ogilvie et al. |
| 6,302,914 B1 | 10/2001 | Michelson |
| 6,309,395 B1 | 10/2001 | Smith et al. |
| 6,325,805 B1 | 12/2001 | Ogilvie et al. |
| 6,328,738 B1 | 12/2001 | Suddaby |
| H2009 H | 1/2002 | Martin et al. |
| 6,336,928 B1 | 1/2002 | Guerin et al. |
| 6,340,369 B1 | 1/2002 | Ferree |
| 6,342,074 B1 | 1/2002 | Simpson |
| 6,344,058 B1 | 2/2002 | Ferree |
| 6,360,126 B1 | 2/2002 | Levisman |
| 6,352,557 B1 | 3/2002 | Ferree |
| 6,365,069 B2 | 3/2002 | DeCarlo, Jr. et al. |
| 6,364,880 B1 | 4/2002 | Michelson |
| 6,368,351 B1 | 4/2002 | Glenn et al. |
| 6,371,989 B1 | 4/2002 | Chauvin et al. |
| 6,375,635 B1 | 4/2002 | Moutafis et al. |
| 6,375,655 B1 | 4/2002 | Zdeblick et al. |
| 6,387,096 B1 | 5/2002 | Hyde, Jr. |
| 6,409,765 B1 | 6/2002 | Bianchi et al. |
| 6,416,551 B1 | 7/2002 | Keller |
| 6,419,702 B1 | 7/2002 | Ferree |
| 6,436,101 B1 | 8/2002 | Hamada |
| 6,436,140 B1 | 8/2002 | Liu et al. |
| 6,436,142 B1 | 8/2002 | Paes et al. |
| 6,443,989 B1 | 9/2002 | Jackson |
| 6,443,990 B1 | 9/2002 | Aebi et al. |
| 6,447,544 B1 | 9/2002 | Michelson |
| 6,447,547 B1 | 9/2002 | Michelson |
| 6,451,017 B1 | 9/2002 | Moutafis et al. |
| 6,451,057 B1 | 9/2002 | Chen et al. |
| 6,454,806 B1 | 9/2002 | Cohen et al. |
| 6,454,807 B1 | 9/2002 | Jackson |
| 6,467,556 B2 | 10/2002 | Alsruhe |
| 6,471,724 B2 | 10/2002 | Zdeblick et al. |
| 6,478,823 B1 | 11/2002 | Michelson |
| D467,657 S | 12/2002 | Scribner |
| 6,491,724 B1 | 12/2002 | Ferree |
| 6,500,206 B1 | 12/2002 | Bryan |
| 6,506,051 B2 | 1/2003 | Levisman |
| 6,611,493 B1 | 1/2003 | Moutafis et al. |
| D469,871 S | 2/2003 | Sand |
| 6,520,976 B1 | 2/2003 | Gage |
| 6,520,991 B2 | 2/2003 | Huene |
| 6,524,318 B1 | 2/2003 | Longhini et al. |
| 6,533,791 B1 | 3/2003 | Betz et al. |
| 6,562,074 B2 | 5/2003 | Gerbec et al. |
| 6,565,574 B2 | 5/2003 | Michelson |
| 6,569,201 B2 | 5/2003 | Moumene et al. |
| 6,576,016 B1 | 6/2003 | Hochshuler et al. |
| 6,579,290 B1 | 6/2003 | Hardcastle et al. |
| 6,595,998 B2 | 7/2003 | Johnson et al. |
| 6,613,091 B1 | 9/2003 | Zdeblick et al. |
| 6,613,093 B2 | 9/2003 | DeCarlo, Jr. et al. |
| 6,616,669 B2 | 9/2003 | Ogilvie et al. |
| 6,620,356 B1 | 9/2003 | Wong et al. |
| 6,641,613 B2 | 11/2003 | Sennett |
| 6,641,614 B1 | 11/2003 | Wagner et al. |
| 6,645,206 B1 | 11/2003 | Zdeblick et al. |
| 6,648,915 B2 | 11/2003 | Sazy |
| 6,648,917 B2 | 11/2003 | Gerbec et al. |
| 6,648,918 B2 | 11/2003 | Ferree |
| 6,652,533 B2 | 11/2003 | O'Neil |
| 6,666,891 B2 | 12/2003 | Boehm, Jr. et al. |
| 6,669,710 B2 | 12/2003 | Moutafis et al. |
| 6,673,113 B2 | 1/2004 | Ralph et al. |
| 6,679,887 B2 | 1/2004 | Nicholson et al. |
| 6,685,742 B1 | 2/2004 | Jackson |
| 6,695,851 B2 | 2/2004 | Zdeblick et al. |
| 6,695,882 B2 | 2/2004 | Bianchi et al. |
| 6,699,288 B2 | 3/2004 | Moret |
| 6,706,070 B1 | 3/2004 | Wagner et al. |
| 6,709,438 B2 | 3/2004 | Dixon et al. |
| 6,719,760 B2 | 4/2004 | Dorchak et al. |
| 6,719,795 B1 | 4/2004 | Cornwall et al. |
| 6,719,796 B2 | 4/2004 | Cohen et al. |
| 6,719,797 B1 | 4/2004 | Ferree |
| 6,723,096 B1 | 4/2004 | Dorchak et al. |

(56) References Cited

U.S. PATENT DOCUMENTS

| | | |
|---|---|---|
| 6,723,126 B1 | 4/2004 | Berry |
| 6,730,125 B1 | 5/2004 | Lin |
| 6,730,126 B2 | 5/2004 | Boehm, Jr. et al. |
| 6,733,535 B2 | 5/2004 | Michelson |
| 6,743,255 B2 | 6/2004 | Ferree |
| 6,743,257 B2 | 6/2004 | Castro |
| 6,746,487 B2 | 6/2004 | Scifert et al. |
| 6,764,491 B2 | 7/2004 | Frey et al. |
| 6,770,074 B2 | 8/2004 | Michelson |
| 6,773,437 B2 | 8/2004 | Ogilvie et al. |
| 6,773,460 B2 | 8/2004 | Jackson |
| 6,800,093 B2 | 10/2004 | Nicholson et al. |
| 6,821,298 B1 | 11/2004 | Jackson |
| 6,823,871 B2 | 11/2004 | Schmieding |
| 6,824,565 B2 | 11/2004 | Muhanna et al. |
| 6,830,574 B2 | 12/2004 | Heckele et al. |
| 6,835,206 B2 | 12/2004 | Jackson |
| 6,852,126 B2 | 2/2005 | Ahlgren |
| 6,852,129 B2 | 2/2005 | Gerbec et al. |
| 6,863,673 B2 | 3/2005 | Gerbec et al. |
| 6,869,430 B2 | 3/2005 | Balbierz et al. |
| 6,890,728 B2 | 5/2005 | Dolecek et al. |
| 6,899,712 B2 | 5/2005 | Moutafis et al. |
| 6,905,512 B2 | 6/2005 | Paes et al. |
| 6,923,792 B2 | 8/2005 | Staid et al. |
| 6,923,814 B1 | 8/2005 | Hildebrand et al. |
| 6,929,646 B2 | 8/2005 | Gambale |
| 6,942,665 B2 | 9/2005 | Gambale |
| 6,955,691 B2 | 10/2005 | Chae et al. |
| 6,960,182 B2 | 11/2005 | Moutafis et al. |
| 6,962,592 B2 | 11/2005 | Gattuma et al. |
| 6,969,523 B1 | 11/2005 | Mattern et al. |
| 6,972,035 B2 | 12/2005 | Michelson |
| 6,974,480 B2 | 12/2005 | Messerli et al. |
| 6,991,653 B2 | 1/2006 | White et al. |
| 6,994,728 B2 | 2/2006 | Zubok et al. |
| 6,997,929 B2 | 2/2006 | Manzi et al. |
| 7,004,946 B2 | 2/2006 | Parker et al. |
| 7,008,431 B2 | 3/2006 | Simonson |
| 7,014,640 B2 | 3/2006 | Kemppainen et al. |
| 7,025,742 B2 | 4/2006 | Rubenstein et al. |
| 7,025,769 B1 | 4/2006 | Ferree |
| 7,033,317 B2 | 4/2006 | Pruitt |
| 7,041,136 B2 | 5/2006 | Goble et al. |
| 7,041,137 B2 | 5/2006 | Fulton et al. |
| 7,066,961 B2 | 6/2006 | Hichelson |
| D524,443 S | 7/2006 | Blain |
| 7,070,598 B2 | 7/2006 | Lim et al. |
| 7,077,864 B2 | 7/2006 | Byrd, III et al. |
| 7,087,055 B2 | 8/2006 | Lim et al. |
| 7,094,257 B2 | 8/2006 | Mujwid et al. |
| 7,122,017 B2 | 10/2006 | Moutafis et al. |
| 7,128,760 B2 | 10/2006 | Michelson |
| 7,135,043 B2 | 11/2006 | Nakahara et al. |
| 7,156,874 B2 | 1/2007 | Paponneau et al. |
| 7,169,182 B2 | 1/2007 | Errico et al. |
| 7,182,782 B2 | 2/2007 | Kirschman |
| 7,204,825 B2 | 4/2007 | Cimino et al. |
| 7,204,853 B2 | 4/2007 | Gordon et al. |
| 7,207,992 B2 | 4/2007 | Ritland |
| D541,940 S | 5/2007 | Blain |
| 7,211,112 B2 | 5/2007 | Baynham et al. |
| 7,214,186 B2 | 5/2007 | Ritland |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,223,292 B2 | 5/2007 | Messerli et al. |
| 7,232,463 B2 | 6/2007 | Falahee |
| 7,238,186 B2 | 7/2007 | Zdeblick et al. |
| 7,238,203 B2 | 7/2007 | Bagga et al. |
| 7,255,703 B2 | 8/2007 | Mujwid et al. |
| 7,267,691 B2 | 9/2007 | Keller et al. |
| 7,273,498 B2 | 9/2007 | Bianchi et al. |
| 7,282,063 B2 | 10/2007 | Cohen et al. |
| 7,288,093 B2 | 10/2007 | Michelson |
| 7,311,713 B2 | 12/2007 | Johnson et al. |
| 7,316,070 B2 | 1/2008 | Green |
| 7,316,714 B2 | 1/2008 | Gordon et al. |
| 7,329,283 B2 | 2/2008 | Estes et al. |
| 7,337,538 B2 | 3/2008 | Moutafis et al. |
| 7,341,590 B2 | 3/2008 | Ferree |
| 7,341,591 B2 | 3/2008 | Grinberg |
| 7,357,284 B2 | 4/2008 | Jauvin |
| 7,357,804 B2 | 4/2008 | Binder, Jr. et al. |
| 7,361,178 B2 | 4/2008 | Hearn et al. |
| 7,364,657 B2 | 4/2008 | Mandrusov et al. |
| 7,371,239 B2 | 5/2008 | Dec et al. |
| 7,377,923 B2 | 5/2008 | Purcell et al. |
| 7,387,643 B2 | 6/2008 | Michelson |
| 7,399,041 B2 | 7/2008 | Prentner et al. |
| D574,495 S | 8/2008 | Petersen |
| 7,406,775 B2 | 8/2008 | Funk et al. |
| 7,410,334 B2 | 8/2008 | McGrew |
| 7,410,478 B2 | 8/2008 | Yano |
| 7,410,501 B2 | 8/2008 | Michelson |
| 7,413,065 B2 | 8/2008 | Gauthier |
| 7,421,772 B2 | 9/2008 | Gao et al. |
| 7,429,270 B2 | 9/2008 | Baumgartner et al. |
| D579,562 S | 10/2008 | Anderson et al. |
| 7,430,945 B2 | 10/2008 | Gauthier et al. |
| 7,431,711 B2 | 10/2008 | Moutafis et al. |
| 7,431,735 B2 | 10/2008 | Liu et al. |
| 7,442,208 B2 | 10/2008 | Mathieu et al. |
| 7,445,636 B2 | 11/2008 | Michelson |
| 7,455,157 B2 | 11/2008 | Kimes et al. |
| D582,552 S | 12/2008 | Berberich |
| 7,461,803 B2 | 12/2008 | Boemer |
| 7,473,255 B2 | 1/2009 | McGarty et al. |
| 7,476,226 B2 | 1/2009 | Weikel et al. |
| 7,478,577 B1 | 1/2009 | Wheeler |
| 7,481,766 B2 | 1/2009 | Lee et al. |
| 7,481,813 B1 | 1/2009 | Purcell |
| 7,485,145 B2 | 2/2009 | Purcell |
| D589,626 S | 3/2009 | Petersen |
| 7,501,073 B2 | 3/2009 | Wen et al. |
| 7,503,933 B2 | 3/2009 | Michelson |
| 7,503,934 B2 | 3/2009 | Eisermann et al. |
| 7,503,936 B2 | 3/2009 | Trieu |
| D590,943 S | 4/2009 | Petersen |
| D590,945 S | 4/2009 | Berberich |
| 7,513,901 B2 | 4/2009 | Scifert et al. |
| D593,202 S | 5/2009 | Petersen |
| 7,531,003 B2 | 5/2009 | Reindel |
| 7,534,265 B1 | 5/2009 | Boyd |
| 7,534,270 B2 | 5/2009 | Ball |
| D594,119 S | 6/2009 | Berberich et al. |
| 7,547,308 B2 | 6/2009 | Bertagnoli et al. |
| 7,553,320 B2 | 6/2009 | Molz, IV et al. |
| D597,669 S | 8/2009 | Petersen |
| D598,096 S | 8/2009 | Petersen |
| D599,015 S | 8/2009 | Petersen |
| 7,569,074 B2 | 8/2009 | Eisermann et al. |
| 7,578,820 B2 | 8/2009 | Moore et al. |
| D600,806 S | 9/2009 | Horton et al. |
| D601,261 S | 9/2009 | Horton et al. |
| 7,582,058 B1 | 9/2009 | Miles et al. |
| 7,582,107 B2 | 9/2009 | Trail et al. |
| 7,588,599 B2 | 9/2009 | Sweeney |
| 7,595,043 B2 | 9/2009 | Hedrick et al. |
| D603,502 S | 11/2009 | Petersen |
| 7,615,078 B2 | 11/2009 | White et al. |
| 7,618,423 B1 | 11/2009 | Valentine et al. |
| 7,618,458 B2 | 11/2009 | Biedermann et al. |
| 7,621,951 B2 | 11/2009 | Glenn et al. |
| 7,621,968 B1 | 11/2009 | Zdeblick et al. |
| 7,625,374 B2 | 12/2009 | Branch et al. |
| 7,632,276 B2 | 12/2009 | Fishbein |
| 7,632,281 B2 | 12/2009 | Errico et al. |
| D608,001 S | 1/2010 | Reardon et al. |
| 7,655,027 B2 | 2/2010 | Michelson |
| 7,655,043 B2 | 2/2010 | Peterman et al. |
| 7,655,046 B2 | 2/2010 | Dryer et al. |
| 7,658,766 B2 | 2/2010 | Melkent et al. |
| D611,147 S | 3/2010 | Hanson et al. |

(56) References Cited

U.S. PATENT DOCUMENTS

| | | |
|---|---|---|
| 7,671,014 B2 | 3/2010 | Beals et al. |
| 7,674,265 B2 | 3/2010 | Smith et al. |
| 7,674,297 B2 | 3/2010 | Falahee |
| 7,677,418 B2 | 3/2010 | Henniges et al. |
| 7,678,148 B2 | 3/2010 | Peterman |
| 7,686,805 B2 | 3/2010 | Michelson |
| 7,691,133 B2 | 4/2010 | Partin et al. |
| 7,693,562 B2 | 4/2010 | Marino et al. |
| 7,699,852 B2 | 4/2010 | Frankel et al. |
| 7,703,727 B2 | 4/2010 | Selness |
| 7,704,279 B2 | 4/2010 | Moskowitz et al. |
| D615,653 S | 5/2010 | Horton |
| 7,708,761 B2 | 5/2010 | Petersen |
| 7,708,778 B2 | 5/2010 | Gordon et al. |
| 7,717,685 B2 | 5/2010 | Moutafis et al. |
| 7,722,530 B2 | 5/2010 | Davison |
| 7,722,613 B2 | 5/2010 | Sutterlin et al. |
| 7,722,674 B1 | 5/2010 | Grotz |
| 7,723,291 B2 | 5/2010 | Beals et al. |
| 7,727,280 B2 | 6/2010 | MoLuen |
| 7,728,868 B2 | 6/2010 | Razzaque et al. |
| 7,730,563 B1 | 6/2010 | Sklar et al. |
| 7,731,751 B2 | 6/2010 | Butler et al. |
| 7,734,327 B2 | 6/2010 | Colquhoun |
| 7,740,634 B2 | 6/2010 | Orbay et al. |
| 7,740,661 B2 | 6/2010 | Baratz et al. |
| 7,744,555 B2 | 6/2010 | DiMauro et al. |
| 7,744,637 B2 | 6/2010 | Johnson et al. |
| 7,744,973 B2 | 6/2010 | Schoenle et al. |
| D620,108 S | 7/2010 | Eitenmueller et al. |
| 7,749,231 B2 | 7/2010 | Bonvallet et al. |
| 7,749,253 B2 | 7/2010 | Zucherman et al. |
| 7,749,255 B2 | 7/2010 | Johnson et al. |
| 7,749,269 B2 | 7/2010 | Peterman et al. |
| 7,749,270 B2 | 7/2010 | Peterman |
| 7,749,273 B2 | 7/2010 | Cauthen et al. |
| 7,749,274 B2 | 7/2010 | Razian |
| 7,749,276 B2 | 7/2010 | Fitz |
| 7,749,279 B2 | 7/2010 | Twomey et al. |
| 7,749,555 B2 | 7/2010 | Zanella et al. |
| 7,751,865 B2 | 7/2010 | Jascob et al. |
| 7,753,911 B2 | 7/2010 | Ray et al. |
| 7,753,912 B2 | 7/2010 | Raymond et al. |
| 7,753,914 B2 | 7/2010 | Ruhling et al. |
| 7,753,938 B2 | 7/2010 | Aschmann et al. |
| 7,753,940 B2 | 7/2010 | Veldman et al. |
| 7,753,958 B2 | 7/2010 | Gordon et al. |
| 7,753,962 B2 | 7/2010 | Melder |
| 7,758,501 B2 | 7/2010 | Frasier et al. |
| 7,758,616 B2 | 7/2010 | LeHuec et al. |
| 7,758,617 B2 | 7/2010 | Lott et al. |
| 7,758,644 B2 | 7/2010 | Trieu |
| 7,758,648 B2 | 7/2010 | Castlemen et al. |
| 7,763,025 B2 | 7/2010 | Assell et al. |
| 7,763,028 B2 | 7/2010 | Lim et al. |
| 7,763,035 B2 | 7/2010 | Melkent et al. |
| 7,763,055 B2 | 7/2010 | Foley |
| 7,763,078 B2 | 7/2010 | Peterman et al. |
| 7,763,080 B2 | 7/2010 | Southworth |
| D621,509 S | 8/2010 | Lovell |
| D622,395 S | 8/2010 | Iott et al. |
| D622,843 S | 8/2010 | Horton |
| D622,851 S | 8/2010 | Horton |
| 7,766,914 B2 | 8/2010 | McCormack et al. |
| 7,766,918 B2 | 8/2010 | Allard et al. |
| 7,766,930 B2 | 8/2010 | DiPoto et al. |
| 7,766,940 B2 | 8/2010 | Kwak et al. |
| 7,766,967 B2 | 8/2010 | Francis |
| 7,766,969 B2 | 8/2010 | Justin et al. |
| 7,769,422 B2 | 8/2010 | DiSilvestro et al. |
| 7,771,143 B2 | 8/2010 | Bharadwaj et al. |
| 7,771,473 B2 | 8/2010 | Thramann |
| 7,771,475 B2 | 8/2010 | Michelson |
| 7,771,476 B2 | 8/2010 | Justis et al. |
| 7,771,479 B2 | 8/2010 | Humphreys et al. |
| 7,776,040 B2 | 8/2010 | Markworth et al. |
| 7,776,046 B2 | 8/2010 | Boyd et al. |
| 7,776,047 B2 | 8/2010 | Fanger et al. |
| 7,776,049 B1 | 8/2010 | Curran et al. |
| 7,776,075 B2 | 8/2010 | Bruneau et al. |
| 7,776,090 B2 | 8/2010 | Winslow et al. |
| 7,776,091 B2 | 8/2010 | Mastrorio |
| 7,776,094 B2 | 8/2010 | McKinley et al. |
| 7,776,095 B2 | 8/2010 | Peterman et al. |
| 7,776,594 B2 | 8/2010 | Bays et al. |
| 7,780,707 B2 | 8/2010 | Johnson et al. |
| 7,780,734 B2 | 8/2010 | Johnson et al. |
| 7,785,351 B2 | 8/2010 | Gordon et al. |
| D623,748 S | 9/2010 | Horton et al. |
| D623,749 S | 9/2010 | Horton et al. |
| 7,789,914 B2 | 9/2010 | Michelson |
| 7,794,396 B2 | 9/2010 | Gattani et al. |
| 7,794,480 B2 | 9/2010 | Gordon et al. |
| 7,794,501 B2 | 9/2010 | Edie et al. |
| 7,799,034 B2 | 9/2010 | Johnson et al. |
| 7,799,036 B2 | 9/2010 | Davison et al. |
| 7,799,053 B2 | 9/2010 | Haid et al. |
| 7,799,054 B2 | 9/2010 | Kwak et al. |
| 7,799,055 B2 | 9/2010 | Lim |
| 7,799,056 B2 | 9/2010 | Sankaran |
| 7,799,076 B2 | 9/2010 | Sybert et al. |
| 7,799,078 B2 | 9/2010 | Embry et al. |
| 7,799,081 B2 | 9/2010 | McKinley |
| 7,799,082 B2 | 9/2010 | Gordon et al. |
| 7,799,083 B2 | 9/2010 | Smith et al. |
| 7,803,159 B2 | 9/2010 | Perez-Cruet et al. |
| 7,806,901 B2 | 10/2010 | Stad et al. |
| 7,811,327 B2 | 10/2010 | Hansell et al. |
| 7,811,329 B2 | 10/2010 | Ankney et al. |
| 7,815,681 B2 | 10/2010 | Ferguson |
| 7,819,801 B2 | 10/2010 | Miles et al. |
| 7,819,921 B2 | 10/2010 | Grotz |
| D627,460 S | 11/2010 | Horton |
| D627,468 S | 11/2010 | Richter et al. |
| 7,824,328 B2 | 11/2010 | Gattani et al. |
| 7,824,332 B2 | 11/2010 | Fakhrai |
| 7,824,410 B2 | 11/2010 | Simonson |
| 7,824,445 B2 | 11/2010 | Biro et al. |
| 7,824,703 B2 | 11/2010 | Scifert et al. |
| 7,828,804 B2 | 11/2010 | Li et al. |
| 7,828,845 B2 | 11/2010 | Estes et al. |
| 7,828,848 B2 | 11/2010 | Chauvin et al. |
| 7,828,849 B2 | 11/2010 | Lim |
| 7,837,713 B2 | 11/2010 | Petersen |
| 7,837,732 B2 | 11/2010 | Zucherman et al. |
| 7,837,734 B2 | 11/2010 | Zucherman et al. |
| D628,694 S | 12/2010 | Donnez |
| D629,896 S | 12/2010 | Horton |
| 7,846,188 B2 | 12/2010 | Moskowitz et al. |
| 7,846,206 B2 | 12/2010 | Oglaza et al. |
| 7,846,210 B2 | 12/2010 | Perez-Cruet et al. |
| 7,850,733 B2 | 12/2010 | Baynham et al. |
| 7,850,736 B2 | 12/2010 | Eisermann et al. |
| D631,156 S | 1/2011 | Halder et al. |
| 7,867,277 B1 | 1/2011 | Tohmeh |
| 7,875,034 B2 | 1/2011 | Josse et al. |
| 7,875,078 B2 | 1/2011 | Wysocki et al. |
| D631,967 S | 2/2011 | Horton |
| 7,879,098 B1 | 2/2011 | Simmons, Jr. |
| 7,892,261 B2 | 2/2011 | Bonutti |
| 7,897,164 B2 | 3/2011 | Scifert |
| 7,897,564 B2 | 3/2011 | Beals et al. |
| 7,905,840 B2 | 3/2011 | Pimenta et al. |
| 7,905,886 B1 | 3/2011 | Curran et al. |
| 7,909,869 B2 | 3/2011 | Gordon et al. |
| 7,918,891 B1 | 4/2011 | Curran et al. |
| 7,922,766 B2 | 4/2011 | Grob et al. |
| 7,927,361 B2 | 4/2011 | Oliver et al. |
| D637,721 S | 5/2011 | Horton |
| 7,935,124 B2 | 5/2011 | Frey et al. |
| 7,938,857 B2 | 5/2011 | Garcia-Bengochea et al. |
| 7,939,092 B2 | 5/2011 | McKay et al. |
| 7,951,180 B2 | 5/2011 | Moskowitz et al. |
| 7,961,107 B2 | 5/2011 | Staid et al. |

(56) References Cited

U.S. PATENT DOCUMENTS

| | | |
|---|---|---|
| 7,964,208 B2 | 6/2011 | Spagnoli et al. |
| D641,872 S | 7/2011 | Solingen et al. |
| D641,873 S | 7/2011 | Solingen et al. |
| D641,874 S | 7/2011 | Solingen et al. |
| D642,268 S | 7/2011 | Qureshi |
| 7,972,363 B2 | 7/2011 | Moskowitz et al. |
| 7,985,256 B2 | 7/2011 | Grotz et al. |
| 7,985,526 B2 | 7/2011 | Sweeney et al. |
| D643,921 S | 8/2011 | Davila |
| 8,021,430 B2 | 9/2011 | Michelson |
| D647,202 S | 10/2011 | Scifert |
| 8,052,723 B2 | 11/2011 | Gordon et al. |
| D650,481 S | 12/2011 | Gottlieb et al. |
| 8,075,623 B2 | 12/2011 | Johnson et al. |
| 8,080,041 B2 | 12/2011 | Boehm, Jr. et al. |
| 8,080,621 B2 | 12/2011 | Beals et al. |
| 8,088,163 B1 | 1/2012 | Kleiner |
| 8,097,035 B2 | 1/2012 | Glenn et al. |
| 8,105,382 B2 | 1/2012 | Olmos et al. |
| D653,757 S | 2/2012 | Binder |
| 8,113,602 B2 | 2/2012 | Heimler |
| 8,118,870 B2 | 2/2012 | Gordon et al. |
| 8,118,871 B2 | 2/2012 | Gordon et al. |
| 8,123,755 B2 | 2/2012 | Johnson et al. |
| 8,123,810 B2 | 2/2012 | Gordon et al. |
| D655,414 S | 3/2012 | Cuschieri et al. |
| D656,610 S | 3/2012 | Kleiner |
| 8,128,700 B2 | 3/2012 | Delurio et al. |
| 8,142,437 B2 | 3/2012 | McLean et al. |
| 8,147,550 B2 | 4/2012 | Gordon et al. |
| 8,148,326 B2 | 4/2012 | Beals et al. |
| 8,162,990 B2 | 4/2012 | Potash et al. |
| D660,428 S | 5/2012 | Hohl |
| 8,167,887 B2 | 5/2012 | McLean |
| 8,172,903 B2 | 5/2012 | Gordon et al. |
| 8,187,332 B2 | 5/2012 | McLuen |
| 8,197,544 B1 | 6/2012 | Manzi et al. |
| 8,198,238 B2 | 6/2012 | Beals et al. |
| 8,202,274 B2 | 6/2012 | McLean |
| 8,206,395 B2 | 6/2012 | McLean et al. |
| 8,206,398 B2 | 6/2012 | Johnson et al. |
| 8,216,314 B2 | 7/2012 | Richelsoph |
| 8,221,501 B2 | 7/2012 | Eisermann et al. |
| 8,221,502 B2 | 7/2012 | Branch, Jr. |
| 8,241,331 B2 | 8/2012 | Arnin |
| 8,246,572 B2 | 8/2012 | Cantor et al. |
| D667,542 S | 9/2012 | Kleiner |
| 8,257,370 B2 | 9/2012 | Moskowitz et al. |
| 8,262,666 B2 | 9/2012 | Baynham et al. |
| 8,262,736 B2 | 9/2012 | Michelson |
| 8,267,440 B2 | 9/2012 | Gordon et al. |
| 8,273,129 B2 | 9/2012 | Baynham et al. |
| 8,277,510 B2 | 10/2012 | Kleiner |
| 8,282,683 B2 | 10/2012 | McLaughlin et al. |
| 8,292,960 B2 | 10/2012 | Kleiner |
| 8,293,232 B2 | 10/2012 | Beals et al. |
| 8,303,601 B2 | 11/2012 | Bandeira et al. |
| 8,303,659 B2 | 11/2012 | Errico et al. |
| 8,308,804 B2 | 11/2012 | Krueger |
| 8,317,025 B1 | 11/2012 | Kolozs et al. |
| 8,317,802 B1 | 11/2012 | Manzi et al. |
| 8,317,866 B2 | 11/2012 | Palmatier et al. |
| 8,328,818 B1 | 12/2012 | Seifert et al. |
| 8,337,531 B2 | 12/2012 | Johnson et al. |
| 8,337,532 B1 | 12/2012 | McLean et al. |
| 8,337,562 B2 | 12/2012 | Landry et al. |
| D674,900 S | 1/2013 | Janice et al. |
| 8,343,193 B2 | 1/2013 | Johnson et al. |
| 8,349,014 B2 | 1/2013 | Barreiro et al. |
| 8,353,913 B2 | 1/2013 | Moskowitz et al. |
| 8,361,152 B2 | 1/2013 | McCormack et al. |
| 8,366,748 B2 | 2/2013 | Kleiner |
| 8,366,777 B2 | 2/2013 | Matthis et al. |
| 8,372,120 B2 | 2/2013 | James |
| 8,377,071 B2 | 2/2013 | Lim et al. |
| 8,382,842 B2 | 2/2013 | Greenhalgh et al. |
| D677,791 S | 3/2013 | Danacioglu et al. |
| 8,394,108 B2 | 3/2013 | McLean et al. |
| 8,394,129 B2 | 3/2013 | Morgenstern Lopez et al. |
| 8,398,713 B2 | 3/2013 | Weiman |
| D681,205 S | 4/2013 | Farris et al. |
| 8,414,622 B2 | 4/2013 | Potash |
| 8,419,795 B2 | 4/2013 | Sweeney |
| 8,430,885 B2 | 4/2013 | Manzi et al. |
| 8,435,298 B2 | 5/2013 | Weiman |
| 8,436,299 B2 | 5/2013 | Chauvin et al. |
| 8,439,929 B1 | 5/2013 | Sharratt et al. |
| 8,444,696 B2 | 5/2013 | Michelson |
| 8,444,697 B1 | 5/2013 | Butler |
| 8,454,621 B2 | 6/2013 | DeRidder et al. |
| 8,454,664 B2 | 6/2013 | McLean |
| 8,460,389 B2 | 6/2013 | DeLurio et al. |
| 8,475,500 B2 | 7/2013 | Potash |
| 8,480,748 B2 | 7/2013 | Poulos |
| 8,491,657 B2 | 7/2013 | Attia et al. |
| 8,496,706 B2 | 7/2013 | Ragab et al. |
| 8,512,347 B2 | 8/2013 | McCormack et al. |
| 8,512,348 B2 | 8/2013 | Chabansky et al. |
| 8,512,383 B2 | 8/2013 | McLean |
| 8,512,407 B2 | 8/2013 | Butler et al. |
| 8,518,087 B2 | 8/2013 | Lopez et al. |
| 8,518,114 B2 | 8/2013 | Marik |
| 8,518,120 B2 | 8/2013 | Glerum et al. |
| 8,606,635 B2 | 8/2013 | Palmatier et al. |
| 8,523,906 B2 | 9/2013 | McLean et al. |
| 8,523,946 B1 | 9/2013 | Swann |
| 8,529,627 B2 | 9/2013 | Baynham |
| 8,535,353 B2 | 9/2013 | Johnson et al. |
| D692,133 S | 10/2013 | Steinwachs et al. |
| 8,545,567 B1 | 10/2013 | Krueger |
| 8,556,975 B2 | 10/2013 | Lechoslaw et al. |
| 8,556,979 B2 | 10/2013 | Glerum et al. |
| 8,562,654 B2 | 10/2013 | McLean et al. |
| 8,562,685 B2 | 10/2013 | Ullrich, Jr. et al. |
| 8,568,481 B2 | 10/2013 | Dimos et al. |
| 8,574,299 B2 | 11/2013 | Barreiro et al. |
| 8,574,300 B2 | 11/2013 | McManus et al. |
| 8,579,907 B2 | 11/2013 | Lim et al. |
| 8,579,980 B2 | 11/2013 | DeLurio et al. |
| 8,579,981 B2 | 11/2013 | Lim et al. |
| 8,585,761 B2 | 11/2013 | Theofilos |
| 8,591,585 B2 | 11/2013 | McLaughlin et al. |
| D696,399 S | 12/2013 | Kleiner |
| 8,597,333 B2 | 12/2013 | Morgenstern Lopez et al. |
| 8,597,360 B2 | 12/2013 | McLuen et al. |
| 8,603,168 B2 | 12/2013 | Gordon et al. |
| 8,623,054 B2 | 1/2014 | McCormack et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| D700,322 S | 2/2014 | Kleiner |
| D700,332 S | 2/2014 | Tyber |
| 8,641,739 B2 | 2/2014 | McLean et al. |
| 8,641,767 B2 | 2/2014 | Landry et al. |
| 8,641,769 B2 | 2/2014 | Malandain |
| 8,647,386 B2 | 2/2014 | Gordon et al. |
| 8,657,826 B2 | 2/2014 | McLean et al. |
| 8,663,281 B2 | 3/2014 | McLean et al. |
| 8,685,031 B2 | 4/2014 | Kleiner |
| 8,685,095 B2 | 4/2014 | Miller et al. |
| 8,696,720 B2 | 4/2014 | Lazarof |
| 8,702,798 B2 | 4/2014 | Matthis et al. |
| 8,709,086 B2 | 4/2014 | Glerum |
| 8,709,088 B2 | 4/2014 | Kleiner et al. |
| 8,715,351 B1 | 5/2014 | Pinto |
| 8,727,975 B1 | 5/2014 | Pfabe et al. |
| 8,747,444 B2 | 6/2014 | Moskowitz et al. |
| 8,753,345 B2 | 6/2014 | McCormack et al. |
| 8,753,347 B2 | 6/2014 | McCormack et al. |
| 8,753,398 B2 | 6/2014 | Gordon et al. |
| 8,763,377 B2 | 6/2014 | McCormack et al. |
| 8,768,443 B2 | 6/2014 | Ullrich, Jr. et al. |
| D708,323 S | 7/2014 | Reyes et al. |
| D708,747 S | 7/2014 | Curran et al. |

(56) References Cited

U.S. PATENT DOCUMENTS

| | | |
|---|---|---|
| 8,771,360 B2 | 7/2014 | Jimenez et al. |
| 8,778,025 B2 | 7/2014 | Ragab et al. |
| 8,778,027 B2 | 7/2014 | Medina |
| 8,784,450 B2 | 7/2014 | Moskowitz et al. |
| 8,790,407 B2 | 7/2014 | Chauvin et al. |
| 8,795,366 B2 | 8/2014 | Varela |
| 8,808,304 B2 | 8/2014 | Weiman et al. |
| 8,808,305 B2 | 8/2014 | Kleiner |
| 8,808,383 B2 | 8/2014 | Kwak et al. |
| 8,814,940 B2 | 8/2014 | Curran et al. |
| 8,821,396 B1 | 9/2014 | Miles et al. |
| 8,828,019 B1 | 9/2014 | Raymond et al. |
| 8,828,062 B2 | 9/2014 | McCormack et al. |
| 8,828,066 B2 | 9/2014 | Lazarof |
| 8,834,472 B2 | 9/2014 | McCormack et al. |
| 8,840,622 B1 | 9/2014 | Vellido et al. |
| 8,840,668 B1 | 9/2014 | Donahoe et al. |
| 8,845,640 B2 | 9/2014 | McLean et al. |
| 8,845,727 B2 | 9/2014 | Gottlieb et al. |
| 8,845,731 B2 | 9/2014 | Weiman |
| 8,845,732 B2 | 9/2014 | Weiman |
| 8,845,734 B2 | 9/2014 | Weiman |
| D714,933 S | 10/2014 | Kawamura |
| 8,852,242 B2 | 10/2014 | Morgenstern Lopez et al. |
| 8,852,243 B2 | 10/2014 | Morgenstern Lopez et al. |
| 8,852,279 B2 | 10/2014 | Weiman |
| 8,852,281 B2 | 10/2014 | Phelps |
| 8,852,282 B2 | 10/2014 | Farley et al. |
| 8,862,244 B2 | 10/2014 | Simonson |
| 8,864,830 B2 | 10/2014 | Malandain |
| 8,864,833 B2 | 10/2014 | Glerum et al. |
| 8,868,598 B2 | 10/2014 | Seifert et al. |
| 8,868,638 B2 | 10/2014 | Michelson |
| 8,870,882 B2 | 10/2014 | Kleiner |
| 8,870,959 B2 | 10/2014 | Arnin |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,708 B2 | 11/2014 | Thalgott |
| 8,894,711 B2 | 11/2014 | Varela |
| 8,894,712 B2 | 11/2014 | Varela |
| 8,900,313 B2 | 12/2014 | Barreiro et al. |
| 8,906,028 B2 | 12/2014 | Kleiner |
| 8,906,099 B2 | 12/2014 | Poulos |
| 8,920,607 B2 | 12/2014 | Malandain |
| D721,808 S | 1/2015 | Oi |
| 8,926,701 B2 | 1/2015 | De Lurio et al. |
| 8,926,704 B2 | 1/2015 | Glerum et al. |
| 8,932,295 B1 | 1/2015 | Greenhalgh |
| 8,940,048 B2 | 1/2015 | Butler et al. |
| 8,945,137 B1 | 2/2015 | Greenhalgh et al. |
| D723,682 S | 3/2015 | Kleiner |
| D724,213 S | 3/2015 | Tyber |
| 8,968,406 B2 | 3/2015 | Arnin |
| 8,968,408 B2 | 3/2015 | Schaller et al. |
| 8,974,464 B2 | 3/2015 | Johnson et al. |
| 8,974,534 B2 | 3/2015 | Krueger |
| 8,986,389 B2 | 3/2015 | Lim et al. |
| 8,992,621 B2 | 3/2015 | Chauvin et al. |
| 8,992,622 B2 | 3/2015 | Ullrich, Jr. et al. |
| 8,998,992 B2 | 4/2015 | Seifert et al. |
| 9,005,293 B2 | 4/2015 | Moskowitz et al. |
| 9,034,040 B2 | 5/2015 | Seifert et al. |
| 9,034,041 B2 | 5/2015 | Wolters et al. |
| 9,039,767 B2 | 5/2015 | Raymond et al. |
| 9,039,771 B2 | 5/2015 | Glerum et al. |
| 9,055,985 B2 | 6/2015 | Lazarof |
| 9,060,877 B2 | 6/2015 | Kleiner |
| D735,336 S | 7/2015 | Lovell |
| 9,078,769 B2 | 7/2015 | Farin |
| 9,084,686 B1 | 7/2015 | McLean et al. |
| 9,095,447 B2 | 8/2015 | Barreiro et al. |
| 9,096,446 B2 | 8/2015 | Landry et al. |
| 9,101,488 B2 | 8/2015 | Malandain |
| 9,107,766 B1 | 8/2015 | McLean et al. |
| 9,113,962 B2 | 8/2015 | McLean et al. |
| 9,114,026 B1 | 8/2015 | McLean et al. |
| 9,119,730 B2 | 9/2015 | Glerum et al. |
| 9,125,757 B2 | 9/2015 | Weiman |
| 9,138,277 B2 | 9/2015 | Fitzpatrick |
| 9,149,302 B2 | 10/2015 | McLean et al. |
| 9,149,364 B2 | 10/2015 | McManus et al. |
| 9,173,694 B2 | 11/2015 | Kleiner |
| 9,174,147 B2 | 11/2015 | Hoogenakker et al. |
| 9,180,017 B2 | 11/2015 | Poulos |
| 9,186,193 B2 | 11/2015 | Kleiner et al. |
| 9,186,262 B2 | 11/2015 | McLuen et al. |
| 9,192,484 B2 | 11/2015 | Landry et al. |
| 9,204,974 B2 | 12/2015 | Glerum et al. |
| 9,211,196 B2 | 12/2015 | Glerum et al. |
| 9,216,094 B2 | 12/2015 | McLean et al. |
| 9,216,095 B2 | 12/2015 | Glerum et al. |
| 9,226,777 B2 | 1/2016 | Potash et al. |
| 9,233,007 B2 | 1/2016 | Sungarian et al. |
| D750,249 S | 2/2016 | Grimberg et al. |
| 9,247,943 B1 | 2/2016 | Kleiner |
| 9,271,846 B2 | 3/2016 | Lim et al. |
| 9,283,089 B2 | 3/2016 | McKay |
| 9,295,500 B2 | 3/2016 | Marigowda |
| 9,301,854 B2 | 4/2016 | Moskowitz et al. |
| 9,320,610 B2 | 4/2016 | Alheidt et al. |
| 9,320,615 B2 | 4/2016 | Suedkamp et al. |
| 9,361,848 B2 | 5/2016 | Glerum et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,358,134 B2 | 6/2016 | Malandain |
| 9,368,123 B2 | 6/2016 | McLuen et al. |
| 9,381,094 B2 | 7/2016 | Barreiro et al. |
| 9,398,961 B2 | 7/2016 | Malandain |
| 9,402,739 B2 | 8/2016 | Weiman |
| 9,408,707 B2 | 8/2016 | Oglaza et al. |
| 9,408,708 B2 | 8/2016 | Greenhalgh |
| 9,414,938 B2 | 8/2016 | Miller et al. |
| 9,427,264 B2 | 8/2016 | Kleiner |
| 9,439,692 B1 | 9/2016 | Schlesinger et al. |
| 9,439,782 B2 | 9/2016 | Kleiner |
| 9,439,783 B2 | 9/2016 | McLean et al. |
| 9,445,866 B2 | 9/2016 | Seifert et al. |
| 9,445,919 B2 | 9/2016 | Palmatier |
| 9,445,921 B2 | 9/2016 | McLean |
| 9,452,063 B2 | 9/2016 | Glerum et al. |
| 9,456,830 B2 | 10/2016 | Greenhalgh |
| 9,480,578 B2 | 11/2016 | Pinto |
| 9,486,324 B2 | 11/2016 | Hochschuler et al. |
| 9,486,328 B2 | 11/2016 | Jimenez |
| 9,492,287 B2 | 11/2016 | Glerum et al. |
| 9,498,200 B2 | 11/2016 | Pfabe et al. |
| 9,498,347 B2 | 11/2016 | McLean |
| 9,498,351 B2 | 11/2016 | Vigliotti et al. |
| 9,510,954 B2 | 12/2016 | Glerum et al. |
| 9,510,955 B2 | 12/2016 | Marino et al. |
| 9,517,140 B2 | 12/2016 | McLean et al. |
| 9,517,141 B2 | 12/2016 | McLean et al. |
| 9,517,142 B2 | 12/2016 | Pinto et al. |
| 9,526,627 B2 | 12/2016 | Tabor et al. |
| 9,526,628 B2 | 12/2016 | Krueger |
| 9,532,821 B2 | 1/2017 | Moskowitz et al. |
| 9,539,108 B2 | 1/2017 | Glerum et al. |
| 9,545,250 B2 | 1/2017 | Pfabe et al. |
| 9,545,279 B2 | 1/2017 | James et al. |
| 9,545,313 B2 | 1/2017 | Raymond et al. |
| 9,545,318 B2 | 1/2017 | Johnson et al. |
| 9,545,319 B2 | 1/2017 | Farin |
| 9,549,824 B2 | 1/2017 | McAfee |
| 9,566,168 B2 | 2/2017 | Glerum et al. |
| 9,579,124 B2 | 2/2017 | Gordon et al. |
| 9,579,215 B2 | 2/2017 | Suedkamp et al. |
| 9,585,767 B2 | 3/2017 | Robinson |
| 9,592,131 B2 | 3/2017 | Sandstrom et al. |
| 9,597,200 B2 | 3/2017 | Glerum et al. |
| 9,603,713 B2 | 3/2017 | Moskowitz et al. |
| 9,610,175 B2 | 4/2017 | Barreiro et al. |
| 9,622,791 B2 | 4/2017 | McCormack et al. |

(56) References Cited

U.S. PATENT DOCUMENTS

| | | |
|---|---|---|
| 9,622,875 B2 | 4/2017 | Moskowitz et al. |
| 9,629,666 B2 | 4/2017 | McCormack et al. |
| 9,629,668 B2 | 4/2017 | McLean et al. |
| 9,629,729 B2 | 4/2017 | Grimberg et al. |
| 9,642,712 B2 | 5/2017 | Schaller et al. |
| 9,655,660 B2 | 5/2017 | McLean et al. |
| 9,655,743 B2 | 5/2017 | Johnson et al. |
| 9,662,223 B2 | 5/2017 | Matthis et al. |
| 9,665,747 B1 | 5/2017 | Glerum et al. |
| 9,668,881 B1 | 6/2017 | Greenhalgh et al. |
| 9,675,385 B2 | 6/2017 | Moskowitz et al. |
| 9,675,469 B2 | 6/2017 | Landry et al. |
| 9,681,889 B1 | 6/2017 | Greenhalgh et al. |
| 9,687,360 B2 | 6/2017 | Baynham et al. |
| 9,707,094 B2 | 7/2017 | Protopsaltis et al. |
| 9,717,403 B2 | 8/2017 | Kleiner et al. |
| 9,730,802 B1 | 8/2017 | Harvey |
| D797,290 S | 9/2017 | Kleiner |
| 9,763,700 B1 | 9/2017 | Gregory |
| 9,801,734 B1 | 10/2017 | Stein |
| 9,826,988 B2 | 11/2017 | Kleiner |
| 9,861,395 B2 | 1/2018 | Potash et al. |
| 9,861,496 B2 | 1/2018 | Kleiner |
| 9,937,053 B2 | 4/2018 | Melkent |
| 9,962,272 B1 | 5/2018 | Daffinson |
| 9,980,737 B2 | 5/2018 | Thommen et al. |
| 9,993,353 B2 | 6/2018 | Sandhu |
| 10,179,054 B2 | 1/2019 | Kleiner |
| 10,245,159 B1* | 4/2019 | Kleiner ............... A61F 2/4455 |
| 10,973,656 B2* | 4/2021 | Kleiner ............... A61F 2/4611 |
| 2002/0010472 A1 | 1/2002 | Kuslich et al. |
| 2002/0040243 A1 | 4/2002 | Attali et al. |
| 2002/0045945 A1 | 4/2002 | Liu et al. |
| 2002/0049448 A1 | 4/2002 | Sand et al. |
| 2002/0058947 A1 | 5/2002 | Hochschuler et al. |
| 2002/0099377 A1 | 7/2002 | Zucherman et al. |
| 2002/0116006 A1 | 8/2002 | Cohen |
| 2002/0161444 A1 | 10/2002 | Cho |
| 2002/0165613 A1 | 11/2002 | Lin et al. |
| 2003/0009169 A1 | 1/2003 | Young et al. |
| 2003/0023306 A1 | 1/2003 | Liu et al. |
| 2003/0083748 A1 | 5/2003 | Lee et al. |
| 2003/0125739 A1 | 7/2003 | Bagga et al. |
| 2003/0135279 A1 | 7/2003 | Michelson |
| 2003/0149482 A1 | 8/2003 | Michelson |
| 2003/0171812 A1 | 9/2003 | Grunberg et al. |
| 2003/0229358 A1 | 12/2003 | Errico et al. |
| 2004/0002713 A1 | 1/2004 | Olson et al. |
| 2004/0024466 A1 | 2/2004 | Heerklotz |
| 2004/0073314 A1 | 4/2004 | White et al. |
| 2004/0087947 A1 | 5/2004 | Lim et al. |
| 2004/0087956 A1 | 5/2004 | Weikel et al. |
| 2004/0133211 A1 | 7/2004 | Raskin et al. |
| 2004/0133217 A1 | 7/2004 | Watschke |
| 2004/0133280 A1 | 7/2004 | Trieu |
| 2004/0143330 A1 | 7/2004 | Sazy |
| 2004/0148027 A1 | 7/2004 | Errico et al. |
| 2004/0153158 A1 | 8/2004 | Errico et al. |
| 2004/0162616 A1 | 8/2004 | Simonton et al. |
| 2004/0167532 A1 | 8/2004 | Olson, Jr. et al. |
| 2004/0176853 A1 | 9/2004 | Sennett et al. |
| 2004/0215201 A1 | 10/2004 | Lieberman |
| 2004/0230211 A1 | 11/2004 | Moutafis et al. |
| 2004/0254643 A1 | 12/2004 | Jackson |
| 2005/0070900 A1 | 3/2005 | Serhan et al. |
| 2005/0070912 A1 | 3/2005 | Voellmicke |
| 2005/0080443 A1 | 4/2005 | Fallin et al. |
| 2005/0096601 A1 | 5/2005 | Doyle |
| 2005/0107878 A1 | 5/2005 | Conchy |
| 2005/0112091 A1 | 5/2005 | DiMauro et al. |
| 2005/0118550 A1 | 6/2005 | Turri |
| 2005/0124993 A1 | 6/2005 | Chappuis |
| 2005/0124994 A1 | 6/2005 | Berger et al. |
| 2005/0149035 A1 | 7/2005 | Pimenta et al. |
| 2005/0149192 A1 | 7/2005 | Zucherman et al. |
| 2005/0159765 A1 | 7/2005 | Moutafis et al. |
| 2005/0165405 A1 | 7/2005 | Tsou |
| 2005/0171641 A1 | 8/2005 | Boehm, Jr. et al. |
| 2005/0192669 A1 | 9/2005 | Zdeblick et al. |
| 2005/0203625 A1 | 9/2005 | Boehm et al. |
| 2005/0216002 A1 | 9/2005 | Simonson |
| 2005/0216018 A1 | 9/2005 | Sennett |
| 2005/0251146 A1 | 11/2005 | Martz et al. |
| 2005/0251257 A1 | 11/2005 | Mitchell et al. |
| 2005/0261781 A1 | 11/2005 | Sennett et al. |
| 2005/0278026 A1 | 12/2005 | Gordon et al. |
| 2005/0278036 A1 | 12/2005 | Leonard et al. |
| 2005/0283150 A1 | 12/2005 | Moutafis et al. |
| 2005/0283245 A1 | 12/2005 | Gordon et al. |
| 2006/0004367 A1 | 1/2006 | Alamin et al. |
| 2006/0015184 A1 | 1/2006 | Winterbottom et al. |
| 2006/0058807 A1 | 3/2006 | Landry et al. |
| 2006/0068585 A1 | 3/2006 | Oberlaender et al. |
| 2006/0069436 A1 | 3/2006 | Sutton et al. |
| 2006/0095136 A1 | 5/2006 | MoLuen |
| 2006/0100304 A1 | 5/2006 | Vresilovic et al. |
| 2006/0100705 A1 | 5/2006 | Puno et al. |
| 2006/0111779 A1 | 5/2006 | Petersen |
| 2006/0111780 A1 | 5/2006 | Petersen |
| 2006/0116770 A1 | 6/2006 | White et al. |
| 2006/0122597 A1 | 6/2006 | Jones et al. |
| 2006/0122701 A1 | 6/2006 | Kiester |
| 2006/0142858 A1 | 6/2006 | Colleran et al. |
| 2006/0154366 A1 | 7/2006 | Brown et al. |
| 2006/0156170 A1 | 7/2006 | Hanson et al. |
| 2006/0167461 A1 | 7/2006 | Hawkins et al. |
| 2006/0190081 A1 | 8/2006 | Kraus |
| 2006/0195192 A1 | 8/2006 | Gordon et al. |
| 2006/0229550 A1 | 10/2006 | Staid et al. |
| 2006/0229729 A1 | 10/2006 | Gordon |
| 2006/0241764 A1 | 10/2006 | Michelson |
| 2006/0241774 A1 | 10/2006 | Attali et al. |
| 2006/0247650 A1 | 11/2006 | Yerby et al. |
| 2006/0247791 A1 | 11/2006 | McKay et al. |
| 2006/0264808 A1 | 11/2006 | Staid et al. |
| 2006/0264964 A1 | 11/2006 | Scifert et al. |
| 2007/0003598 A1 | 1/2007 | Trieu |
| 2007/0010824 A1 | 1/2007 | Malandain et al. |
| 2007/0016195 A1 | 1/2007 | Winslow et al. |
| 2007/0043376 A1 | 2/2007 | Leatherbury et al. |
| 2007/0043442 A1 | 2/2007 | Abernathie |
| 2007/0060030 A1 | 3/2007 | Kim |
| 2007/0067034 A1 | 3/2007 | Chirico et al. |
| 2007/0073110 A1 | 3/2007 | Larson et al. |
| 2007/0073294 A1 | 3/2007 | Chin et al. |
| 2007/0073406 A1 | 3/2007 | Gordon et al. |
| 2007/0088007 A1 | 4/2007 | Ng |
| 2007/0093850 A1 | 4/2007 | Harris et al. |
| 2007/0123985 A1 | 5/2007 | Errico et al. |
| 2007/0172790 A1 | 7/2007 | Doucette, Jr. et al. |
| 2007/0186496 A1 | 8/2007 | Beckman et al. |
| 2007/0208423 A1 | 9/2007 | Messerli et al. |
| 2007/0213596 A1 | 9/2007 | Hamada |
| 2007/0213717 A1 | 9/2007 | Trieu |
| 2007/0213718 A1 | 9/2007 | Trieu |
| 2007/0213822 A1 | 9/2007 | Trieu |
| 2007/0213826 A1 | 9/2007 | Smith et al. |
| 2007/0225219 A1 | 9/2007 | Boden et al. |
| 2007/0225811 A1 | 9/2007 | Scifert et al. |
| 2007/0242869 A1 | 10/2007 | Rochester |
| 2007/0250166 A1 | 10/2007 | McKay |
| 2007/0264300 A1 | 11/2007 | Scifert et al. |
| 2007/0265632 A1 | 11/2007 | Scifert et al. |
| 2007/0270951 A1 | 11/2007 | Davis et al. |
| 2007/0270954 A1 | 11/2007 | Wu |
| 2007/0270963 A1 | 11/2007 | Melkent |
| 2007/0276406 A1 | 11/2007 | Mahoney et al. |
| 2007/0282447 A1* | 12/2007 | Yedlicka ............ A61B 17/1671 |
| | | 606/86 R |
| 2007/0288007 A1 | 12/2007 | Burkus et al. |
| 2007/0293948 A1 | 12/2007 | Bagga et al. |
| 2008/0003255 A1 | 1/2008 | Kerr et al. |
| 2008/0009929 A1 | 1/2008 | Harris et al. |
| 2008/0021559 A1 | 1/2008 | Thramann |

(56) References Cited

U.S. PATENT DOCUMENTS

| | | |
|---|---|---|
| 2008/0033440 A1 | 2/2008 | Moskowitz et al. |
| 2008/0051902 A1 | 2/2008 | Dwyer |
| 2008/0058606 A1 | 3/2008 | Miles et al. |
| 2008/0065219 A1 | 3/2008 | Dye |
| 2008/0071284 A1 | 3/2008 | Lechmann et al. |
| 2008/0086142 A1 | 4/2008 | Kohm et al. |
| 2008/0125856 A1 | 5/2008 | Perez-Cruet et al. |
| 2008/0147191 A1 | 6/2008 | Lopez et al. |
| 2008/0154375 A1 | 6/2008 | Serhan et al. |
| 2008/0154377 A1 | 6/2008 | Voellmicke |
| 2008/0154381 A1 | 6/2008 | Parrish |
| 2008/0161924 A1 | 7/2008 | Viker |
| 2008/0172127 A1 | 7/2008 | Perez-Cruet et al. |
| 2008/0177294 A1 | 7/2008 | O'Neil et al. |
| 2008/0183204 A1 | 7/2008 | Greenhalgh et al. |
| 2008/0195058 A1 | 8/2008 | Moutafis et al. |
| 2008/0195101 A1 | 8/2008 | Lechot et al. |
| 2008/0228225 A1 | 9/2008 | Trautwein et al. |
| 2008/0243126 A1 | 10/2008 | Gutierrez et al. |
| 2008/0249569 A1 | 10/2008 | Waugh et al. |
| 2008/0255564 A1 | 10/2008 | Michelson |
| 2008/0260598 A1 | 10/2008 | Gross et al. |
| 2008/0265666 A1 | 10/2008 | Fisher et al. |
| 2008/0269904 A1 | 10/2008 | Voorhies |
| 2008/0288071 A1 | 11/2008 | Bivani et al. |
| 2008/0300598 A1 | 12/2008 | Barreiro et al. |
| 2009/0043312 A1 | 2/2009 | Koulisis |
| 2009/0043394 A1 | 2/2009 | Zdeblick et al. |
| 2009/0076440 A1 | 3/2009 | Moutafis et al. |
| 2009/0076556 A1 | 3/2009 | McGarity et al. |
| 2009/0088765 A1 | 4/2009 | Butler et al. |
| 2009/0098184 A1 | 4/2009 | Govil et al. |
| 2009/0099660 A1 | 4/2009 | Scifert et al. |
| 2009/0105718 A1 | 4/2009 | Zhang et al. |
| 2009/0124860 A1 | 5/2009 | Miles et al. |
| 2009/0124980 A1 | 5/2009 | Chen |
| 2009/0125066 A1 | 5/2009 | Krau et al. |
| 2009/0142385 A1 | 6/2009 | Gross et al. |
| 2009/0182429 A1 | 7/2009 | Humphreys et al. |
| 2009/0187194 A1 | 7/2009 | Hamada |
| 2009/0192350 A1 | 7/2009 | Meja |
| 2009/0192403 A1 | 7/2009 | Gharib et al. |
| 2009/0198241 A1 | 8/2009 | Phan |
| 2009/0198243 A1 | 8/2009 | Melsheimer |
| 2009/0198245 A1 | 8/2009 | Phan |
| 2009/0198337 A1 | 8/2009 | Phan |
| 2009/0198338 A1 | 8/2009 | Phan |
| 2009/0198339 A1 | 8/2009 | Kleiner et al. |
| 2009/0203967 A1 | 8/2009 | Branch et al. |
| 2009/0204148 A1 | 8/2009 | Lenke |
| 2009/0204159 A1 | 8/2009 | Justis et al. |
| 2009/0204220 A1 | 8/2009 | Trieu |
| 2009/0222011 A1 | 9/2009 | Lehuec et al. |
| 2009/0228107 A1 | 9/2009 | Michelson |
| 2009/0234455 A1 | 9/2009 | Moskowitz et al. |
| 2009/0246244 A1 | 10/2009 | McKay et al. |
| 2009/0248163 A1 | 10/2009 | King et al. |
| 2009/0259108 A1 | 10/2009 | Miles et al. |
| 2009/0264892 A1 | 10/2009 | Beyar et al. |
| 2009/0275995 A1 | 11/2009 | Truckai et al. |
| 2009/0281551 A1 | 11/2009 | Frey |
| 2009/0292361 A1 | 11/2009 | Lopez |
| 2009/0299477 A1 | 12/2009 | Clayton et al. |
| 2009/0299478 A1 | 12/2009 | Carls et al. |
| 2009/0306671 A1 | 12/2009 | McCormack et al. |
| 2009/0306692 A1 | 12/2009 | Barrington et al. |
| 2010/0004752 A1 | 1/2010 | White et al. |
| 2010/0010367 A1 | 1/2010 | Foley et al. |
| 2010/0010524 A1 | 1/2010 | Barrington et al. |
| 2010/0016903 A1 | 1/2010 | Matityahu et al. |
| 2010/0016972 A1 | 1/2010 | Jansen et al. |
| 2010/0016973 A1 | 1/2010 | de Villiers et al. |
| 2010/0021518 A1 | 1/2010 | Scifert et al. |
| 2010/0023057 A1 | 1/2010 | Aeschlimann et al. |
| 2010/0030065 A1 | 2/2010 | Farr et al. |
| 2010/0036226 A9 | 2/2010 | Marino et al. |
| 2010/0036442 A1 | 2/2010 | Lauryssen et al. |
| 2010/0042221 A1 | 2/2010 | Boyd |
| 2010/0049325 A1 | 2/2010 | Biedermann et al. |
| 2010/0057208 A1 | 3/2010 | Dryer |
| 2010/0063516 A1 | 3/2010 | Parmer et al. |
| 2010/0063554 A1 | 3/2010 | Branch et al. |
| 2010/0070041 A1 | 3/2010 | Peterman et al. |
| 2010/0076335 A1 | 3/2010 | Gharib et al. |
| 2010/0076445 A1 | 3/2010 | Pagano |
| 2010/0076446 A1 | 3/2010 | Gorek |
| 2010/0082036 A1 | 4/2010 | Reiley et al. |
| 2010/0087828 A1 | 4/2010 | Krueger et al. |
| 2010/0087875 A1 | 4/2010 | McGahan et al. |
| 2010/0100141 A1 | 4/2010 | de Villiers et al. |
| 2010/0105986 A1 | 4/2010 | Miles et al. |
| 2010/0105987 A1 | 4/2010 | Miles et al. |
| 2010/0112029 A1 | 5/2010 | Scifert |
| 2010/0114147 A1 | 5/2010 | Biyani |
| 2010/0121365 A1 | 5/2010 | O'Sullivan et al. |
| 2010/0121453 A1 | 5/2010 | Peterman |
| 2010/0125333 A1 | 5/2010 | Zdeblick et al. |
| 2010/0125338 A1 | 5/2010 | Fitz |
| 2010/0131020 A1 | 5/2010 | Heinz et al. |
| 2010/0137690 A1 | 6/2010 | Miles et al. |
| 2010/0137923 A1 | 6/2010 | Greenhalgh et al. |
| 2010/0145390 A1 | 6/2010 | McCarthy et al. |
| 2010/0145452 A1 | 6/2010 | Blaylock et al. |
| 2010/0145461 A1 | 6/2010 | Landry et al. |
| 2010/0152853 A1 | 6/2010 | Kirschman |
| 2010/0160923 A1 | 6/2010 | Sand et al. |
| 2010/0160982 A1 | 6/2010 | Justis et al. |
| 2010/0161062 A1 | 6/2010 | Foley et al. |
| 2010/0161074 A1 | 6/2010 | McKay |
| 2010/0168755 A1 | 7/2010 | Reiley et al. |
| 2010/0168862 A1 | 7/2010 | Edie et al. |
| 2010/0174326 A1 | 7/2010 | Selover et al. |
| 2010/0185286 A1 | 7/2010 | Allard |
| 2010/0185287 A1 | 7/2010 | Allard |
| 2010/0185288 A1 | 7/2010 | Carls |
| 2010/0191241 A1 | 7/2010 | McCormack et al. |
| 2010/0191334 A1 | 7/2010 | Keller |
| 2010/0191336 A1 | 7/2010 | Greenhalgh |
| 2010/0191337 A1 | 7/2010 | Zamani et al. |
| 2010/0198140 A1 | 8/2010 | Lawson |
| 2010/0199483 A1 | 8/2010 | Justis et al. |
| 2010/0204795 A1 | 8/2010 | Greenhalgh |
| 2010/0204798 A1 | 8/2010 | Gerbec et al. |
| 2010/0211176 A1 | 8/2010 | Greenhalgh |
| 2010/0217398 A1 | 8/2010 | Keller |
| 2010/0222784 A1 | 9/2010 | Schwab et al. |
| 2010/0222824 A1 | 9/2010 | Simonson |
| 2010/0228294 A1 | 9/2010 | LeHuec et al. |
| 2010/0228351 A1 | 9/2010 | Ankney et al. |
| 2010/0234848 A1 | 9/2010 | Sutterlin et al. |
| 2010/0234952 A1 | 9/2010 | Peterman |
| 2010/0234957 A1 | 9/2010 | Zdeblick et al. |
| 2010/0241231 A1 | 9/2010 | Marino et al. |
| 2010/0249933 A1 | 9/2010 | Trieu |
| 2010/0249934 A1 | 9/2010 | Melkent |
| 2010/0256767 A1 | 10/2010 | Melkent |
| 2010/0256768 A1 | 10/2010 | Lim et al. |
| 2010/0262241 A1 | 10/2010 | Eisermann et al. |
| 2010/0262245 A1 | 10/2010 | Alfaro et al. |
| 2010/0266689 A1 | 10/2010 | Simonton et al. |
| 2010/0280622 A1 | 11/2010 | McKinley |
| 2010/0286778 A1 | 11/2010 | Eisermann et al. |
| 2010/0286779 A1 | 11/2010 | Thibodeau |
| 2010/0286780 A1 | 11/2010 | Dryer et al. |
| 2010/0286784 A1 | 11/2010 | Curran et al. |
| 2010/0298938 A1 | 11/2010 | Humphreys et al. |
| 2010/0305575 A1 | 12/2010 | Wilkinson et al. |
| 2010/0312103 A1 | 12/2010 | Gorek et al. |
| 2010/0312290 A1 | 12/2010 | McKinley et al. |
| 2010/0312347 A1 | 12/2010 | Arramon et al. |
| 2010/0331847 A1 | 12/2010 | Wilkinson et al. |
| 2010/0331891 A1 | 12/2010 | Culbert et al. |
| 2011/0014687 A1 | 1/2011 | Spagnoli et al. |
| 2011/0015638 A1 | 1/2011 | Pischl et al. |

(56) References Cited

U.S. PATENT DOCUMENTS

| | | |
|---|---|---|
| 2011/0015742 A1 | 1/2011 | Hong |
| 2011/0015748 A1 | 1/2011 | Molz, IV et al. |
| 2011/0020768 A1 | 1/2011 | Spagnoli et al. |
| 2011/0021427 A1 | 1/2011 | Amsden et al. |
| 2011/0028393 A1 | 2/2011 | Vickers et al. |
| 2011/0029086 A1 | 2/2011 | Glazer et al. |
| 2011/0054538 A1 | 3/2011 | Zehavi et al. |
| 2011/0071527 A1 | 3/2011 | Nelson et al. |
| 2011/0093005 A1 | 4/2011 | Strokosz et al. |
| 2011/0093074 A1 | 4/2011 | Glerum et al. |
| 2011/0106162 A1 | 5/2011 | Ballard et al. |
| 2011/0137349 A1 | 6/2011 | Moskowitz et al. |
| 2011/0144687 A1 | 6/2011 | Kleiner |
| 2011/0160777 A1 | 6/2011 | Spagnoli et al. |
| 2011/0184412 A1 | 7/2011 | Scifert et al. |
| 2011/0208226 A1 | 8/2011 | Fatone et al. |
| 2011/0208312 A1 | 8/2011 | Moskowitz et al. |
| 2011/0213372 A1 | 9/2011 | Keefer et al. |
| 2011/0218627 A1 | 9/2011 | Rampersaud et al. |
| 2011/0230970 A1 | 9/2011 | Lynn et al. |
| 2011/0238184 A1 | 9/2011 | Zdeblick et al. |
| 2011/0257478 A1 | 10/2011 | Kleiner et al. |
| 2012/0022603 A1 | 1/2012 | Kirschman |
| 2012/0022651 A1 | 1/2012 | Akyuz et al. |
| 2012/0029635 A1 | 2/2012 | Schoenhoeffer et al. |
| 2012/0035668 A1 | 2/2012 | Manninen et al. |
| 2012/0035729 A1 | 2/2012 | Glerum et al. |
| 2012/0058451 A1 | 3/2012 | Lazarof |
| 2012/0059472 A1 | 3/2012 | Weiman |
| 2012/0059481 A1 | 3/2012 | Abernathie et al. |
| 2012/0065613 A1 | 3/2012 | Pepper et al. |
| 2012/0065687 A1 | 3/2012 | Ballard et al. |
| 2012/0071981 A1 | 3/2012 | Farley et al. |
| 2012/0078315 A1 | 3/2012 | Sweeney |
| 2012/0089185 A1 | 4/2012 | Gabelberger |
| 2012/0109319 A1 | 5/2012 | Perisic |
| 2012/0123546 A1 | 5/2012 | Medina |
| 2012/0158146 A1 | 6/2012 | Glerum et al. |
| 2012/0197311 A1 | 8/2012 | Kirschman |
| 2012/0197405 A1 | 8/2012 | Cuevas et al. |
| 2012/0215316 A1 | 8/2012 | Mohr et al. |
| 2012/0245691 A1 | 9/2012 | Reimels |
| 2012/0259335 A1 | 10/2012 | Scifert et al. |
| 2012/0277861 A1 | 11/2012 | Steele et al. |
| 2012/0330419 A1 | 12/2012 | Moskowitz et al. |
| 2012/0330421 A1 | 12/2012 | Weiman |
| 2013/0006364 A1 | 1/2013 | McCormack et al. |
| 2013/0006365 A1 | 1/2013 | Pepper et al. |
| 2013/0006366 A1 | 1/2013 | Farley et al. |
| 2013/0013070 A1 | 1/2013 | McCormack et al. |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0053962 A1 | 2/2013 | Moskowitz et al. |
| 2013/0073041 A1 | 3/2013 | Scifert et al. |
| 2013/0103153 A1 | 4/2013 | Blackwell et al. |
| 2013/0103154 A1 | 4/2013 | Trieu et al. |
| 2013/0110168 A1 | 5/2013 | McCormack et al. |
| 2013/0110169 A1 | 5/2013 | Hynes et al. |
| 2013/0110248 A1 | 5/2013 | Zipnick |
| 2013/0116791 A1 | 5/2013 | Theofilos |
| 2013/0144388 A1 | 6/2013 | Emery et al. |
| 2013/0158669 A1 | 6/2013 | Sungarian |
| 2013/0168664 A1 | 6/2013 | Palmatier et al. |
| 2013/0178940 A1 | 7/2013 | Farley |
| 2013/0204371 A1 | 8/2013 | McLuen et al. |
| 2013/0211525 A1 | 8/2013 | McLuen |
| 2013/0231747 A1 | 9/2013 | Olmos et al. |
| 2013/0297028 A1 | 11/2013 | Zipnick |
| 2013/0297029 A1 | 11/2013 | Kana et al. |
| 2013/0310935 A1 | 11/2013 | Swann |
| 2014/0012383 A1 | 1/2014 | Triplett et al. |
| 2014/0088712 A1 | 3/2014 | Gage |
| 2014/0100657 A1 | 4/2014 | McCormack et al. |
| 2014/0107790 A1 | 4/2014 | Combrowski |
| 2014/0156006 A1 | 6/2014 | Bannigan et al. |
| 2014/0172103 A1 | 6/2014 | O'Neil et al. |
| 2014/0172106 A1 | 6/2014 | To et al. |
| 2014/0207239 A1 | 7/2014 | Barreiro |
| 2014/0228955 A1 | 8/2014 | Weiman |
| 2014/0236296 A1 | 8/2014 | Wagner et al. |
| 2014/0236297 A1 | 8/2014 | Iott et al. |
| 2014/0236298 A1 | 8/2014 | Pinto |
| 2014/0249629 A1 | 9/2014 | Moskowitz et al. |
| 2014/0257405 A1 | 9/2014 | Zappacosta et al. |
| 2014/0257490 A1 | 9/2014 | Himmelberger et al. |
| 2014/0276581 A1 | 9/2014 | Lou et al. |
| 2014/0276896 A1 | 9/2014 | Harper |
| 2014/0277497 A1 | 9/2014 | Bennett et al. |
| 2014/0287055 A1 | 9/2014 | Kunjachan |
| 2014/0288652 A1 | 9/2014 | Boehm et al. |
| 2014/0296916 A1 | 10/2014 | McCormack et al. |
| 2014/0296985 A1 | 10/2014 | Balasubramanian et al. |
| 2014/0303675 A1 | 10/2014 | Mishra |
| 2014/0303731 A1 | 10/2014 | Glerum |
| 2014/0303732 A1 | 10/2014 | Rhoda et al. |
| 2014/0309268 A1 | 10/2014 | Arnou |
| 2014/0309548 A1 | 10/2014 | Merz et al. |
| 2014/0309697 A1 | 10/2014 | Iott et al. |
| 2014/0309714 A1 | 10/2014 | Mercanzini et al. |
| 2014/0367846 A1 | 12/2014 | Nakagawa et al. |
| 2014/0371721 A1 | 12/2014 | Anderson et al. |
| 2015/0081021 A1 | 3/2015 | Ciupik |
| 2015/0094814 A1 | 4/2015 | Emerick |
| 2015/0106824 A1 | 4/2015 | Moskowitz et al. |
| 2015/0216518 A1 | 8/2015 | McCormack et al. |
| 2015/0230931 A1 | 8/2015 | Greenhalgh |
| 2015/0230934 A1 | 8/2015 | Chauvin et al. |
| 2015/0351925 A1 | 12/2015 | Emerick |
| 2015/0374507 A1 | 12/2015 | Wolters et al. |
| 2016/0008040 A1 | 1/2016 | McCormack et al. |
| 2016/0015527 A1 | 1/2016 | McManus et al. |
| 2016/0015529 A1 | 1/2016 | Reimels |
| 2016/0030191 A1 | 2/2016 | McLuen et al. |
| 2016/0058579 A1 | 3/2016 | Aeschlimann et al. |
| 2016/0089247 A1 | 3/2016 | Nichols |
| 2016/0120660 A1 | 5/2016 | Melkent |
| 2016/0135961 A1 | 5/2016 | Aeschlimann et al. |
| 2016/0143748 A1 | 5/2016 | Lim et al. |
| 2016/0166396 A1 | 6/2016 | McClintock |
| 2016/0193056 A1 | 7/2016 | McKay |
| 2016/0213482 A1 | 7/2016 | Alheidt et al. |
| 2016/0228261 A1 | 8/2016 | Emery et al. |
| 2016/0242932 A1 | 8/2016 | McLuen et al. |
| 2016/0296340 A1 | 10/2016 | Gordon et al. |
| 2016/0296344 A1 | 10/2016 | Greenhalgh et al. |
| 2016/0302943 A1 | 10/2016 | Oglaza et al. |
| 2016/0310291 A1 | 10/2016 | Greenhalgh |
| 2016/0317315 A1 | 11/2016 | Weiman |
| 2016/0324659 A1 | 11/2016 | Malandain |
| 2016/0324661 A1 | 11/2016 | Miller et al. |
| 2016/0364131 A1 | 12/2016 | Seifert et al. |
| 2016/0374826 A1 | 12/2016 | Palmatier et al. |
| 2016/0374830 A1 | 12/2016 | Moskowitz et al. |
| 2017/0036468 A1 | 2/2017 | McCormack et al. |
| 2017/0036676 A1 | 2/2017 | Schaller et al. |
| 2017/0086986 A1 | 3/2017 | McAfee |
| 2017/0100256 A1 | 4/2017 | Hleihil |
| 2017/0119539 A1 | 5/2017 | Glerum et al. |
| 2017/0119540 A1 | 5/2017 | Greenhalgh |
| 2017/0119541 A1 | 5/2017 | Greenhalgh |
| 2017/0119542 A1 | 5/2017 | Logan et al. |
| 2017/0119546 A1 | 5/2017 | Farin |
| 2017/0128229 A1 | 5/2017 | Suedkamp et al. |
| 2017/0165083 A1 | 6/2017 | Greenhalgh |
| 2017/0224397 A1 | 8/2017 | Grimberg |
| 2017/0238984 A1 | 8/2017 | Kleiner |
| 2017/0325969 A1 | 11/2017 | McLean |

(56) References Cited

U.S. PATENT DOCUMENTS

| | | |
|---|---|---|
| 2017/0364514 A1 | 12/2017 | Greenhalgh et al. |
| 2018/0064451 A1 | 3/2018 | Kleiner |

FOREIGN PATENT DOCUMENTS

| | | |
|---|---|---|
| AU | 2011203582 | 8/2011 |
| CA | 1337842 | 1/1996 |
| CA | 2447257 | 12/1996 |
| CN | 2668075 | 1/2005 |
| CN | 1621015 | 6/2005 |
| CN | 2730336 | 10/2005 |
| CN | 101268963 | 9/2008 |
| CN | 201861800 | 6/2011 |
| CN | 202191381 | 4/2012 |
| CN | 202235781 | 5/2012 |
| CN | 203001182 | 6/2013 |
| CN | 103356310 | 10/2013 |
| DE | 4012622 | 7/1991 |
| DE | 4416605 | 6/1995 |
| DE | 10241948 | 4/2004 |
| DE | 102005033608 | 1/2007 |
| DE | 102010004133 | 9/2011 |
| DE | 102012203256 | 9/2013 |
| EP | 0635246 | 1/1995 |
| EP | 0880950 | 12/1998 |
| EP | 1290985 | 3/2003 |
| EP | 1382315 | 1/2004 |
| EP | 1532949 | 5/2005 |
| EP | 1541096 | 6/2005 |
| EP | 1889587 | 2/2008 |
| EP | 2213263 | 8/2010 |
| EP | 2226039 | 9/2010 |
| EP | 2510904 | 10/2012 |
| ES | 2067421 | 3/1995 |
| ES | 2099008 | 5/1997 |
| FR | 2707477 | 1/1995 |
| FR | 2708192 | 2/1995 |
| FR | 2717068 | 9/1995 |
| FR | 2790946 | 9/2000 |
| FR | 2803741 | 7/2001 |
| FR | 2815845 | 5/2002 |
| FR | 2866228 | 8/2005 |
| FR | 2866229 | 8/2005 |
| FR | 2874814 | 3/2006 |
| FR | 2943529 | 10/2010 |
| FR | 2943530 | 10/2010 |
| FR | 2981261 | 4/2013 |
| JP | H09-327468 | 12/1997 |
| JP | 2002-052331 | 2/2002 |
| JP | 2005-137418 | 6/2005 |
| JP | 2008-054710 | 3/2008 |
| JP | 2008126085 | 6/2008 |
| JP | 2009-534140 | 9/2009 |
| JP | 2009-535115 | 10/2009 |
| KR | 20010112139 | 12/2001 |
| KR | 20020025647 | 4/2002 |
| KR | 20030012142 | 2/2003 |
| KR | 100410823 | 12/2003 |
| KR | 20040064577 | 7/2004 |
| KR | 20050064501 | 6/2005 |
| KR | 20080001064 | 1/2008 |
| KR | 20080042341 | 5/2008 |
| KR | 100953930 | 4/2010 |
| KR | 20120119812 | 10/2012 |
| KR | 20130082281 | 7/2013 |
| RU | 2063730 | 7/1996 |
| RU | 2210343 | 8/2003 |
| RU | 105157 | 6/2011 |
| RU | 2460499 | 9/2012 |
| RU | 131611 | 8/2013 |
| SU | 988281 | 1/1983 |
| SU | 1424826 | 9/1988 |
| WO | WO 1990/000037 | 1/1990 |
| WO | WO 95/22402 | 8/1995 |
| WO | WO 1995/031158 | 11/1995 |
| WO | WO 1997/000054 | 1/1997 |
| WO | WO 99/08627 | 2/1999 |
| WO | WO 1999/026562 | 6/1999 |
| WO | WO 2000/074605 | 12/2000 |
| WO | WO 02/17801 | 3/2002 |
| WO | WO 2003/092507 | 11/2003 |
| WO | WO 2004/012634 | 2/2004 |
| WO | WO 2005/037149 | 4/2005 |
| WO | WO 2005/071190 | 8/2005 |
| WO | WO 2006/081843 | 8/2006 |
| WO | WO 2006/117463 | 11/2006 |
| WO | WO 2006/134262 | 12/2006 |
| WO | WO 2007/009107 | 1/2007 |
| WO | WO 2007/028706 | 3/2007 |
| WO | WO 2007/122006 | 11/2007 |
| WO | WO 2007/127666 | 11/2007 |
| WO | WO 2008/132322 | 11/2008 |
| WO | WO 2009/064787 | 5/2009 |
| WO | WO 2010/148112 | 12/2010 |
| WO | WO 2011/142761 | 11/2011 |
| WO | WO 2012/031267 | 3/2012 |
| WO | WO 2012/145048 | 10/2012 |
| WO | WO 2013/152257 | 10/2013 |

OTHER PUBLICATIONS

"BAK® Vista® Radiolucent Interbody Fusion System", Zimmer Website, as early as Oct. 25, 2005, available at www.zimmerindia.com/z/ctl/op/global/action/1/id/7809/template/MP/prcat/M6/prod/y, printed on Jun. 8, 2009, pp. 1-2.

"Facet Joint Syndrome," The Cleveland Clinic Foundation, copyright 1995-2008, printed Nov. 19, 2008, available at www.my.clevelandclinic.org/disorders/facet_joint_syndrome/hic_facet_joint_syndrome.aspx, 2 pages.

"Graft Delivery Devices," Nordson Medical, Aug. 2015, 8 pages.

"Rapid Graft Delivery System," Seaspine, 2017, 2 pages.

"Screws, Cages or Both", Spine Universe Website, as early as Aug. 18, 2002, available at www.spineuniverse.com/displayarticle.php/article1363.html, printed on Jun. 8, 2009, pp. 1-13.

"StaXX XD Expandable Device," SpineWave, 2014, retrieved at http://www.spinewave.com/products/xd_us.html, 1 page.

"University of Maryland Spine Program: A Patient's Guide to Anterior Lumbar Interbody Fusion with Intervertebral Cages", University of Maryland Medical Center website, as early as 2003, available at www.umm.edu/spinecenter/education/anterior_lumbar_interbody_fusion_with_intervertebral_cages.htm, printed on Jun. 8, 2009, pp. 1-4.

"Vertebral column," from Wikipedia, the free encyclopedia, printed May 19, 2009, retrieved from www.en.wikipedia.org/wiki/Vertebral_column, 6 pages.

"Zygapophysial joint," from Wikipedia, the free encyclopedia, printed May 19, 2009, retrieved from www.en.wikipedia.org/wiki/Zygapophysial_joint, 2 pages.

Ehrenberg, "The 3-D Printing Revolution," Science News, Mar. 9, 2013, pp. 20-25.

Newton, "EOS Teams with Medical Implant Designer to Advance 3D Printing in Medicine," Graphic Speak, 2012, 2 pages.

Ray, "Facet Joint Disorders and Back Pain," published on Spine-Health, Dec. 10, 2002, available at www.spine-health.com/conditions/arthritis/facet-joint-disorders-and-back-pain, 1 page.

Staehler, "Spine Surgery for a Cervical Herniated Disc," published on Spine-Health, Jun. 12, 2002, available at www.spine-health.com/conditions/herniated-disc/spine-surgery-a-cervical-herniated-disc, 2 pages.

Staehler, "Summary of Cervical Herniated Disc Treatment Options," published on Spine-Health, Jun. 12, 2002, available at www.spine-health.com/conditions/herniated-disc/summary-cervical-herniated-disc-treatment-options, 1 page.

Ullrich, "Anterior Cervical Spinal Fusion Surgery," published on Spine-Health, Oct. 7, 2005, available at www.spine-health.com/treatment/back-surgery/anterior-cervical-spinal-fusion-surgery, 2 pages.

Ullrich, "Cervical Spinal Instrumentation," published on Spine-Health, Oct. 7, 2006, available at www.spine-health.com/treatment/back-surgery/cervical-spinal-instrumentation, 2 pages.

(56) References Cited

OTHER PUBLICATIONS

Wascher, "Anterior cervical decompression and spine fusion procedure," published on Spine-Health, Aug. 29, 2001, available at www.spine-health.com/treatment/spinal-fusion/anterior-cervical-decompression-and-spine-fusion-procedure, 2 pages.
International Search Report for International (PCT) Patent Application No. PCT/US11/52278, mailed Jan. 18, 2012 2 pages.
Written Opinion for International (PCT) Patent Application No. PCT/US11/52278, mailed Jan. 18, 2012 5 pages.
International Preliminary Report on Patentability for International (PCT) Patent Application No. PCT/US11/52278, mailed Apr. 4. 2013 7 pages.
Official Action for Australian Patent Application No. 2011305680, dated Jan. 31, 2014, 2 pages.
Notice of Acceptance for Australian Patent Application No. 2011305680, dated Aug. 27, 2014, 2 pages.
Official Action for Canadian Patent Application No. 2,811,018, dated Feb. 6, 2014, 2 pages.
Official Action for Canadian Patent Application No. 2,811,018, dated Dec. 8, 2014, 3 pages.
Notice of Allowance for Canadian Patent Application No. 2,811,018, dated Sep. 17, 2015, 1 page.
Official Action for European Patent Application No. 11827323.4, dated Jul. 21, 2014, 3 pages.
Extended European Search Report for European Patent Application No. 11827323.4, dated Oct. 17, 2014, 9 pages.
Official Action for European Patent Application No. 11827323.4, dated Jun. 16, 2016, 6 pages.
Official Action for European Patent Application No. 11827323.4, dated Aug. 14, 2017, 5 pages.
Official Action (with English translation) for Israeli Patent Application No. 224873, dated Mar. 15, 2016, 3 pages.
Official Action (English translation) for Japanese Patent Application No. 2013-529407, mailed Aug. 4, 2015, 3 pages.
Official Action (with English translation) for Japanese Patent Application No. 2013-529407, mailed Apr. 5, 2016, 7 pages.
International Search Report and Written Opinion for International (PCT) Patent Application No. PCT/US2013/023992 mailed Apr. 26, 2013, 8 pages.
International Preliminary Report on Patentability for International (PCT) Patent Application No. PCT/US2013/023992 mailed Aug. 14, 2014, 6 pages.
Notice of Allowance for Japanese Patent Application No. 2013-25835, mailed Mar. 28, 2014, 2 pages (includes English translation).
Official Action for Canadian Patent Application No. 153952, dated Apr. 15, 2014, 1 page.
Notice of Allowance (with English translation) for Chinese Patent Application No. 201530104963.1, mailed Sep. 6, 2015, 5 pages.
Notice of Allowance (with English translation) for Chinese Patent Application No. 201530389193.X, mailed Dec. 8, 2015, 4 pages.
Extended European Search Report for European Patent Application No. 18153790.3, dated Jun. 14, 2018, 11 pages.
International Search Report for International (PCT) Patent Application No. PCT/US2009/033488, mailed Mar. 25. 2009, 2 pages.
Written Opinion for International (PCT) Patent Application No. PCT/US2009/033488, mailed Mar. 25, 2009, 9 pages.
Notice of Allowance for U.S. Appl. No. 14/887,598, mailed Dec. 19, 2016 10 pages.

\* cited by examiner

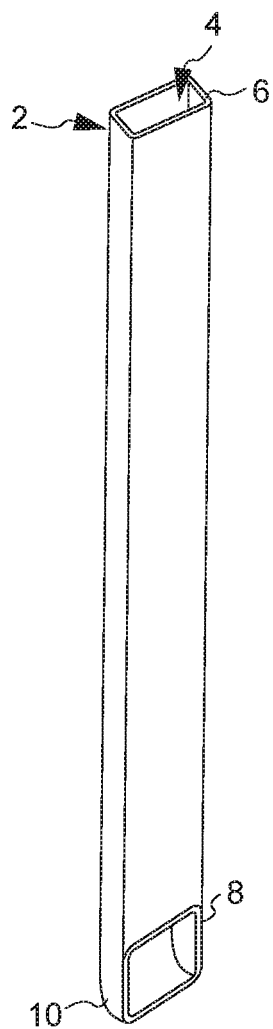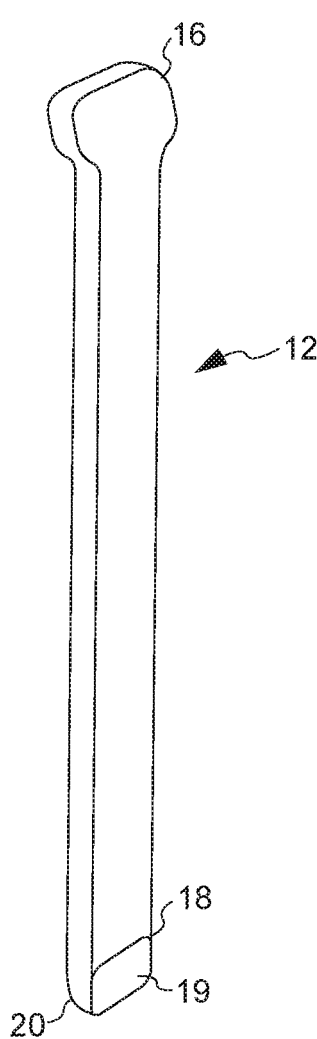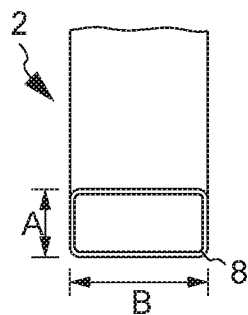
FIG. 1A
FIG. 1B
FIG. 1C

SECTION A-A

SECTION A-A

SECTION A-A

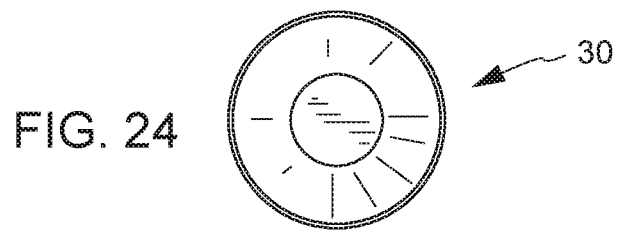
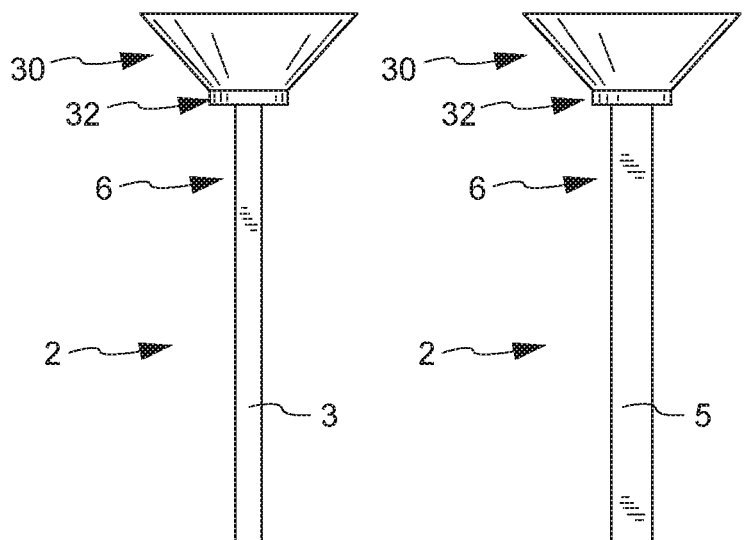
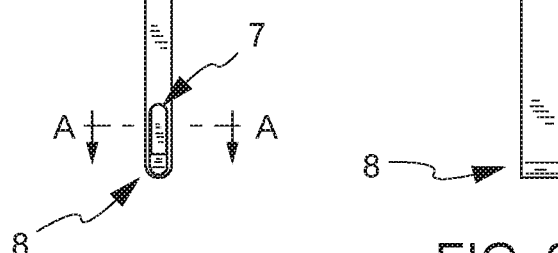
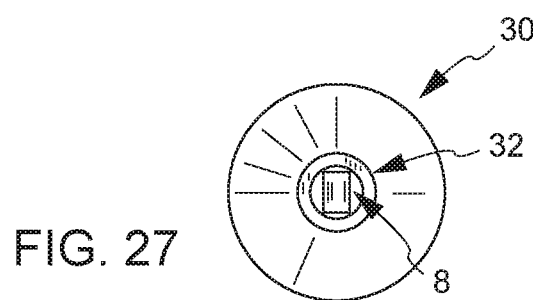
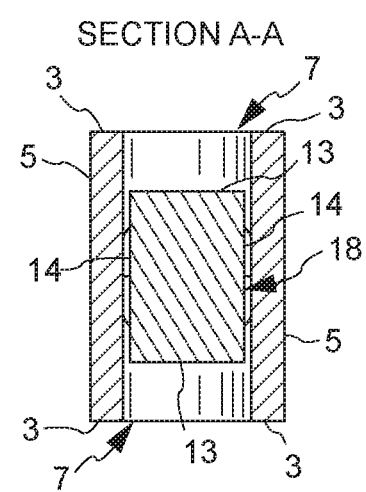

- 1ml DISK REMOVAL = 6.6+/-0.9ml
- 2ml DISK REMOVAL = 8.4+/-2.8ml
- 3ml DISK REMOVAL = 8.8+/-2.0ml
- 4ml DISK REMOVAL = 10.2+/-3.5ml
- 5ml DISK REMOVAL = 12.1+/-1.9ml
- 6ml DISK REMOVAL = 11.6+/-2.4ml
- 7ml DISK REMOVAL = 11.1+/-3.1ml
- 8ml DISK REMOVAL = 12.3+/-2.3ml

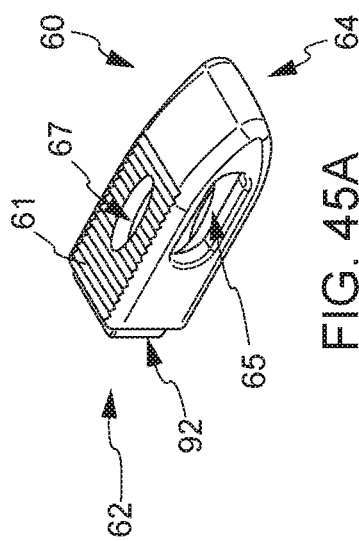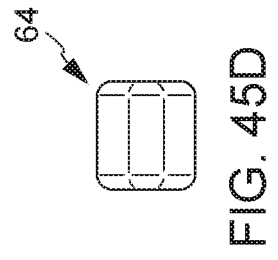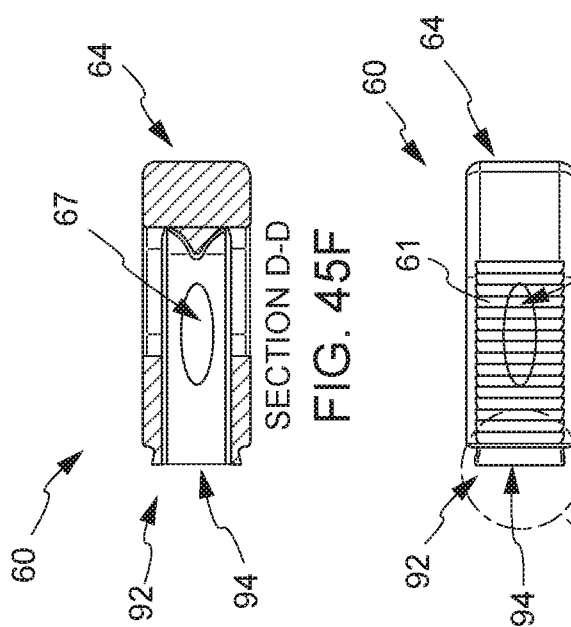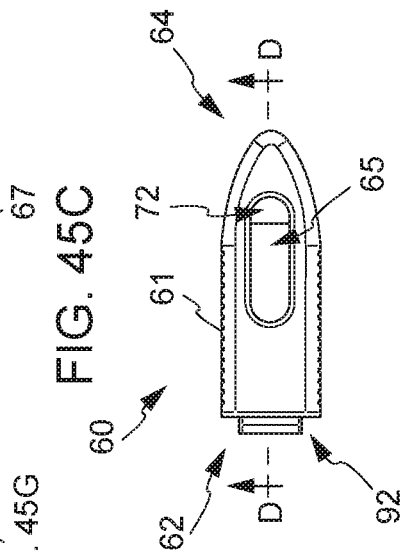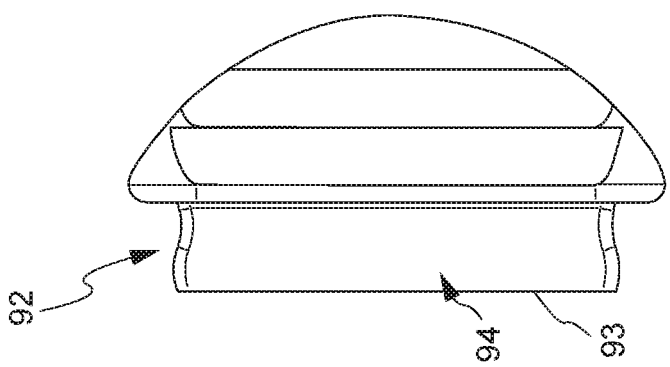

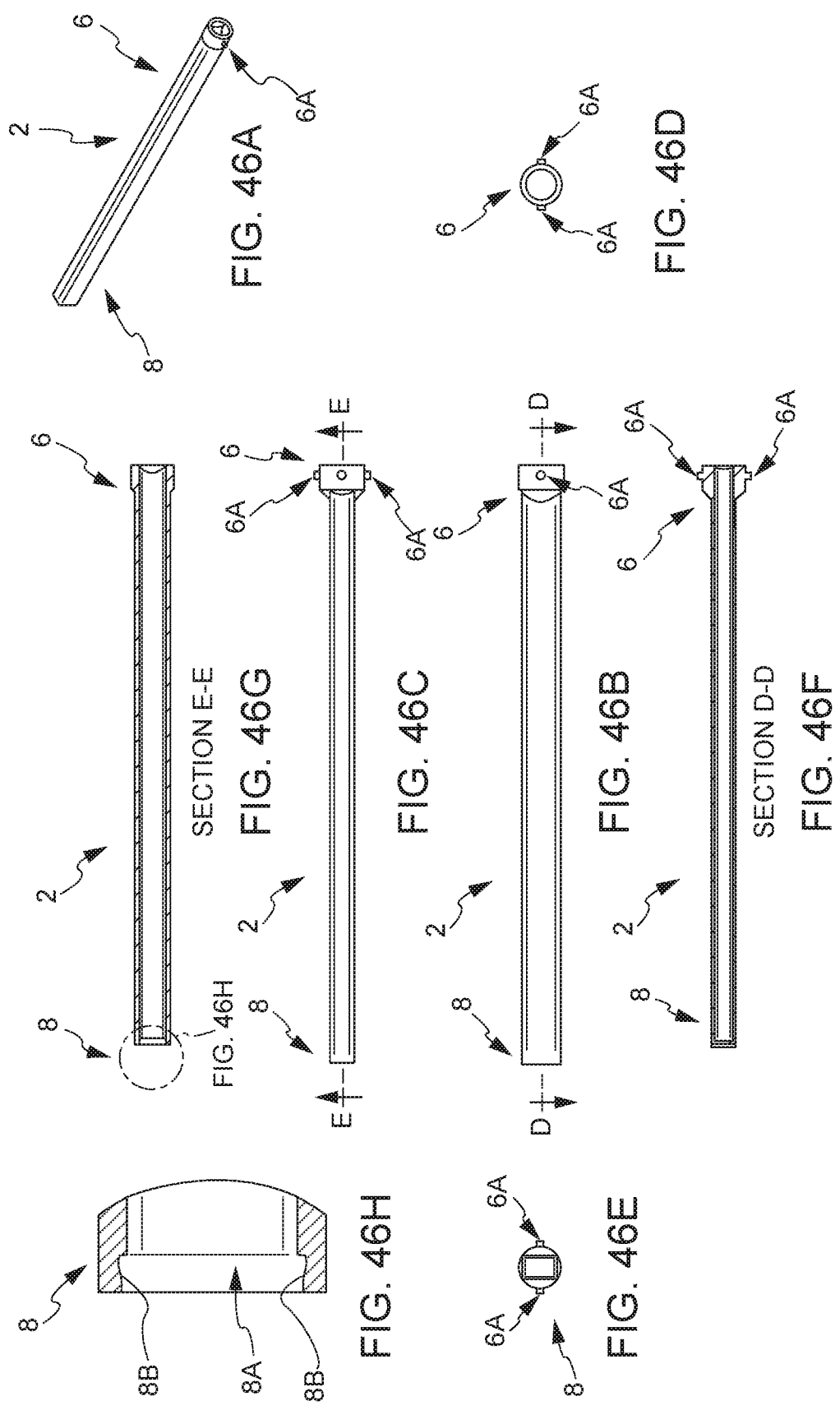

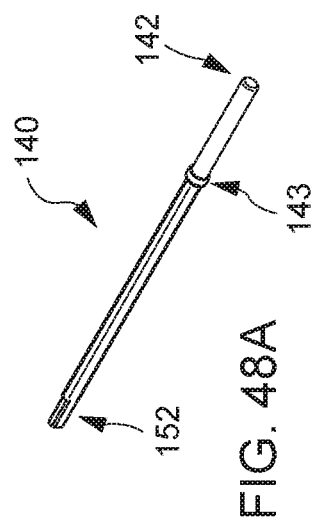
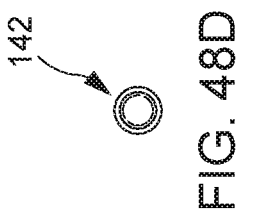
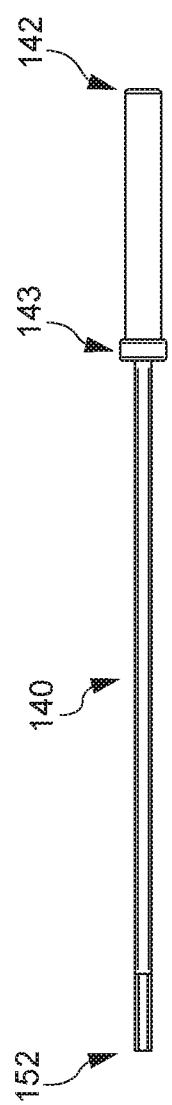
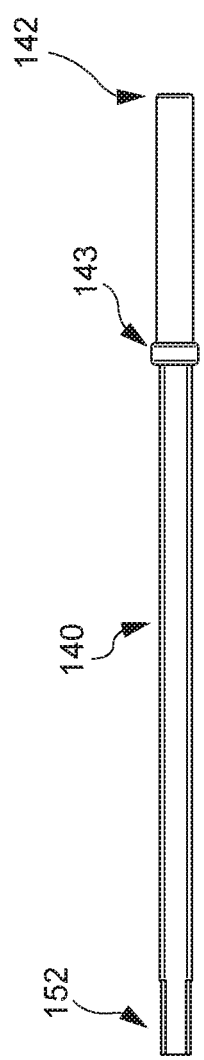
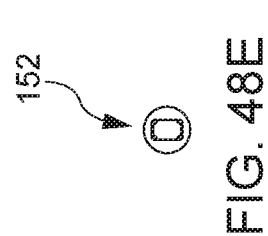
FIG. 48A
FIG. 48D
FIG. 48C
FIG. 48B
FIG. 48E

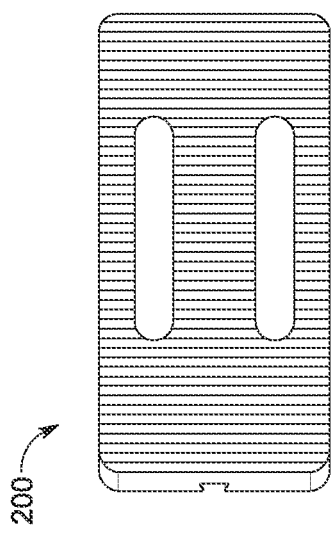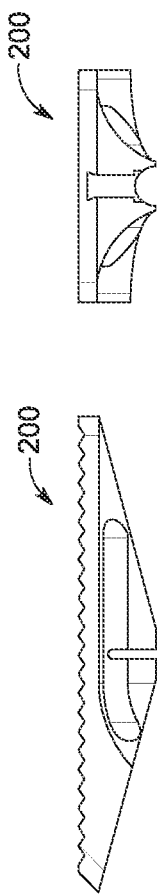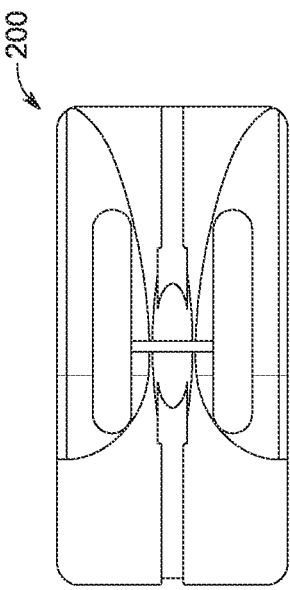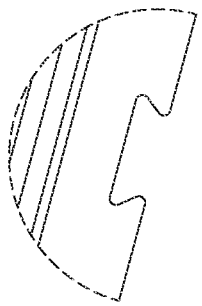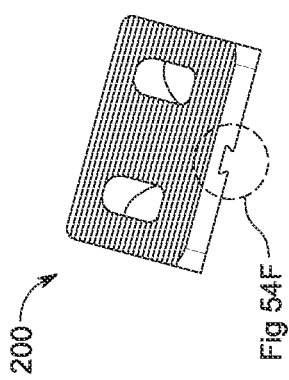
FIG. 54A FIG. 54B FIG. 54C FIG. 54D FIG. 54E FIG. 54F

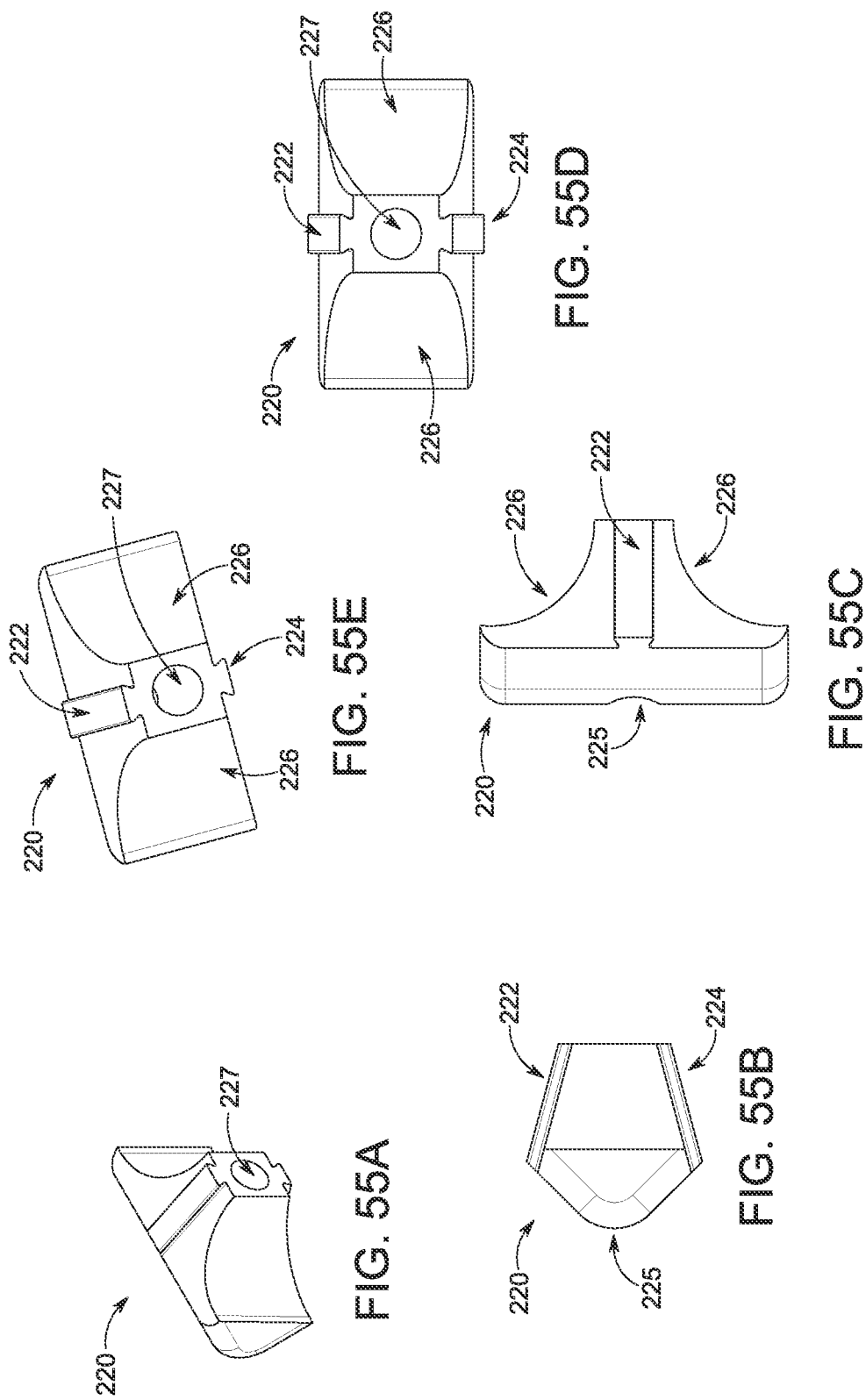

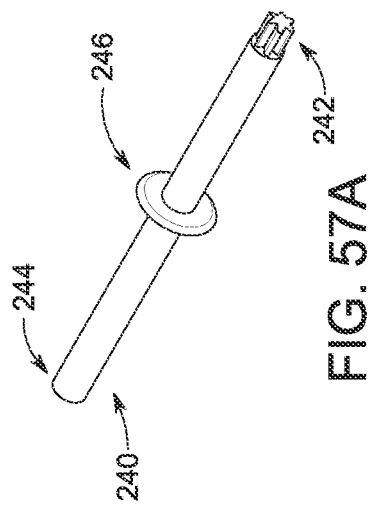
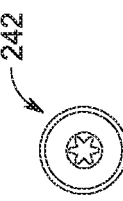
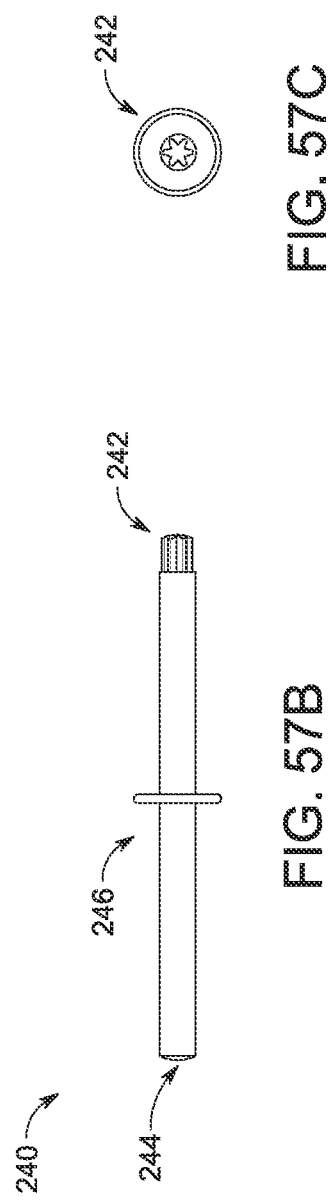
FIG. 57A
FIG. 57C
FIG. 57B

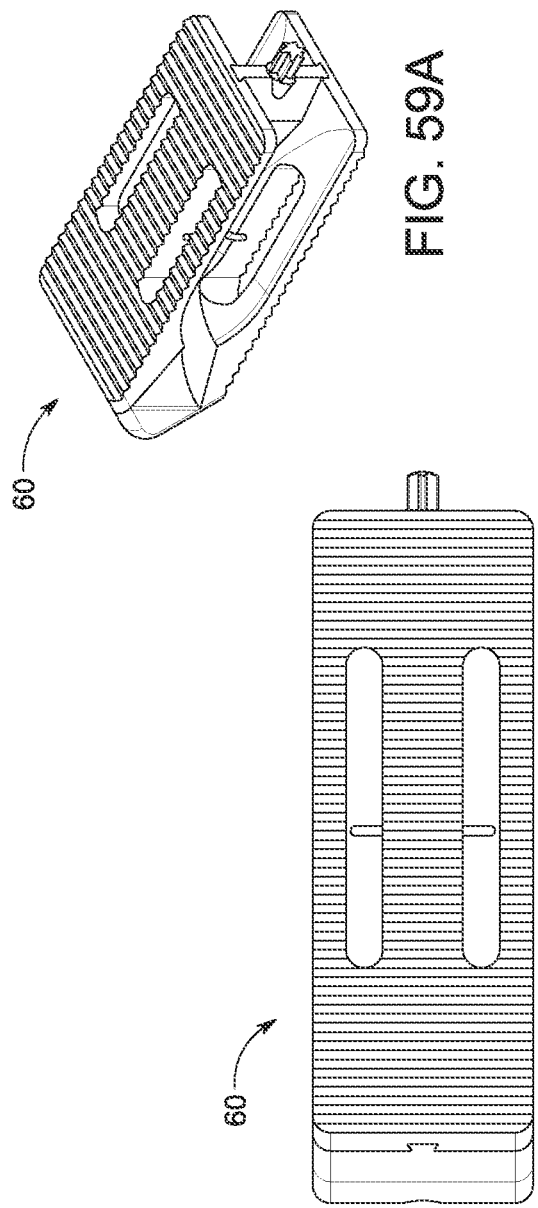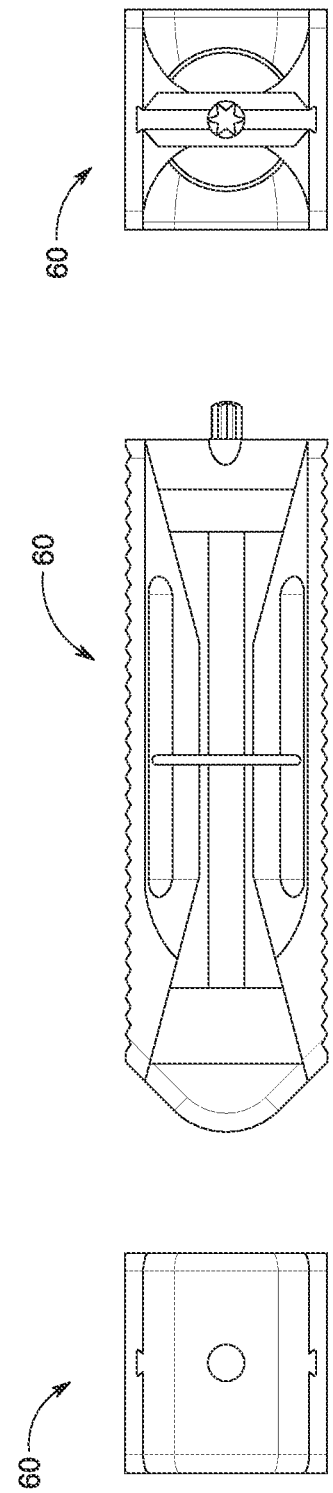

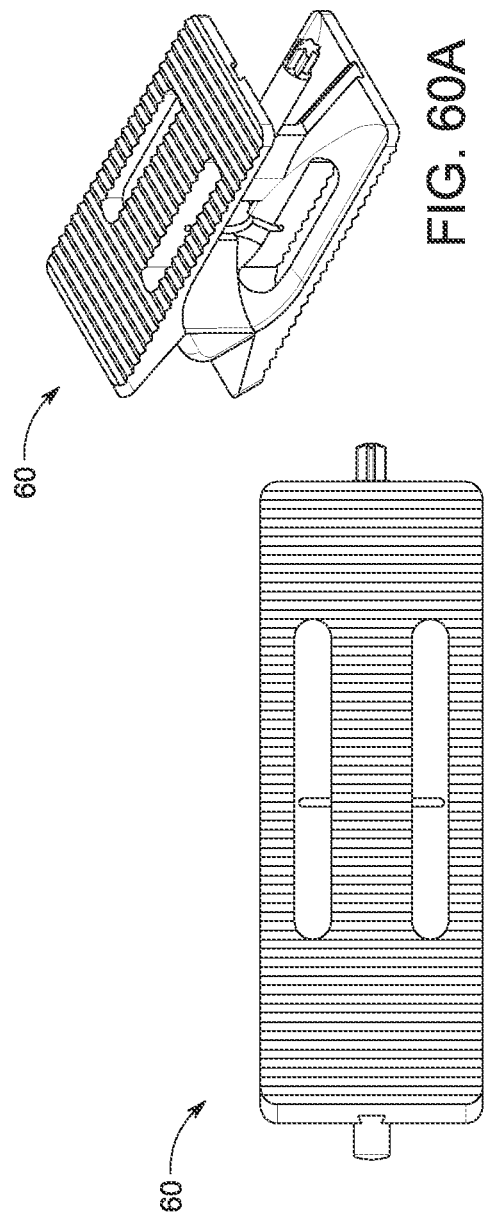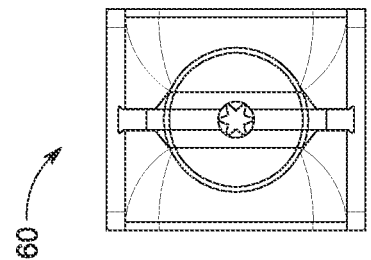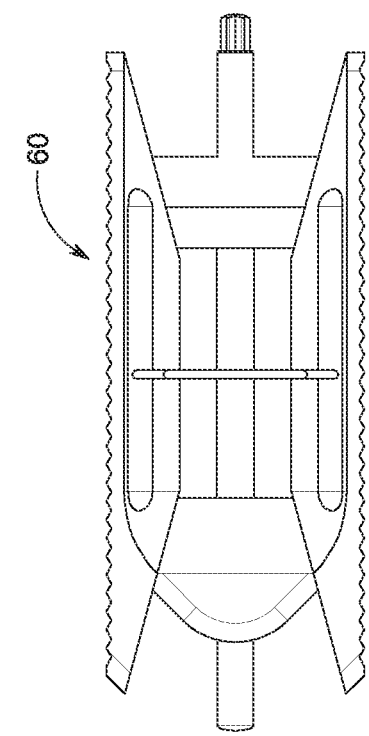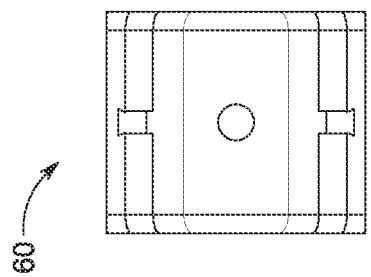

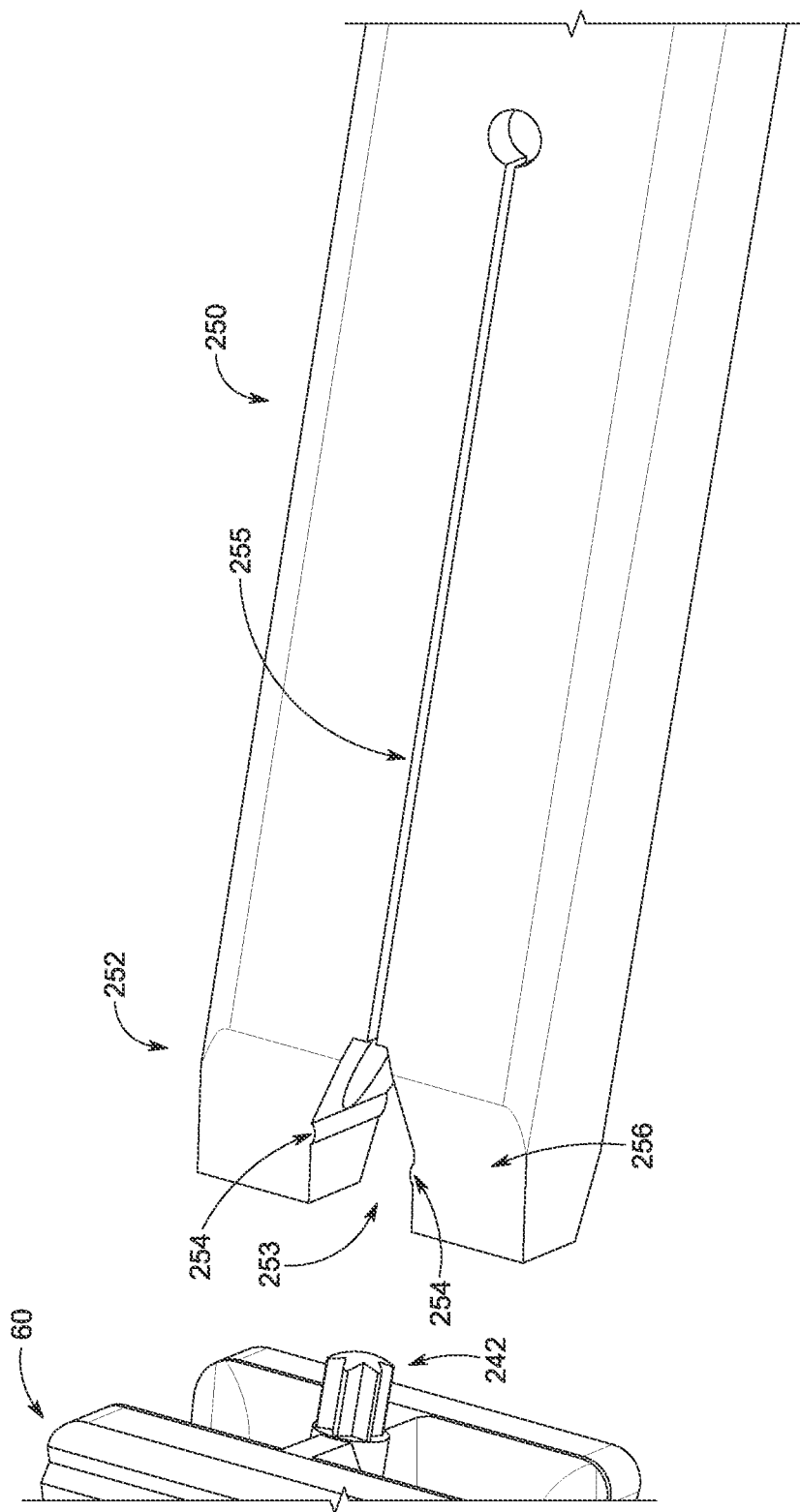

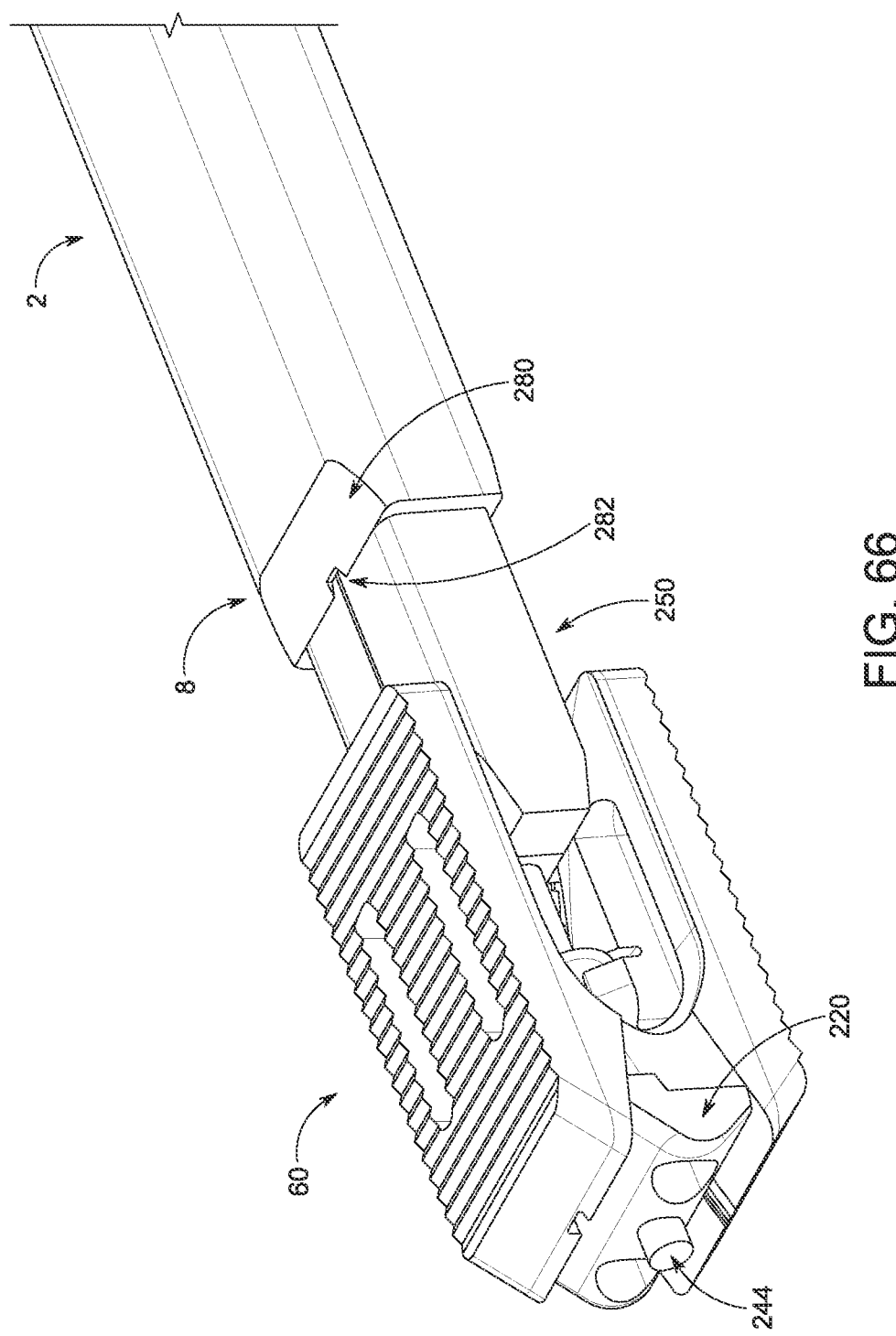

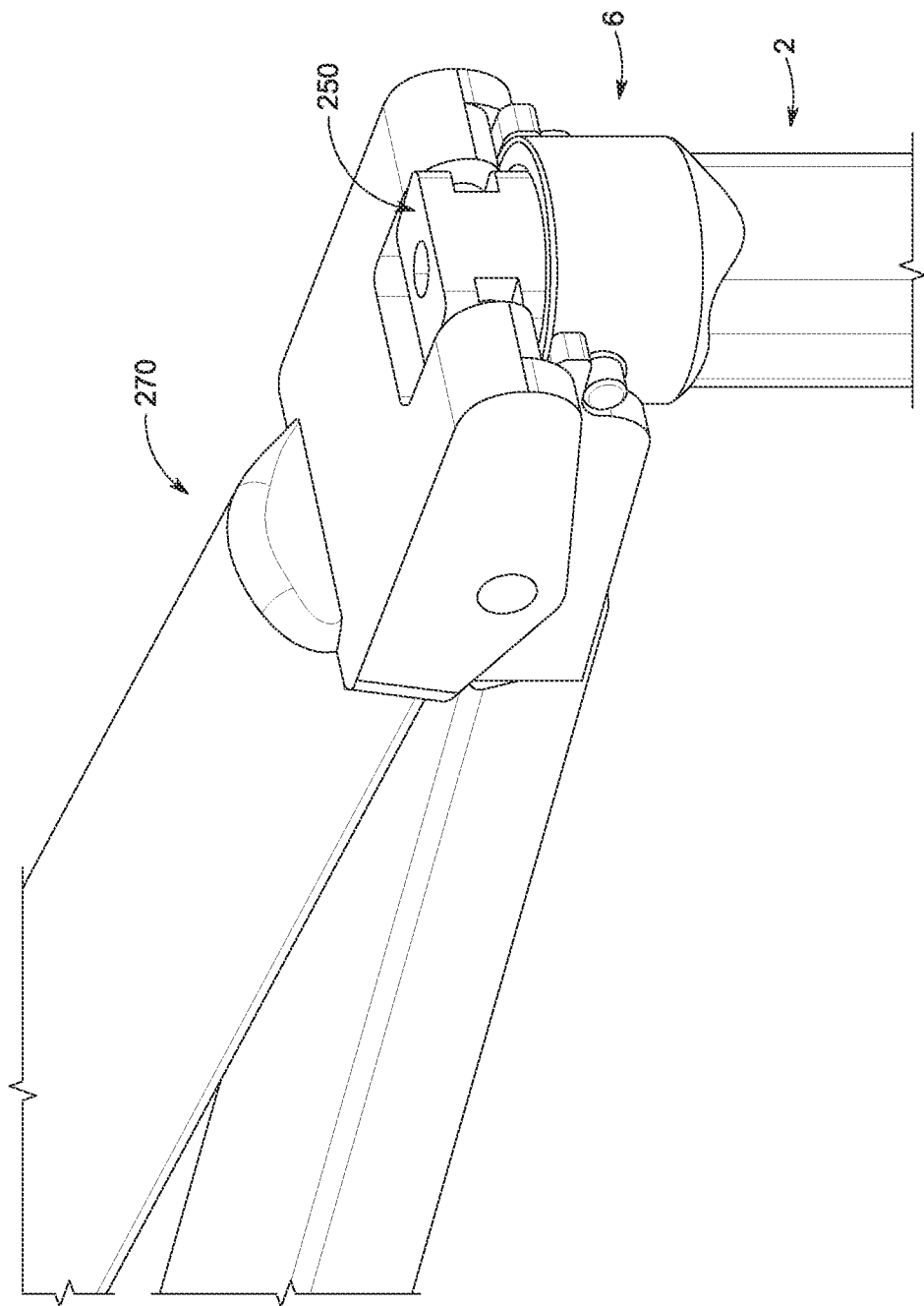

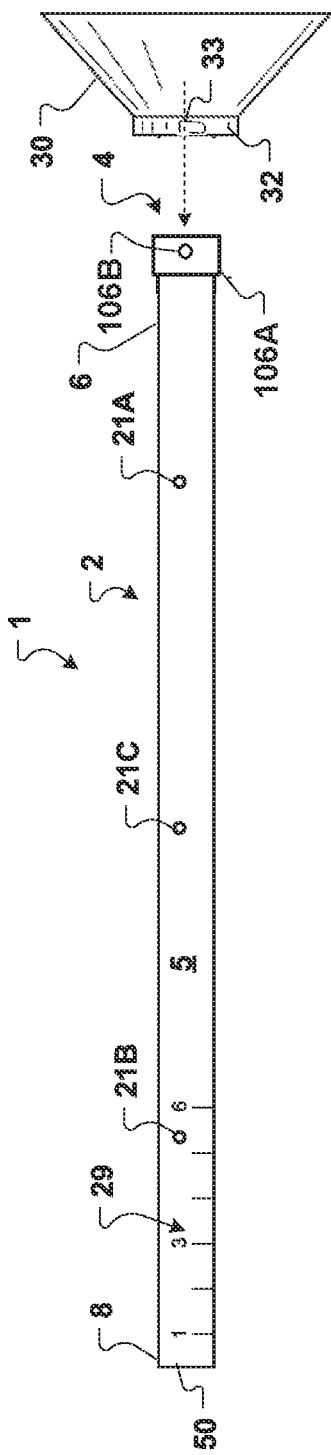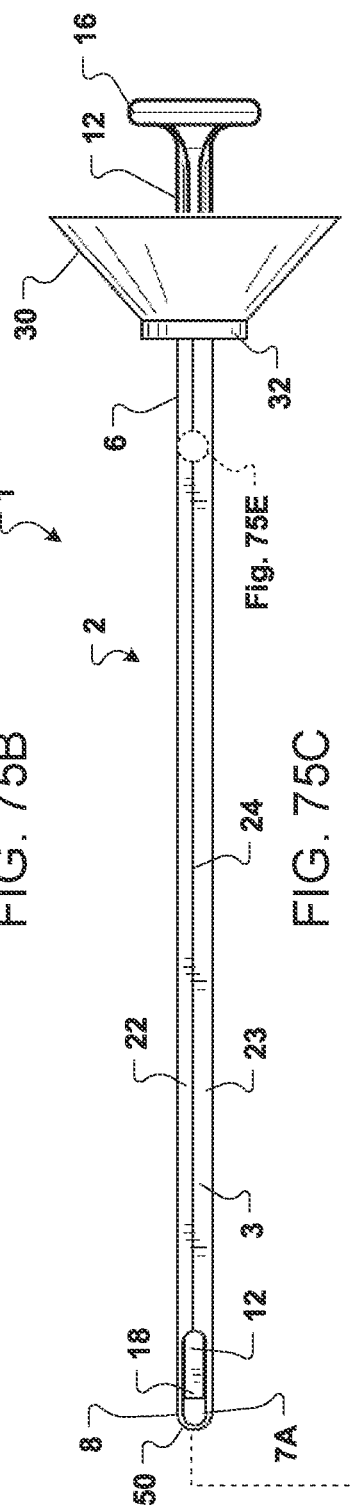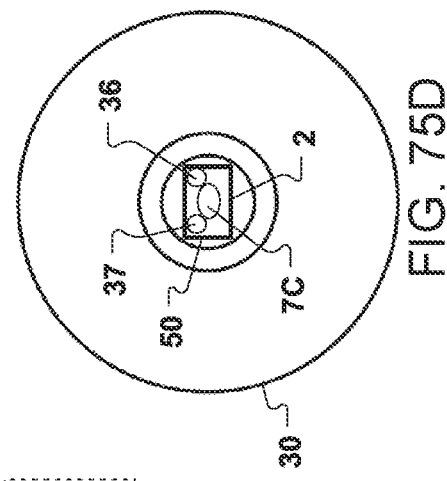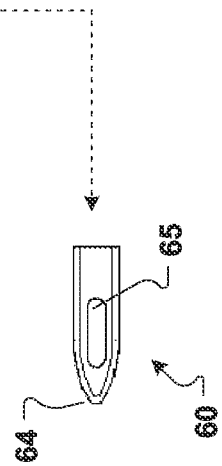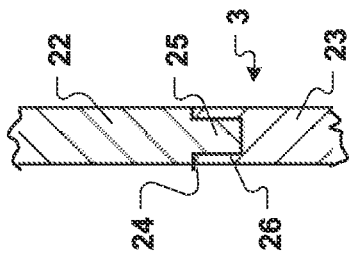

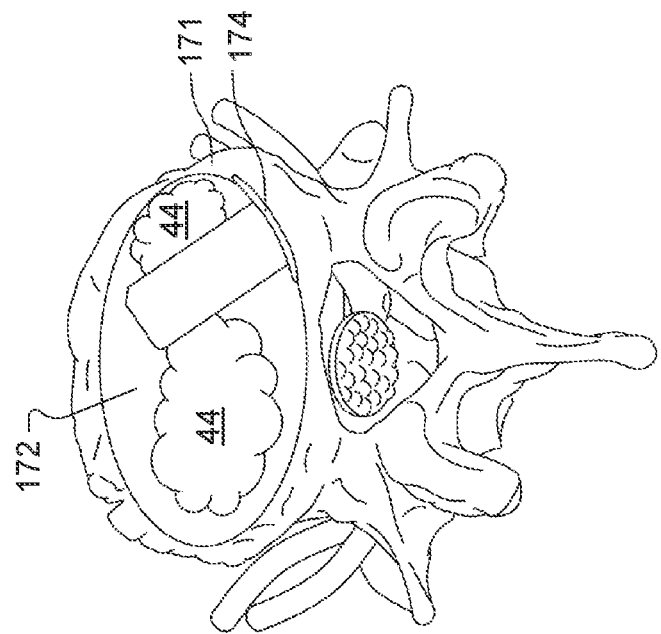
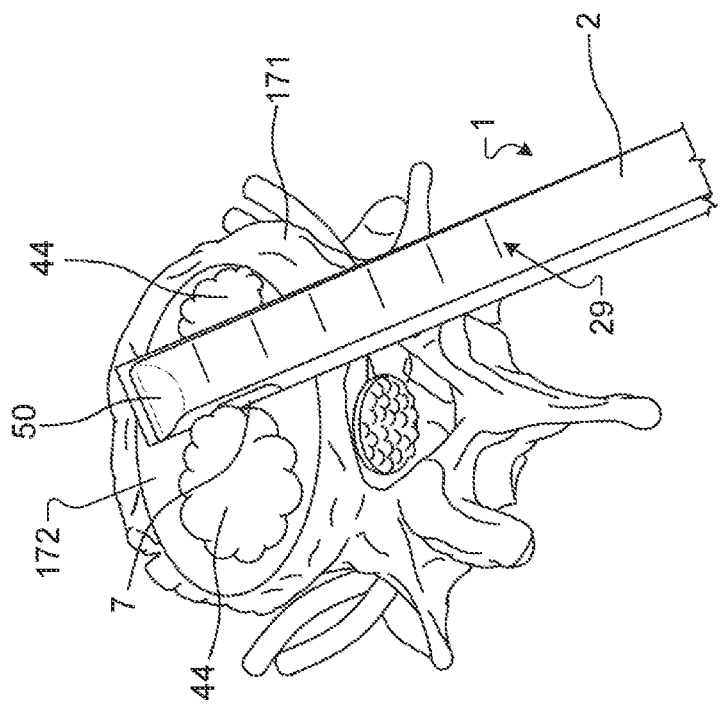
FIG. 77A
FIG. 77B

BONE GRAFT DELIVERY SYSTEM AND METHOD FOR USE

RELATED APPLICATIONS

This application is a continuation of U.S. patent application Ser. No. 17/203,655, filed Mar. 16, 2021, which is a continuation of U.S. patent application Ser. No. 16/373,410, filed Apr. 2, 2019 (now U.S. Pat. No. 10,973,656, issued Apr. 14, 2021), which is a continuation-in-part of U.S. patent application Ser. No. 16/198,754, filed Nov. 21, 2018 (now U.S. Pat. No. 10,245,159, issued Apr. 2, 2019), which is a continuation-in-part of U.S. patent application Ser. No. 15/486,511, filed Apr. 13, 2017 (now U.S. Pat. No. 10,195,053, issued Feb. 5, 2019), which is a continuation of U.S. patent application Ser. No. 14/887,598, filed Oct. 20, 2015 (now U.S. Pat. No. 9,629,729, issued Apr. 25, 2017), which is a continuation-in-part of U.S. patent application Ser. No. 14/263,963, filed Apr. 28, 2014 (now U.S. Pat. No. 9,186,193, issued Nov. 17, 2015), which is a continuation-in-part of U.S. patent application Ser. No. 14/088,148, filed Nov. 22, 2013 (now U.S. Pat. No. 8,709,088, issued Apr. 29, 2014), which is a continuation of U.S. patent application Ser. No. 13/947,255, filed Jul. 22, 2013 (now U.S. Pat. No. 8,685,031, issued Apr. 1, 2014), which is a continuation-in-part of U.S. patent application Ser. No. 13/714,971, filed Dec. 14, 2012 (now U.S. Pat. No. 9,173,694, issued Nov. 3, 2015), which is a continuation-in-part of U.S. patent application Ser. No. 13/367,295, filed Feb. 6, 2012 (now U.S. Pat. No. 9,060,877, issued Jun. 23, 2015), which is a continuation-in-part of U.S. patent application Ser. No. 12/886,452, filed Sep. 20, 2010 (now U.S. Pat. No. 8,906,028, issued Dec. 9, 2014), which claims the benefit of U.S. Provisional Application No. 61/243,664, filed on Sep. 18, 2009. This application also claims the benefit of U.S. Provisional Application No. 62/696,093, filed on Jul. 10, 2018. The disclosures of each of the above-referenced applications is incorporated herein by reference in its entirety.

FIELD OF THE INVENTION

This disclosure relates to orthopedic surgery, and more specifically to an apparatus and method for integrated delivery of bone graft material during the placement of surgical cages or other medical implants in a patient's spine.

BACKGROUND OF THE INVENTION

According to the American Academy of Orthopedic Surgeons, about 250,000 spinal fusion surgeries are performed every year, mostly on adults between the ages of 45 to 64. Spinal fusion is a process by which two or more of the vertebrae that make up the spinal column are fused together with bone grafts and internal devices (such as rods) that heal into a single solid bone. Spinal fusion can eliminate unnatural motion between the vertebrae and, in turn, reduce pressure on nerve endings. In addition, spinal fusion can be used to treat, for example, injuries to spinal vertebrae caused by trauma; protrusion and degeneration of the cushioning disc between vertebrae (sometimes called slipped disc or herniated disc); abnormal curvatures (such as scoliosis or kyphosis); and weak or unstable spine caused by infections or tumors.

Individuals who suffer degenerative disc disease, natural spine deformations, a herniated disc, spine injuries or other spine disorders may require surgery on the affected region to relieve the individual from pain and prevent further injury to the spine and nerves. Spinal surgery may involve removal of damaged joint tissue, insertion of a tissue implant and/or fixation of two or more adjacent vertebral bodies. In some instances a medical implant is also inserted, such as a fusion cage. The surgical procedure will vary depending on the nature and extent of the injury. Generally, there are five main types of lumbar fusion, including: posterior lumbar fusion ("PLF"), posterior lumbar interbody fusion ("PLIF"), anterior lumbar interbody fusion ("ALIF"), circumferential 360 fusion, and transforaminal lumbar interbody fusion ("TLIF"). More recently, direct lateral interbody fusion ("D-LIF") has become available. A posterior approach is one that accesses the surgical site from the patient's back, an anterior approach is one that accesses the surgical site from the patient's front or chest, and a direct lateral approach is one that accesses the surgical site from the patient's side. There are similar approaches for fusion in the interbody or cervical spine regions. For a general background on some of these procedures and the tools and apparatus used in certain procedures, see U.S. Prov. Pat. Appl. No. 61/120,260 filed on Dec. 5, 2008, the entire disclosure of which is incorporated by reference in its entirety. In addition, further background on procedures and tools and apparatus used in spinal procedures is found in U.S. patent application Ser. No. 12/632,720 filed on Dec. 7, 2009, now U.S. Pat. No. 8,366,748, the entire disclosure of which is incorporated by reference in its entirety.

Vertebrectomy, or the removal or excision of a vertebra, is another type of spinal surgery that may be necessary to alleviate pain and/or correct spinal defects, such as when disk material above and below a particular vertebra protrudes from the spine and contacts the spinal cord. Once the problematic vertebra is removed, a specialized fusion cage (also called a vertebrectomy cage) may be inserted into its place to restore structural continuity to the spine.

Some disadvantages of traditional methods of spinal surgery include, for example, the pain associated with the procedure, the length of the procedure, the complexity of implements used to carry out the procedure, the prolonged hospitalization required to manage pain, the risk of infection due to the invasive nature of the procedure, and the possible requirement of a second procedure to harvest autograft bone from the iliac crest or other suitable site on the patient for generating the required quantity of cancellous and/or cortical bone.

A variety of semisolid bone graft materials are available on the market which ostensibly increase spinal fusion rates without the morbidity of autograft bone harvest. Each of the manufacturers espouses their product as the most advantageous for healing. These products all have similar handling characteristics and the literature reveals that they have similar healing prospects. They come in a syringe and it is up to the surgeon to apply the selected material to the target site. The most common site for application is to the disk space after it has been prepared to a bleeding bed and ready to accept a cage and/or the grafting material. This represents a long and narrow channel even in open procedures. The surgeon is left to his own devices as to how to get the graft from its container to the active site. The devices which have been used have included a "caulking gun" construct and a variety of barrel shaft with a plunger design.

Bone graft typically includes crushed bone (cancellous and cortical), or a combination of these (and/or other natural materials), and may further comprise synthetic biocompatible materials. Bone graft of this type is intended to stimulate growth of healthy bone. As used herein, "bone graft" shall mean materials made up entirely of natural materials, entirely of synthetic biocompatible materials, or any combination of these materials. Bone graft often is provided by the supplier in a gel or slurry form, as opposed to a dry or granule form. Many companies provide various forms of bone graft in varying degrees of liquidity and viscosity, which may cause problems in certain prior art delivery devices in both prepackaged or packaged by the surgeon embodiments. In addition, the method of delivery of bone graft to a particular location varies depending on the form of the bone graft utilized.

Autogenous bone (bone from the patient) or allograft bone (bone from another individual) are the most commonly used materials to induce bone formation. Generally, small pieces of bone are placed into the space between the vertebrae to be fused. Sometimes larger solid pieces of bone are used to provide immediate structural support. Autogenous bone is generally considered superior at promoting fusion. However, this procedure requires extra surgery to remove bone from another area of the patient's body such as the pelvis or fibula. Thus, it has been reported that about 30 percent of patients have significant pain and tenderness at the graft harvest site, which may be prolonged, and in some cases outlast the back pain the procedure intended to correct. Similarly, allograft bone and other bone graft substitutes, although eliminating the need for a second surgery, have drawbacks in that they have yet to be proven as cost effective and efficacious substitutes for autogenous bone fusion.

An alternative to autogenous or allograft bone is the use of growth factors that promote bone formation. For example, studies have shown that the use of bone morphogenic proteins ("BMPs") results in better overall fusion, less time in the operating room and, more importantly, fewer complications for patients because it eliminates the need for the second surgery. However, use of BMPs, although efficacious in promoting bone growth, can be prohibitively expensive.

Another alternative is the use of a genetically engineered version of a naturally occurring bone growth factor. This approach also has limitations. Specifically, surgeons have expressed concerns that genetically engineered BMPs can dramatically speed the growth of cancerous cells or cause non-cancerous cells to become more sinister. Another concern is unwanted bone creation. There is a chance that bone generated by genetically engineered BMPs could form over the delicate nerve endings in the spine or, worse, somewhere else in the body.

Regenerative medicine, which harnesses the ability of regenerative cells, e.g., stem cells (i.e., the unspecialized master cells of the body) to renew themselves indefinitely and develop into mature specialized cells, may be a means of circumventing the limitations of the prior-art techniques. Stem cells, i.e., both embryonic and adult stem cells, have been shown to possess the nascent capacity to become many, if not all, of the 200+ cell and tissue types of the body, including bone. Recently, adipose tissue has been shown to be a source of adult stem cells (See e.g. Zuk, Patricia Z. et al., "Multilineage Cells from Human Adipose Tissue: Implication for Cell-Based Therapies," Tissue Engineering, April 2001, 7:211-28; Zuk, Patricia A. et al., "Human Adipose Tissue Is A Source Of Multipotent Stem Cells," Molecular Biology of the Cell, 2002, 13:4279-4295). Adipose tissue (unlike marrow, skin, muscle, liver and brain) is comparably easy to harvest in relatively large amounts with low morbidity (See e.g. Commons, G. W., Halperin, B., and Chang, C. C. (2001) "Large-volume liposuction: a review of 631 consecutive cases over 12 years" Plast. Reconstr. Surg. 108, 1753-63; Katz, B. E., Bruck, M. C. and Coleman, W. P. 3 (2001b) "The benefits of powered liposuction versus traditional liposuction: a paired comparison analysis" Dermatol. Surg. 27, 863-7). Accordingly, given the limitations of the prior art spinal fusion techniques, there exists a need for a device that incorporates regenerative cells, e.g., stem cells that possess the ability to induce bone formation.

Many different methods and approaches have been attempted to induce bone formation or to promote spinal fusion. The traditional devices for inserting bone graft impair the surgeon's visualization of the operative site, which can lead to imprecise insertion of bone graft and possible harm to the patient. The caulking gun and the collection of large barrel/plunger designs typically present components at the top of their structure which block the view of the surgical site. The surgeon must then resort to applying pressure to the surgical site to approximate the location of the device's delivery area. Such rough maneuvering can result in imprecise placement of bone graft, and in some cases, rupture of the surgical area by penetrating the annulus and entering the abdominal cavity. Also, in some surgical procedures, the devices for inserting bone graft material are applied within a cannula inserted or placed in the surgical area, further limiting the size and/or profile of the bone graft insertion device. When a cannula is involved, some traditional devices such as the large barrel/plunger designs and/or the chalking gun designs simply cannot be used as they cannot be inserted within the cannula.

Traditional devices for inserting bone graft deliver the bone graft material at the bottom of the delivery device along the device's longitudinal axis. Such a delivery method causes the bone grafting material to become impacted at the bottom of the delivery device which jams the device and promotes risk of rupture of the surgical area by penetrating the annulus and entering the abdominal cavity. Further, traditional devices that deliver bone graft material along their longitudinal axis may cause rupture of the surgical area or harm to the patient because of the ensuing pressure imparted by the ejected bone graft material from the longitudinal axis of the device. Furthermore, the graft material is distributed only in the longitudinal axis and does not fill in the peripheral areas of the disk.

As mentioned, the method of delivery of bone graft to a particular location varies depending on the form of the bone graft utilized. For example, in the case of slurry type bone graft, various dispensing devices have been developed having applicators designed to accommodate this type of bone graft. One such device is disclosed by U.S. Pat. No. 5,925,051 issued to Mikhail on Jul. 20, 1999 ("Mikhail"), the disclosure of which is incorporated herein by reference in its entirety. Mikhail provides a caulking gun type dispenser for introducing bone graft in an enlarged bone (e.g. femoral) cavity. The device preferably includes a barrel pre-loaded with bone graft and a cannulated ejector positioned over a multi-section guide wire. This arrangement purports to accomplish both ejecting bone graft from the barrel and compacting the bone graft material while being guided on the guide wire. Mikhail, however, is designed solely for use with slurry-type bone graft, and does not accommodate bone graft in granule form, which often varies in size among granules and does not have the same "flow" or viscosity characteristics as slurry-type bone graft. Thus, the applicator of Mikhail is insufficient for introducing most bone graft to a surgical site in a patient.

U.S. Pat. No. 6,019,765 issued to Thornhill et al. on Feb. 1, 2000 ("Thornhill") also teaches a bone graft delivery device and is incorporated herein by reference in its entirety. The bone graft device applicator of Thornhill is used to apply bone graft to an artificial joint without having to remove a previously implanted prosthesis component. The applicator device includes a hollow tube with an actuation mechanism for discharging the bone graft from the device via a nozzle coupled to a distal end of the tube. The bone graft delivery device of Thornhill may include various components for loading the device with the bone graft, and may further include a plurality of nozzles each having a geometry suited for a particular application. Like Mikhail, the Thornhill delivery device is designed for use with bone slurry, and requires much custom instrumentation and different sized parts to achieve success in many bone graft delivery applications, which in turn increases the time to assemble and use the delivery device and may create further problems during the surgical operation.

U.S. Pat. No. 5,697,932 issued to Smith et al. on Dec. 16, 1997 ("Smith") discloses yet another bone graft delivery system and method and is incorporated herein by reference in its entirety. In Smith, a hollow tube of pre-loaded bone graft and a plunger are used to facilitate delivery of the bone graft to a bone graft receiving area. A positioning structure is provided on the plunger to maintain the plunger in a desirable position with respect to the hollow tube. Adjunct positioning means may also be provided to ensure that the plunger remains in the desirable position during the packing of bone graft into the bone graft receiving area. Like the devices of Thornhill and Mikhail, the device disclosed by Smith is clearly designed solely for slurry type bone graft, and does not provide an effective opening for receiving the desired amount of bone graft. Furthermore, the hollow tube shown by Smith is narrow and does not have a footing or other apparatus associated with the delivery device for preventing the device from penetrating, for example, the abdominal region of a patient, which may occur during tamping or packing of the bone graft. This in turn may cause serious injury to a patient if not controlled, and for these reasons the device of Smith is also insufficient for delivery of bone graft to a surgical site.

Traditional devices for inserting a fusion cage or other medical implants into a patient's spine or other surgical area are distinct and separate from traditional devices that deliver bone graft material to the surgical site. For example, once an implant has been positioned, then bone growth material is packed into the internal cavity of the fusion cage. Also, sometimes the process is reversed, i.e., the bone growth is inserted first, and then the implant. These bone growth inducing substances come into immediate contact with the bone from the vertebral bone structures which project into the internal cavity through the apertures. Two devices are thus traditionally used to insert bone graft material into a patient's spine and to position and insert a fusion cage. These devices thus necessitate a disc space preparation followed by introduction of the biologic materials necessary to induce fusion and, in a separate step, application of a structural interbody fusion cage.

The problems associated with separate administration of the biologic material bone graft material and the insertion of a fusion cage include applying the graft material in the path of the cage, restricting and limiting the biologic material dispersed within the disk space, and requiring that the fusion cage be pushed back into the same place that the fusion material delivery device was, which can lead to additional trauma to the delicate nerve structures.

Fusion cages provide a space for inserting a bone graft between adjacent portions of bone. Such cages are often made of titanium and are hollow, threaded, and porous in order to allow a bone graft contained within the interior of the cage of grow through the cage into adjacent vertebral bodies. Such cages are used to treat a variety of spinal disorders, including degenerative disc diseases such as Grade I or II spondylolistheses of the lumbar spine.

Surgically implantable intervertebral fusion cages are well known in the art and have been actively used to perform spinal fusion procedures for many years. Their use became popularized during the mid 1990's with the introduction of the BAK Device from the Zimmer Inc., a specific intervertebral fusion cage that has been implanted worldwide more than any other intervertebral fusion cage system. The BAK system is a fenestrated, threaded, cylindrical, titanium alloy device that is capable of being implanted into a patient as described above through an anterior or posterior approach, and is indicated for cervical and lumbar spinal surgery. The BAK system typifies a spinal fusion cage in that it is a highly fenestrated, hollow structure that will fit between two vertebrae at the location of the intervertebral disc.

Spinal fusion cages may be placed in front of the spine, a procedure known as anterior lumbar interbody fusion, or ALIF, or placed in back of the spine. The cages are generally inserted through a traditional open operation, though laparoscopic or percutaneous insertion techniques may also be used. Cages may also be placed through a posterior lumbar interbody fusion, or PLIF, technique, involving placement of the cage through a midline incision in the back, or through a direct lateral interbody fusion, or D-LIF, technique, involving placement of the cage through an incision in the side.

A typical procedure for inserting a common threaded and impacted fusion cage is as follows. First, the disc space between two vertebrae of the lumbar spine is opened using a wedge or other device on a first side of the vertebrae. The disk space is then prepared to receive a fusion cage. Conventionally, a threaded cage is inserted into the bore and the wedge is removed. A disk space at the first side of the vertebrae is then prepared, and a second threaded fusion cage inserted into the bore. Alternatively, the disk space between adjacent vertebrae may simply be cleared and a cage inserted therein. Often, only one cage is inserted obliquely into the disk space. Use of a threaded cage may be foregone in favor of a rectangular or pellet-shaped cage that is simply inserted into the disk space. Lastly, bone graft material may be inserted into the surgical area using separate tools and devices.

U.S. Pat. No. 4,743,256 issued to Brantigan ("Brantigan") discloses a traditional spinal back surgical method involving the implantation of a spinal fusion cage. The cage surfaces are shaped to fit within prepared endplates of the vertebrae to integrate the implant with the vertebrae and to provide a permanent load-bearing strut for maintaining the disc space. Brantigan teaches that these cages typically consist of a homogeneous nonresorbable material such as carbon-reinforced polymers such as polyether ether ketone (PEEK) or polyether ketone ether ketone ketone ("PEKEKK"). Although these cages have demonstrated an ability to facilitate fusion, a sufficient fusion is sometimes not achieved between the bone chips housed within the cage and the vertebral endplates. In particular, achieving a complete fusion in the middle portion of the cage has been particularly problematic. As shown in FIG. 6 herein, the upper U and lower L surfaces of these cages C have large transverse pores P which facilitate bone ingrowth, and these pores lead to an inner void space IVS which houses bone graft (not shown) which facilitates the desired fusion. In any case, Brantigan teaches the separate process and procedure for the insertion of a fusion cage and the insertion of bone graft. Indeed, local bone graft harvested from the channel cuts into the vertebrae to receive the plug supplements the fusion.

U.S. Pat. Appl. Pub. 2007/0043442 of Abernathie et al. ("Abernathie") discloses another traditional spinal surgical method involving the implantation of a spinal fusion cage. Abernathie relates generally to an implantable device for promoting the fusion of adjacent bony structures, and a method of using the same. More specifically, Abernathie relates to an expandable fusion cage that may be inserted into an intervertebral space, and a method of using the same. Abernathie includes an aperture in the fusion cage to allow bone growth therethrough, as a separate procedure to the insertion of the fusion cage.

Traditional fusion cages are available in a variety of designs and composed of a variety of materials. The cages or plugs are commonly made of an inert metal substrate such as stainless steel, cobalt-chromium-molybdenum alloys, titanium or the like having a porous coating of metal particles of similar substrate metal, preferably titanium or the like as disclosed, for example, in the Robert M. Pilliar U.S. Pat. No. 3,855,638 issued Dec. 24, 1974 and U.S. Pat. No. 4,206,516 issued Jun. 10, 1980. These plugs may take the form of flat sided cubical or rectangular slabs, cylindrical rods, cruciform blocks, and the like.

U.S. Pat. No. 5,906,616 issued to Pavlov et al. ("Pavlov") discloses a fusion cage of various cylindrical and conical shapes and a method of insertion. Like Brantigan, Pavlov teaches the separate process and procedure for the insertion of a fusion cage and the insertion of bone graft. U.S. Pat. No. 5,702,449 ("McKay") discloses a spinal implant comprising a cage made of a porous biocompatible material reinforced by an outer sleeve made of a second material which is relatively stronger under the compressive load of the spine than the biocompatible material. U.S. Pat. No. 6,569,201 issued to Moumene et al. ("Moumene") teaches a bone fusion device having a structural bioresorbable layer disposed upon the outer surface of a non-resorbable support. As the bioresorbable structural layer resorbs over time, the load upon the bone graft housed within the non-resorbable support increases. Published PCT Application No. WO 99/08627 ("Gresser") discloses a fully bioresorbable interbody fusion device, as well as homogeneous composite devices containing at least 25% resorbable materials. U.S. Pat. No. 7,867,277 issued to Tohmeh discloses a spinal fusion implant of bullet shaped end.

U.S. Pat. No. 7,846,210 issued to Perez-Cruet et al. ("Perez-Cruet") discloses an interbody device assembly consisting of a fusion device and an insertion device. The insertion device positions the fusion device between two vertebrae, provides bone graft material, and then detaches from the fusion device, leaving the fusion device in place to restore disc space height. However, the Perez-Cruet device is designed to receive bone graft material from its insertion device and distribute the material away from the fusion device. In most embodiments of the fusion device, a center plate is positioned immediately downstream of the received bone graft material and directs the bone graft to opposing sides of the fusion device. (See, for example, FIG. 20 depicting plate 308 directing bone graft material 392 along the exterior sides of the fusion device 302). As such, the Perez-Cruet fusion device is unlikely to completely fill the areas near of its fusion cage and deliver bone graft material to the surrounding bone graft site. Furthermore, none of the Perez-Cruet fusion device embodiments feature a defined interior space or a cage-style design. Indeed, the Perez-Cruet fusion device explicitly teaches away from a contained-interior, fusion-cage-style device, asserting that its fusion device fills all of the disc space as opposed to a cage design, which contains the bone material. Furthermore, the Perez-Cruet does not feature a distal tip that functions to precisely position the fusion device and stabilize the device during delivery of bone graft material.

U.S. Pat. No. 7,985,256 issued to Grotz et al. ("Grotz") discloses an expandable spinal implant for insertion between opposed vertebral end plates. The implant is a cylinder block of slave cylinders; a central cavity between the cylinders receives bone graft material and pistons positioned within the cylinders provide a corrective bone engaging surface for expanding against a first vertebral end plate. The insertion tool used to place the spinal implant includes a handle and hollow interior for housing hydraulic control lines and a bone graft supply line. The Grotz system does not allow precise positioning or delivery of bone graft material without an implant and requires a complex and bulky insertion tool.

U.S. Pat. Appl. Pub. 2010/0198140 to Lawson ("Lawson") discloses a tool comprising a cannula with an open slot at the distal end and a closed tip. Lawson's tool employs tamps to push bone aside and open up a void for filling; solid bone pellets are then rammed down the hollow interior of the cannula by a tamper and delivered to the surgical site. Lawson does not allow precise positioning or delivery of viscous bone graft material and has no capability to interconnect or integrate with an implant such as a bone graft fusion cage.

U.S. Pat. Appl. Pub. 2010/0262245 to Alfaro et al. ("Alfaro") discloses a delivery system for an intervertebral spacer and a bone grafting material comprising a spacer disengagingly attached to a hollow handle. The handle comprises a chamber and bone grafting material-advancing means for introducing bone grafting material from the chamber into the spacer and the intervertebral spaces. The Alfaro system does not allow precise positioning or delivery of bone graft material through a distal tip that precisely positions the fusion device and stabilizes the device during delivery of bone graft material, and does not allow primarily lateral injection of bone graft fusion material.

The prior art bone graft delivery devices listed above typically must come pre-loaded with bone graft, or alternatively require constant loading (where permissible) in order to constantly have the desired supply of bone graft available. Moreover, these bone graft delivery devices generally cannot handle particulate bone graft of varying or irregular particulate size. Furthermore, the prior art devices for inserting a fusion cage or other medical implant into a patient's spine or other surgical area are commonly distinct and separate from traditional devices that deliver bone graft material to the surgical site. As such, two devices are traditionally used to insert bone graft material into a patient's spine and to position and insert a fusion cage. The problems associated with separate administration of the biologic material bone graft material and the insertion of a fusion cage include applying the graft material in the path of the cage, restricting and limiting the biologic material dispersed within the disk space, and requiring that the fusion cage be pushed back into the same place that the fusion material delivery device was, which can lead to additional trauma to the delicate nerve structures. These problems can be a great inconvenience, cause avoidable trauma to a patient and make these prior art devices unsuitable in many procedures.

Therefore, there is a long-felt need for an apparatus and method integrated precision delivery of bone graft material during the placement of surgical cages or other medical implants in a patient's spine. The present invention solves these needs. The present invention allows biologic material to flow directly to the fusion cage and be dispersed within the disc space in a single step, and can precisely and simply deliver particulate bone graft of varying or irregular particulate size. Thus, the present invention allows application of bone graft material through a detachable fusion cage, eliminates otherwise restriction of the volume of biologic material that may be dispersed within the disk space, and eliminates the requirement that the fusion cage be pushed back into the same place that the fusion material delivery device was, which can lead to additional trauma to the delicate nerve structures.

SUMMARY OF THE INVENTION

Certain embodiments of the present disclosure relate to an apparatus and method for the integrated delivery of bone graft material during the placement of surgical cages or other medical implants in a patient's spine. The integrated fusion cage and delivery device (the "device") is comprised generally of a tubular member and a plunger for expelling bone graft from the tubular member, through a surgical fusion cage, and into a bone graft receiving area, then disengaging the fusion cage at the surgical site in a human patient. Thus, the apparatus and method allows the biologic material to flow directly into and through the fusion cage and be dispersed within the disc space in a single step, and leave the detachable fusion cage in the surgical area. In one embodiment, the integrated fusion cage is an expandable integrated fusion cage. Other embodiments and alternatives to this device are described in greater detail below.

By way of providing additional background, context, and to further satisfy the written description requirements of 35 U.S.C. § 112, the following references are incorporated by reference in their entireties for the express purpose of explaining the nature of the surgical procedures in which bone graft is used and to further describe the various tools and other apparatus commonly associated therewith: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. Pub. No. 2008/0255564 to Michelson.

By way of providing additional background, context, and to further satisfy the written description requirements of 35 U.S.C. § 112, the following references are incorporated by reference in their entireties for the express purpose of explaining the nature of the surgical procedures in which fusion cages are used and to further describe the various tools and other apparatus commonly associated therewith: U.S. Pat. No. 6,569,201 to Moumene et al.; U.S. Pat. No. 6,159,211 to Boriani et al.; U.S. Pat. No. 4,743,256 to Brantigan; U.S. Pat. Appl. 2007/0043442 to Abernathie et al.; U.S. Pat. Nos. 3,855,638 and 4,206,516 to Pilliar; U.S. Pat. No. 5,906,616 issued to Pavlov et al.; U.S. Pat. No. 5,702,449 to McKay; U.S. Pat. No. 6,569,201 to Moumene et al.; PCT Appl. No. WO 99/08627 to Gresser; U.S. Pat. Appl. Pub. 2012/0022651 to Akyuz et al.; U.S. Pat. Appl. Pub. 2011/0015748 to Molz et al.; U.S. Pat. Appl. Pub. 2010/0249934 to Melkent; U.S. Pat. Appl. Pub. 2009/0187194 to Hamada; U.S. Pat. No. 7,867,277 issued to Tohmeh; U.S. Pat. No. 7,846,210 to Perez-Cruet et al.; U.S. Pat. No. 7,985,256 issued to Grotz et al.; U.S. Pat. Appl. Pub. 2010/0198140 to Lawson; and U.S. Pat. Appl. Pub. 2010/0262245 to Alfaro et al.

By way of providing additional background and context, the following references are also incorporated by reference in their entireties for the purpose of explaining the nature of spinal fusion and devices and methods commonly associated therewith: U.S. Pat. No. 7,595,043 issued to Hedrick et al.; U.S. Pat. No. 6,890,728 to Dolecek et al.; U.S. Pat. No. 7,364,657 to Mandrusov, and U.S. Pat. No. 8,088,163 to Kleiner.

In addition, by way of providing additional background and context, the following references are also incorporated by reference in their entireties for the purpose of explaining the nature of spinal fusion and devices and methods commonly associated therewith: U.S. Pat. No. D647,202 entitled "Bone Marrow Harvesting Device" to Scifert issued Oct. 18, 2011; U.S. Pat. No. 7,897,164 entitled "Compositions and Methods for Nucleus Pulposus Regeneration" to Seifert issued Mar. 1, 2011; US Pat. Appl. No. 2010/0112029 entitled "Compositions and Methods for Nucleus Pulposus Regeneration" to Scifert issued May 6, 2010; US Pat. Appl. No. 2010/0021518 entitled "Foam Carrier for Bone Grafting" to Scifert issued Jan. 28, 2010; U.S. Pat. No. 7,824,703 entitled "Medical Implants with Reservoir(s), and Materials Preparable From Same" to Scifert, et al., issued Nov. 2, 2010; US Pat. Appl. No. 2006/0247791 entitled "Multi-Purpose Medical Implant Devices" to McKay, et al., issued Nov. 2, 2006; US Pat. Appl. No. 2007/0225811 entitled "Conformable Orthopedic Implant" to Scifert, et al., issued Sep. 27, 2007; U.S. Pat. No. 6,746,487 entitled "Intramedullary Trial Fixation Device" to Scifert, et al., issued Jun. 9, 2004; US Pat. Appl. No. 2013/0073041 entitled "Medical Implants With Reservoir(s), and Materials Preparable From Same" to Scifert et al., issued Mar. 21, 2013; US Pat. Appl. No. 2010/0266689 entitled "Tissue Augmentation With Active Agent For Wound Healing" to Simonton et al., issued Oct. 21, 2010; US Pat. Application No. 2011/0028393 entitled "Flowable Paste And Putty Bone Void Filler" to Vickers et al., issued Feb. 3, 2011; US Pat. Appl. No. 2009/0099660 entitled "Instrumentation To Facilitate Access Into The Intervertebral Disc Space And Introduction Of Materials Therein" to Scifert issued Apr. 16, 2009; US Pat. Appl. No. 2011/0014587 entitled "System And Methods Of Preserving An Oral Socket" to Spagnoli et al., issued Jan. 20, 2011; U.S. Pat. No. 8,148,326 entitled "Flowable Carrier Matrix and Methods for Delivering to a Patient" to Beals et al., issued Apr. 3, 2012; US Pat. Appl. No. 2008/0260598 entitled "Devices, Methods and Systems for Hydrating a Medical Implant Material" to Gross et al., issued Oct. 23, 2008; US Pat. Appl. No. 2007/0265632 entitled "Bone Cutting Template and Method of Treating Bone Fractures" to Seifert et al., issued Nov. 15, 2007; U.S. Pat. No. 8,293,232 entitled "Flowable Carrier Matrix and Methods for Delivering to a Patient" to Beals et al., issued Oct. 23, 2012; U.S. Pat. No. 8,198,238 entitled "Flowable Carrier Matrix and Methods for Delivering to a Patient" to Beals et al., issued Jun. 12, 2012; U.S. Pat. No. 7,939,092 entitled "Cohesive Osteogenic Putty and Materials Therefor" to McKay et al., issued May 10, 2011; US Pat. Appl. No. 2007/0264300 entitled "Therapeutic Agent Carrier and Method of Treating Bone Fractures" to Scifert et al., issued Nov. 15, 2007; US Pat. Appl. No. 2011/0020768 entitled "Implantable Screw and System for Socket Preservation" to Spagnoli et al., issued Jan. 27, 2011; US Pat. Appl. No. 2012/0065687 entitled "Multi-Radius Vertebral Rod with a Varying Stiffness" to Ballard et al., issued Mar. 15, 2012; US Pat. No. 2007/0225219 entitled "Intramedullary Drug Delivery Device and Method of Treating Bone Fractures" to Boden et al., issued Sep. 27, 2007; U.S. Pat. No. 7,723,291 entitled "Release of BMP, Bioactive Agents and/or Cells Via a Pump into a Carrier Matrix" to Beals et al., issued May 25, 2010; U.S. Pat. No. 7,671,014 entitled "Flowable Carrier Matrix And Methods For Delivering To A Patient" to Beals et al., issued Mar. 2, 1010; U.S. Pat. No. 7,897,564 entitled "Flowable Carrier Matrix and Methods for Delivering to a Patient" to Beals et al., issued Mar. 1, 2011; US Pat. Application No. 2011/0160777 entitled "System and Methods of Maintaining Space for Augmentation of the Alveolar Ridge" to Spagnoli et al., issued Jun. 30, 2011; US Pat. Application No. 2009/0246244 entitled "Malleable Multi-Component Implants and Materials Therefor" to McKay et al., issued Oct. 1, 2009; US Pat. Application No. 2009/0246244 entitled "Malleable Multi-Component Implants and Materials Therefor" to McKay et al., issued Oct. 1, 2009; US Pat. No. 2013/0110169 entitled "Vertebral Rod System and Methods of Use" to Hynes, et al., issued May 2, 2013; US Pat. Appl. No. 2011/0184412 entitled "Pre-Assembled Construct With One Or More Non-Rotating Connectors For Insertion Into a Patient" to Scifert, et al., issued Jul. 28, 2011; U.S. Pat. No. 7,964,208 entitled "System and Methods of Maintaining Space For Augmentation of the Alveolar Ridge" to Spagnoli, et al., issued Jun. 21, 2011; U.S. Pat. No. 8,080,521 entitled "Flowable Carrier Matrix and Methods for Delivering to a Patient" to Beals, et al., issued Dec. 20, 2011; US Pat. Appl. No. 2009/0142385 entitled "Compositions for Treating Bone Defects" to Gross, et al., issued Jun. 4, 2009; U.S. Pat. No. 7,578,820 entitled "Devices and Techniques for a Minimally Invasive Disc Space Preparation and Implant Insertion" to Moore, et al., issued Aug. 25, 2009; US Pat. Appl. No. 2010/0305575 entitled "Methods and Apparatus for Performing Knee Arthroplasty" to Wilkinson, et al., issued Dec. 2, 2010; US Pat. Appl. No. 2011/0021427 entitled "Biphasic Calcium Phosphate Cement for Drug Delivery" to Amsden, et al., issued Jan. 27, 2011; US Pat. Appl. No. 2012/0259335 entitled "Patello-Femoral Joint Implant and Instrumentation" to Scifert, et al., issued Oct. 11, 2012; US Pat. Appl. No. 2011/0106162 entitled "Composite Connecting Elements for Spinal Stabilization Systems" to Ballard, et al., issued May 5, 2011; US Pat. Appl. No. 2004/0073314 entitled "Vertebral Body and Disc Space Replacement Devices" to White, et al., issued Apr. 15, 2004; U.S. Pat. No. 7,513,901 entitled "Graft Syringe Assembly" to Scifert, et al., issued Apr. 7, 2009; US Pat. Appl. No. 2010/0004752 entitled "Vertebral Body and Disc Space Replacement Devices" to White, et al., issued Jan. 7, 2010; U.S. Pat. No. 7,615,078 entitled "Vertebral Body and Disc Space Replacement Devices" to White, et al., issued Nov. 10, 2009; U.S. Pat. No. 6,991,653 entitled "Vertebral Body and Disc Space Replacement Devices" to White, et al., issued Jan. 31, 2006; US Pat. Appl. No. 2010/0331847 entitled "Methods and Apparatus for Performing Knee Arthroplasty" to Wilkinson, et al., issued Dec. 30, 2010; US Pat. Appl. No. 2006/0116770 entitled "Vertebral Body and Disc Space Replacement Devices" to White, et al., issued Jun. 1, 2006; and U.S. Pat. No. 8,246,572 entitled "Bone Graft Applicator" to Cantor, et al., issued Aug. 21, 2012.

According to varying embodiments described herein, the present invention is capable of integrated delivery of bone graft material during the placement of surgical cages or other medical implants into a patient's spine. The delivery of the bone graft material may be to any area of the body, and in particular to the intervertebral joints of the spine, for achieving bone graft fusion. Also, the invention may be used in the repair of a bone joint or in connection with the implantation of prosthetic devices in the body, including, by way of example but not limitation, the hip, knee and a variety of spinal joints. Additionally, the present invention may be used in primary surgery, in which a bone graft is being supplied to promote new bone growth or to reconstruct a joint for the first time, as well as in revision surgery, in which a follow-up procedure is being performed in an area that has previously been subject to one or more surgeries. Further, the invention may be used in any application where an implant and/or material is to be delivered with precision to a confined area where access is restricted.

Although well suited for use in human patients, and although much of the discussion of the present invention is directed toward use in humans, advantages offered by the present invention may be realized in the veterinary and scientific fields for the benefit and study of all types of animals and biological systems. Additionally, although the fusion cages of the present invention are particularly well-suited for implantation into the spinal column between two target vertebrae, and although much of the discussion of the present invention is directed toward their use in spinal applications, advantages offered by embodiments of the present invention may also be realized by implantation at other locations within a patient where the fusion of two or more bony structures may be desired. As one of skill in the art will appreciate, the present invention has applications in the general field of skeletal repair and treatment, with particular application to the treatment of spinal injuries and diseases. It should be appreciated, however that the principles of the present invention can also find application in other areas, specifically where there is a desire to constrain added fluid material to particular regions. For example, the present invention finds application in methods where the objective is to confine added material to predetermined areas of interest and to prohibit the undesired translocation of such material until an operation is complete and/or until a predetermined later time.

According to various embodiments of the present disclosure, one aspect of the invention is to provide an integrated fusion cage and graft delivery device that comprises a tubular member, which is substantially hollow or contains at least one inner lumen and that has a generally rectangular cross-sectional shape. This generally rectangular cross-sectional shape offers a larger amount of surface area through which bone graft material may be inserted and ejected from the hollow tubular member. Furthermore, this generally rectangular shape is more congruent with the size or shape of the annulotomy of most disc spaces, which frequently are accessed by a bone graft delivery device for delivery of bone graft. However, as one skilled in the art would appreciate, the tool cross-section need not be limited to a generally rectangular shape. For example, cross-sections of an oval shape or those with at least one defined angle to include obtuse, acute, and right angles can provide a shape in some situations that is more congruent with the size or shape of the annulotomy of a particular disc space. A substantially round shape may also be employed that provides the surgeon with an indication of directional orientation.

The phrase "removably attached" and/or "detachable" is used herein to indicate an attachment of any sort that is readily releasable.

The phrase "integrated fusion cage", "spinal fusion implant", "biological implant" and/or "fusion cage" is used here to indicate a biological implant.

In various embodiments, the fusion cage may be designed in variable heights and lengths so that it fits snugly into the prepared disk space.

In one embodiment of the fusion cage, the fusion cage is of rectangular cross-section, such that one pair of opposite sides, for example a height first pair of sides, has a dimension of approximately 8-14 mm, and a second pair of opposite sides, for example a length dimension, of approximately 22-36 mm. One skilled in the art will appreciate that the exact dimensions of the fusion cage may be adapted to conform to particulars of the surgical site, for example, the relative sizing between the particular vertebrae in which bone graft material and/or a fusion cage is to be inserted. In other embodiments of the fusion cage, the fusion cage is of a substantially cylindrical shape. For example, a preferred embodiment of a fusion cage for use in an ALIF procedure forms a substantially cylindrical shape, with a height of approximately 8-14 mm and a diameter of less than about 36 millimeters. As another example, a preferred embodiment of a fusion cage for use in conjunction with a vertebrectomy has a substantially cylindrical shape with a height equal to or greater than the height of the vertebra (or the collective height of the vertebrae) it is intended to replace and a diameter of less than about 36 millimeters. Preferably, the separation "zone" between the cage and the hollow filling tube is at one end of the cage, preferably the end of the cage (when implanted) closer to the incision site.

A preferred method of using the integrated fusion cage and graft delivery device comprises precisely inserting the integrated fusion cage and graft delivery device, in one or more of the embodiments contained herein, into the surgical area. The integrated fusion cage and graft delivery device is then filled with bone graft material in its one or more substantially hollow tubes, the one or more plungers are inserted into the one or more hollow tubes, and the one or more plunger are pushed into the one or more hollow tubes, guided precisely as enabled by the minimal profile of the device, therein controllably depositing the bone graft material into the surgical area through and into the surgical implant cage. The surgical implant device may then be selectably detached from the integrated fusion cage and graft delivery device so as to remain at the surgical site.

Another method of using the integrated fusion cage and graft delivery device comprises inserting the integrated fusion cage and graft delivery device into a prepared disk space, such that the fusion cage portion fits snugly into the prepared disk space (the fusion cage is designed in variable heights and lengths so as to fit snugly into the prepared disk space), pushing the plunger through the hollow shaft so as to push biological fusion material (e.g. bone graft) through the hollow shaft to flow the biological material through the fusion cage's open lateral and/or medial portals in communication with the hollow tube and plunger, thereby delivering biological material into the prepared disk space, after which the fusion cage is detached from the hollow tube and left in the disk space. Thus, the fusion cage is left in the disk space with a maximum and/or optimal amount of biological material delivered within the fusion cage and/or surrounding the fusion cage in the disk space.

In another embodiment for the integrated fusion cage and graft delivery device, the detachable fusion cage is detachable by way of receipt of an electrical, mechanical, pneumatic, hydraulic or other communication imparted by the user upon the plunger and/or hollow tube so as to detach the fusion cage and thereby deposit the fusion cage into the surgical area.

In another embodiment for the integrated fusion cage and graft delivery device, the detachable fusion cage is detachable by way of a Luer taper or Luer fitting connection, such as in a Luer-Lok® or Luer-Slip® configuration or any other Luer taper or Luer fitting connection configuration. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2009/0124980 to Chen.

In another embodiment for the integrated fusion cage and graft delivery device, the detachable fusion cage is detachable by way of a pedicle dart by threadable rotation to achieve attachment, detachment, and axial movement. Other ways include a quick key insertion, an external snap detent, or magnetic attraction or any other structure. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2009/0187194 to Hamada.

In another embodiment for the integrated fusion cage and graft delivery device, the detachable fusion cage is detachable by use of magnetism. More specifically, the detachable fusion cage can be made to feature a magnetic field pattern and a resulting force R that are adjustable and may be of different character than the rest of the integrated fusion cage and graft delivery device. With permanent magnets, such adjustments can be made mechanically by orienting various permanent magnet polar geometries and corresponding shapes relative to one another. U.S. Pat. No. 5,595,563 to Moisdon describes further background regarding such adjustment techniques, which is hereby incorporated by reference in its entirety. Alternatively or additionally, electromagnets could be used in combination with permanent magnets to provide adjustability. In further embodiments, the magnets and corresponding fields and the resultant magnetic field pattern can include both attraction forces from placement of opposite pole types in proximity to one another and repulsion forces from placement of like pole types in proximity to one another. As used herein, "repulsive magnetic force" or "repulsive force" refers to a force resulting from the placement of like magnetic poles in proximity to one another either with or without attractive forces also being present due to opposite magnetic poles being placed in proximity to one another, and further refers to any one of such forces when multiple instances are present. U.S. Pat. No. 6,387,096 is cited as a source of additional information concerning repulsive forces that are provided together with attractive magnetic forces, which is hereby incorporated by reference. In another alternative embodiment example, one or more of surfaces of the fusion cage are roughened or otherwise include bone-engaging structures to secure purchase with vertebral surfaces. In yet other embodiments, the selectable detachable feature between the detachable fusion cage and the integrated fusion cage and graft delivery device can include one or more tethers, cables, braids, wires, cords, bands, filaments, fibers, and/or sheets; a nonfabric tube comprised of an organic polymer, metal, and/or composite; an accordion or bellows tube type that may or may not include a fabric, filamentous, fibrous, and/or woven structure; a combination of these, or such different arrangement as would occur to one skilled in the art. Alternatively or additionally, the selectable detachable feature between the detachable fusion cage and the integrated fusion cage and graft delivery device can be arranged to present one or more openings between members or portions, where such openings extend between end portions of the fusion cage. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2011/0015748 to Molz et al.

In another embodiment for the integrated fusion cage and graft delivery device, the detachable fusion cage is detachable by use of plasma treatment. The term "plasma" in this context is an ionized gas containing excited species such as ions, radicals, electrons and photons. (Lunk and Schmid, Contrib. Plasma Phys., 28: 275 (1998)). The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces (Ratner, Ultrathin Films (by Plasma deposition), 11 Polymeric Materials Encyclopedia 8444-8451, (1996)). Plasma treatment is an effective method to uniformly alter the surface properties of substrates having different or unique size, shape and geometry including but not limited to bone and bone composite materials. Plasma Treatment may be employed to effect magnetic properties on elements of the integrated fusion cage and graft delivery device, or to provide selectable detachment of the fusion cage. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Pat. No. 7,749,555 to Zanella et al.

One having skill in the art will appreciate that the fusion cage may be selectably detachable to the integrated fusion cage and graft delivery device, for example, by means that mechanically grasp the head, means that attach by vacuum, and means that attach by friction, or other means known to those of skill in the art for attaching the head of an apparatus to the shaft of an apparatus.

Another embodiment of the present invention provides an integrated fusion cage and graft delivery system, by which a hollow tube and/or a hollow tube/plunger assembly can be prepared prior to opening a patient, thus minimizing the overall impact of the grafting aspect of a surgical implantation or other procedure. Moreover, the hollow tube may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

The present invention can be used in veterinary conditions, in the thoracic spine or can be used for insertion of a laterally based disk replacement.

Thus, according to various embodiments of the present disclosure, a method of introducing bone graft material to a desired operating site ("bone graft receiving area") is provided by use of a hollow tubular member comprising a generally rectangular cross-sectional area, whereby the desired operating area is capable of receiving at least one plunger. The one or more plunger having at least one distal end which is designed to accommodate ejecting bone graft or other material to be inserted into the joint space or between intervertebral members in a generally lateral direction, as opposed to a generally longitudinal direction (in relation to the direction of the primary axis of the device).

One skilled in the art will appreciate that the distal end of the tubular device need not be limited to those specific embodiments described above. Other forms, shapes or designs that enable the foregoing aspects of the present invention are hereby incorporated into this disclosure. Forms, shapes and designs that relate to the provision of an end of a tubular device to perform lateral introduction of bone or bone substitute to an operating site are considered to be within the scope of the present disclosure.

One aspect of the present invention provides an integrated fusion cage and graft delivery device system for delivering bone graft, in a partially formed, fully formed or unformed condition to a bone graft receiving area in a body.

In one embodiment, the device is configured to deliver bone graft material substantially laterally from its delivery end, that is substantially not in the axial direction but rather substantially from the side and/or in a radial direction. This is distinctly different than devices that deliver bone graft material along their vertical axis, that is, along or out their bottom end, and/or obstruct the user view of the bone graft and/or fusion cage delivery site, such as that of U.S. Pat. Appl. No. 2010/0087828 to Krueger et al ("Krueger"), U.S. Pat. Appl. No. 2009/0264892 to Beyar et al ("Beyar"), U.S. Pat. Appl. No. 2007/0185496 to Beckman et al ("Beckman"), U.S. Pat. Appl. No. 2009/0275995 to Truckai et al ("Truckai") and U.S. Pat. Appl. No. 2006/0264964 to Scifert et al ("Scifert"). Krueger, Beyar, Beckman, Truckai and Scifert are incorporated by reference in their entireties for all purposes.

In one embodiment, the device is configured to deliver bone graft material so as to completely fill the defined interior of its fusion cage and subsequently deliver bone graft material to the surrounding bone graft site, rather than, for example, to contain the bone material as are the fusion cage designs of U.S. Pat. No. 7,846,210 to Perez-Cruet ("Perez-Cruet"). Further, the fusion device of this application features a distal tip that functions to precisely position the fusion device and stabilize the device during delivery of bone graft material. Perez-Cruet is incorporated by reference in its entirety for all purposes. In addition, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 4,863,476 to Shepperd; U.S. Pat. No. 6,743,255 to Ferree; U.S. Pat. No. 6,773,460 to Jackson; U.S. Pat. No. 6,835,206 to Jackson; U.S. Pat. No. 6,972,035 to Michelson; U.S. Pat. No. 7,771,473 to Thramann; U.S. Pat. No. 7,850,733 to Baynham; U.S. Pat. No. 8,506,635 to Palmatier; U.S. Pat. No. 8,556,979 to Glerum; U.S. Pat. No. 8,628,576 to Triplett; U.S. Pat. No. 8,709,086 to Glerum; U.S. Pat. No. 8,715,351 to Pinto; U.S. Pat. No. 8,753,347 to McCormack; U.S. Pat. No. 8,753,377 to McCormack; U.S. Design Pat. No. D708,323 to Reyes; U.S. Pat. No. 8,771,360 to Jimenez;

U.S. Pat. No. 8,778,025 to Ragab; U.S. Pat. No. 8,778,027 to Medina; U.S. Pat. No. 8,808,383 to Kwak; U.S. Pat. No. 8,814,940 to Curran; U.S. Pat. No. 8,821,396 to Miles; U.S. Patent Application Publication No. 2006/0142858 to Colleran; U.S. Patent Application Publication No. 2008/0086142 to Kohm; U.S. Patent Application Publication No. 2010/0286779 to Thibodean; U.S. Patent Application Publication No. 2011/0301712 to Palmatier; U.S. Patent Application Publication No. 2012/0022603 to Kirschman; U.S. Patent Application Publication No. 2012/0035729 to Glerum; U.S. Patent Application Publication No. 2012/0089185 to Gabelberger; U.S. Patent Application Publication No. 2012/0123546 to Medina; U.S. Patent Application Publication No. 2012/0197311 to Kirschman; U.S. Patent Application Publication No. 2012/0215316 to Mohr; U.S. Patent Application Publication No. 2013/0158664 to Palmatier; U.S. Patent Application Publication No. 2013/0178940; U.S. Patent Application Publication No. 2014/0012383 to Triplett; U.S. Patent Application Publication No. 2014/0156006; U.S. Patent Application Publication No. 2014/0172103 to O'Neil; U.S. Patent Application Publication No. 2014/0172106 to To; U.S. Patent Application Publication No. 2014/0207239 to Barreiro; U.S. Patent Application Publication No. 2014/0228955 to Weiman; U.S. Patent Application Publication No. 2014/0236296 to Wagner; U.S. Patent Application Publication No. 2014/0236297 to Iott; U.S. Patent Application Publication No. 2014/0236298 to Pinto.

Furthermore, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 7,803,159 to Perez-Cruet et al.; U.S. Pat. No. 8,852,282 to Farley et al.; U.S. Pat. No. 8,858,598 to Seifert et al.; U.S. Pat. No. D714,933 to Kawamura; U.S. Pat. No. 8,795,366 to Varela; U.S. Pat. No. 8,852,244 to Simonson; U.S. Patent Application Publication No. 2012/0158146 to Glerum et al.; U.S. Pat. No. 8,852,242 to Morgenstern Lopez et al.; U.S. Pat. No. 8,852,281 to Phelps; U.S. Pat. No. 8,840,668 to Donahoe et al.; U.S. Pat. No. 8,840,622 to Vellido et al.; U.S. Patent Application Publication No. 2014/0257405; U.S. Patent Application Publication No. 2014/0257490 to Himmelberger et al.; U.S. Pat. No. 8,828,019 to Raymond et al.; U.S. Patent Application Publication No. 2014/0288652 to Boehm et al.; U.S. Patent Application Publication No. 2014/0287055 to Kunjachan; U.S. Patent Application Publication No. 2014/0276896 to Harper; U.S. Patent Application Publication No. 2014/0277497 to Bennett et al.; U.S. Patent Application Publication No. 2012/0029635 to Schoenhoeffer et al.; U.S. Patent Application Publication No. 2014/0303675 to Mishra; U.S. Patent Application Publication No. 2014/0303731 to Glerum; U.S. Patent Application Publication No. 2014/0303732 to Rhoda et al.; U.S. Pat. No. 8,852,279 to Weiman; PCT Pub. WO 2012/031267 to Weiman; U.S. Pat. No. 8,845,731 to Weiman; U.S. Pat. No. 8,845,732 to Weiman; U.S. Pat. No. 8,845,734 to Weiman; U.S. Patent Application Publication No. 2014/0296985 to Balasubramanian et al.; U.S. Patent Application Publication No. 2014/0309268 to Arnou; U.S. Patent Application Publication No. 2014/0309548 to Merz et al.; U.S. Patent Application Publication No. 2014/0309697 to Iott et al.; U.S. Patent Application Publication No. 2014/0309714 to Mercanzini et al.; U.S. Pat. No. 8,282,683 to McLaughlin et al.; U.S. Pat. No. 8,591,585 to McLaughlin et al; U.S. Pat. No. 8,394,129 to Morgenstern Lopez et al.; U.S. Patent Application Publication No. 2011/0208226 to Fatone et al.; U.S. Patent Application Publication No. 2010/0114147 to Biyani; U.S. Patent Application Publication No. 2011/0144687 to Kleiner; U.S. Pat. No. 8,852,243 to Morgenstern Lopez et al.; U.S. Pat. No. 8,597,333 to Morgenstern Lopez et al.; U.S. Pat. No. 8,518,087 to Lopez et al.; U.S. Patent Application Publication No. 2012/0071981 to Farley et al.; U.S. Patent Application Publication No. 2013/0006366 to Farley et al.; U.S. Patent Application Publication No. 2012/0065613 to Pepper et al.; U.S. Patent Application Publication No. 2013/0006365 to Pepper et al.; U.S. Patent Application Publication No. 2011/0257478 to Kleiner et al.; U.S. Patent Application Publication No. 2009/0182429 to Humphreys et al.; U.S. Patent Application Publication No. 2005/0118550 to Turri; U.S. Patent Application Publication No. 2009/0292361 to Lopez; U.S. Patent Application Publication No. 2011/0054538 to Zehavi et al.; U.S. Patent Application Publication No. 2005/0080443 to Fallin et al.; U.S. Pat. No. 8,778,025 to Ragab et al.; U.S. Pat. No. 8,628,576 to Triplett et al; U.S. Pat. No. 8,808,304 to Weiman, and U.S. Pat. No. 8,828,019 to Raymond.

All of the following U.S. patents are also incorporated herein by reference in their entirety: U.S. Pat. Nos. 6,595,998; 6,997,929; 7,311,713; 7,749,255; 7,753,912; 7,780,734; 7,799,034; 7,875,078; 7,931,688; 7,967,867; 8,075,623; 8,123,755; 8,142,437; 8,162,990; 8,167,857; 8,197,544; 8,202,274; 8,206,395; 8,206,398; 8,317,802; 8,337,531; 8,337,532; 8,337,562; 8,343,193; 8,349,014; 8,372,120; 8,394,108; 8,414,622; 8,430,885; 8,439,929; 8,454,664; 8,475,500; 8,512,383; 8,523,906; 8,529,627; 8,535,353; 8,562,654; 8,574,299; 8,641,739; 8,657,826; 8,663,281; 8,715,351; 8,727,975; 8,828,019; 8,845,640; 8,864,830; 8,900,313; 8,920,507; 8,974,464; 9,039,767; 9,084,686; 9,095,446; 9,095,447; 9,101,488; 9,107,766; 9,113,962; 9,114,026; 9,149,302; 9,174,147; 9,216,094; 9,226,777; 9,295,500; 9,358,134; 9,381,094; 9,439,692; 9,439,783; 9,445,921; 9,456,830; 9,480,578; 9,498,200; 9,498,347; 9,498,351; 9,517,140; 9,517,141; 9,517,142; 9,545,250; 9,545,279; 9,545,313; 9,545,318; 9,610,175; 9,629,668; 9,655,660; 9,655,743; 9,681,889; 9,687,360; 9,707,094; 9,763,700; 9,861,395; 9,980,737; 9,993,353; U.S. Pat. Pub. 2014/0088712; U.S. Pat. Pub. 2014/0276581; U.S. Pat. Pub. 2014/0371721; U.S. Pat. Pub. 2016/0296344; U.S. Pat. Pub. 2017/0367846; U.S. Pat. Pub. 2017/0354514.

In addition, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 4,863,476 to Shepperd; U.S. Pat. No. 6,743,255 to Ferree; U.S. Pat. No. 6,773,460 to Jackson; U.S. Pat. No. 6,835,206 to Jackson; U.S. Pat. No. 6,972,035 to Michelson; U.S. Pat. No. 7,771,473 to Thramann; U.S. Pat. No. 7,850,733 to Baynham; U.S. Pat. No. 8,506,635 to Palmatier; U.S. Pat. No. 8,556,979 to Glerum; U.S. Pat. No. 8,628,576 to Triplett; U.S. Pat. No. 8,709,086 to Glerum; U.S. Pat. No. 8,715,351 to Pinto; U.S. Pat. No. 8,753,347 to McCormack; U.S. Pat. No. 8,753,377 to McCormack; U.S. Design Pat. No. D708,323 to Reyes; U.S. Pat. No. 8,771,360 to Jimenez; U.S. Pat. No. 8,778,025 to Ragab; U.S. Pat. No. 8,778,027 to Medina; U.S. Pat. No. 8,808,383 to Kwak; U.S. Pat. No. 8,814,940 to Curran; U.S. Pat. No. 8,821,396 to Miles; U.S. Patent Application Publication No. 2006/0142858 to Colleran; U.S. Patent Application Publication No. 2008/0086142 to Kohm; U.S. Patent Application Publication No. 20100286779 to Thibodeau; U.S. Patent Application Publication No. 20110301712 to Palmatier; U.S. Patent Application Publication No.

20120022603 to Kirschman; U.S. Patent Application Publication No. 20120035729 to Glerum; U.S. Patent Application Publication No. 20120089185 to Gabelberger; U.S. Patent Application Publication No. 20120123546 to Medina; U.S. Patent Application Publication No. 20120197311 to Kirschman; U.S. Patent Application Publication No. 20120215316 to Mohr; U.S. Patent Application Publication No. 20130158664 to Palmatier; U.S. Patent Application Publication No. 20130178940; U.S. Patent Application Publication No. 20140012383 to Triplett; U.S. Patent Application Publication No. 20140156006; U.S. Patent Application Publication No. 20140172103 to O'Neil; U.S. Patent Application Publication No. 20140172106 to To; U.S. Patent Application Publication No. 20140207239 to Barreiro; U.S. Patent Application Publication No. 20140228955 to Weiman; U.S. Patent Application Publication No. 20140236296 to Wagner; U.S. Patent Application Publication No. 20140236297 to Iott; U.S. Patent Application Publication No. 20140236298 to Pinto.

Furthermore, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 7,803,159 to Perez-Cruet et al.; U.S. Pat. No. 8,852,282 to Farley et al.; U.S. Pat. No. 8,858,598 to Seifert et al.; U.S. Pat. No. D714,933 to Kawamura; U.S. Pat. No. 8,795,366 to Varela; U.S. Pat. No. 8,852,244 to Simonson; U.S. Patent Application Publication No. 2012/0158146 to Glerum et al.; U.S. Pat. No. 8,852,242 to Morgenstern Lopez et al.; U.S. Pat. No. 8,852,281 to Phelps; U.S. Pat. No. 8,840,668 to Donahoe et al.; U.S. Pat. No. 8,840,622 to Vellido et al.; U.S. Patent Application Publication No. 20140257405; U.S. Patent Application Publication No. 20140257490 to Himmelberger et al.; U.S. Pat. No. 8,828,019 to Raymond et al.; U.S. Patent Application Publication No. 20140288652 to Boehm et al.; U.S. Patent Application Publication No. 20140287055 to Kunjachan; U.S. Patent Application Publication No. 20140276896 to Harper; U.S. Patent Application Publication No. 20140277497 to Bennett et al.; U.S. Patent Application Publication No. 20120029635 to Schoenhoeffer et al.; U.S. Patent Application Publication No. 20140303675 to Mishra; U.S. Patent Application Publication No. 20140303731 to Glerum; U.S. Patent Application Publication No. 20140303732 to Rhoda et al.; U.S. Pat. No. 8,852,279 to Weiman; PCT WO2012031267 to Weiman; U.S. Pat. No. 8,845,731 to Weiman; U.S. Pat. No. 8,845,732 to Weiman; U.S. Pat. No. 8,845,734 to Weiman; U.S. Patent Application Publication No. 20140296985 to Balasubramanian et al.; U.S. Patent Application Publication No. 20140309268 to Arnou; U.S. Patent Application Publication No. 20140309548 to Merz et al.; U.S. Patent Application Publication No. 20140309697 to Iott et al.; U.S. Patent Application Publication No. 20140309714 to Mercanzini et al.; U.S. Pat. No. 8,282,683 to McLaughlin et al.; U.S. Pat. No. 8,591,585 to McLaughlin et al; U.S. Pat. No. 8,394,129 to Morgenstern Lopez et al.; U.S. Patent Application Publication No. 20110208226 to Fatone et al.; U.S. Patent Application Publication No. 20100114147 to Biyani; U.S. Patent Application Publication No. 20110144687 to Kleiner; U.S. Pat. No. 8,852,243 to Morgenstern Lopez et al.; U.S. Pat. No. 8,597,333 to Morgenstern Lopez et al.; U.S. Pat. No. 8,518,087 to Lopez et al.; U.S. Patent Application Publication No. 20120071981 to Farley et al.; U.S. Patent Application Publication No. 20130006366 to Farley et al.; U.S. Patent Application Publication No. 20120065613 to Pepper et al.; U.S. Patent Application Publication No. 20130006365 to Pepper et al.; U.S. Patent Application Publication No. 20110257478 to Kleiner et al.; U.S. Patent Application Publication No. 20090182429 to Humphreys et al.; U.S. Patent Application Publication No. 20050118550 to Turri; U.S. Patent Application Publication No. 20090292361 to Lopez; U.S. Patent Application Publication No. 20110054538 to Zehavi et al.; U.S. Patent Application Publication No. 20050080443 to Fallin et al.; U.S. Pat. No. 8,778,025 to Ragab et al.; U.S. Pat. No. 8,628,576 to Triplett et al; U.S. Pat. No. 8,808,304 to Weiman, and U.S. Pat. No. 8,828,019 to Raymond.

One of ordinary skill in the art will appreciate that embodiments of the present disclosure may have various sizes. The sizes of the various elements of embodiments of the present disclosure may be sized based on various factors including, for example, the anatomy of the implant patient, the person or other device operating the apparatus, the implant location, physical features of the implant including, for example, with, length and thickness, and the size of operating site or the size of the surgical tools being used with the device.

One or ordinary skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, as polyether ether ketone (PEEK), carbon fiber, ABS plastic, polyurethane, rubber, latex, synthetic rubber, and other fiber-encased resinous materials, synthetic materials, polymers, and natural materials. The plunger element could be flexible, semi-rigid, or rigid and made of materials such as stainless steel, titanium alloy, aluminum alloy, chromium alloy, and other metals or metal alloys. Similarly, the tubular element could be flexible, semi-rigid, or rigid and made of materials such as stainless steel, titanium alloy, aluminum alloy, chromium alloy, and other metals or metal alloys. In certain embodiments, the plunger and hollow tube are composed of plastic and are intended for one use only and then discarded. In another embodiment, some or all elements of the device, or portions of some or all of the elements, are luminescent. Also, in another embodiment, some or all elements of the device, or portions of some or all of the elements, include lighting elements. In another embodiment, the hollow tube and/or plunger are made of a substantially transparent material and/or are rigidly opaque.

In one embodiment of the fusion cage, the fusion cage comprises a polymer, such as PEEK, titanium and composite materials.

In another embodiment, a bone graft material delivery system is provided. The delivery system includes an elongate hollow tube constructed to receive bone graft material, said elongate hollow tube being generally linear and having an extended axis, a generally rectangular cross-section, a proximal end, a distal end with at least one opening, a hollow interior extending from said proximal end to said distal end, and indicia formed on an exterior surface of said elongate hollow tube. The delivery system also includes a plunger adapted to extend in said elongate hollow tube, said plunger having a shaft and a distal portion with an exterior surface contoured to form a substantially congruent fit with said hollow interior of said elongate hollow tube such that said plunger is precluded from rotating within said elongate hollow tube, wherein teeth are formed along a longitudinal axis of said plunger shaft, and wherein said plunger is adapted to urge bone graft material through said elongate hollow tube to deliver bone graft material through said at least one opening of said distal end.

In a further embodiment, a bone graft material delivery system is provided. The delivery system includes an elongate hollow tube constructed to receive bone graft material, said elongate hollow tube being generally linear and having an extended axis, a generally rectangular cross-section, a proximal end, a distal end, a hollow interior extending from said proximal end to said distal end, and indicia formed on an exterior surface of said elongate hollow tube, wherein said distal end of said elongate hollow tube is at least partially open. The delivery system also includes a plunger adapted to extend in said elongate hollow tube, said plunger having a shaft and a distal portion with an exterior surface contoured to form a substantially congruent fit with said hollow interior of said elongate hollow tube such that said plunger is precluded from rotating within said elongate hollow tube, wherein teeth are formed along a longitudinal axis of said plunger shaft, and wherein said plunger is adapted to urge bone graft material through said elongate hollow tube to deliver bone graft material through said at least partially open distal end.

In a still further embodiment, a bone graft material delivery system is provided. The delivery system includes an elongate hollow tube constructed to receive bone graft material, said elongate hollow tube being generally linear and having an extended axis, a generally rectangular cross-section, a proximal end, a distal end with at least one opening, a hollow interior extending from said proximal end to said distal end, and indicia formed on an exterior surface of said elongate hollow tube and configured to indicate how far said elongate hollow tube has been inserted into a surgical site, wherein said distal end of said elongate hollow tube comprises a wedge or a bullet shaped distal tip. The delivery system also includes a plunger adapted to extend in said elongate hollow tube, said plunger having a shaft and a distal portion with an exterior surface contoured to form a substantially congruent fit with said hollow interior of said elongate hollow tube such that said plunger is precluded from rotating within said elongate hollow tube, wherein teeth are formed along a longitudinal axis of said plunger shaft, and wherein said plunger is adapted to urge bone graft material through said elongate hollow tube to deliver bone graft material through said at least one opening of said distal end.

One of ordinary skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

Embodiments of the present disclosure present several advantages over the prior art including, for example, the speed of the procedure, the minimally invasive aspect of the procedure, the ability to introduce the implant material to the implant site with minimal risk and damage to the surrounding tissue, the lower risk of infection, more optimally placed implant material, a more stable delivery device which is designed to reduce the likelihood of the implant material becoming dislodged prior to fixation, and fewer tools in a surgical site due to the integration of several components required to provide bone graft to a bone graft receiving area.

Further, the lower profile of the device allows improved viewing of the area intended for receipt of bone graft material, and use of a reduced set and size of elements therein provided a less expensive device. Also, the device disclosed provides that substantially all of the bone graft material may be ejected from the device and delivered to the surgical site, rather than wasted as unretrievable matter remaining inside the device. The ability to remove substantially all of the bone graft material is of significant benefit because the bone graft material is expensive and/or hard to obtain.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the claims set forth herein, taken in conjunction with this Summary of the Invention, define the invention. The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the claims set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

FIG. 1A is a front perspective view of the device for delivering bone graft;

FIG. 1B is a front perspective view of the plunger of the device;

FIG. 1C is a cross sectional view of a portion of the device shown in FIG. 1A;

FIG. 24 is a top plan view of the device shown in FIG. 22;

FIG. 25 is a front elevation view of the device shown in FIG. 22;

FIG. 26 is a right elevation view of the device shown in FIG. 22;

FIG. 27 is a bottom plan view of the device shown in FIG. 22;

FIG. 28 is a cross-sectional view of section A-A of FIG. 25;

FIGS. 45A-G provide scaled views of one embodiment of the fusion cage element of yet another embodiment of the integrated fusion cage and graft delivery device configured to operate with the hollow tube of FIGS. 46A-H, plunger of FIGS. 47A-D and ejection tool of FIGS. 48A-E;

FIGS. 46A-H provide scaled views of one embodiment of the hollow tube (aka snap on cannula) of the integrated fusion cage and graft delivery device configured to operate with the fusion cage element of FIGS. 45A-G, plunger of FIGS. 47A-D and ejection tool of FIGS. 48A-E;

FIGS. 48A-E provide scaled views of one embodiment of the ejection tool (aka cage insertion tool) of the integrated fusion cage and graft delivery device configured to operate with the fusion cage element of FIGS. 45A-G, hollow tube of FIGS. 46A-H and plunger of FIGS. 47A-D;

FIGS. 54A-F provide scaled views of the upper plate component of the device shown in FIG. 51;

FIGS. 55A-E provide scaled views of the front block component of the device shown in FIG. 51;

FIGS. 57A-C provide scaled views of the expansion screw component of the device shown in FIG. 51;

FIGS. 59A-E provide scaled views of the device shown in FIG. 58, the fusion cage in an unexpanded state;

FIGS. 60A-E provide scaled views of the device shown in FIG. 58, the fusion cage in an expanded state;

FIG. 63B is a close-up partial left rear perspective view of the devices of FIG. 63A;

FIG. 66 is a left front perspective view of the devices of FIG. 63A, shown with the fusion cage and installer/impactor components in an engaged state, with the hollow tube component engaged with the installer/impactor component;

FIG. 68B is a close-up partial perspective view of the devices of FIG. 68A;

FIG. 75D is a front elevation view of the hollow tubular member of FIG. 75A and illustrating an optional opening at the distal end;

FIG. 75E is an expanded cross sectional view of a portion of the hollow tubular member;

FIG. 75F illustrates devices used to prepare bone graft material according to one embodiment of the present disclosure;

FIG. 75G is a cross-sectional view of a surgical site and a bone graft delivery device according to one embodiment of the present disclosure;

FIG. 76 is a cross-sectional view of an intervertebral disc space and a bone graft delivery device;

FIG. 77A is a cross-sectional view of a surgical site and a bone graft delivery device according to one embodiment of the present disclosure;

Figure 78:
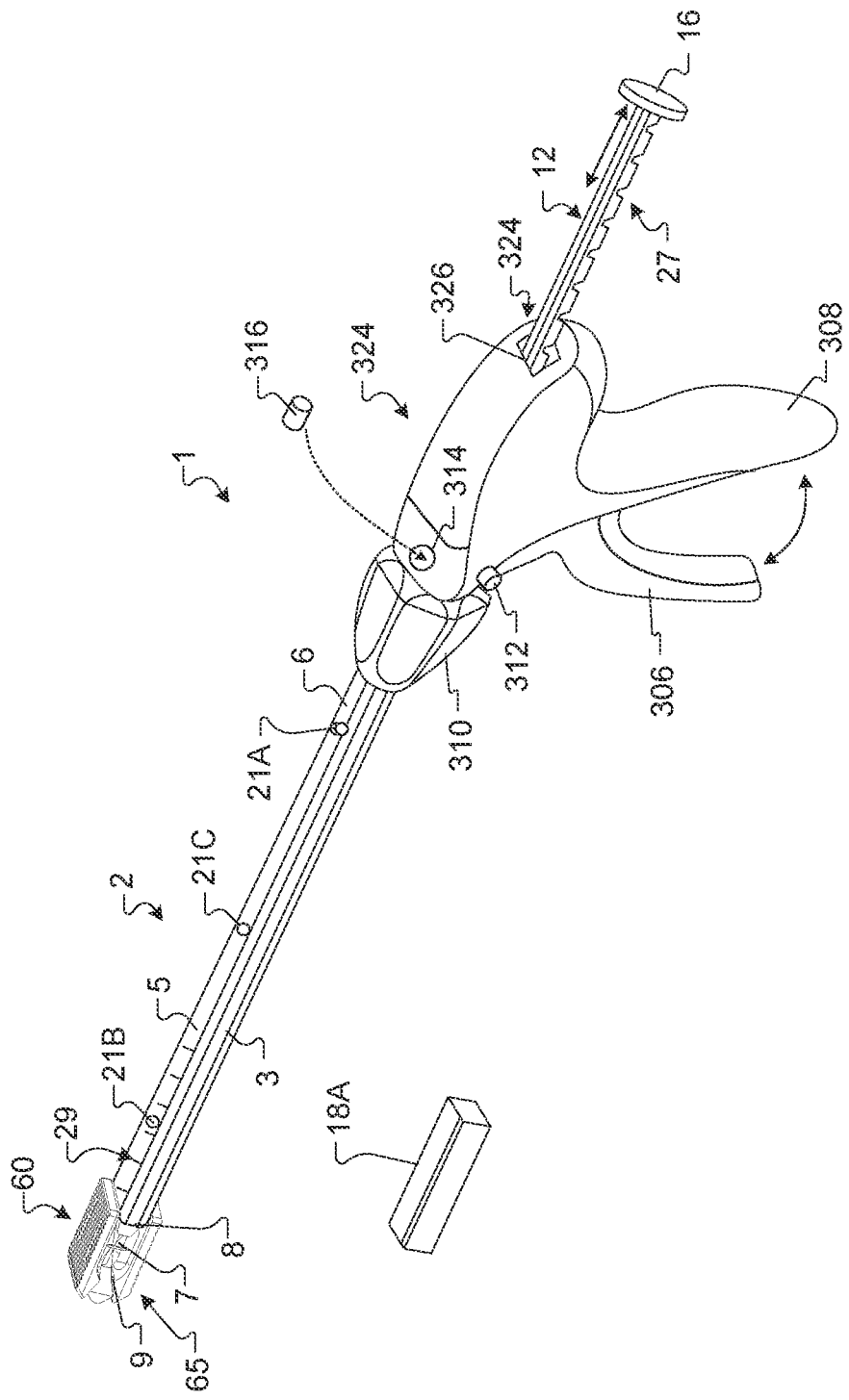
Figure 79:
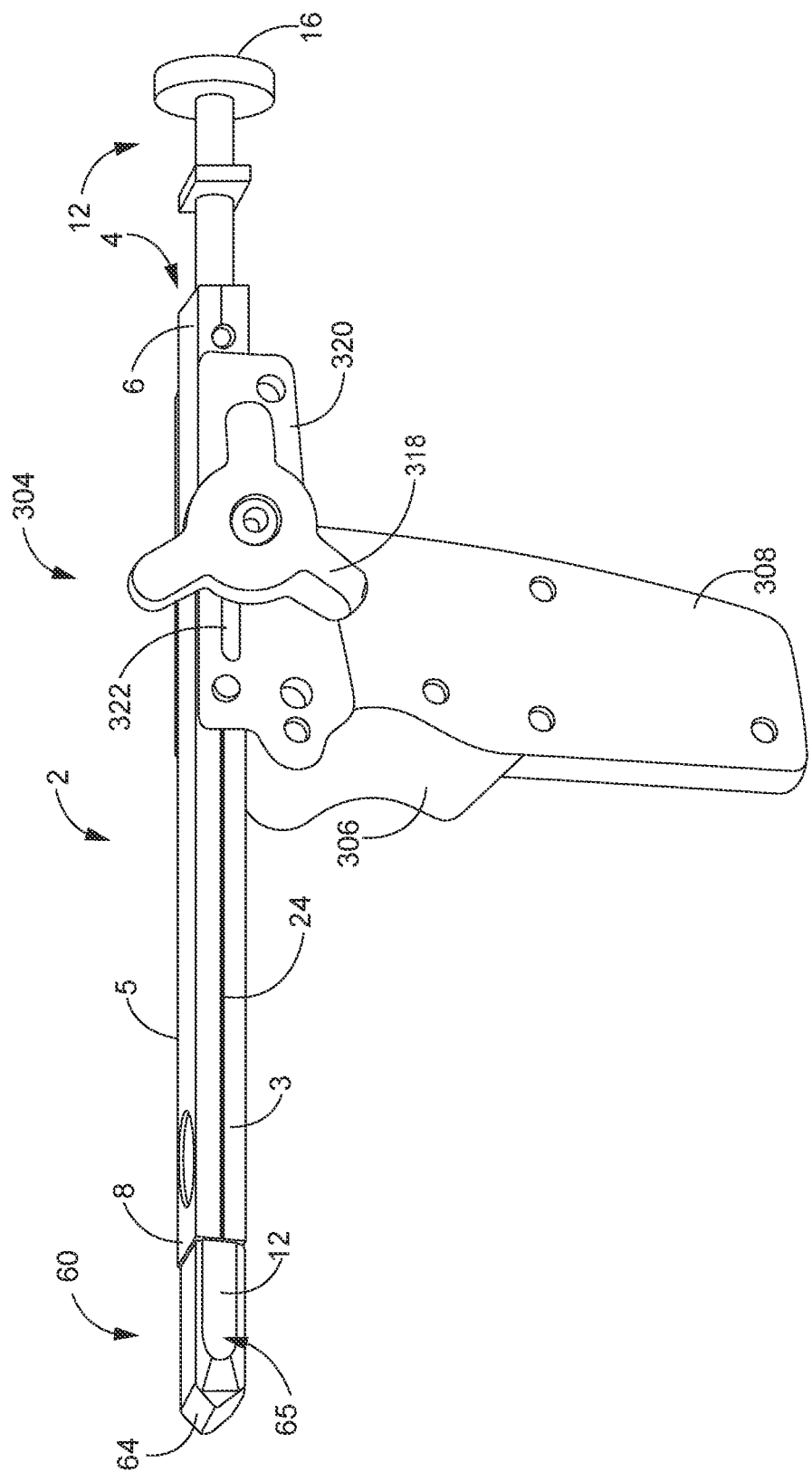

FIG. 77B another cross-sectional view of the surgical site of FIG. 77A after the bone graft delivery device has been removed therefrom;

FIG. 78 is a side perspective view of another embodiment of a device for delivering bone graft; and FIG. 79 is a side perspective view of still another integrated fusion cage and graft delivery device of the present disclosure.

To provide further clarity to the Detailed Description provided herein in the associated drawings, the following list of components and associated numbering are provided as follows:

1 Integrated fusion cage and graft delivery device
2 Hollow tube
3 Hollow tube first (side) exterior surface
4 Opening (of Hollow tube)
5 Hollow tube second (top) exterior surface
6 First (or proximal) end (of Hollow tube)
6A Knob
6B Pin
7 Hollow tube first distal opening
7A opening
7B opening
7C opening
8 Second (or distal) end (of Hollow tube)
8A Hollow tube cage clamp
8B Hollow tube cage clamp radial surface
9 Hollow tube distal interior ramp
9A Hollow tube distal interior ramp surface
10 Curved surface (of Hollow tube)
10A Curved interior surface (of Hollow tube)
11 Footing (of Hollow tube)
12 Plunger
13 Plunger distal first surface
14 Plunger distal second surface
15 Plunger distal third surface
16 Handle (of Plunger)
16A Plunger stop
17 Plunger medial portion
18 Second (or distal) end (of Plunger)
18A Pusher
19 Horizontal surface (of Plunger)
20 Curved surface (of Plunger)
21 Vent port
21A first vent port
21B second vent port
21C third vent port
22 First portion
23 Second portion
24 Joint or plane
25 Peg or pin
26 Recess
27 Teeth or notches of plunger
28 Lumen
29 Indicia to indicate depth of insertion of distal end
30 Funnel
32 Sleeve (of Funnel)
33 Slot for pin of bayonet mount
34 Opening (of Funnel)
35 Vent channel in plunger pusher
36 Endoscope, camera, or image sensing device
37 Lighting element
40 Disc space
42 Syringe
42A First Device (syringe)
42B Second Device (syringe)
44 Bone graft material
44A First bone graft component
44B Second bone graft component
46 Luer lock device
48 Bore
50 Wedge-shaped Second/distal end (of Hollow tube)

52 Wedge-shaped Second end (of Plunger)
60 Fusion Cage
61 Fusion cage surface texture
62 Fusion Cage First End
64 Fusion Cage Second (or Distal) End
65 Fusion Cage First Opening Pair
66 Fusion Cage First End Opening
67 Fusion Cage Second Opening Pair
68 Fusion Cage Medial Opening
69 Fusion Cage Lateral Opening
70 Fusion Cage Medial Surfaces
72 Fusion Cage Internal Ramps
80 Hollow Tube Locking Tabs
82 Fusion Cage Locking Slots
90 Break-off Collar
92 Fusion Cage Collar
93 Fusion Cage Collar Face
94 Fusion Cage Collar Cavity
96 Fusion Cage Tab Extension
97 Fusion Cage Tab Extension Latch
100 Connector Conduit
102 Connectors
106A Collar
106B Projection
110 ALIF Fusion Cage
112 ALIF Fusion Cage Portals
114 ALIF Fusion Cage Chamber
116 ALIF Fusion Cage Break-off Collar
120 D-LIF Fusion Cage
122 D-LIF Fusion Cage Portals
124 D-LIF Fusion Cage Chamber
126 D-LIF Fusion Cage Break-off Collar
130 Vertebrectomy Fusion Cage
132 Vertebrectomy Fusion Cage Porous Wall Portion
134 Vertebrectomy Fusion Cage Chamber
136 Vertebrectomy Fusion Cage Break-off Collar
138 Vertebrectomy Fusion Cage Impervious Wall Portion
140 Ejection Tool
142 Ejection Tool First (Proximal) End
143 Ejection Tool Stop
144 Ejection Tool Cover
145 Ejection Tool Cover Cavity
146 Spring Cover
147 Spring Cover Attachment
148 Spring
149 Ejection Tool Wings
150 Ejection Tool Wings Cavity
151 Ejection Tool L-cut
152 Ejection Tool Second (Distal) End
160 Ejection Tool Rod
170 Bone graft deliver device
171 Spine
172 Surgical site
172A Disc space
174 Path for fusion cage
200 Upper Plate
201 Upper Plate Front
202 Upper Plate Rear
203 Upper Plate Opening
204 Upper Plate Surface Texture
205 Upper Plate Track
206 Upper Plate Slot
209 Upper Plate Ridge
210 Lower Plate
211 Lower Plate Front
212 Lower Plate Rear
213 Lower Plate Opening
214 Lower Plate Surface Texture
215 Lower Plate Track
216 Lower Plate Slot
217 Plate Tab
218 Plate Nose
219 Lower Plate Ridge
220 Front Block
222 Front Block Upper Rail
224 Front Block Lower Rail
225 Front Block Nose
226 Front Block Ramp
227 Front Block Aperture
228 Block Spine
230 Rear Block
231 Rear Block Groove
232 Rear Block Upper Rail
234 Rear Block Lower Rail
236 Rear Block Ramp
237 Rear Block Aperture
238 Rear Block Aft
239 Rear Block Detent
240 Expansion Screw
242 Expansion Screw Head
244 Expansion Screw Tip
246 Expansion Screw Disk
250 Installer/Impactor
252 Installer/Impactor Tip
253 Installer/Impactor Aperture
254 Installer/Impactor Ridge
255 Installer/Impactor Channel
256 Installer/Impactor Ramp
258 Installer/Impactor Handle
260 Expansion Driver
268 Expansion Driver Handle
270 Removal Pliers
280 Hollow Tube External Ramp
282 Hollow Tube Notch
284 Hollow Tube Slot
285 Hollow Tube Slot Aperture
290 Cam
292 Nose Cone
294 Ramps
300 Adaptor
304 Grip
306 Trigger
308 Handle
310 Knob
312 Switch or button
314 Loading port
316 Capsule or package of bone graft material
318 Knob of grip
320 Flange
322 Slot
324 Channel
326 Proximal opening of channel
400 Prior Art Fusion Cage
400' Modified Prior Art Fusion Cage
A Height of Opening (in Hollow tube)
B Width of Opening (in Hollow tube)

DESCRIPTION OF THE PREFERRED EMBODIMENTS

The present invention relates to a device and method for integrated delivery of bone graft material and a fusion cage to any portion of a patient which requires bone graft material and/or a fusion cage. Thus, for example, the foregoing description of the various embodiments contemplates delivery to, for example, a window cut in a bone, where access to such window for bone grafting is difficult to obtain because of orientation of such window, presence of muscle tissue, risk of injury or infection, etc. The integrated fusion cage and graft delivery device is formed such that the one or more hollow tubes and/or plungers may be helpful in selectively and controllably placing bone graft material and a fusion cage in or adjacent to such window. The integrated fusion cage and graft delivery device is formed to allow delivery of bone graft material and/or a fusion cage in a direction other than solely along the longitudinal axis of the device, and in some embodiments transverse to the primary axis used by the surgeon or operator of the device when inserting the device into a cannula or other conduit to access the surgical site. This same concept applies to other areas of a patient, whether or not a window has been cut in a bone, for example in a vertebral disc space, and may be used whether this is a first surgery to the area or a follow-up surgery. The present invention also contemplates the delivery of bone graft material and/or a fusion cage with or without the use of a plunger, and with or without the use of various other tools described in greater detail herein.

Referring now to FIGS. 1-33 and 36-45, several embodiments of the present invention are shown.

In regard to FIG. 1A, an integrated fusion cage and graft delivery device portion is shown, which is comprised of a hollow tubular member or hollow tube or contains at least one inner lumen 2, which has a first proximate end 6 (which is referred to elsewhere in this specification as the "graspable end" of hollow tube 2), and a second distal end 8, with a general hollow structure therebetween. Thus, as shown in FIG. 1, the hollow tube 2 allows bone graft material to be inserted into the opening 4 at the graspable end 6 of the hollow tube 2, and ultimately exited from the hollow tube 2 through the second end 8. According to a preferred embodiment, the hollow tube 2 also comprises at least one sloped or curved surface 10 at or near the second end 8 of the hollow tube 2. Although a generally rectangular cross-section is depicted, the cross-section need not be limited to a generally rectangular shape. For example, cross-sections of an oval shape or those with at least one defined angle to include obtuse, acute, and right angles can provide a shape in some situations that is more congruent with the size or shape of the annulotomy of a particular disc space.

Referring now in detail to FIG. 1B, a plunger 12 is shown for use with the hollow tube 2 of FIG. 1A. The plunger 12 is generally of the same geometry as the hollow portion of the hollow tube 2, extending at least the same length of hollow tube 2. The plunger 12 may include, as depicted in FIG. 1B, at least one knob or handle 16 for grasping by a user of the plunger 12. As with the interior of the hollow tube 2 at its second end 8, the plunger 12 also comprises at least one sloped or curved surface 20 at or adjacent to a second end 18 of the plunger 12. The plunger 12 terminates in a generally flat, horizontal surface 19, which corresponds to the opening at the second end 8 of the hollow tube 2 shown in FIG. 1A. Thus, in cooperation, the plunger 12 may be inserted into the opening 4 of the hollow tube 2 shown in FIG. 1A, and extended the entire length of the hollow tube 2, at least to a point where the horizontal surface 19 of plunger 12 is in communication with the second end 8 of the hollow tube 2. This configuration permits a user to eject substantially all of the bone graft material that is placed into the hollow tube 2 during a surgical procedure. One skilled in the art will appreciate that the plunger need not terminate in a generally flat, horizontal surface to affect the substantial removal of all of the bone graft material placed into the hollow tube; more specifically, any shape that allows conformance between the internal contour of the distal end of the hollow tube and the distal end of the plunger will affect the substantial removal of the bone graft material.

In the embodiment, of FIG. 1A-C, a contoured leading edge is provided on the plunger to correspond with the internal contour of distal end of the hollow tube of the delivery device. This contoured plunger serves several purposes: First, it maintains the plunger in a desirable rotational position with respect to the hollow tube (i.e., prevents the plunger from inadvertently or intentionally being manipulated to rotate about the longitudinal axis of the hollow tube). Second, it ensures that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. Alternative positioning means may also be provided to ensure that the plunger remains in the desirable position during delivery of bone graft into the hollow tube, for example by a machined bevel or edge on the outer surface of the plunger, and a corresponding groove in the interior surface of the hollow tube, which must be aligned when inserting the plunger in the hollow tube.

Referring now to FIG. 1C, an elevation view of the hollow tube 2 shown in FIG. 1A is shown in detail. The second end 8 of the hollow tube 2 has an opening with a height A and width B according to the needs of the surgeon, the location of the bone graft receiving area, the nature of the surgical operation to be performed, and the quantity and type of bone graft that is being inserted in (and ultimately ejected from) this integrated fusion cage and graft delivery device. According to a preferred embodiment, the height A of the opening at the second end 8 of the hollow tube 2 is in the range of 4 mm to 9 mm, and in a most preferred embodiment is about 7 mm. According to a preferred embodiment, the width B of the opening at the second end 8 of the hollow tube 2 is in the range of 7 mm to 14 mm, and in a most preferred embodiment is about 10 mm.

Referring to FIGS. 1A-C, it is to be understood that although these particular drawings reflect an embodiment where the second end 8 of the hollow tube 2, and the second end 18 of the plunger 12 comprise a curved or sloped surface which extends at least a certain distance laterally away from the generally longitudinal axis of the hollow tube 2/plunger 12, that in other embodiments, the second end 8 of the hollow tube 2 (and thereby, the second end 18 of the plunger 12) do not extend a lateral distance away, but rather terminate along the longitudinal wall of the hollow tube 2. In this embodiment, the hollow tube 2 may have a second end 8 which has an opening that is carved out of the side of the wall of the hollow tube 2, such that it appears as a window in the tubular body of hollow tube 2. According to this embodiment, the horizontal face 19 of the plunger 12 would also be a face on the outer surface of plunger 12, without extending any lateral distance away from the body of plunger 12. According to this embodiment, the plunger 12 would still retain the curved or sloped surface at the opposite end of the horizontal face 19 (referred to in FIG. 1B as 20) and similarly the hollow tube 2 would still comprise a sloped or curved surface 10 opposite the opening at second end 8. It is to be expressly understood that other variations which deviate from the drawing FIGS. 1A-C are also contemplated with the present invention, so long as that the opening at the second end 8 of hollow tube 2 is oriented to permit bone graft to be exited from the hollow tube 2 in a generally lateral direction (in relation to the longitudinal direction of the axis of the hollow tube 2).

According to another embodiment, the plunger 12 shown in FIG. 1B may further comprise a secondary handle (not shown in FIG. 1B), which includes an opening about at least one end of secondary handle such that it is permitted to couple with handle 16 of plunger 12. In this fashion, the secondary handle may be larger, contain one or more rings or apertures for placing a user's hand and/or fingers, or may simply be of a more ergonomic design, for accommodating use of the plunger 12 during a surgical operation. The secondary handle, according to this embodiment, is selectively removable, which permits a surgeon to use the secondary handle for inserting the plunger 12, and then at a later point remove the secondary handle, for instance, to improve visibility through the incision or through the hollow tube 2, and/or to determine whether substantially all of the bone graft material has been ejected from the hollow tube 2.

Figures 2, 3:
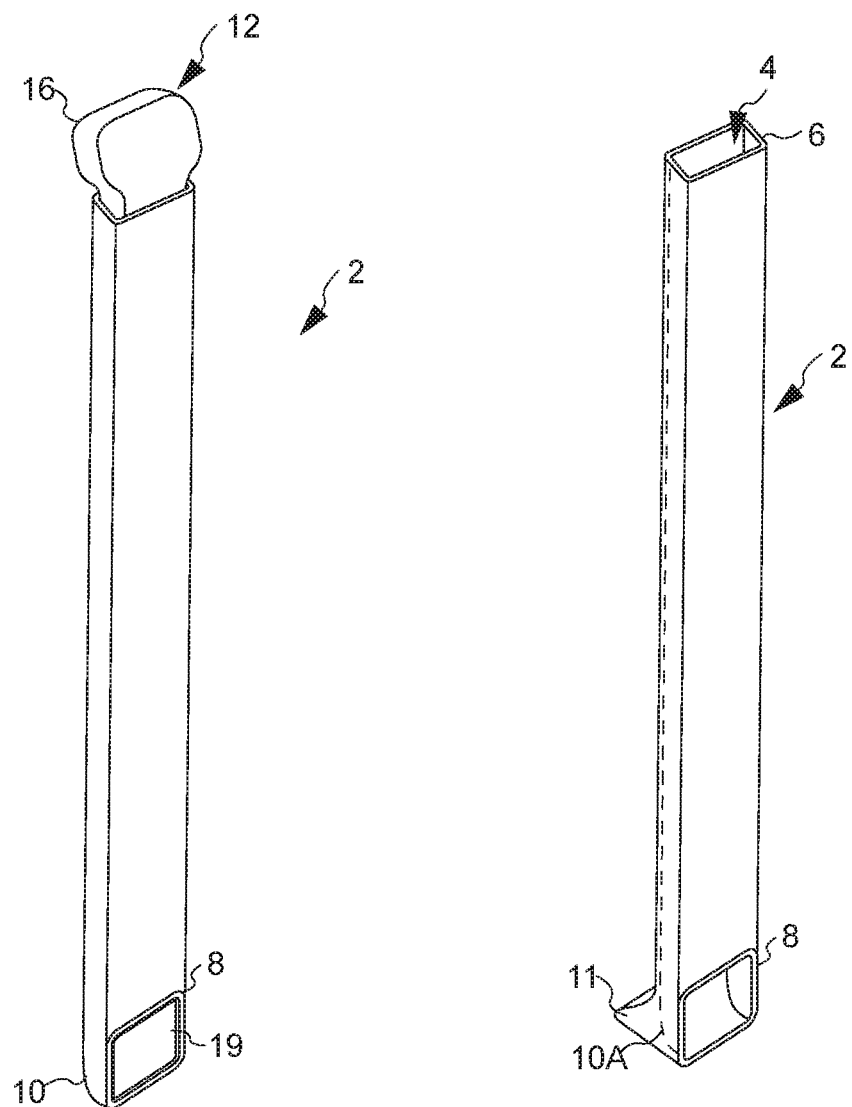
FIG. 2 is another front perspective view of the device of FIGS. 1A and 1B, showing the relationship between the tubular and plunger portions of the device.
FIG. 3 is a front perspective view of the device according to one alternative embodiment where the tubular portion includes a foot section and where the plunger portion has been fully inserted into the tubular portion.

Referring now in detail to FIG. 2, the plunger 12 is shown inserted into the hollow tube 2, such that the horizontal face 19 is substantially planar with the opening at the second end 8 of the hollow tube 2. As described above, the geometry of plunger 12 is such that it fits snuggly or tightly in the interior of the hollow tube 2. This configuration is such that the sloped or curved surface 10 of the hollow tube 2 is substantially congruent to the sloped or curved surface 20 (not shown in FIG. 2), thereby allowing the plunger to be inserted into the hollow tube 2 and allowing substantially all of bone graft material which is placed into the hollow tube 2 to be ejected by the user.

Referring now in detail to FIG. 3, an alternate embodiment of the present invention is shown. According to this embodiment, the hollow tube 2 comprises a footing 11 at the second end 8 of the hollow tube 2. This footing 11 extends in a lateral direction, opposite the direction of the opening at the second end 8 of the hollow tube 2. The purpose of this footing 11 is to prevent injury to the annulus of a patient, or other sensitive anatomy adjacent the bone graft receiving area. This footing 11 is helpful when a surgeon or other user of the integrated fusion cage and graft delivery device is using the plunger 12 to drive bone graft through the hollow tube 2, or using another tool, such as a tamp, mallet, or other driving or impacting device to strike the plunger 12 and/or hollow tube 2 during the surgical procedure. Without the footing 11, the hollow tube 2 would have a generally angular second end 8, which may cause damage to the patient during these types of procedures. Thus, the footing 11 prevents the second end 8 of the hollow tube 2 from penetrating the annulus or other sensitive anatomy of the patient.

According to this embodiment, the footing 11 may also operate to ensure a fixed position of the second end 8 of the hollow tube 2 in the surgical site. This in turn allows a user to ensure that bone graft ejecting the second end 8 of the hollow tube 2 is being ejected laterally, and in the desired direction. This may be important, for example, when the integrated fusion cage and graft delivery device is placed within a disc space, and bone graft is being ejected laterally from the second end 8 of the hollow tube 2 in a specific direction. In other embodiments, the footing 11 may also serve as a visual marker for the surgeon, as it extends away from the horizontal wall of the hollow tube 2, and is therefore visible at the second end 8 of the hollow tube 2. As shown in FIG. 3, the presence of the footing 11 does not affect the interior slope or curved surface 10A of the hollow tube 2, so that the plunger 12 of the design shown in FIG. 1B may still be used with the hollow tube 2 of this alternate embodiment.

Figure 4:
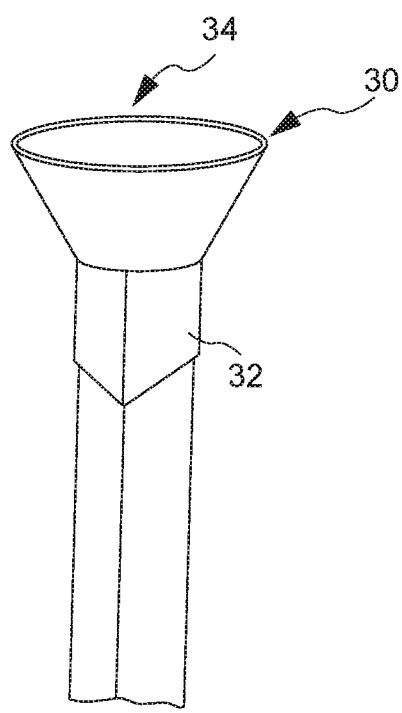
FIG. 4 is a partial front perspective view of another alternative embodiment of the device where the tubular portion includes a funnel at its proximal end designed to receive bone graft.

Referring now in detail to FIG. 4, a removable funnel 30 is shown, which comprises an opening 34 which is generally larger in diameter or dimension when compared to the opening 4 of the hollow tube 2. This removable funnel 30 further comprises a sleeve 32, the sleeve 32 having an internal cross-section which is substantially congruent with the external cross-section of the first end 6 of the hollow tube 2. Thus, according to this embodiment, the funnel 30 is selectively removable from the first end 6 of the hollow tube 2, and may allow a surgeon to more easily place new or additional bone graft into the hollow tube 2 by way of the opening 34 of the funnel 30. This funnel 30 may be used in connection with a hollow tube 2 that has been pre-filled with bone graft, or a hollow tube which is not pre-filled with bone graft. Thus, the funnel may be selectively positioned on the first end 6 of the hollow tube 2 at any point during the surgical operation when the surgeon desires new or additional bone graft be placed in the hollow tube 2 of the integrated fusion cage and graft delivery device.

Figure 5:
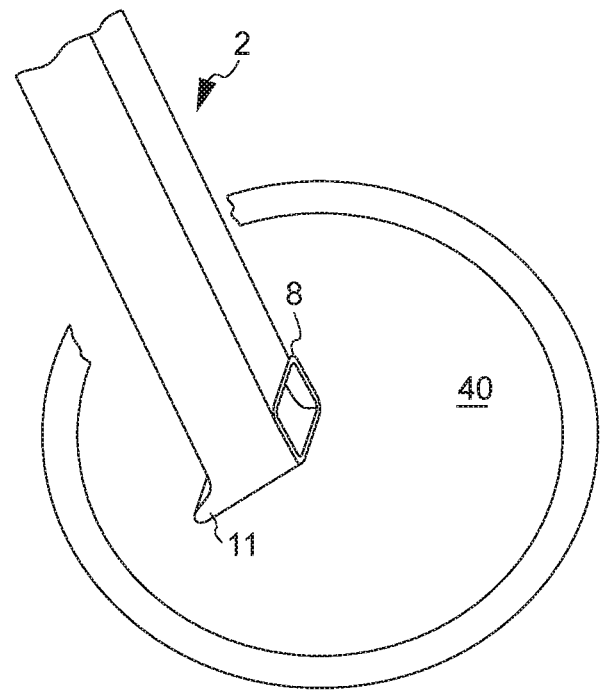
FIG. 5 is a partial front perspective view of the device according to one embodiment where the device is positioned in a disc space during a surgical operation.

Referring now in detail to FIG. 5, one particular application of the integrated fusion cage and graft delivery device is shown in a perspective view. Here, the integrated fusion cage and graft delivery device is shown with the embodiment of the hollow tube 2 further comprising a footing 11, and a second end opening for ejecting bone graft in a generally lateral direction, here in the interior of a disc space 40. The disc is shown with an opening on one end for inserting the second end 8 of the hollow tube 2 of the integrated fusion cage and graft delivery device. As opposed to prior art integrated fusion cage and graft delivery devices which have an opening at a second end that is open to the longitudinal axis of the delivery device, the present invention comprises a lateral opening, which as shown in FIG. 5 allows a surgeon to eject bone mill into the lateral direction and thereby into the opened areas of the disc space 40. A surgeon has the option to rotate the direction of the opening in the second end 8 of the hollow tube 2 for ejecting additional bone graft to other open areas in the disc space 40. Once the disc space 40 is substantially full of bone graft, the surgeon may remove the hollow tube 2 without disturbing the disc or anatomy of the patient. The surgeon may also accomplish the delivery of bone graft without displacing any cage or other structural implantable device which may be present in or adjacent the disc space. One skilled in the art will appreciate that the hollow tube 2 further comprising a footing 11, and a second end opening for ejecting bone graft in a generally lateral direction, may affect the delivery of bone graft in a lateral direction simultaneous with delivery in a longitudinal direction.

Figure 6:
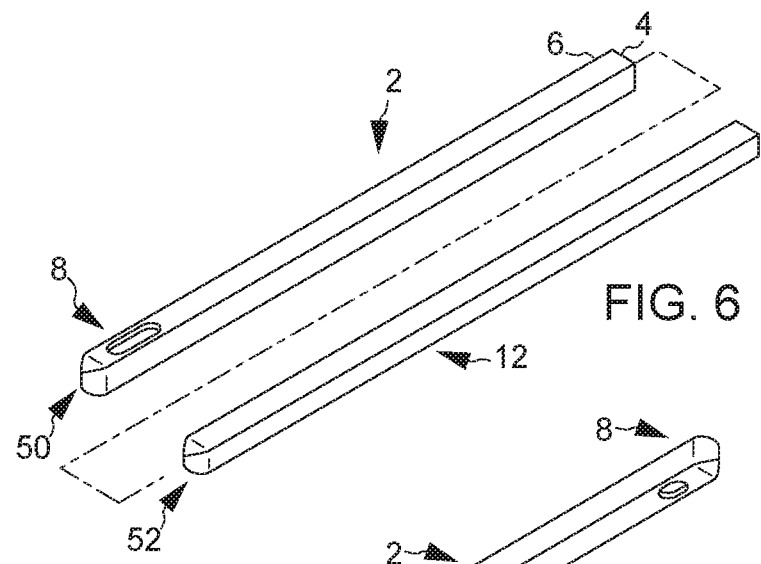
FIG. 6 is a front perspective view of one embodiment of the device, showing the relationship between the tubular and plunger portions where the tubular portion includes two lateral facing openings at the distal end of the tubular portion and a wedge-shaped distal end of the tubular member.

Referring now to FIGS. 6-10D, a preferred embodiment of the device is shown. In regard to FIG. 6, an integrated fusion cage and graft delivery device portion is shown, comprised of a hollow tubular member 2, which has a first proximate end 6 and a second distal end 8, with a general hollow structure therebetween. The generally hollow tube 2 is shown with one of two lateral openings at the distal end 8 of the tubular member 2 viewable (the other is viewable in FIG. 7). Also in FIG. 6, the plunger member 12 is shown. The manner of insertion of plunger member 12 into tubular member 2 is also provided. Thus, as shown in FIG. 6, the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2.

Furthermore, regarding FIG. 6, a preferred embodiment of the distal end 8 of the tubular member 2 and the distal end 18 of the plunger member 12 is provided. The configuration provided, a wedge-shaped end 50 of the tubular member 2 and a wedge-shaped end 52 of the plunger 12, allows substantially all of the bone graft material to be removed and thus inserted into the surgical area when the plunger 12 is fully inserted into the tubular member 2. The wedge-shaped feature 50 of the distal end 8 of the tubular member 2 and the wedge-shaped end 52 of the distal end 18 of the plunger member 12 is discussed in additional detail with respect to FIGS. 8 and 9 below. The ability to remove substantially all of the bone graft material is an important feature of the invention because bone graft material is traditionally expensive and may require surgery to obtain.

Figure 7:
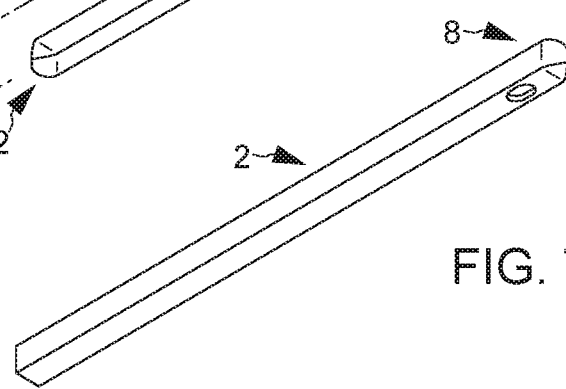
FIG. 7 is another front perspective view of the tubular portion of the device of FIG. 6 showing the second of two lateral openings at the distal end of the tubular portion and a wedge-shaped distal end of the tubular member.

Referring now to FIG. 7, a perspective view of a preferred embodiment of the hollow tubular member 2 is provided. Consistent with FIG. 6, the generally hollow tube 2 is shown with one of two lateral openings at the distal end 8 of the tubular member 2 viewable (the other is viewable in FIG. 6). Thus, in operation the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2. In this configuration, bone graft material is ejected into the surgical area in two lateral directions. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular), and/or one or more lateral openings may comprise a first pair of edges and a second pair of edges, wherein the first pair of edges are straight and the second pair of edges are not straight.

Figure 8:
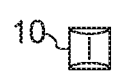
FIG. 8 is a front elevation view of the distal end of the tubular portion of the device of FIG. 6.

Referring now to FIG. 8, an elevation view of the wedge-shaped distal end 50 of the tubular member 2 is provided. In this embodiment, the distal end 52 of the plunger 12 would conform to the same shape, to allow close fitting of the plunger and the hollow tubular member.

This contoured plunger, corresponding to the contoured tubular member, serves several purposes: First, it maintains the plunger in a desirable rotational position with respect to the hollow tube (i.e., prevent the plunger from inadvertently or intentionally being manipulated to rotate about the longitudinal axis of the hollow tube); Second, it ensures that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. One skilled in the art will appreciate that the plunger 12 need not terminate in a wedge-shape surface 52 to affect the substantial removal of all of the bone graft material placed into the hollow tube 2; more specifically, any shape that allows conformance between the internal contour of the distal end of the hollow tube and the distal end of the plunger will affect the substantial removal of the bone graft material.

Figure 9:
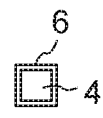
FIG. 9 is a bottom elevation view of the proximal end of the tubular device of FIG. 6.

Referring now to FIG. 9, an elevation view of the opening 4 of the proximal end 6 of the hollow tubular member 2 is provided. As shown in FIG. 9, the opening 4 at the proximal end 6 of the hollow tube 2 allows deposit of bone graft material. In this configuration, the cross-section of the opening 4 at the proximal end 6 of the hollow tube 2 is generally square. Although a generally square cross-section is depicted, the cross-section need not be limited to a generally square shape. For example, cross-sections of an oval shape or those with at least one defined angle to include obtuse, acute, and right angles can provide a shape in some situations that is more congruent with the size or shape of the annulotomy of a particular disc space.

Figure 10A:
FIG. 10A is a top plan view of the device of FIG. 6 with the plunger portion fully inserted into the tubular portion.
Figure 10B:
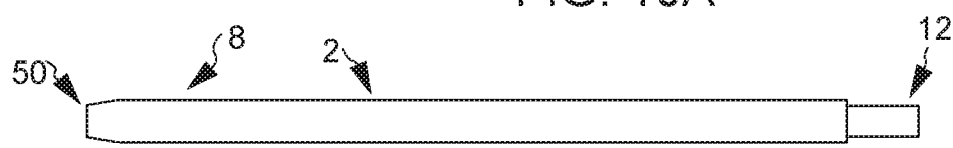
FIG. 10B is a left elevation view of the device of FIG. 6 with the plunger portion fully inserted into the tubular portion.
Figure 10C:
FIG. 10C is a bottom plan view of the device of FIG. 6 with the plunger portion fully inserted into the tubular portion.
Figure 10D:
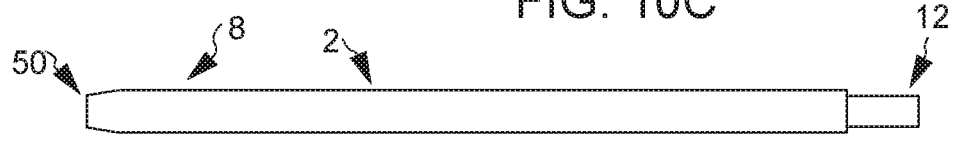
FIG. 10D is a right elevation view of the device of FIG. 6 with the plunger portion fully inserted into the tubular portion.
Figure 11A:
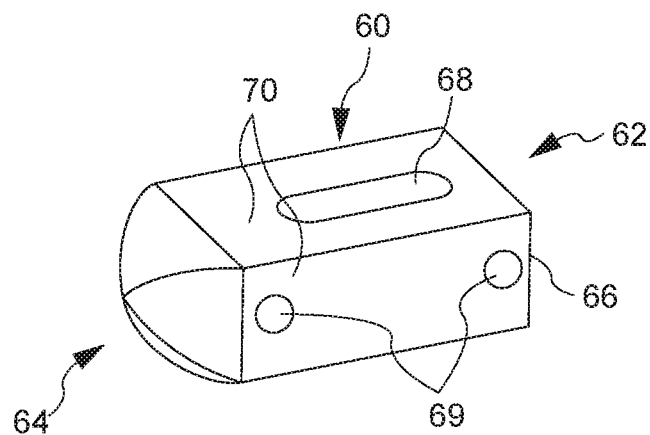
FIG. 11A is a front perspective view of one embodiment of the fusion cage of the device, showing a tapered proximal end and medial openings.
Figure 11B:
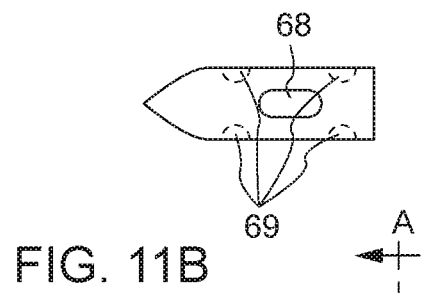
FIG. 11B is a top plan view of the fusion cage of FIG. 11A.
Figure 11C:
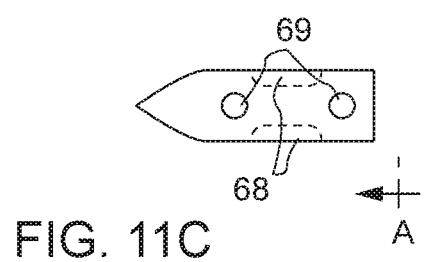
FIG. 11C is a left elevation view of the fusion cage of FIG. 11A.
Figure 11D:
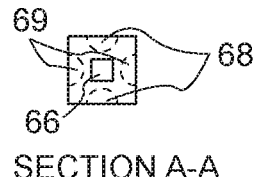
FIG. 11D is a rear elevation view of the fusion cage of FIG. 11A.

Referring to FIGS. 10A-D, sequential elevation views of the square-shaped embodiment of the integrated fusion cage and graft delivery device 1 are provided, depicting the complete insertion of the plunger 12 into the hollow tubular member 2. In each of FIGS. 10A-D, the wedge-shaped distal end 50 of the tubular member 2 is depicted. Also, each of FIGS. 10A-D depict the additional length of the plunger element 12 when inserted into the tubular member 2. FIG. 10A shows one of two lateral openings at the distal end 8 of the hollow tubular member 2. FIG. 10C shows another of the two lateral openings at the distal end 8 of the hollow tubular member 2. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular).

Referring to FIGS. 11A-D, a fusion cage 60 of an integrated fusion cage and graft delivery device 1 portion is shown, which is comprised of an integrated fusion cage 60 that comprises a first proximal end 62 and a second distal end 64 wherein the first proximal end contains an opening 66 adapted to allow fitting and/or engagement to the distal end 8 of the hollow tube 2. This fitting and/or engagement may be over the external surface of the hollow tube 2 or inside the interior of the hollow tube 2. Further, the integrated fusion cage 60 may comprise one or more medial openings 68 that align with one or more openings at the distal end 8 of the hollow tube 2. Further, the integrated fusion cage 60 may contain non-smooth surfaces, such as belts or striations, along one or more medial surfaces 70 of the integrated fusion cage 60. The integrated fusion cage 60 is configured such that when a plunger 12, once fully inserted into the hollow tube 2, is substantially congruent with the hollow interior portion of the hollow tube 2, e.g. both the plunger 12 and the hollow tube 2 are substantially the same shape and/or class and bone graft material is delivered through the integrated fusion cage 60 into the surgical area.

In a preferred embodiment, the fusion cage 60 has a tapered tip, and several open channels along the medial and lateral surfaces. In a preferred embodiment, the fusion cage 60 and/or the bone graft delivery portion of the integrated fusion cage and graft delivery device is of oblong or rectangular or square shape. The integrated fusion cage and graft delivery device 1 is designed to avoid blocking or impacting bone graft material into a surgical disc space, thereby limiting the bone graft material that may be delivered, and not allowing available fusion space to be fully exploited for fusion.

In a preferred embodiment, the fusion cage 60 has a keel-shaped tip to separate disk and prevent annular penetration. Also, the fusion cage 60 may have dual portals for bone graft discharge, with the medial openings 68 larger than the lateral openings 69. Further, the fusion cage may be designed in variable heights and lengths so that it fits snugly into the prepared disk space.

Figure 12A:
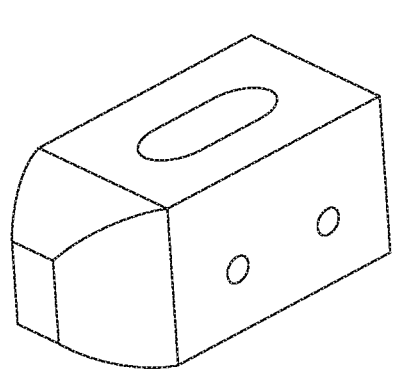
FIG. 12A is a front perspective view of another embodiment of the fusion cage of the device.
Figure 12B:
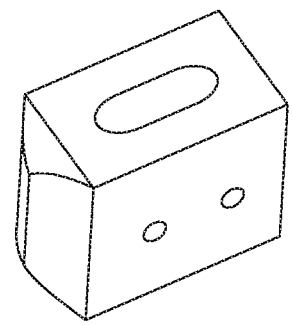
FIG. 12B is a front perspective view of yet another embodiment of the fusion cage of the device.
Figure 12C:
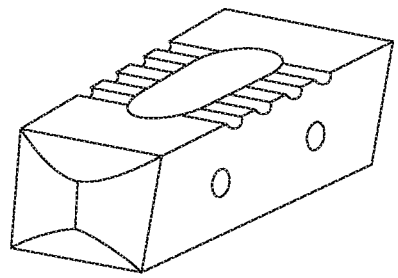
FIG. 12C is a front perspective view of yet another embodiment of the fusion cage of the device.

Referring now to FIGS. 12A-C, two alternate embodiments of the fusion cage 60 are provided. FIG. 12A shows an embodiment of the integrated fusion cage 60 with a second distal end 64 tapered to a flat rectangular shape end. FIG. 12B shows an embodiment of the integrated fusion cage 60 with a second distal end 64 tapered to a wedged-shaped end. Such a configuration would be, for example, would be conformal with the wedge-shaped second end 50 of the hollow tube 2, as shown in FIGS. 6-8. FIG. 12C shows an embodiment of the integrated fusion cage 60 with belts of striations imparted to the upper medial surface 70 of the fusion cage 60.

Figure 13:
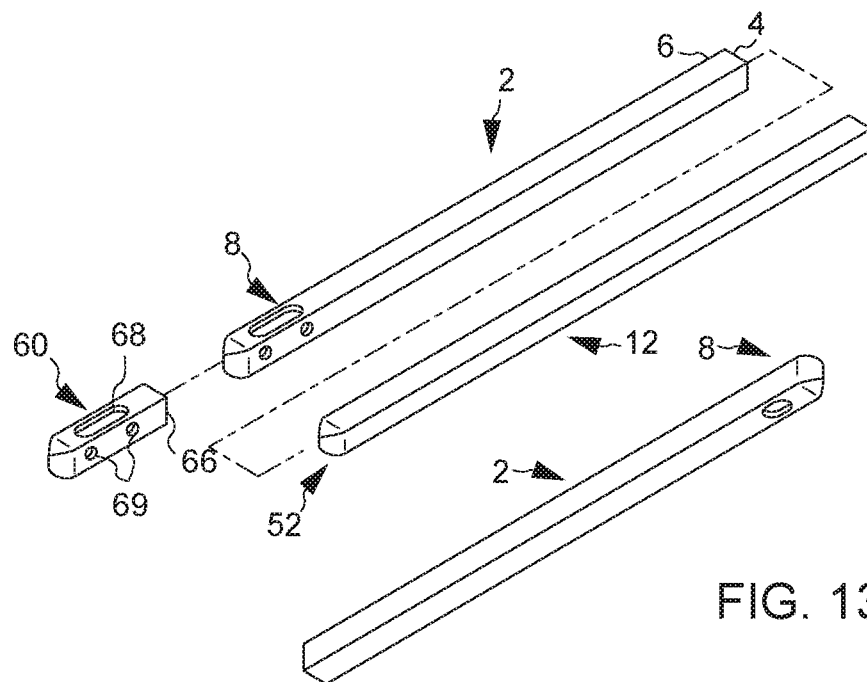
FIG. 13 is a front perspective view of one embodiment of the device, showing the relationship between the tubular and plunger portions where the tubular portion includes two lateral facing openings at the distal end of the tubular portion and a wedge-shaped distal end of the tubular member, and a fusion cage fitting over the exterior distal end of the tubular member.
Figure 14A:
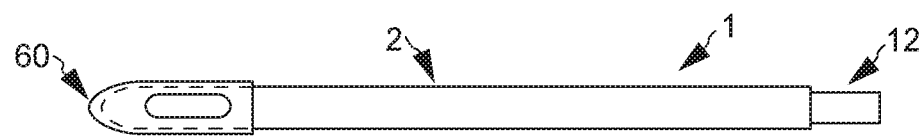
FIG. 14A is a top plan view of the device of FIG. 13 with the plunger portion fully inserted into the tubular portion and the fusion cage fully inserted over the tubular portion.
Figure 14B:
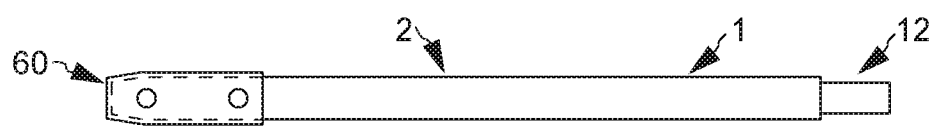
FIG. 14B is a left elevation view of the device of FIG. 13 with the plunger portion fully inserted into the tubular portion and the fusion cage fully inserted over the tubular portion.
Figure 14C:
FIG. 14C is a bottom plan view of the device of FIG. 13 with the plunger portion fully inserted into the tubular portion and the fusion cage fully inserted over the tubular portion.
Figure 14D:
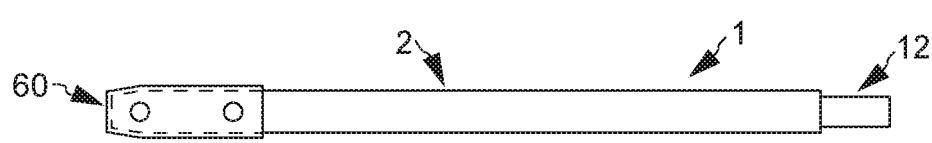
FIG. 14D is a right elevation view of the device of FIG. 13 with the plunger portion fully inserted into the tubular portion and the fusion cage fully inserted over the tubular portion.

In regard to FIG. 13, an integrated fusion cage and graft delivery device 1 is shown, comprised of a hollow tubular member 2, which has a first proximate end 6 and a second distal end 8, with a general hollow structure therebetween. The generally hollow tube 2 is shown with one of two lateral openings at the distal end 8 of the tubular member 2 viewable. Also in FIG. 13, the plunger member 12 is shown and the fusion cage 60. The manner of insertion of plunger member 12 into tubular member 2 is also provided, as is the manner of insertion of fusion cage 60 over tubular member 2 and into the fusion cage first end opening 66. Thus, as shown in FIG. 13, the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2 and through the medial openings 68 and/or the lateral openings 69 of the fusion cage 60. In one embodiment as shown in FIG. 13, the lateral openings at the distal end 8 of the hollow tubular member 2 are preferably disposed within a distance from the distal end 8 not exceeding 25% of the total distance (or length) of the hollow tube member 2, more preferably not exceeding 15% of this identified distance, and most preferably not exceeding 10% of this identified distance. In one embodiment as shown in FIG. 13, the lateral openings at the distal end 8 of the hollow tubular member 2 are preferably disposed within a distance from the distal end 8 not exceeding 10 cm of the total distance (or length) of the hollow tube member 2, more preferably not exceeding 8 cm of this identified distance, and most preferably not exceeding 5 cm of this identified distance.

Referring to FIGS. 14A-D, sequential elevation views of the square-shaped embodiment of the integrated fusion cage and graft delivery device 1 are provided, depicting sequential elevation views of the integrated fusion cage and graft delivery device 1 with the plunger portion 12 fully inserted into the tubular portion 2 and the fusion cage 60 fully inserted over the tubular portion 2. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral and medial openings may vary, for example the distal end 8 of the tubular member 2 may have more than two openings that are of different shape (e.g. oval, rectangular).

Referring to FIGS. 15A-D, a fusion cage 60 of an integrated fusion cage and graft delivery device portion is shown, which is comprised of an integrated fusion cage 60 that comprises a first proximal end 62 and a second distal end 64 wherein the first proximal end contains an opening 66 adapted to allow fitting and/or engagement to the distal end 8 of the hollow tube 2. This fitting and/or engagement may be over the external surface of the hollow tube 2 or inside the interior of the hollow tube 2. Further, the integrated fusion cage 60 may contain non-smooth surfaces, such as belts or striations, along one or more medial surfaces 70 of the integrated fusion cage 60. The integrated fusion cage 60 is configured such that when a plunger 12, once fully inserted into the hollow tube 2, is substantially congruent with the hollow interior portion of the hollow tube 2, e.g. both the plunger 12 and the hollow tube 2 are substantially the same shape and/or class and bone graft material is delivered through the integrated fusion cage 60 into the surgical area.

In a preferred embodiment, the fusion cage 60 has a tapered tip, and several open channels along the medial and lateral surfaces. In a preferred embodiment, the fusion cage 60 is of a square shape and the bone graft delivery portion of the integrated fusion cage and graft delivery device is of a cylindrical shape. The integrated fusion cage and graft delivery device 1 is designed to avoid blocking or impacting bone graft material into a surgical disc space, thereby limiting the bone graft material that may be delivered, and not allowing available fusion space to be fully exploited for fusion.

Figure 15A:
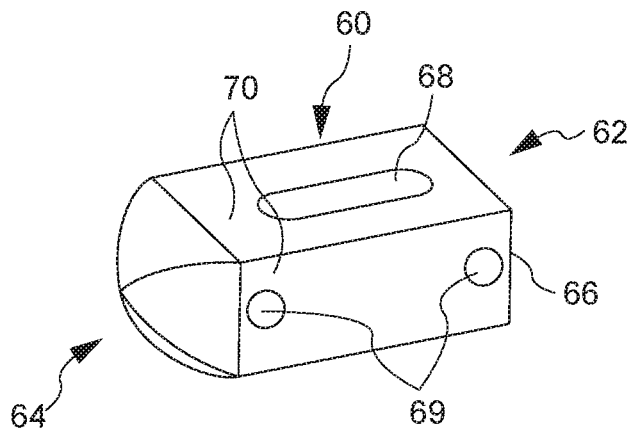
FIG. 15A is a front perspective view of another embodiment of the fusion cage of the device.
Figure 15B:
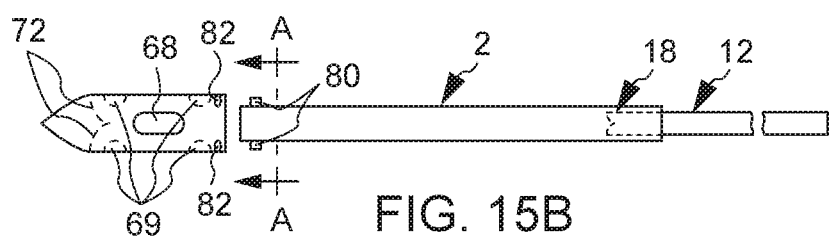
FIG. 15B is a top plan view of another embodiment of the device wherein the fusion cage of the device includes internal ramps and locking slots configured to engage locking tabs of the tubular portion, and the plunger includes a tapered tip.

In a preferred embodiment, the fusion cage 60 has a keel-shaped tip to separate disk and prevent annular penetration and has internal ramps 72 which assist in directing the bone graft material to one or more lateral openings 69. As the plunger 12 is inserted into the hollow tube 2, bone graft material is directed by the fusion cage internal ramps 72 out the lateral openings 69, and bone additionally bone graft material may flow out the one or more medial openings 68. The plunger end 18 may be configured to be conformal with the internal ramps 72 of the fusion cage 60, as depicted in FIG. 15B. Also, the fusion cage 60 may have dual portals for bone graft discharge, with the medial openings 68 larger than the lateral openings 69. Further, the fusion cage may be designed in variable heights and lengths so that it fits snugly into the prepared disk space.

Figure 15C:
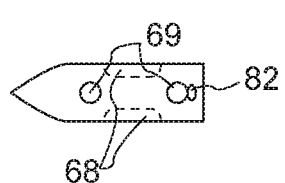
FIG. 15C is a left elevation view of the fusion cage of FIG. 15B.
Figure 15D:
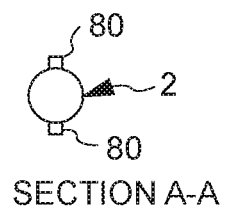
FIG. 15D is a front elevation view of the tubular portion of FIG. 15B.

In a preferred embodiment as shown in FIGS. 15B-D, the hollow tube 2 is of cylindrical shape and includes one or more locking tabs 80 configured to engage one or more locking slots 82 of the fusion cage 60. The locking tabs 80 may permanently or not permanently engage the locking slots 82, and may be of shape to include rectangular, circular and oblong. The instruments used with the integrated fusion cage and graft delivery device described above in its varying embodiments may include one or more tamps, preferably having a configuration which at least in part corresponds in shape and contour of the hollow tube portion of the delivery device. The one or more tamps may be adapted to correspond further to the shape and contour of the graspable end of the plunger, for use in driving the plunger through the hollow tube portion of the delivery device to ensure any remaining bone graft located in the hollow tube is delivered to the graft receiving area.

Figure 16:
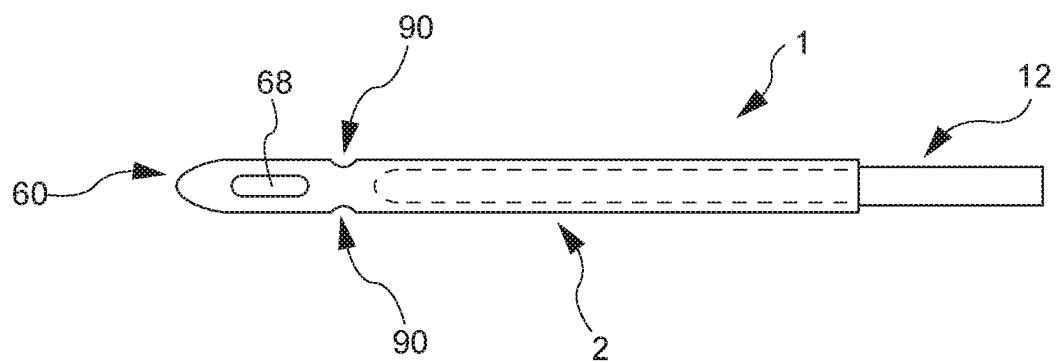
FIG. 16 is a top plan view of another embodiment of the device with the plunger portion partial inserted into the tubular portion and the fusion cage engaged with the tubular portion via a break-off collar.

In the embodiment of the device of FIG. 16, the hollow tube 2 engages with the fusion cage 60 via a break-off collar 90 and the plunger 12 inserts into the interior of the hollow tube 2. The plunger 12 is depicted partially inserted into the hollow tube 2. The break-off collar 90 may be severed by any of several means, to include application of torsion and/or rotational force and/or lateral force to break-off collar 90, for example by twisting on the hollow tube 2 and/or the plunger 12.

Figure 17A:
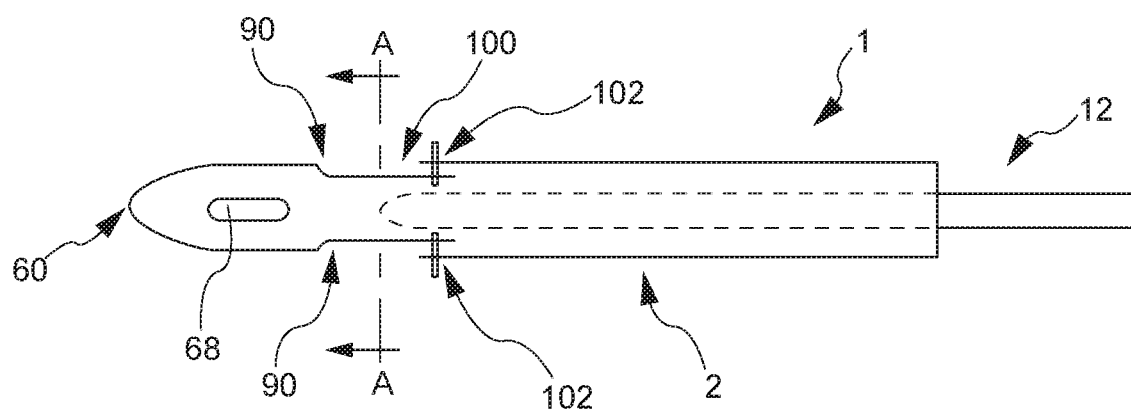
FIG. 17A is a top plan view of another embodiment of the device wherein the fusion cage engages with a connector conduit which in turn engages with the tubular portion.
Figure 17B:
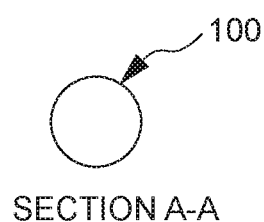
FIG. 17B is a cross-sectional view of section A-A of FIG. 17A.
Figure 18A:
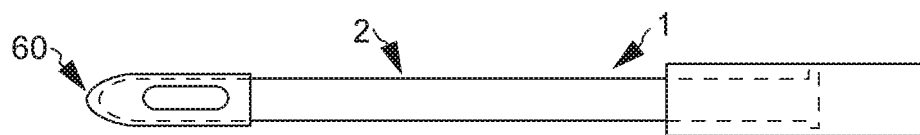
FIG. 18A is a top plan view of another embodiment of the device wherein the tubular portion comprises a telescoping feature.
Figure 18B:
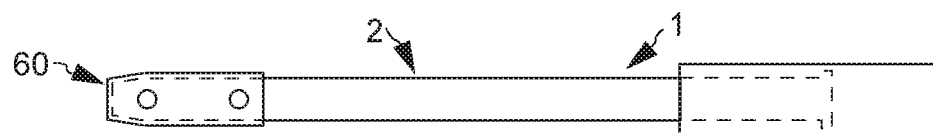
FIG. 18B is a left elevation view of the device of FIG. 18A.
Figure 18C:
FIG. 18C is a bottom plan view of the device of FIG. 18A.
Figure 18D:
FIG. 18D is a right elevation view of the device of FIG. 18A.
Figure 19A:
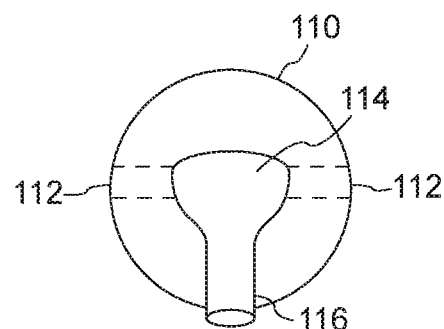
FIG. 19A is a top plan view of a fusion cage of an embodiment of the device particularly adapted for use in anterior lumbar interbody fusion procedures.
Figure 19B:
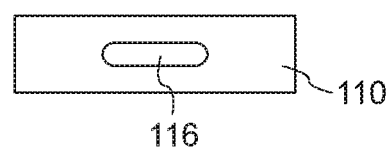
FIG. 19B is a front elevation view of the device of FIG. 19A.
Figure 19C:
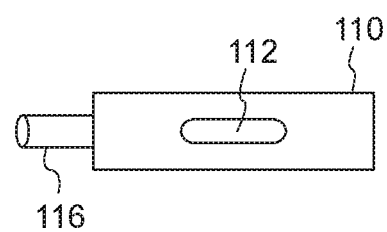
FIG. 19C is a left elevation view of the device of FIG. 19A.
Figure 19D:
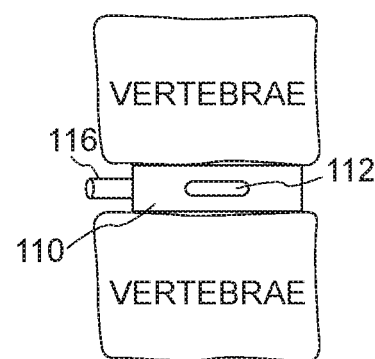
FIG. 19D is a view of the device of FIG. 19A inserted between vertebrae.
Figure 20A:
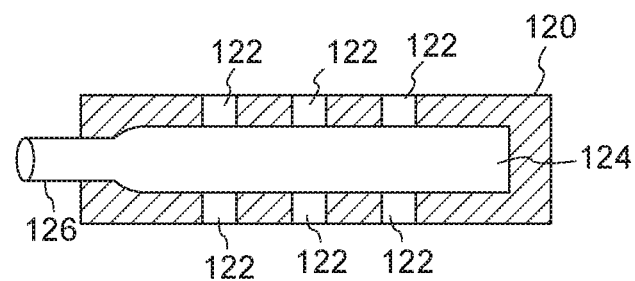
FIG. 20A is a cross-sectional top plan view of a fusion cage of an embodiment of the device particularly adapted for use in direct lateral interbody fusion procedures.
Figure 20B:
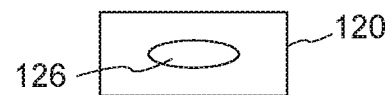
FIG. 20B is a front elevation view of the device of FIG. 20A.
Figure 20C:
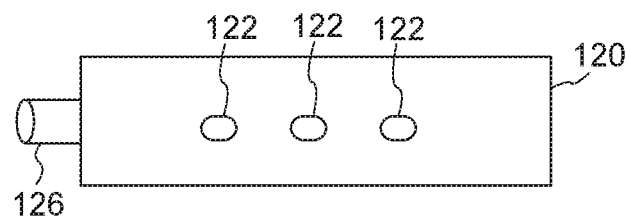
FIG. 20C is a left elevation view of the device of FIG. 20A.
Figure 20D:
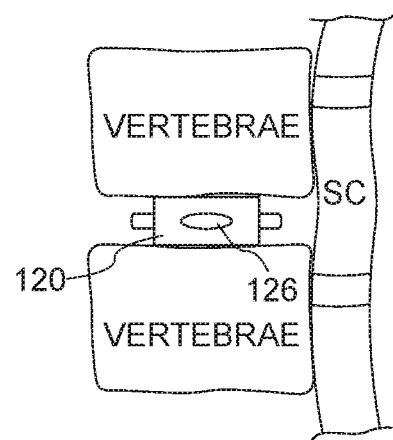
FIG. 20D is a view of the device of FIG. 20A inserted between vertebrae.
Figures 21A, 21B:
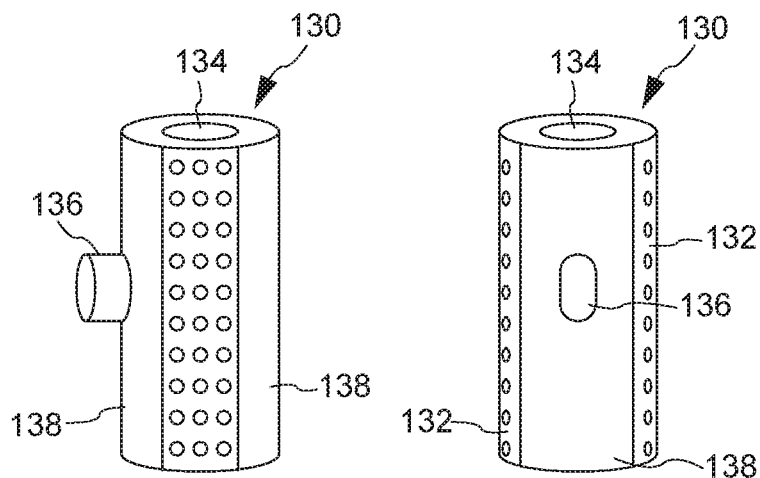
FIG. 21A is a front perspective view of a fusion cage of an embodiment of the device particularly adapted for use in connection with vertebrectomy procedures.
FIG. 21B is a left perspective view of the device of FIG. 21A.
Figures 21C, 21D:
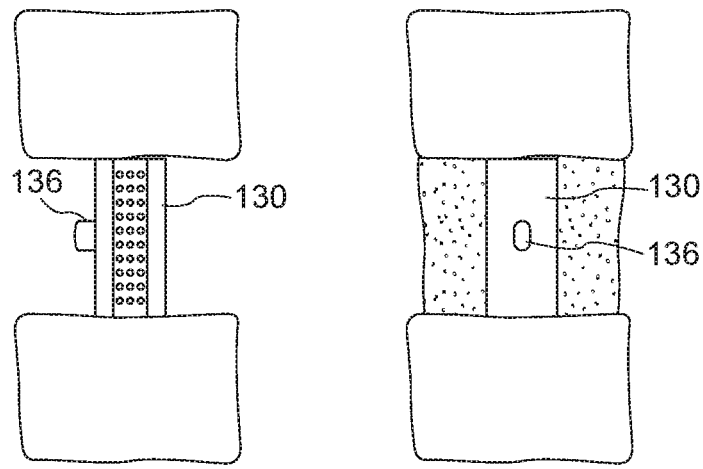
FIG. 21C is a front elevation view of the device of FIG. 21A inserted into a surgical site.
FIG. 21D is a left elevation view of the device of FIG. 21A inserted into a surgical site.

In the embodiment of the device of FIG. 17A-B, the hollow tube 2 engages with a connector conduit 100 which in turn connects with the fusion cage 60 via a break-off collar 90. One or more connectors 102 connect the hollow tube 2 with the connector conduit 100. The hollow tube 2 fits over the connector conduit 100. The one or more connectors 102 fit through the hollow tube 2 and the connector conduit 100. The break-off collar 90 may be severed by any of several means, to include application of torsion and/or rotational force and/or lateral force to break-off collar 90, for example by twisting on the hollow tube 2 and/or the plunger 12. In one embodiment of the connector conduit 100, as shown in FIG. 17B, the connector conduit 100 is of circular cross-section.

Referring to FIGS. 18A-D, sequential elevation views of the square-shaped embodiment of the integrated fusion cage and graft delivery device 1 are provided, depicting sequential elevation views of the integrated fusion cage and graft delivery device 1 with telescoping tubular portion 2 and the fusion cage 60 fully inserted over the tubular portion 2. One skilled in the art will appreciate that the openings at the distal end 8 of the hollow tubular member 2 need not be positioned exclusively on one or more lateral sides of the distal end of the tubular member to allow bone graft material to be provided to the surgical site in other than a purely axial or longitudinal direction.

In an embodiment of the invention particularly suited for ALIF procedures, a fusion cage 110 as shown in FIGS. 19A-D comprises a hollow internal chamber 114 in fluid communication with bone graft discharge portals 112 and a charging portal 116, which comprises a break-off collar in some embodiments such as those depicted in FIGS. 17A-D. The fusion cage 110 has a substantially cylindrical shape, with the discharge portals 112 located opposite each other on the curved lateral portion of the fusion cage 110 and the charging portal 116 located substantially in between the discharge portals 112 on the curved anterior portion of the fusion cage 110. The curved posterior portion of the fusion cage 110 is substantially devoid of portals from the internal chamber 114 to the exterior of the fusion cage 110. The charging portal 116 is adapted to receive a hollow tube such as the hollow tube 2 shown in other embodiments described herein. Bone graft material enters the internal chamber 114 through a hollow tube connected to the charging portal 116, and exits the internal chamber 114 through the discharge portals 112. The discharge portals 112 are positioned so that when the fusion cage 110 is properly positioned in between two vertebrae, bone graft material discharged therethrough fills the space in between the vertebrae on the lateral sides of the spine, but does not discharge into or fill the anterior or posterior space in between the vertebrae. In embodiments of fusion cage 110 comprising a break-off collar, once the fusion cage 110 is properly positioned and the desired amount of bone graft material has been inserted into the chamber 114 and discharged through the discharge portals 112, the break-off collar is severed from the fusion cage 110 (as described with respect to other embodiments herein) and removed from the patient's body.

In embodiments that do not comprise a break-off collar, the charging portal 116 of fusion cage 110 is adapted to removably receive a hollow tube (such as the hollow tube 2 shown in other embodiments described herein). For example, the walls of the charging portal 116 may be threaded so that the hollow tube can be screwed into the charging portal 116.

The fusion cage 110 preferably has a height of from about 8 millimeters to about 14 millimeters, and a diameter of less than about 36 millimeters. The fusion cage 110 is made from polyether ether ketone (PEEK), titanium, a composite material, or any other material suitable for implantation in a human body. The fusion cage 110 comprises, in some embodiments, ramps within internal chamber 114 to guide bone graft material to discharge portals 112.

In an embodiment of the invention particularly suited for D-LIF procedures, a fusion cage 120 as shown in FIGS. 20A-D comprises a hollow internal chamber 124 in fluid communication with bone graft discharge portals 122 and a charging portal 126, which in some embodiments—including the embodiment shown in FIGS. 20A-D—comprises a break-off collar. The fusion cage 120 is substantially shaped as a rectangular prism, with the discharge portals 122 located on opposite sides of the fusion cage 120 and the charging portal 126 located on a lateral face of the fusion cage 120. The opposite lateral face of the fusion cage 120 is devoid of portals from the internal chamber 124 to the exterior of the fusion cage 120. The charging portal 126 is adapted to receive a hollow tube such as the hollow tube 2 shown in other embodiments described herein. Bone graft material enters the chamber 124 through a hollow tube connected to the charging portal 126, and exits the internal chamber 124 through the discharge portals 122. The discharge portals 122 are positioned so that when the fusion cage 120 is properly positioned in between two vertebrae, bone graft material discharged therethrough fills the space in between the vertebrae towards the anterior and posterior of the spine, but does not discharge into or fill the lateral space in between the vertebrae. As with other embodiments described herein, in embodiments that comprise a break-off collar, once the fusion cage 120 is properly positioned and the desired amount of bone graft material has been inserted into the chamber 124 through charging portal 126 and discharged through the discharge portals 122, the break-off collar is severed from the fusion cage 120 (as described with respect to other embodiments herein) and removed from the patient's body.

In embodiments that do not comprise a break-off collar, the charging portal 126 is adapted to removably receive a hollow tube (such as the hollow tube 2 shown in other embodiments described herein). For example, the internal walls of charging portal 126 may be threaded so that the hollow tube can be screwed into the charging portal 126.

The fusion cage 120 preferably has a height of from about 8 millimeters to about 14 millimeters, and a length of from about 22 millimeters to about 36 millimeters. The fusion cage 120 is made from polyether ether ketone (PEEK), titanium, a composite material, or any other material suitable for implantation in a human body. The fusion cage 120 comprises, in some embodiments, ramps within internal chamber 124 to guide bone graft material to discharge portals 122.

Referring now to FIGS. 21A-D, in embodiments of the invention particularly suited for use in connection with a vertebrectomy, a fusion cage 130 comprises a substantially cylindrical wall surrounding an internal chamber 134. Thus, the fusion cage 130 has a substantially cylindrical shape. Internal chamber 134 is open at the top and the bottom of fusion cage 130, and lateral portions 132 of the cylindrical wall of the fusion cage 130 are porous to bone graft material (i.e. bone graft slurry). Anterior and posterior portions 138 of the cylindrical wall of fusion cage 130 in between porous portions 132 are impervious to bone graft material. A charging portal 136—which in some embodiments, including the embodiment shown in FIGS. 21A-D, comprises a break-off collar—is positioned on an impervious portion 138 of fusion cage 130. The charging portal 136 is adapted to receive a hollow tube such as the hollow tube 2 shown in other embodiments described herein. Bone graft material enters the chamber 134 through a hollow tube connected to the charging portal 136, and exits the chamber 134 through porous wall portions 132. The porous wall portions 132 are positioned so that when the fusion cage 130 is properly positioned in between two vertebrae, bone graft material discharged therethrough fills the space in between the vertebrae on either side of the spine, but the impervious wall portions 138 prevent bone graft material from discharging into the anterior or posterior space in between the vertebrae, thus preventing bone graft material from pushing against the spinal cord. In embodiments of fusion cage 130 comprising a break-off collar, once the fusion cage 130 is properly positioned and the desired amount of bone graft material has been inserted into the chamber 134 through charging portal 136 and discharged through the porous wall portions 132, the break-off collar 136 is severed from the fusion cage 130 (as described with respect to other embodiments herein) and removed from the patient's body.

In embodiments that do not comprise a break-off collar, the charging portal 136 is adapted to removably receive a hollow tube (such as the hollow tube 2 shown in other embodiments described herein). For example, the internal walls of the charging portal 136 may be threaded so that the hollow tube can be screwed into the charging portal 136.

The fusion cage 130 preferably has a height equal to or greater than the vertebra or vertebrae it is intended to replace, and a diameter of less than about 36 millimeters. The fusion cage 130 is made of polyether ether ketone, titanium, a composite material, or any other material suitable for implantation in a human body. In some embodiments, ramps in the internal chamber 134 guide the bone graft material to the porous lateral faces 132.

Figure 22:
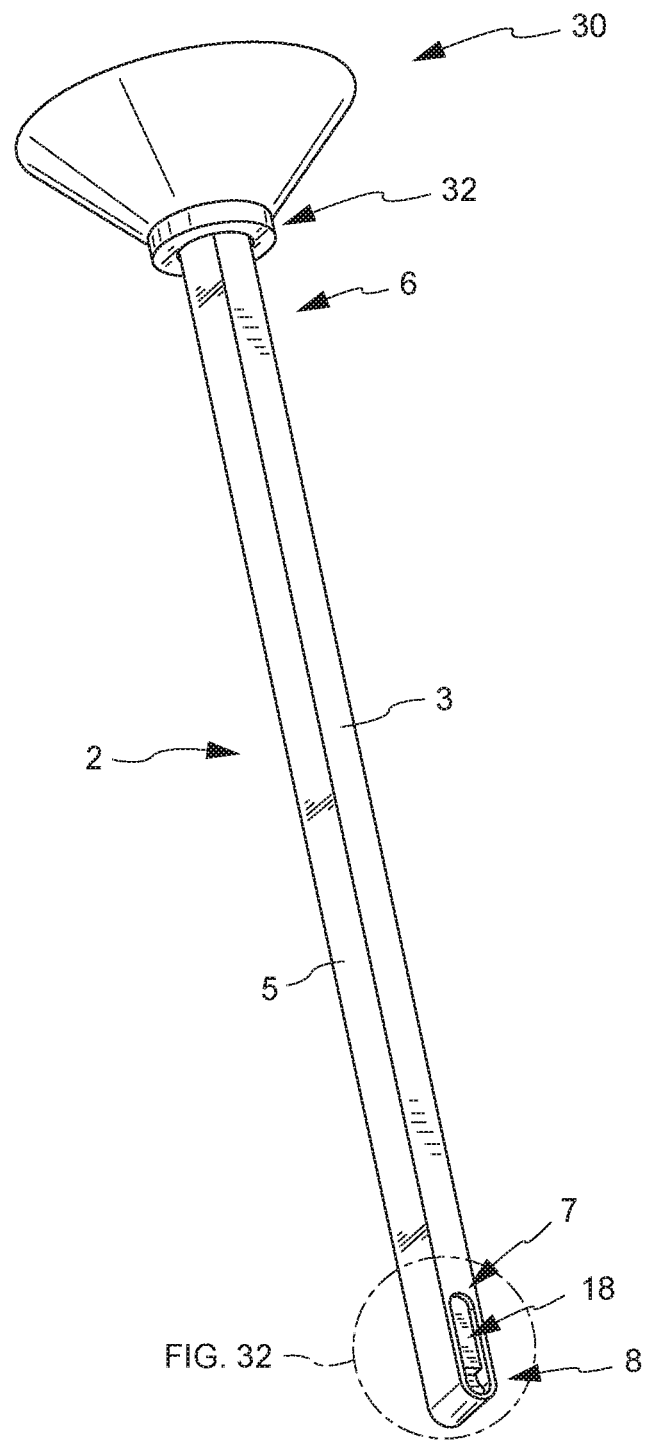
FIG. 22 is a front perspective view of another embodiment of the device for delivering bone graft.

Referring now to FIGS. 22-33, another embodiment of the device for delivering bone graft is provided. In regard to FIGS. 22-28, integrated fusion cage and graft delivery device 1 is shown. FIG. 22 is a perspective view of the device 1, FIG. 23 a perspective exploded view, FIG. 24 a top plan view, FIG. 25 a front elevation view, FIG. 26 a right elevation view, FIG. 27 is a bottom plan view, and FIG. 28 is a cross-sectional view of section A-A of FIG. 25.

Device 1 is comprised of a hollow tubular member or hollow tube 2, a plunger 12 which fits within the hollow tube 2, and a funnel 30. The funnel 30 engages the upper or distal or first end 6 of the hollow tube, and comprises a sleeve 32 and opening 34. Medical material, such as bone graft material, is inserted into opening 34 of funnel 30, which in turn enters hollow tube 2. Hollow tube 2 comprises hollow tube first exterior surface 3, hollow tube second exterior surface 5, first end 6, second end 8, and hollow tube first distal opening 7. Hollow tube 2 is generally of symmetrical shape such that first exterior surface 3 comprises two such surfaces opposite or at 180 degrees from one another, and second exterior surface 5 comprises two such surfaces opposite or at 180 degrees from one another. Also, hollow tube first distal opening 7 is positioned on each of two opposite sides of hollow tube 2 at second end 8, each opening from hollow tube first exterior surface 3.

Figure 23:
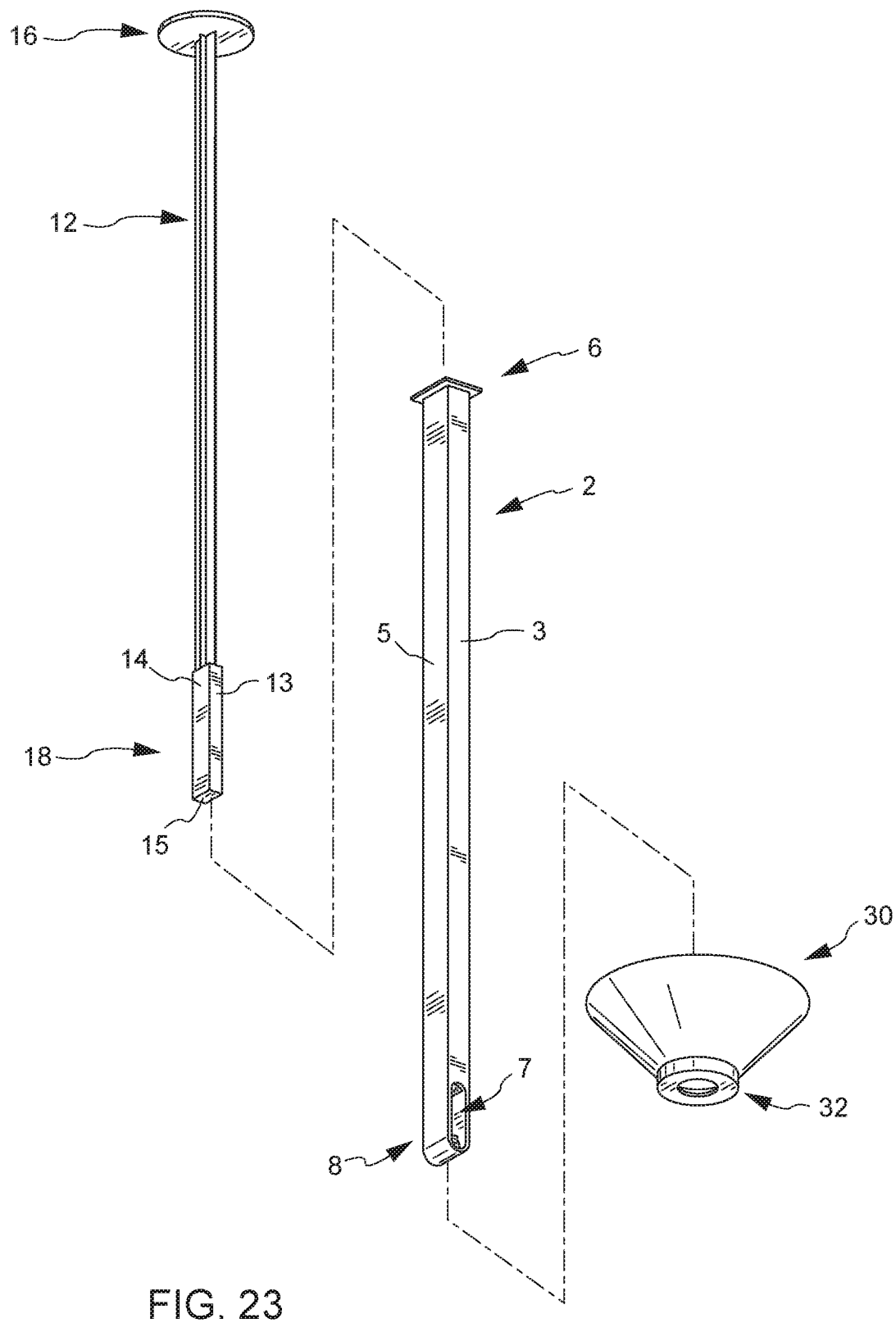
FIG. 23 is a front perspective exploded view of the device shown in FIG. 22.

Funnel 30 is configured with sleeve 32 such that funnel 30 may be positioned at second end 8 of hollow tube 2 such that hollow tube may fit through funnel 30, enabling funnel 30 to move along hollow tube 2 from second end 8 of hollow tube 2 to first end 6 of hollow tube 2 until funnel 30 engages first end 6 of hollow tube, such as at protrusion or shelf depicted in FIG. 23.

Plunger 12 comprises handle 16 at upper or proximal end of plunger 12, plunger distal or second end 18. Plunger second end 18 comprises distal first surface 13, distal second surface 14 and distal third (or bottom) surface 15. Plunger second end 18 is generally of symmetrical shape such that distal first surface 13 comprises two such surfaces opposite or at 180 degrees from one another, and distal third surface 15 comprises two such surfaces opposite or at 180 degrees from one another. Plunger 12 is configured such that second end 18 forms a congruent or conformal engagement with the interior of the hollow tube 2. Stated another way, the plunger second end 18 fits within the hollow tube 2 so as to slide within the hollow tube with minimal to no effective spacing between the exterior surface of the plunger second end 18 and the interior of the hollow tube 2, thereby forcing through bone graft material positioned in the hollow tube 2 through the hollow tube when the plunger 12 (and thus its second end 18) is axially moved from hollow tube first end 6 to hollow tube second end 8.

Figure 29:
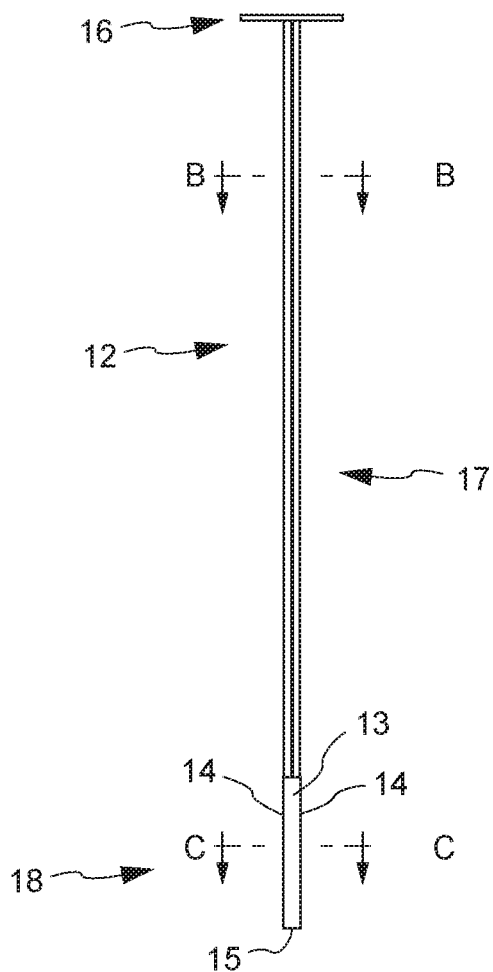
FIG. 29 is a front elevation view of the plunger element of the device shown in FIG. 22.
Figure 30:
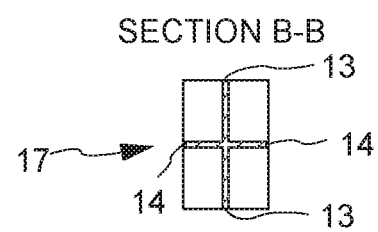
FIG. 30 is a cross-sectional view of section B-B of FIG. 29.
Figure 31:
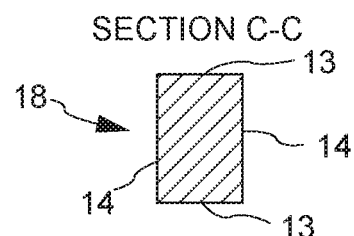
FIG. 31 is a cross-sectional of section C-C of FIG. 29.

In regard to FIGS. 29-31, further features of the plunger 12 are described. FIG. 29 is a front elevation view of the plunger element of the device shown in FIG. 22, FIG. 30 is a cross-sectional view of section B-B of FIG. 29, and FIG. 31 is a cross-sectional of section C-C of FIG. 29. Plunger 12 comprises handle 16 at upper or proximal end of plunger 12, plunger distal or second end 18. Plunger second end 18 comprises distal first surface 13, distal second surface 14 and distal third (or bottom) surface 15. Plunger medial portion 17 forms a cross configuration, as depicted in FIG. 30, such that distal first surfaces 13 are of reduced width relative to width at second end 18. Similarly, plunger distal second surfaces 14, at plunger medial portion 17, are of reduced width relative to width at second end 18. At distal end 18 of plunger 12, plunger cross-section is a rectangle, as depicted in FIG. 31.

Figure 32:
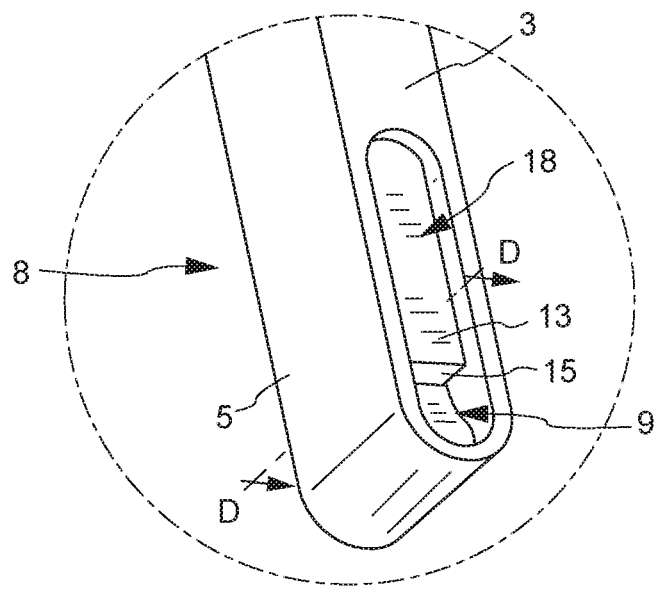
FIG. 32 is a detailed front perspective view of a portion of the device shown in FIG. 22.
Figure 33:
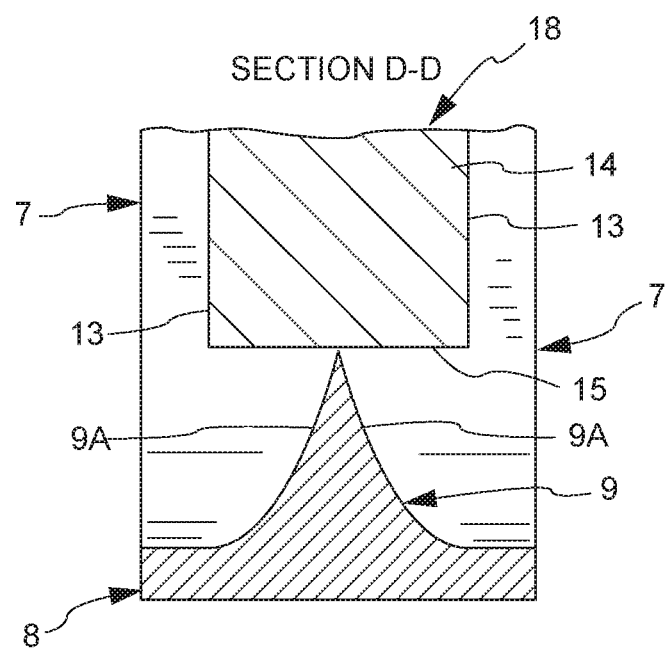
FIG. 33 is a cross-sectional view of section D-D of FIG. 32.

In regard to FIGS. 32 and 33, additional detail of the distal portion of device 1 are provided. FIG. 32 is a detailed view of a portion of the device 1 shown in FIG. 22 and FIG. 33 is a cross-sectional view of section D-D of FIG. 32. Each of FIGS. 32 and 33 depict the device 1 when the plunger 12 is fully inserted into the hollow tube 2, and the plunger distal third surface 15 has engaged and is in contact with the hollow tube distal interior ramp 9. Hollow tube distal interior ramp 9 comprises hollow tube distal interior ramp surfaces 9A, symmetrically positioned about the middle of the hollow tube second end 8. Hollow tube distal interior ramp surfaces 9A are of curvilinear shape forming a terminus, and urge bone graft material, when disposed within the hollow tube 2, to substantially exit the pair of first distal openings 7 of the device 1.

Referring now to FIGS. 36-39 another embodiment of an integrated fusion cage and graft delivery device 1 is provided. With reference to FIGS. 36-39, the integrated fusion cage and graft delivery device 1 comprises plunger 12, hollow tube 2, fusion cage 60 and ejection tool 140. The fusion cage 60 comprises fusion cage second or distal end 64 with tapered end feature and fusion cage first or proximal end 62 comprising fusion cage collar 92, fusion cage collar face 93 and fusion cage collar cavity 94. Hollow tube 2 comprises hollow tube second end 8 which engages fusion cage collar 92 by fitting over fusion cage collar 92 in a press or interference fit. Plunger 12 fits within hollow tube 12, and further may optionally fit within fusion cage collar cavity 94 so as to enter into interior of fusion cage 60 as previously described above.

Ejection tool 140 comprises ejection tool second or distal end 152 and ejection tool first or proximal end 142. Ejection tool second end 152 engages fusion cage collar face 93 to apply force or push fusion cage 60 from engagement with hollow tube 2. Ejection tool second end 152 is configured such that it may not travel past or into the fusion cage. When sufficient axial force is applied to the ejection tool 140 in the direction of the fusion cage 60, the interference fit that secures the fusion cage 60 (at fusion cage collar 92) to hollow tube 2 (at second end 8 of hollow tube) is overcome and the fusion cage 60 is released or disengaged from the hollow tube 2. Ejection tool 140 further comprises an ejection tool L-cut 151 that engages knobs 6A of hollow tube 2. In one embodiment, knobs 6A of hollow tube 2 are configured to additionally or alternatively engage L-cuts of the funnel 30 at funnel sleeve 32 (See FIG. 23). Plunger 16 further comprises handle 16 and plunger stop 16A which engages upper portion of hollow tube 2. Plunger stop 16A may be configured to prevent plunger distal most portion from entering fusion cage collar cavity 94 and therefore further prevent entry into interior of fusion cage 60.

Fusion cage 60 further comprises fusion cage internal ramps 72 as described above. The fusion cage internal ramps 72 may be symmetrical about a centerline of the device 1, and may be linear or sloped inwardly. In one embodiment, plunger stop 16A may be configured to prevent plunger distal most portion from striking or contacting fusion cage internal ramps 72 but otherwise allowing entry into fusion cage collar cavity 94 and therefore also allow entry into interior of fusion cage 60.

Fusion cage 60 further comprises fusion cage first opening or port pair 65 and fusion cage second opening or port pair 67. Fusion cage first opening pair 65 are symmetric about a vertical plane intersecting a centerline of the fusion cage 60, and are located such that at least a portion of the openings are adjacent the tip of the fusion cage internal ramps 72. The fusion cage first opening pair 65 are of an oblong racetrack shape, but in other embodiments may be oval, circular and rectangular. The fusion cage second opening pair 67 are of an oval shape, but in other embodiments may be oblong racetrack, circular and rectangular. The fusion cage may have rounded or no square edges, and may have a non-smooth exterior surface or any or all portions. That is, the fusion cage 60 may have ridges, bumps, contours, sawtooth profile edges along or on top of any or all exterior surfaces, such as surfaces adjacent the fusion cage second opening pair 67 and/or fusion cage first opening pair 65.

Figure 40:
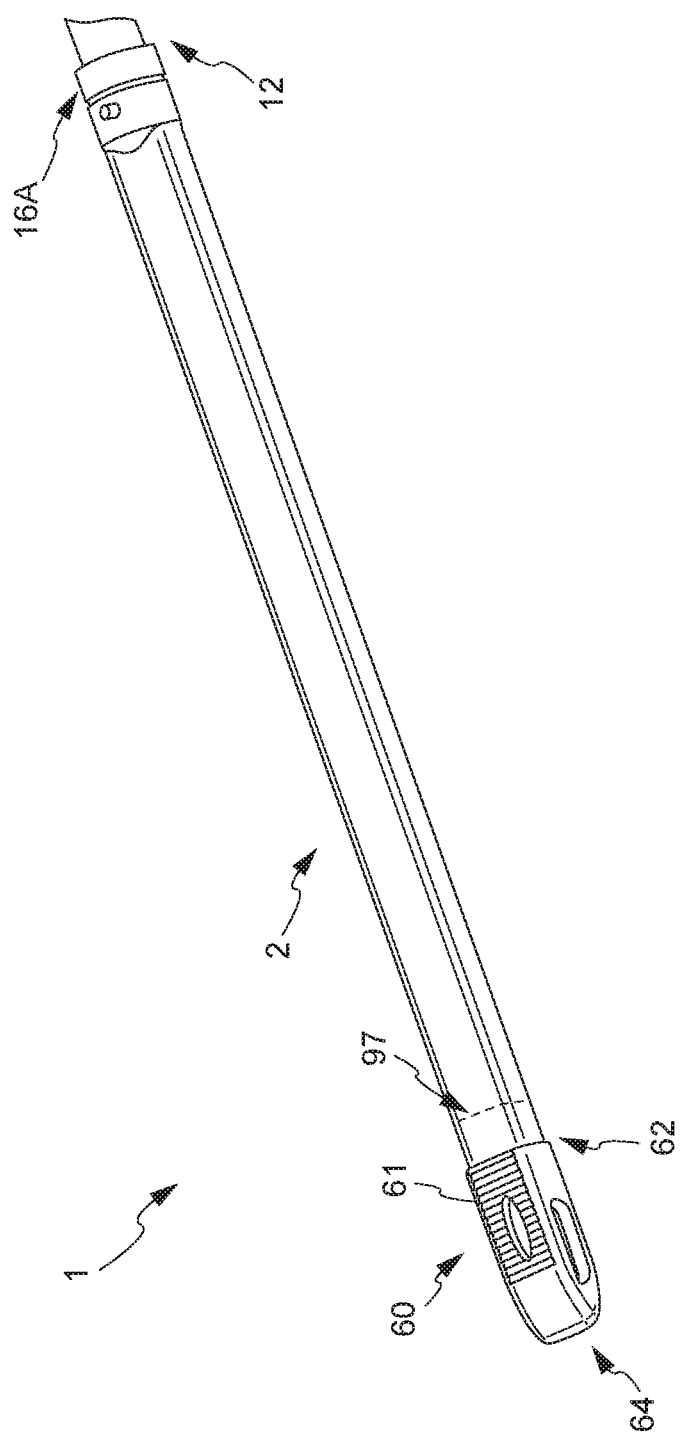
FIG. 40 is a front perspective view of an integrated fusion cage and graft delivery device according to yet another embodiment.
Figure 41:
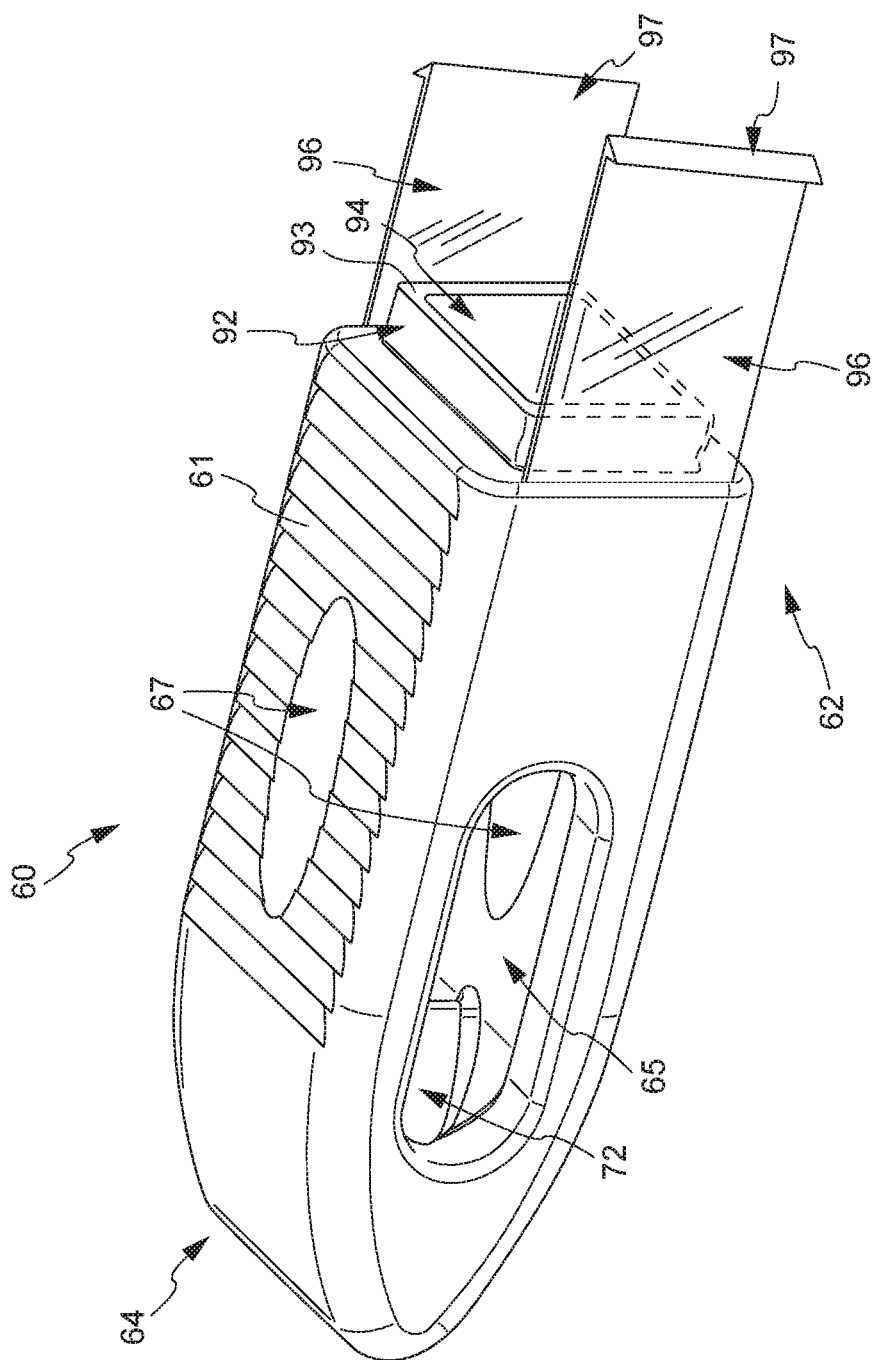
FIG. 41 is a closed-up front perspective view of the device of FIG. 40.

Referring now to FIGS. 40-41, another embodiment of an integrated fusion cage and graft delivery device 1 is provided. FIG. 40 is a front perspective view of an integrated fusion cage and graft delivery device 1, and FIG. 41 is a closed-up front perspective view of a portion of the device of FIG. 40. The embodiment of FIGS. 40-41 comprises a pair of fusion cage tab extensions 96, each of which comprises a fusion cage tab extension latch 97. Integrated fusion cage and graft delivery device 1 comprises plunger 12, hollow tube 2 and fusion cage 60. FIG. 40 depicts the integrated fusion cage and graft delivery device 1 with plunger 12 fully inserted into hollow tube 2 such that plunger stop 16A engages upper portion of hollow tube 2. The fusion cage 60 comprises fusion cage second or distal end 64 with tapered end feature and fusion cage first or proximal end 62 comprising fusion cage collar 92, fusion cage collar face 93 and fusion cage collar cavity 94.

Fusion cage 60 further comprises fusion cage internal ramps 72 as described above. The fusion cage internal ramps 72 may be symmetrical about a centerline of the device 1, and may be linear or sloped inwardly. Fusion cage 60 further comprises fusion cage first opening or port pair 65 and fusion cage second opening or port pair 67. Fusion cage first opening pair 65 are symmetric about a vertical plane intersecting a centerline of the fusion cage 60, and are located such that at least a portion of the openings are adjacent the tip of the fusion cage internal ramps 72. The fusion cage first opening pair 65 are of an oblong racetrack shape, but in other embodiments may be oval, circular and rectangular. The fusion cage second opening pair 67 are of an oval shape, but in other embodiments may be oblong racetrack, circular and rectangular. The fusion cage may have rounded or no square edges. Fusion cage 60 has fusion cage surface texture 61, depicted as a series of lateral sawtooth-like ridges.

Fusion cage tab extensions 96, each of which comprises a fusion cage tab extension latch 97, function, among other things, to increase stability of the interface or connection between the distal end of the hollow tube 2 and the fusion cage 60. The fusion cage tab extension latches 97 may be configured to engage corresponding grooves on the interior surface of the hollow tube 2. The fusion cage tab extensions 96 fit inside the end of the hollow tube and, in one embodiment, provide a force directed outwards to or against the interior of the hollow tube. The vertical height and longitudinal (axial) length of the fusion cage tab extensions 96 provide more secure fit between the hollow tube 2 and the fusion cage 60 by restricting rotational movement, for example, of the hollow tube 2 with respect to the fusion cage 60. After bone graft material is provided to the fusion cage 60 by way of the plunger 12 (as described above), the fusion cage tab extensions 96 may be broken-off by application of a tool, such as the ejection tool 140, engaged with the fusion cage tab extension latches 97 so as to fatigue or otherwise severe the fusion cage tab extensions 96.

Figure 42:
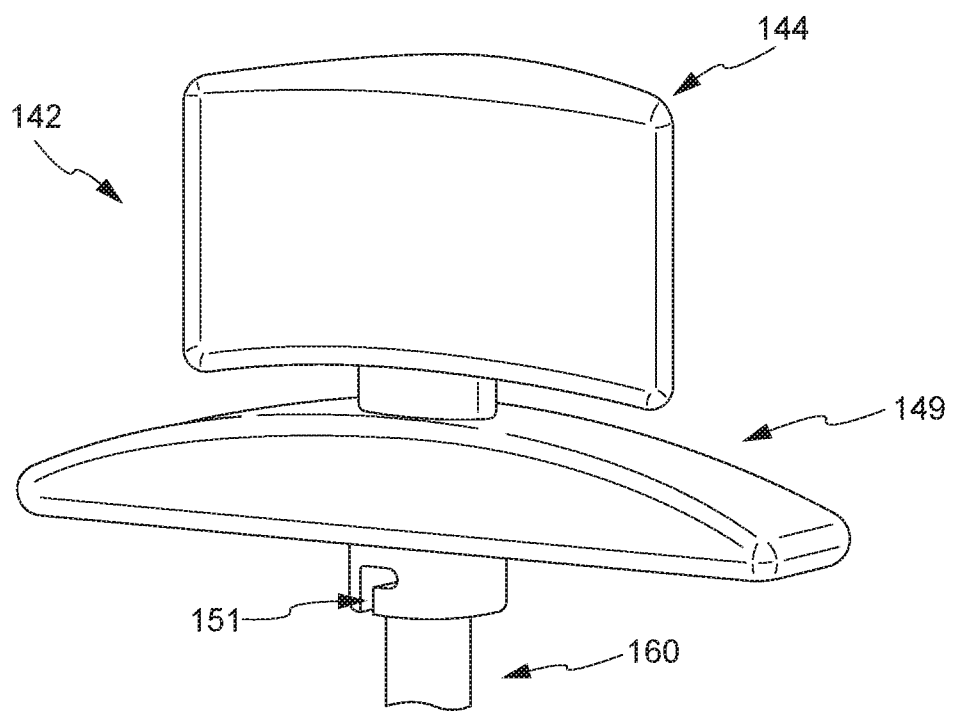
FIG. 42 is a close-up front perspective view of the ejection tool element first end.
Figure 43:
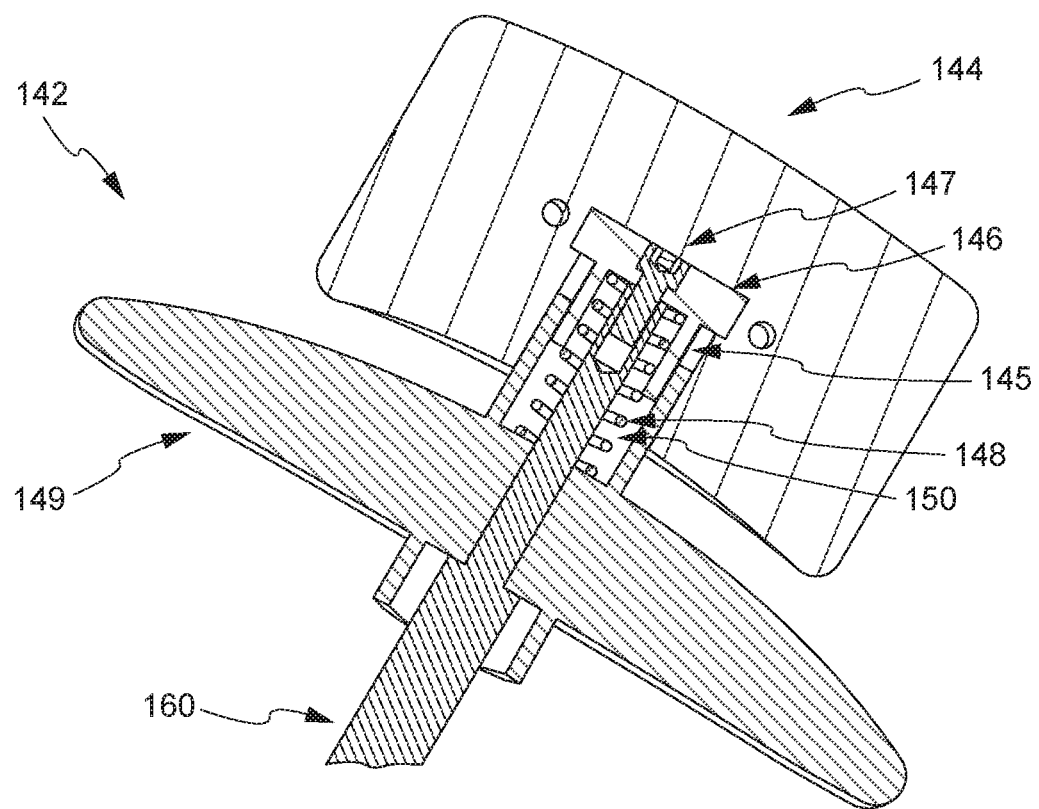
FIG. 43 is a cut-away cross-sectional view of the element of FIG. 42.

Referring now to FIGS. 42-43, another embodiment of the ejection tool 140 of an integrated fusion cage and graft delivery device 1 is provided. FIG. 42 is a close-up front perspective view of the ejection tool first end 142, and FIG. 43 is a cut-away cross-sectional view of FIG. 42. Ejection tool 140 comprises ejection tool cover 144 which engages ejection tool wings 149. Ejection tool 140 engages with hollow tube 2 at hollow tube knobs 6A via ejection tool L-cuts 151. Ejection tool cover 144 comprises cylindrically-shaped ejection tool cover cavity 145 which fits over cylindrically-shaped ejection tool wings cavity 150 and over spring cover 146. Spring cover is secured to ejection tool cover 144 by spring cover attachment 147, which may be a pin, a screw or other means known in the art, and further fits around at least a portion of coiled spring 148. When ejection tool cover 144 is pushed downward toward fusion cage 60, the spring 148 compresses and imparts a force in the opposite direction, thereby returning the ejection tool cover 144 to its original (retracted) position. In use, after securing the ejection tool first end 142 to hollow tube 2 as described above, the user (e.g. surgeon) squeezes the injection tool cover 144 against the ejection tool wings 149, thereby advancing the ejection tool rod 160 downwards inside the hollow tube so as to engage the fusion cage 60 at the fusion cage collar face 93 and release or disengage the fusion cage 60 from the hollow tube 2. The injection tool 140 and hollow tube 2 may then be removed from the surgical site (e.g. spinal disk space) as one unit, leaving the fusion cage in the surgical site.

Figure 44:
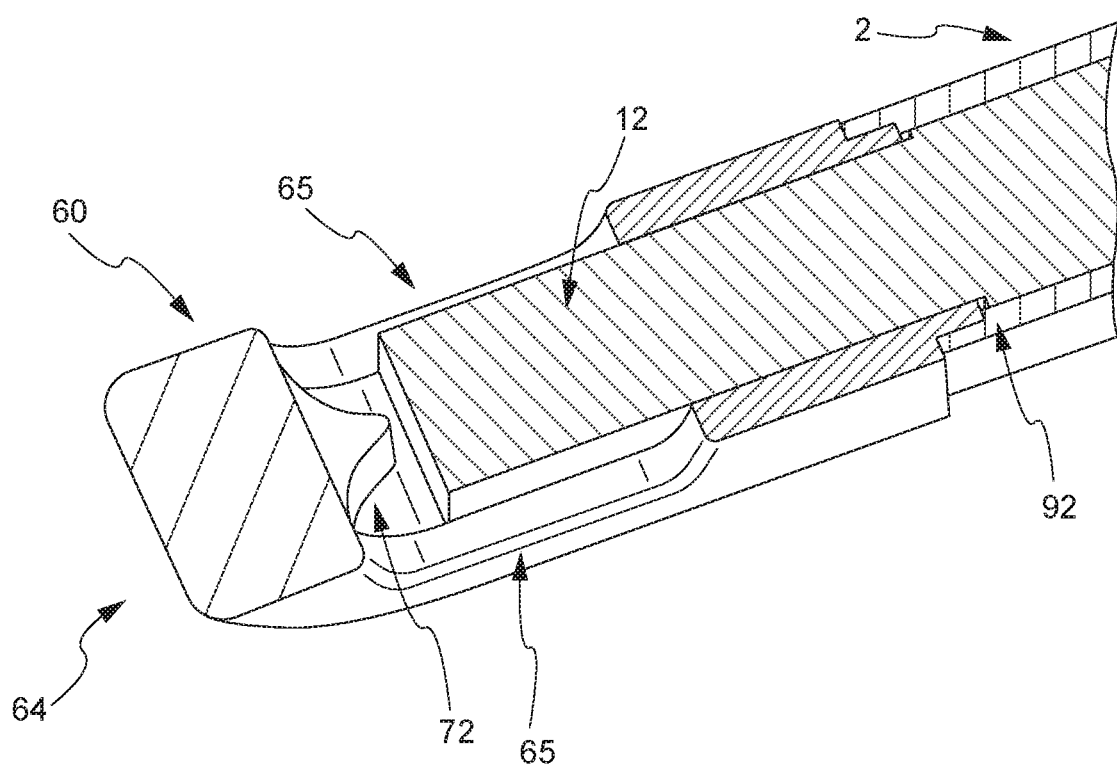
FIG. 44 is a close-up cut-away cross-sectional view of one embodiment of the integrated fusion cage and graft delivery device.
Figure 47A:
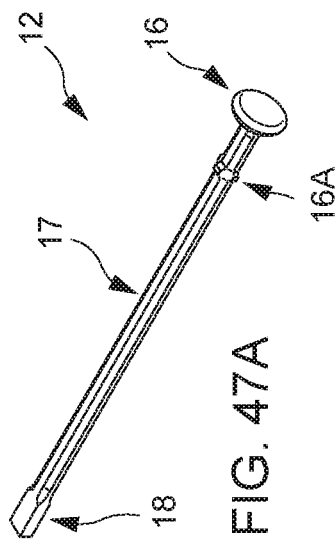
FIGS. 47A-D provide scaled views of one embodiment of the plunger (aka snap on plunger) of the integrated fusion cage and graft delivery device configured to operate with the fusion cage element of FIGS. 45A-G, hollow tube of FIGS. 46A-H, and ejection tool of FIGS. 48A-E.
Figure 47D:
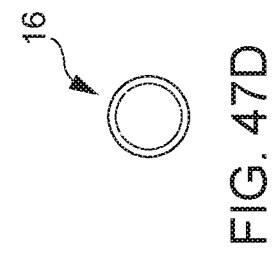
Figure 47C:
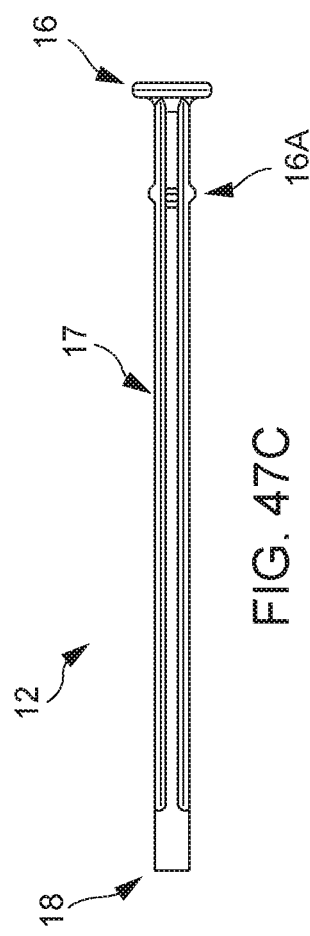
Figure 47B:
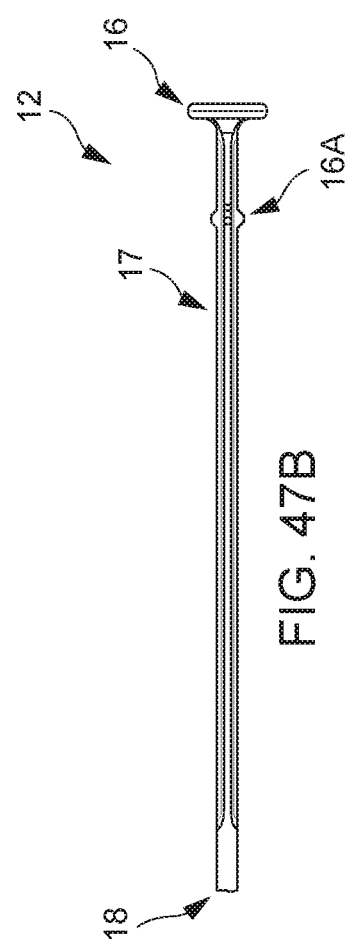

FIG. 44 is a close-up cut-away cross-sectional view of one embodiment of the integrated fusion cage and graft delivery device 1. FIG. 44 depicts a configuration of the integrated fusion cage and graft delivery device 1 wherein the plunger 12 is configured to traverse the length of the hollow tube 2, past the fusion cage collar 92 and into the fusion cage 60, stopping just prior to engaging the tip of the fusion cage internal ramps 72. Fusion cage 60 is depicted with fusion cage first opening pair 65 and fusion cage second end 64.

FIGS. 45-48 are scaled drawings of, respectively, the fusion cage 60, the hollow tube 2, the plunger 12 and the ejection tool 140 of yet another embodiment of the integrated fusion cage and graft delivery device 1, and operate in coordination with one another.

FIGS. 45A-G provide scaled views of one embodiment of the fusion cage element of yet another embodiment of the integrated fusion cage and graft delivery device configured to operate with the hollow tube of FIGS. 46A-H, plunger of FIGS. 47A-D and ejection tool of FIGS. 48A-E. Fusion cage 60 comprises fusion cage second or distal end 64 with tapered end feature and fusion cage first or proximal end 62 comprising fusion cage collar 92, fusion cage collar face 93 and fusion cage collar cavity 94. Fusion cage 60 further comprises fusion cage first opening or port pair 65, fusion cage second opening or port pair 67, fusion cage surface texture 61 and fusion cage internal ramps 72.

FIGS. 46A-H provide scaled views of one embodiment of the hollow tube (aka snap on cannula) of the integrated fusion cage and graft delivery device configured to operate with the fusion cage element of FIGS. 45A-G, plunger of FIGS. 47A-D and ejection tool of FIGS. 48A-E. Hollow tube 2 comprises first end 6 with knobs 6A and second end 8 comprising hollow tube cage clamp 8A and hollow tube cage clamp radial surface 8B. Hollow tube cage clamp radial surface 8B is configured to engage fusion cage collar 92, for example by an interference or friction fit (i.e. to "snap-on"). Other means of connection comprise those known to those skilled in the art, such as a threaded-screw engagement and a tongue and groove engagement.

FIGS. 47A-D provide scaled views of one embodiment of the plunger (aka snap on plunger) of the integrated fusion cage and graft delivery device configured to operate with the fusion cage element of FIGS. 45A-G, hollow tube of FIGS. 46A-H, and ejection tool of FIGS. 48A-E. Plunger 12 comprises handle 16, plunger stop 16A, plunger medial portion 17 and second end 18. Second end 18 may be configured to pass into and/or through fusion cage collar cavity 94.

FIGS. 48A-E provide scaled views of one embodiment of the ejection tool (aka cage insertion tool) of the integrated fusion cage and graft delivery device configured to operate with the fusion cage element of FIGS. 45A-G, hollow tube of FIGS. 46A-H and plunger of FIGS. 47A-D. Ejection tool 140 comprises ejection tool second or distal end 152, ejection tool first or proximal end 142 and ejection tool stop 143. Ejection tool second end 152 engages fusion cage collar face 93 to apply force or push fusion cage 60 from engagement with hollow tube 2. Ejection tool second end 152 is configured such that it may not travel past or into the fusion cage.

A method of use of the integrated fusion cage and graft delivery device 1 as depicted in any of the afore-mentioned embodiments of FIGS. 37-48 would be performed as follows. The fusion cage 60 is attached to the hollow tube 2 by way of the above-discussed interference fit at fusion cage collar 92 and interior surface of distal end of hollow tube 2. Funnel 30 is then attached to upper portion of hollow tube at first or upper or proximal end of hollow tube 2 via knobs 6A. Bone graft or other suitable substance as known to one skilled in the art is inserted at upper or first end 6 of hollow tube 2. Plunger 12 is then inserted into hollow tube 2 at upper or proximal end of hollow tube and pushed or advanced axially down interior of hollow tube, thereby urging or pushing or advancing the bone graft material down the hollow tube 2 toward fusion cage 60. Bone graft then proceeds into the fusion cage 60 whereby it at least substantially fills fusion cage 60 interior and further engages fusion cage internal ramps 72 and emits bone graft material through fusion cage first opening pair 65 and fusion cage second opening pair 67 and thus enters surgical area (e.g. a spinal surgical area). Upon sufficient user (i.e. surgeon) selectable injection of bone graft material into surgical site and fusion cage 60, the plunger 12 is retracted and removed from the hollow tube 2 by opposite axial movement, i.e. by moving the plunger 12 away from the fusion cage 60. The funnel 30 may then be optionally removed. Next, the ejection tool 140 is inserted into hollow tube 2 at upper or proximal end Ejection tool 140 is advanced until ejection tool second end 152 engages fusion cage collar face 93, whereupon downward force is applied to push fusion cage 60 from engagement with hollow tube 2. As discussed, ejection tool second end 152 is configured such that it may not travel past or into the fusion cage. When sufficient axial force is applied to the ejection tool 140 in the direction of the fusion cage 60, the interference fit that secures the fusion cage 60 (at fusion cage collar 92) to hollow tube 2 (at second end 8 of hollow tube) is overcome and the fusion cage 60 is released or disengaged from the hollow tube 2. The engagement tool 140, and the hollow tube 2 in which it is inserted, are then removed from the surgical site, leaving a fusion cage at least substantially filled with bone graft and a surgical site also at least substantially filled with bone graft.

In one embodiment, all or a portion of fusion cage collar 92 is of a material different than the remainder of the fusion cage 60, e.g. comprising a metal alloy. In one embodiment, a portion of the distal end of the hollow tube 2 is of a material different than the remainder of the hollow tube 2, e.g. comprising a metal alloy. In one embodiment, a portion of the distal end of the ejection tool is comprised of a metal alloy.

In one embodiment of the device, the tip of the hollow tube and/or fusion cage may separate under a threshold pressure as applied axially from the inside of the hollow tube or fusion cage respectively. Such a user-selected threshold would allow bone graft material to enter the surgical site if bone graft material becomes clogged in the hollow tube and/or fusion cage.

Figure 49A:
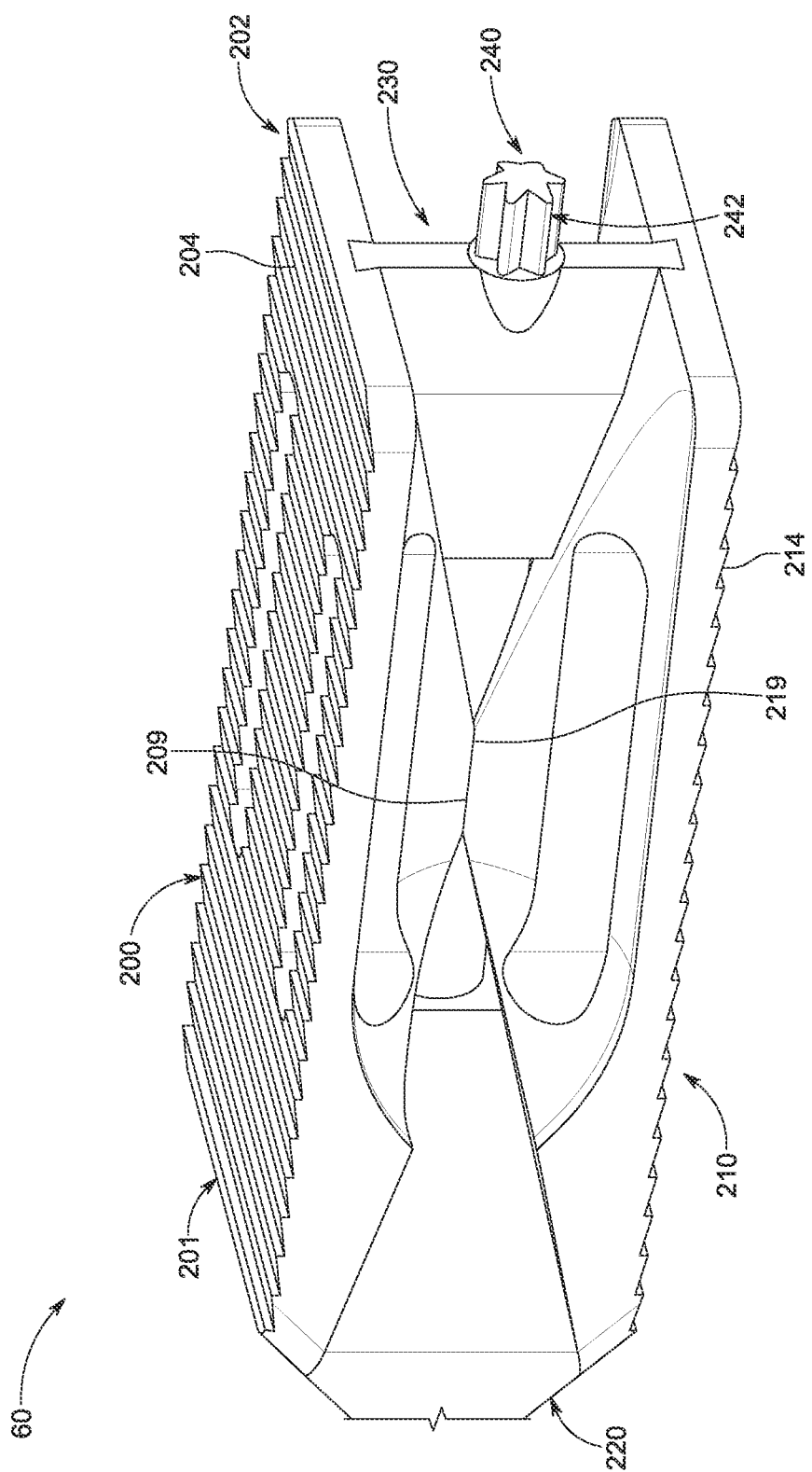
FIG. 49A is a left perspective view of an embodiment of the fusion cage with expandable fusion cage feature, the fusion cage in an unexpanded state.
Figure 49B:
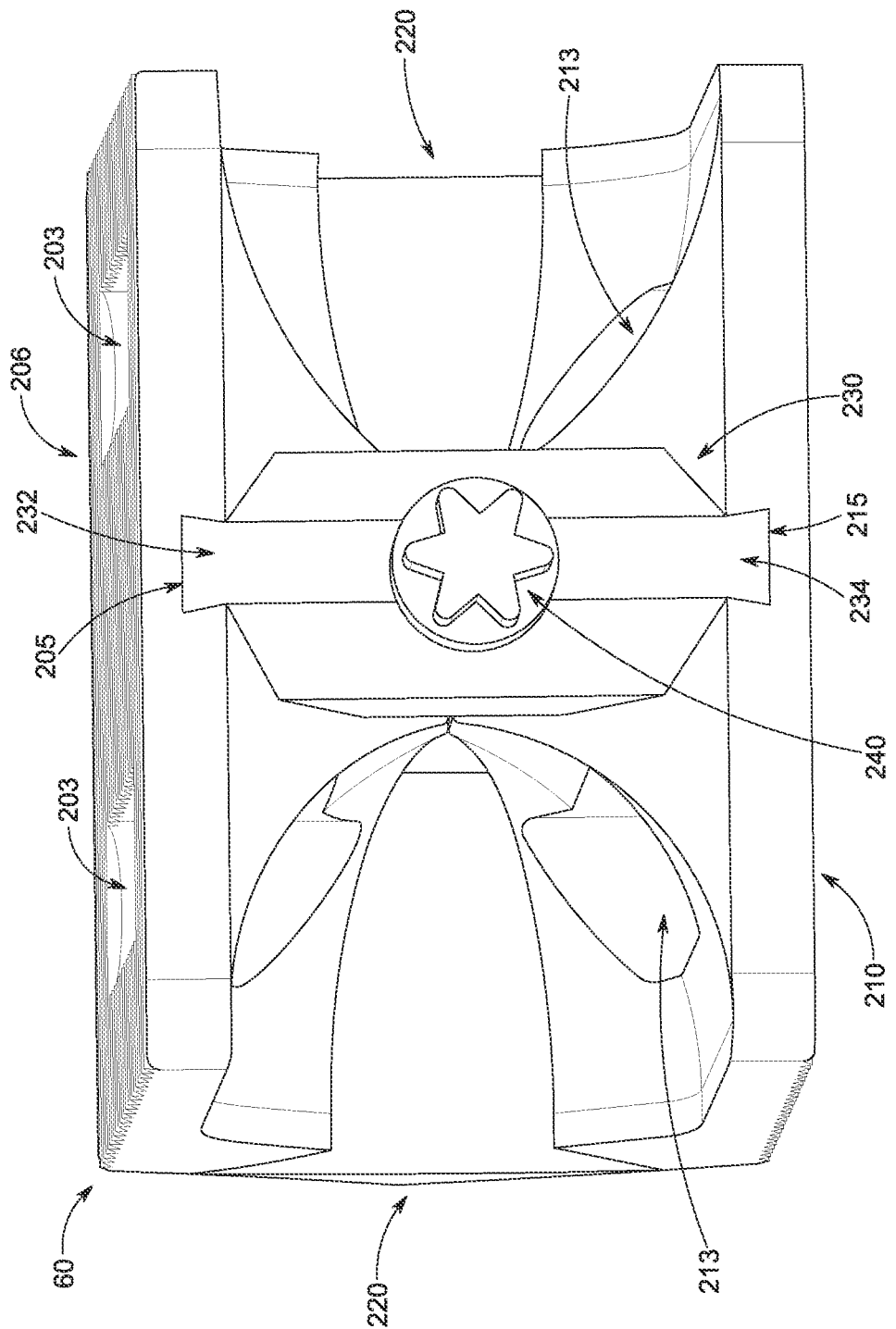
FIG. 49B is a rear perspective view of the device shown in FIG. 49A.
Figure 49C:
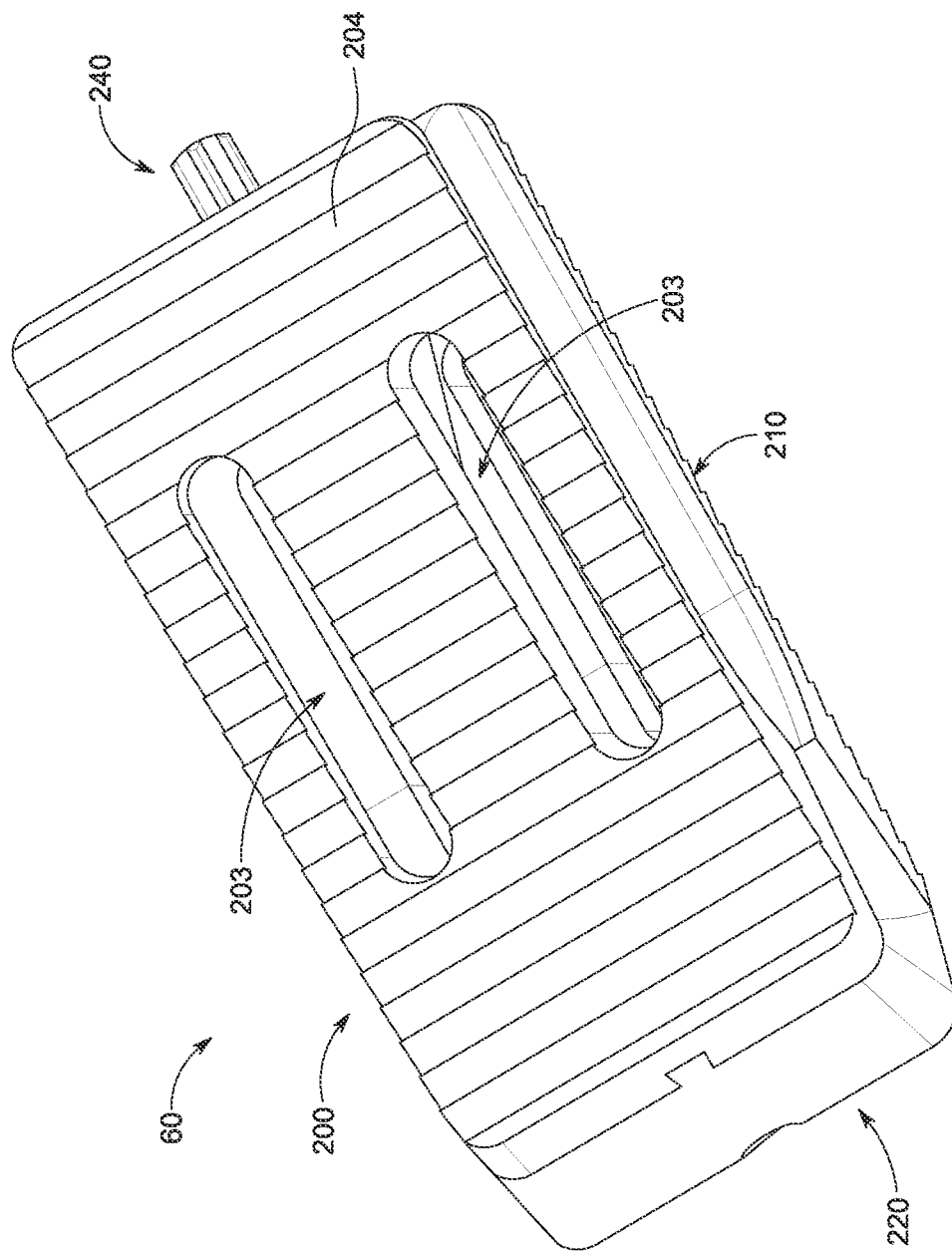
FIG. 49C is a top perspective view of the device shown in FIG. 49A.
Figure 50A:
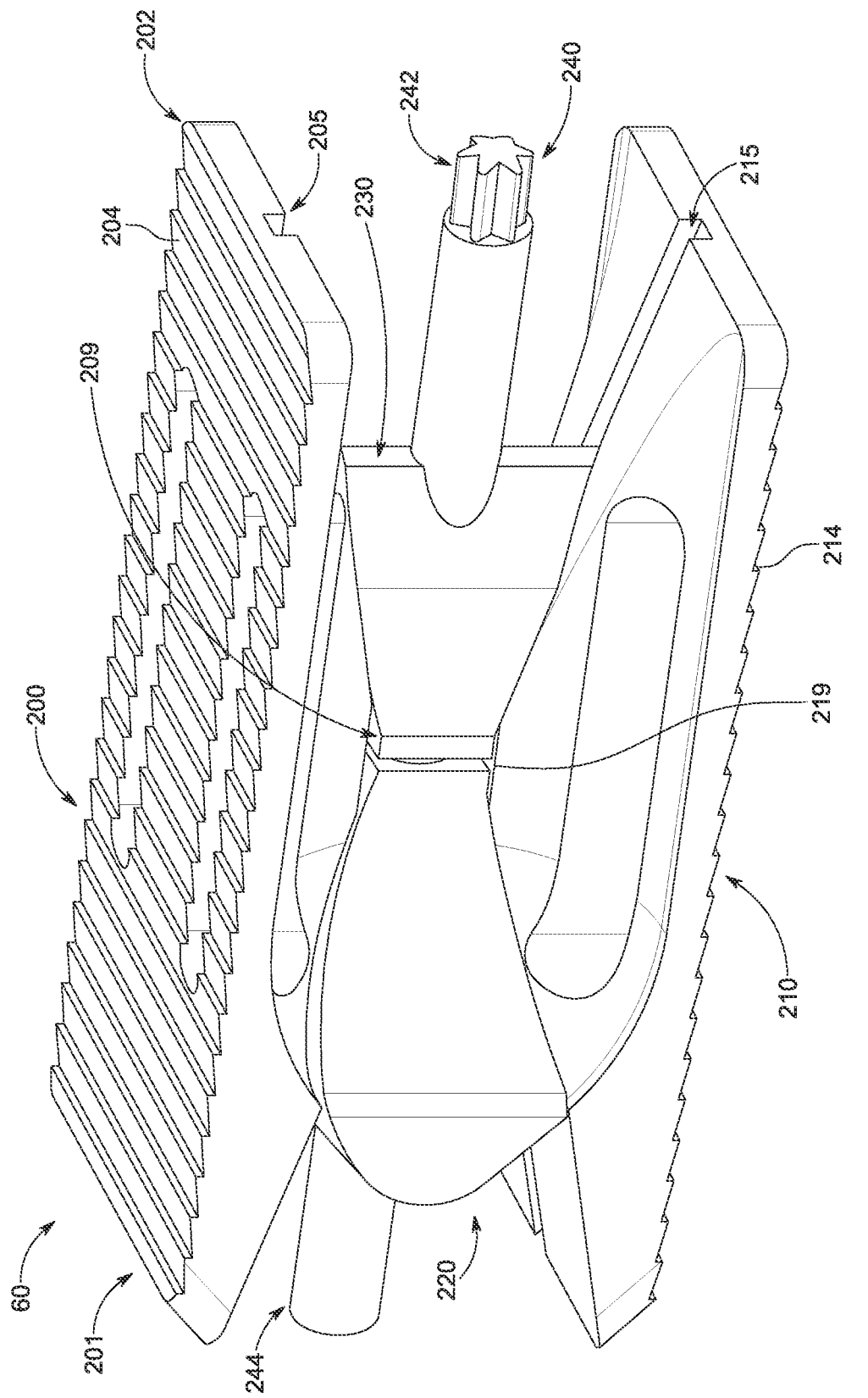
FIG. 50A is a left perspective view of the device shown in FIG. 49A, the fusion cage in an expanded state.
Figure 50B:
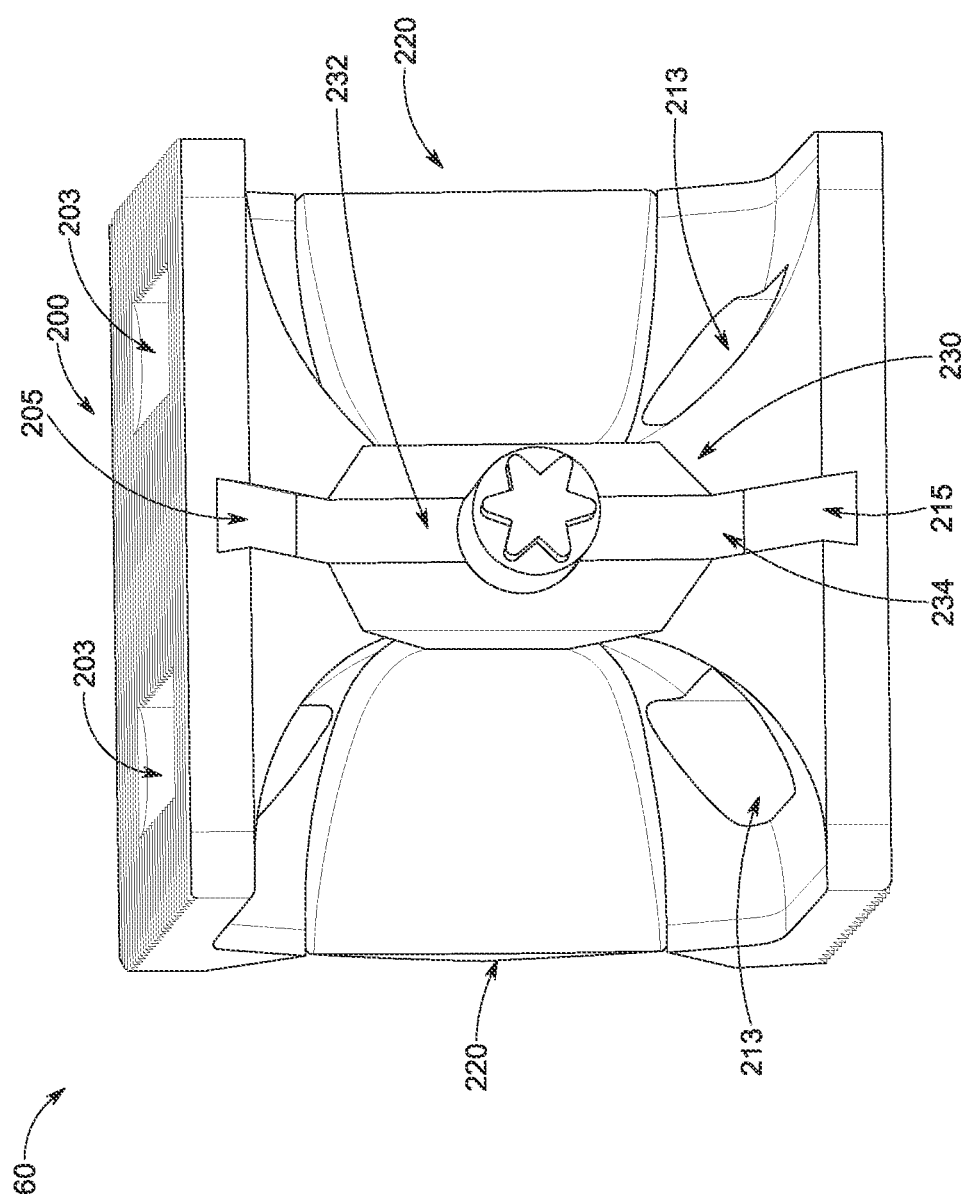
FIG. 50B is a rear perspective view of the device shown in FIG. 50A.
Figure 50C:
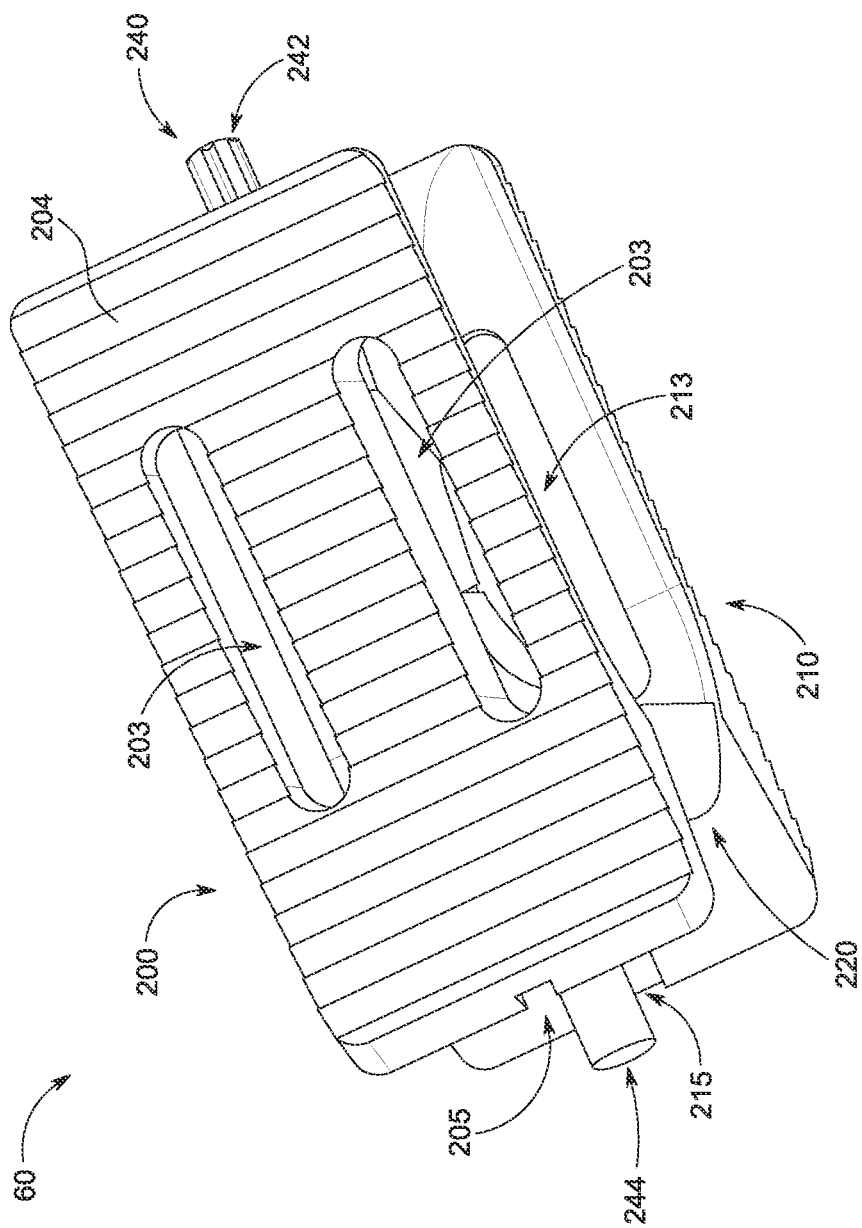
FIG. 50C is a top perspective view of the device shown in FIG. 50A.
Figure 51:
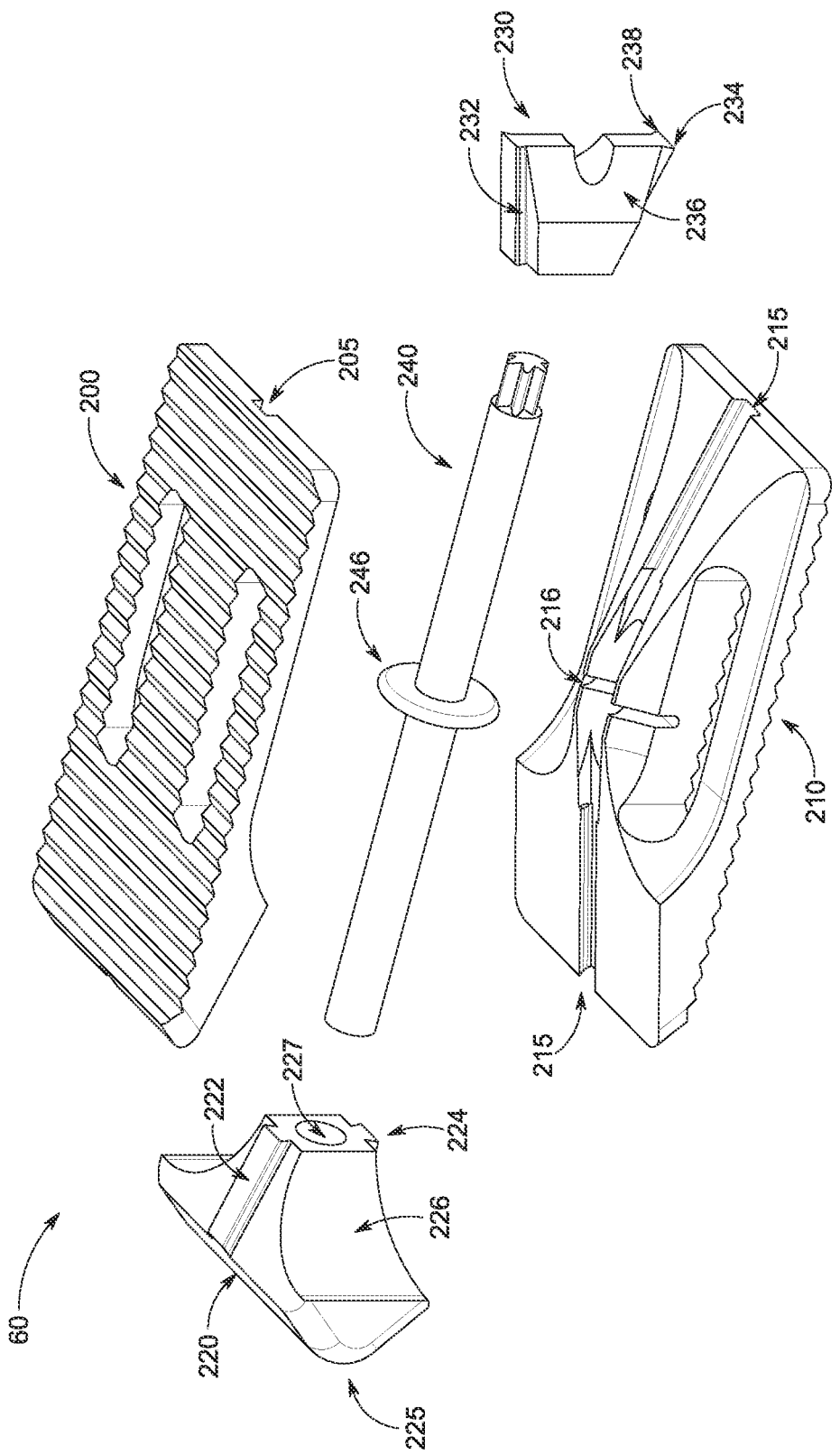
FIG. 51 is a scaled rear perspective exploded view of an embodiment of the fusion cage with expandable fusion cage feature.
Figure 52A:
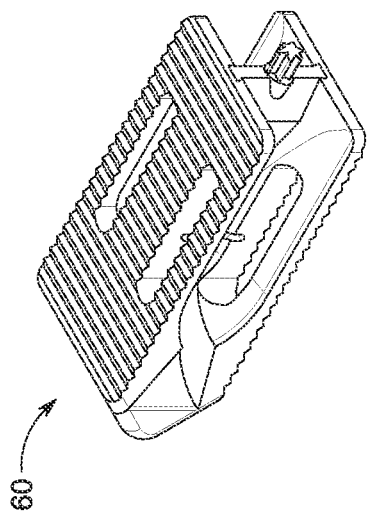
FIGS. 52A-E provide scaled views of the device shown in FIG. 51, the fusion cage in an unexpanded state.
Figure 52E:
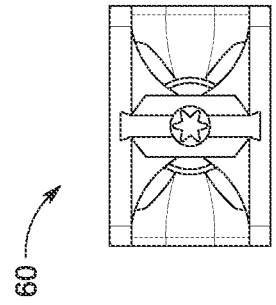
Figure 52C:
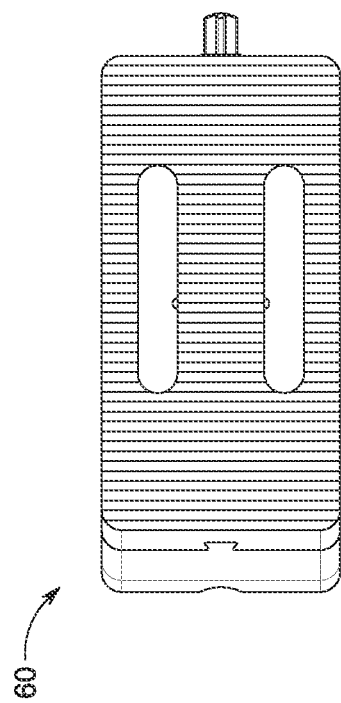
Figure 52B:
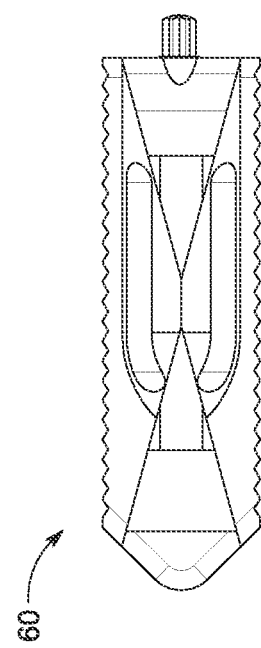
Figure 52D:
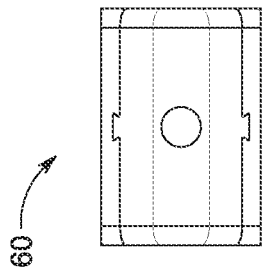
Figure 53A:
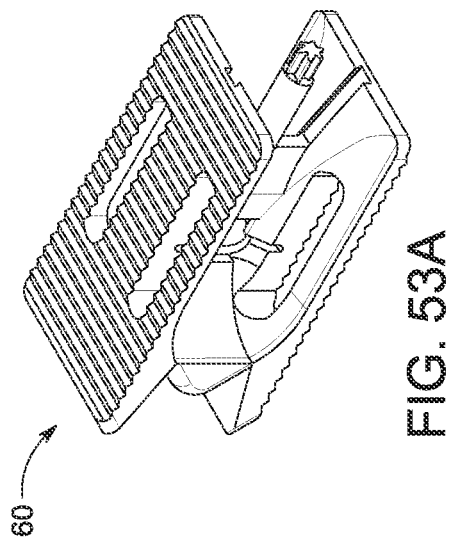
FIGS. 53A-E provide scaled views of the device shown in FIG. 51, the fusion cage in an expanded state.
Figure 53E:
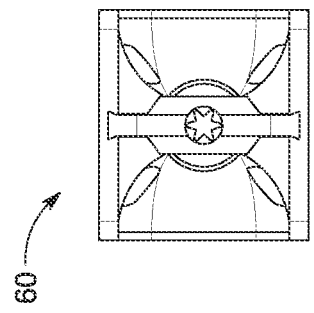
Figure 53C:
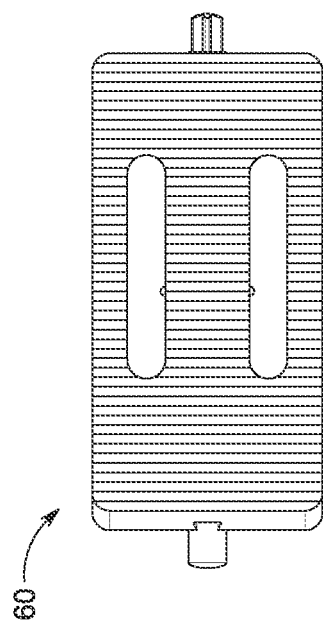
Figure 53B:
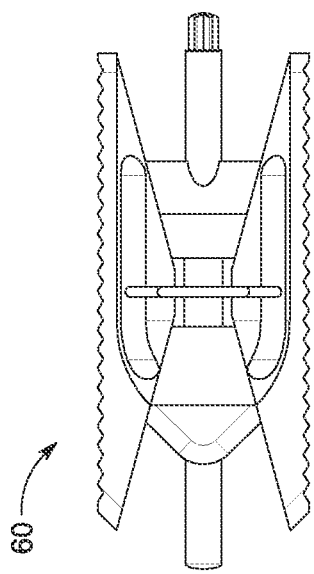
Figure 53D:
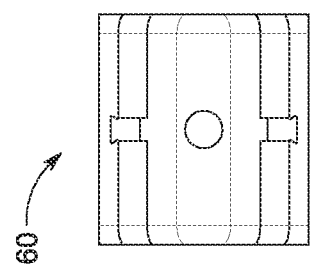
Figure 56F:
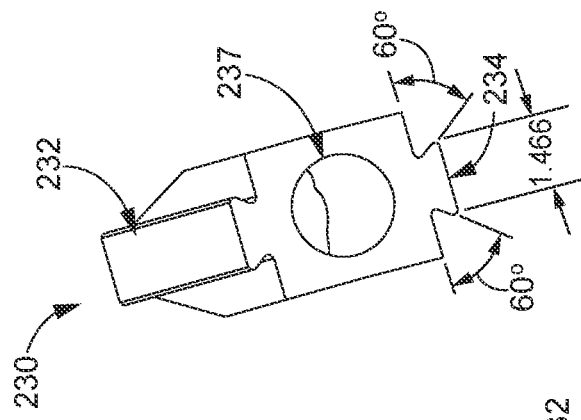
FIGS. 56A-F provide scaled views of the rear block component of the device shown in FIG. 51.
Figure 56E:
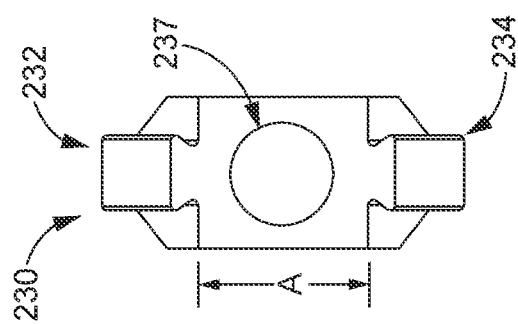
Figure 56C:
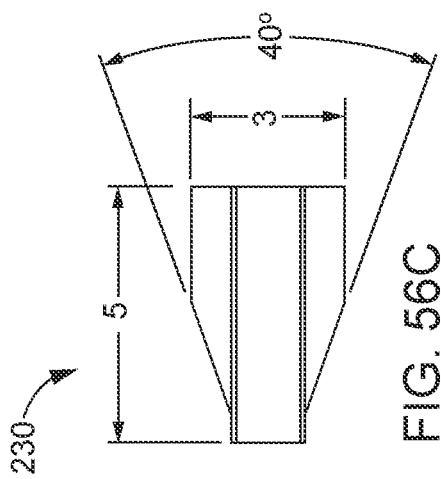
Figure 56B:
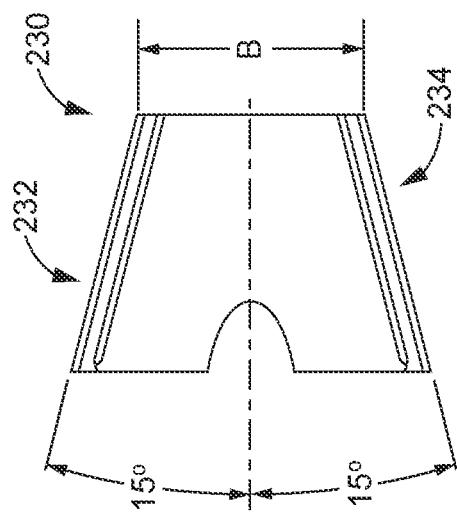
Figure 56A:
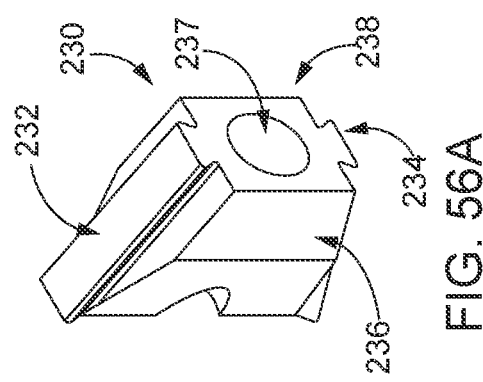
Figure 56D:
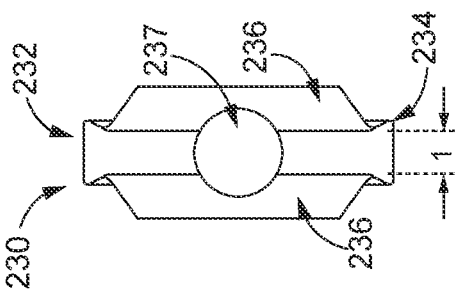
Figure 58:
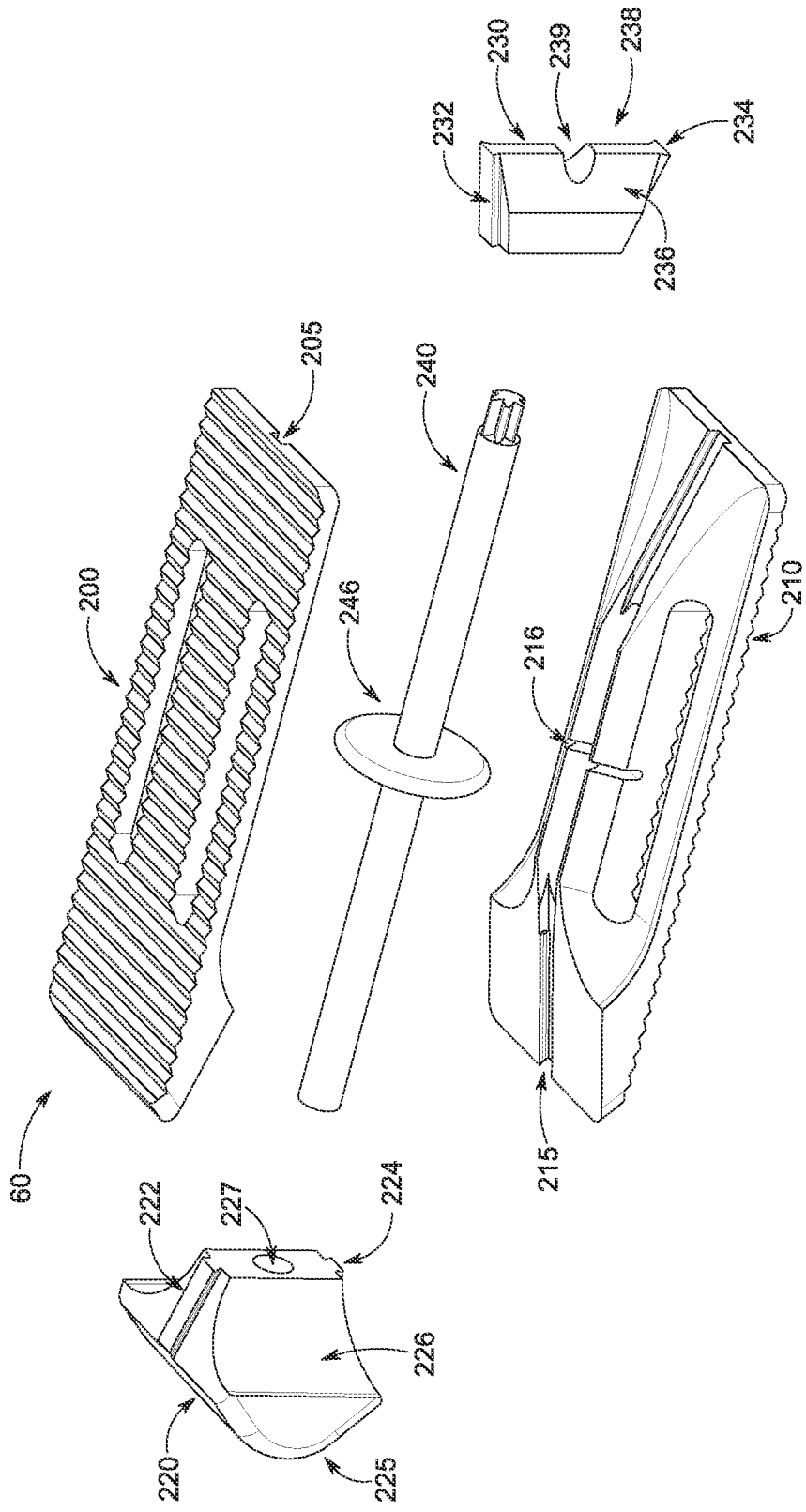
FIG. 58 is a rear perspective exploded view of another embodiment of the fusion cage with expandable fusion cage feature.
Figure 61A:
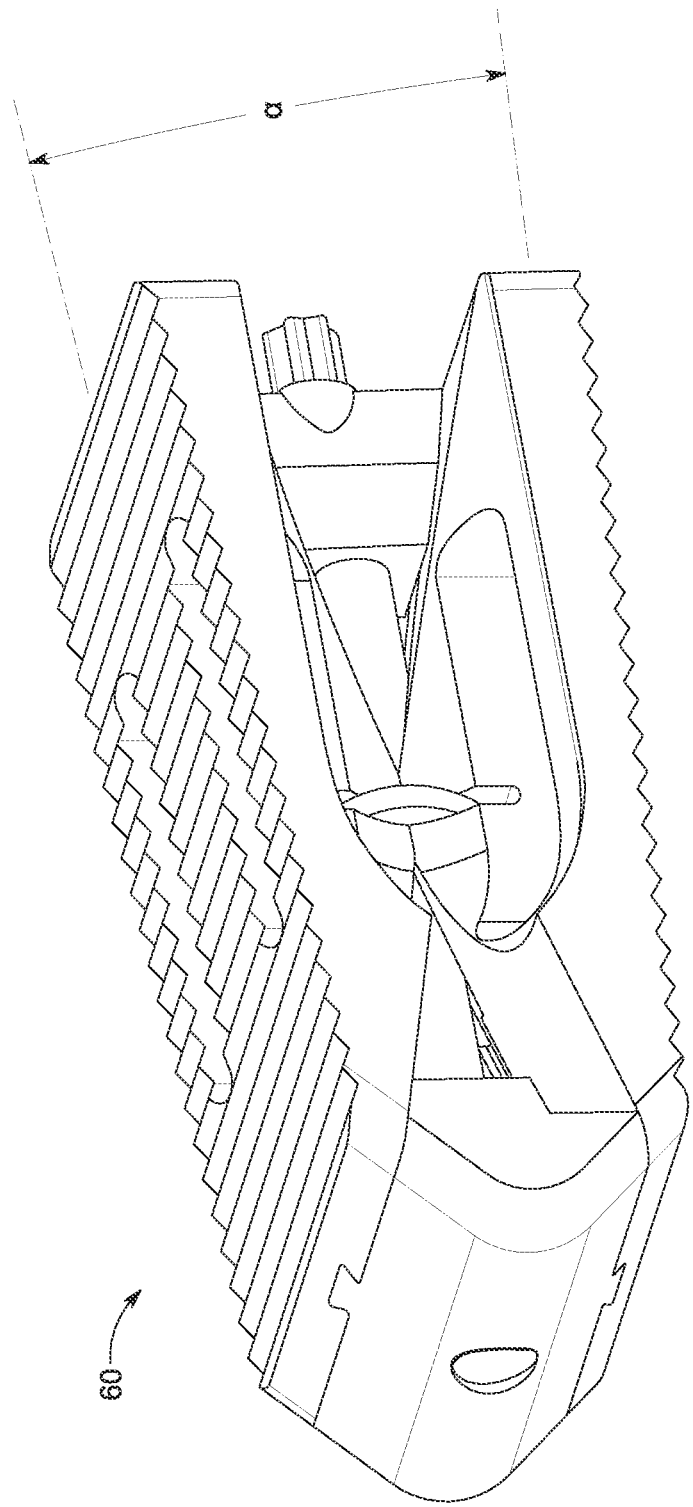
FIG. 61A is a front left perspective view of yet another embodiment of the fusion cage with expandable fusion cage feature, comprising a vertical wedge angle α feature.
Figure 61B:
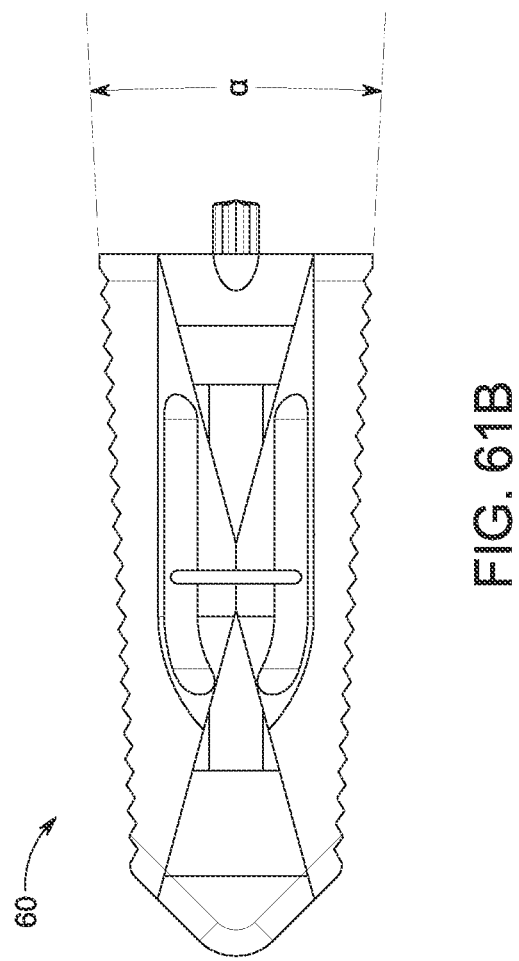
FIG. 61B is a left elevation view of the device of FIG. 61A.
Figure 62A:
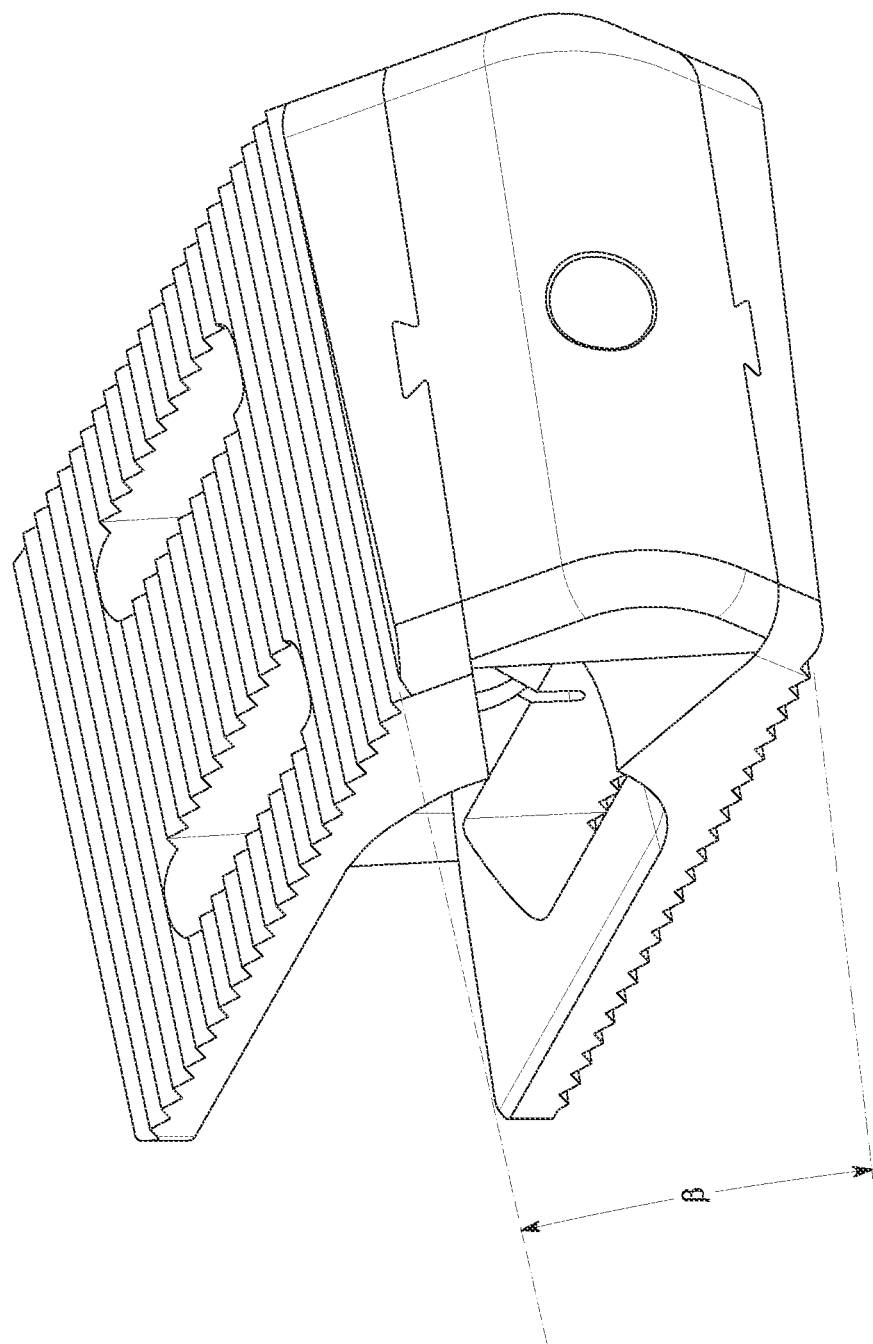
FIG. 62A is a front left perspective view of yet another embodiment of the fusion cage with expandable fusion cage feature, comprising a horizontal wedge angle β feature.
Figure 62B:
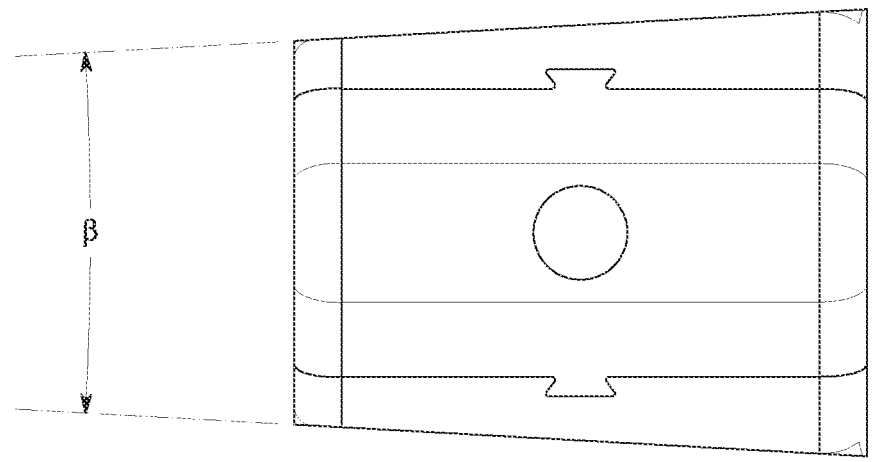
FIG. 62B is a left elevation view of the device of FIG. 62A.
Figure 63A:
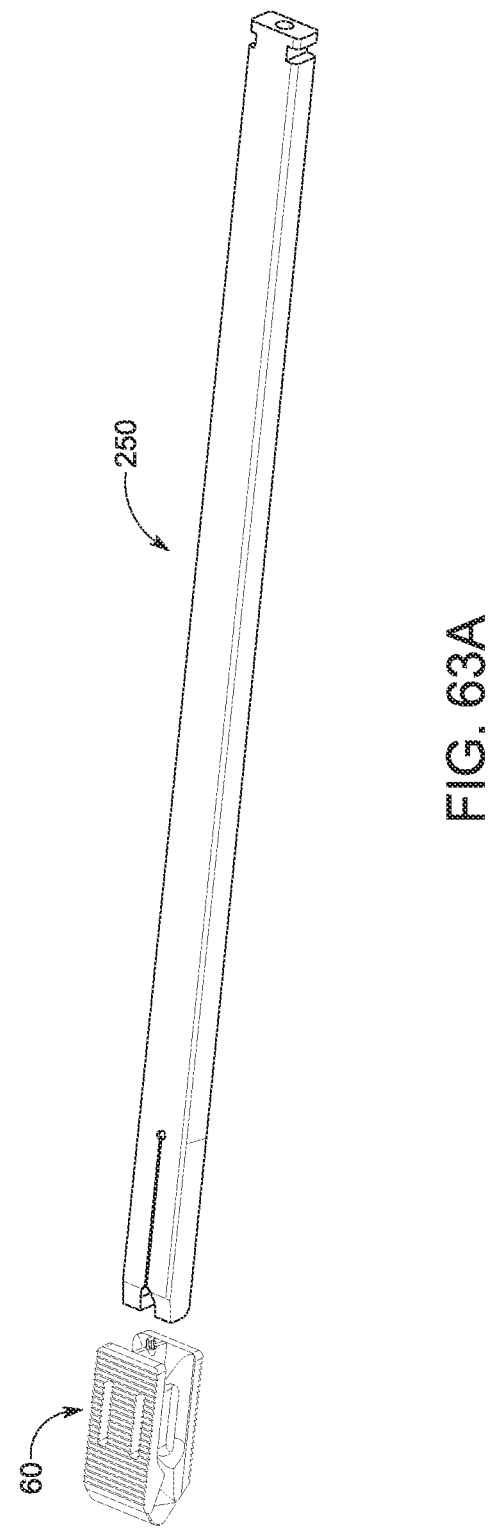
FIG. 63A is a left rear perspective view of a fusion cage with expandable fusion cage feature configured to communicate with an installer/impactor component according to yet another embodiment.
Figure 64:
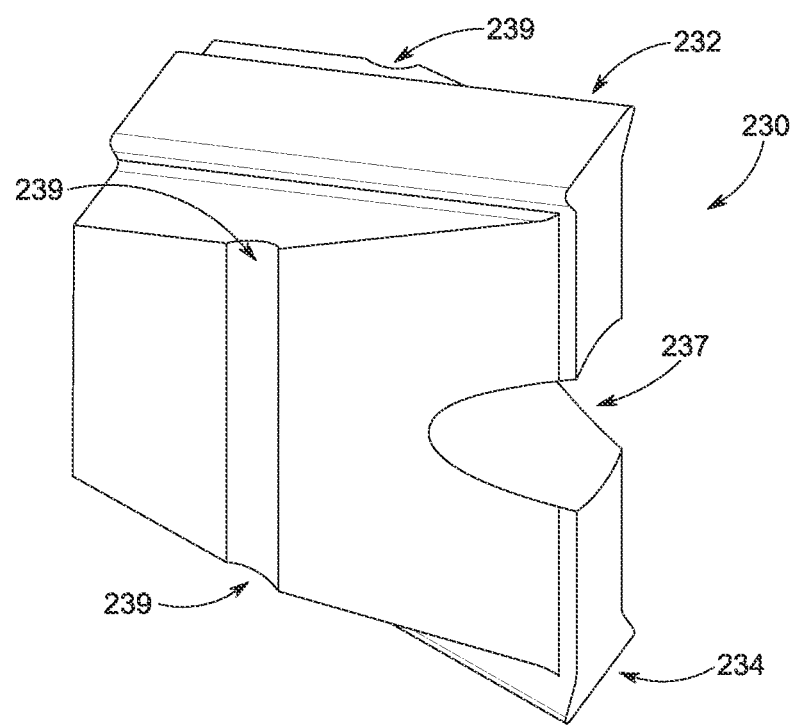
FIG. 64 is a left rear perspective view of the rear block component of the fusion cage of FIG. 63A.

Referring now to FIGS. 49-62, various embodiments and components of a fusion cage 60 with expandable fusion cage feature are depicted. Generally, the fusion cage 60 comprises an upper plate 200, lower plate 210, front block 220, rear block 230, and expansion screw 240. By rotating the expansion screw 240, each of the front block 220 and rear block 230 advance toward the center of the fusion cage 60 while simultaneously advancing each of the lower plate 210 and upper plate 220 away from the center of the fusion cage 60, thereby expanding the overall height of the fusion cage 60. Each of the unexpanded state of the fusion cage 60 and expanded state of the fusion cage 60 are understood most immediately by comparing FIGS. 49A and 50A, respectively. The fusion cage 60 may be expanded in a scalable manner to a maximum threshold height value. At the maximum threshold height value of the fusion cage 60, each of the front block 220 and rear block 230 are unable to continue to advance toward the center of the fusion cage 60 (such a state is shown as FIG. 50A). It is noted that in the embodiments of FIGS. 49-60, the lower plate 210 and upper plate 220 remain substantially parallel in all configurations. Stated another way, the lower plate 210 and upper plate 220 remain substantially parallel in the unexpanded fusion cage 60 state (e.g. FIG. 49A), in the maximum threshold height value expanded state of the fusion cage 60 (e.g. FIG. 50A), and in all states in between. In contrast, in the fusion cage 60 embodiment of FIGS. 61A-B, the lower plate 210 and upper plate 220 maintain a relative vertical wedge angle α, and in the embodiment of FIGS. 62A-B, the lower plate 210 and upper plate 220 maintain a relative horizontal wedge angle β.

Expansion screw 240 comprises expansion screw head 242, expansion screw tip 244 and expansion screw disk 246. The expansion screw 240 rotationally engages each of the front block 220 via front block aperture 227 and rear block 230 via rear block aperture 237. The expansion screw disk 246 engages each of the upper plate 200 via upper plate slot 206 and the lower plate 210 via lower plate slot 216. The expansion screw 240 is configured with opposing screw threads on each side of expansion screw disk 246. Each of the front block aperture 227 and rear block aperture 237 are tapped to accept the expansion screw 240 threads. As such, as the expansion screw 240 is rotated, each of the opposing screw threads engage each of the front block aperture 227 and rear block aperture 237 and advance the respective front block 220 and rear block 230 toward the center of the fusion cage 60. As provided in FIGS. 57A-C, expansion screw 240 comprises left hand threads on a first portion of expansion screw 240 proximal to the expansion screw head 242 and right hand threads on a second portion of expansion screw 240 distal to the expansion screw head 242. Thus, the left hand threads engage the rear block aperture 237 and the right hand threads engage the front block aperture 227. The left hand and right hand threads are symmetrical although in opposite directions such that rotation of the expansion screw 240 results in equal movement of each of the front block 220 and rear block 230. Stated another way, the operation of the expansion screw 240 with respect to the front block 220 and rear block 230 is such that each block advances toward (or retreats from) the center of the fusion cage 60 in equal amounts or distance with rotation of the expansion screw 240.

In an alternate embodiment, the thread configurations (and respective tapped apertures) are reversed. The expansion screw head 242 is fitted with a star terminus so as to engage a star (a.k.a. Torx™) screwdriver. In other embodiments, the expansion screw head 242 is fitted with a star screwhead (i.e. female, i.e. receptor, end) so as to engage a star screwdriver (i.e. a male screwdriver.) In other embodiments, any means of screw drive known to those skilled in the art may be employed, to include slot or regular, Phillips, pozidriv, square, Robertson, hex, hex socket, tri-wing, spanner head, clutch, double-square, triple-square, polydrive, spline drive, double hex, Bristol and pentalobular.

Front block 220 comprises front block upper rail 222, front block lower rail 224, front block nose 225, front block ramp 226 and front block aperture 227. As described above, front block aperture 227 is tapped to engage the threads of expansion screw 240. Each of front block upper rail 222 and front block lower rail 224 engage, respectively, upper plate track 205 and lower plate track 215. Such a configuration or arrangement may be referred to as a dovetail joint slider. As the expansion screw is rotated, front block upper rail 222 moves or slides within upper plate track 205 toward the center of fusion cage and front block lower rail 224 moves or slides within lower plate track 215 toward the fusion cage. Because of the wedged-shaped geometry of each of the front block 220 and rear block 230, such movement toward the center of the fusion cage 60 results in an expansion (in height) of the fusion cage 60. Such movement also causes a reduction in the length of the fusion cage 60, in that the front block nose 225 retreats to the interior of the fusion cage 60, thereby leaving the upper plate front 201 and lower plate front 211, or the expansion screw tip 244, to define the most distal end of the fusion cage 60. Such a change in fusion cage 60 length is apparent by comparing, for example, FIGS. 49A and 50A. In one embodiment, the expansion screw tip 244 is configured such that, when the fusion cage 60 is in a maximum expansion state, the expansion screw tip 244 does not extend beyond a plane between the most distal end of the upper plate front 210 and lower plate front 211. It is noted that in all states of expansion of the fusion cage 60, no aperture is formed at the nose of the fusion cage 60, e.g. between the front block 220 and each of the upper plate 200 and lower plate 210. Stated another way, in all states of expansion of the fusion cage 60, to span unextended state (e.g. FIG. 49a) and maximum extended state (e.g. FIG. 50A), no path for egress of material (e.g. bone graft) is provided from the interior of the fusion cage 60 through the front or nose area (i.e. in a longitudinal direction.) In an alternate embodiment, the front block 220 is configured with one or more apertures, e.g. on one or more of front block ramp 236, so as to allow a path for said egress.

Front block 220 is symmetrical about a vertical plane (i.e. a plane running parallel to each of front block upper rail 222 edge and front block lower rail 224 edge longitudinal axes and bisecting front block aperture 227 at 12 and 6 o'clock positions.) Front block is symmetrical about a horizontal plane (i.e. a plane running parallel to each of front block upper rail 222 surface and front block lower rail 224 surface and bisecting front block aperture 227 at 3 and 9 o'clock positions.)

Rear block 230 comprises rear block groove 231, rear block upper rail 232, rear block lower rail 234, rear block ramp 236, rear block aperture 237, rear block aft 238 and rear block detent 239. As described above, rear block aperture 237 is tapped to engage the threads of expansion screw 240. Each of rear block upper rail 232 and rear block lower rail 234 engage, respectively, upper plate track 205 and lower plate track 215. As the expansion screw is rotated, rear block upper rail 232 moves or slides within upper plate track 205 toward the center of fusion cage and rear block lower rail 234 moves or slides within lower plate track 215 toward the fusion cage. Because of the wedged-shaped geometry of each of the rear block 230 and rear block 230, such movement toward the center of the fusion cage 60 results in an expansion (in height) of the fusion cage 60. The rear block aft 238 is configured such that when the fusion cage 60 is in an unexpended state (e.g. FIG. 49A), the rear block aft 238 is flush with the edges of each of upper plate rear 202 and lower plate rear 212. In one embodiment, the expansion screw head 242 is configured such that, when the fusion cage 60 is in an unexpanded state, the expansion screw head 242 is flush with the edges of each of upper plate rear 202, lower plate rear 212 and rear block aft 238.

Rear block 230 is similarly symmetrical about the same relative axes as front block 220. That is, rear block 230 is symmetrical about a vertical plane (i.e. a plane running parallel to each of rear block upper rail 232 edge and rear block lower rail 234 edge longitudinal axes and bisecting rear block aperture 237 at 12 and 6 o'clock positions.) Rear block is symmetrical about a horizontal plane (i.e. a plane running parallel to each of rear block upper rail 232 surface and rear block lower rail 234 surface and bisecting front block aperture 237 at 3 and 9 o'clock positions.)

Upper plate 200 comprises upper plate front 201, upper plate rear 202, upper plate opening 203, upper plate surface texture 204, upper plate track 205, upper plate slot 206, upper plate ridge 209 and plate tab 217. Upper plate surface texture 204 is formed of consecutive ridges in a lateral orientation, i.e. left-right rather than fore-aft. In alternate embodiments, the upper plate surface texture 204 is formed in a longitudinal direction, i.e. fore-aft rather than left-right. In other alternate embodiments, the upper plate surface texture 204 is of other configurations known to those skilled in the art, to comprise grooves and ridges. Upper plate opening 203 comprises a pair of oval race-track openings. In other embodiments, upper plate opening 203 is a single opening, is of circular shape, is of rectangular shape, or other shapes known to those skilled in the art and/or conventionally used in fusion cages. Upper plate 200 is symmetric about a vertical plane running longitudinally between the two upper plate openings 203 and the upper plate track 205.

Lower plate 210 comprises lower plate front 211, lower plate rear 212, lower plate opening 213, lower plate surface texture 214, lower plate track 215, lower plate slot 216, lower plate ridge 219 and plate tab 217. Lower plate surface texture 214 is formed of consecutive ridges in a lateral orientation, i.e. left-right rather than fore-aft. In alternate embodiments, the lower plate surface texture 214 is formed in a longitudinal direction, i.e. fore-aft rather than left-right. In other alternate embodiments, the lower plate surface texture 214 is of other configurations known to those skilled in the art, to comprise grooves and ridges. Lower plate opening 213 comprises a pair of oval race-track openings. In other embodiments, lower plate opening 213 is a single opening, is of circular shape, is of rectangular shape, or other shapes known to those skilled in the art and/or conventionally used in fusion cages. Lower plate 210 is symmetric about a vertical plane running longitudinally between the two lower plate openings 213 and the lower plate track 215.

When the fusion cage 60 is in the unexpanded state (e.g. FIG. 49A), upper plate ridge 209 and lower plate ridge 219 are in communication, i.e. are touching or substantially touching.

Upper plate 200 and lower plate 210 are identical, and are assembled to form the fusion cage 60 by positioning in opposite orientations. Stated another way, upper plate 200 and lower plate 210 are positioned to mirror one another about a horizontal plane through the center and middle height of the fusion cage 60. Among other things, identical upper plate 200 and lower plate 210 allow fewer unique parts to be used to assemble the fusion cage 60, thereby reducing costs, reducing complexity, and increasing robustness. Also, the fusion cage 60 design is such that the fusion cage remains structural stable and strong while expanded, to include when in the maximum expanded state, as enabled by the type and degree of connections between the wedged blocks and the plates. That is, as enabled by the rail/track connections between the blocks and the plates, and also the adjacent surface connections of the wedged blocks (i.e. the area adjacent the rails of each block) and the plates.

The fusion cage 60 is a modular system in that components may be combined to cover several sizes and configurations. Although each of the upper plate 200 and lower plate 210 are identical, these paired plates may be provided in several sizes. For example, as provided in FIGS. 54A-F, a set of paired (i.e. one upper plate 200 and one lower plate 210) plates may be provided in lengths of 26 mm, 32 mm and 36 mm. Also, the paired wedged blocks (i.e. a front block 220 and a rear block 230) may be provided in assorted sizes, e.g. an 8 mm and an 11 mm size, as depicted in FIGS. 55A-E. Lastly, the expansion screw 240 may be provided in various configurations, as provided in FIGS. 57A-C, to match combinations of paired plates and paired wedged blocks. In one embodiment, the fusion cage 60 may be constructed to range in size from 8×26 mm to 14×36 mm.

In one embodiment, the expansion screw 240 comprises stainless steel and titanium, and the upper plate 200 and lower plate 210 comprise stainless steel, titanium and polyether ether ketone (PEEK.)

Additional components that are configured to engage the fusion cage 60 are provided in FIGS. 63-72. Generally, the additional components comprise those that allow the fusion cage 60 to be positioned at or within a surgical site, to expand and/or contract the fusion cage 60, deliver bone graft material within the fusion cage 60 and to the surrounding surgical site, and detach the fusion cage.

With attention to FIGS. 63-69, a fusion cage 60 with expandable fusion cage feature, as described above, is depicted with an installer/impactor 250 component. The installer/impactor 250 comprises installer/impactor tip 252, installer/impactor aperture 253, installer/impactor ridge 254, installer/impactor channel 255, installer/impactor ramp 256 and installer/impactor handle 258. The installer/impactor aperture 253 is configured to engage the rear block aperture 253 and the installer/impactor ridges 254 are configured to engage the rear block detent 239; once these elements are engaged, the fusion cage 60 may be accurately and reliable positioned at the surgical site. The installer/impactor handle 258, with integrated striking plate, may be used to assist in guiding the fusion cage 60 into place, and further allows a "persuading" with a mallet. The installer/impactor handle 258 attaches in place with, for example, a ball detent or similar feature that secures the installer/impactor handle 250 in place yet allows quick and easy removal.

Figure 65A:
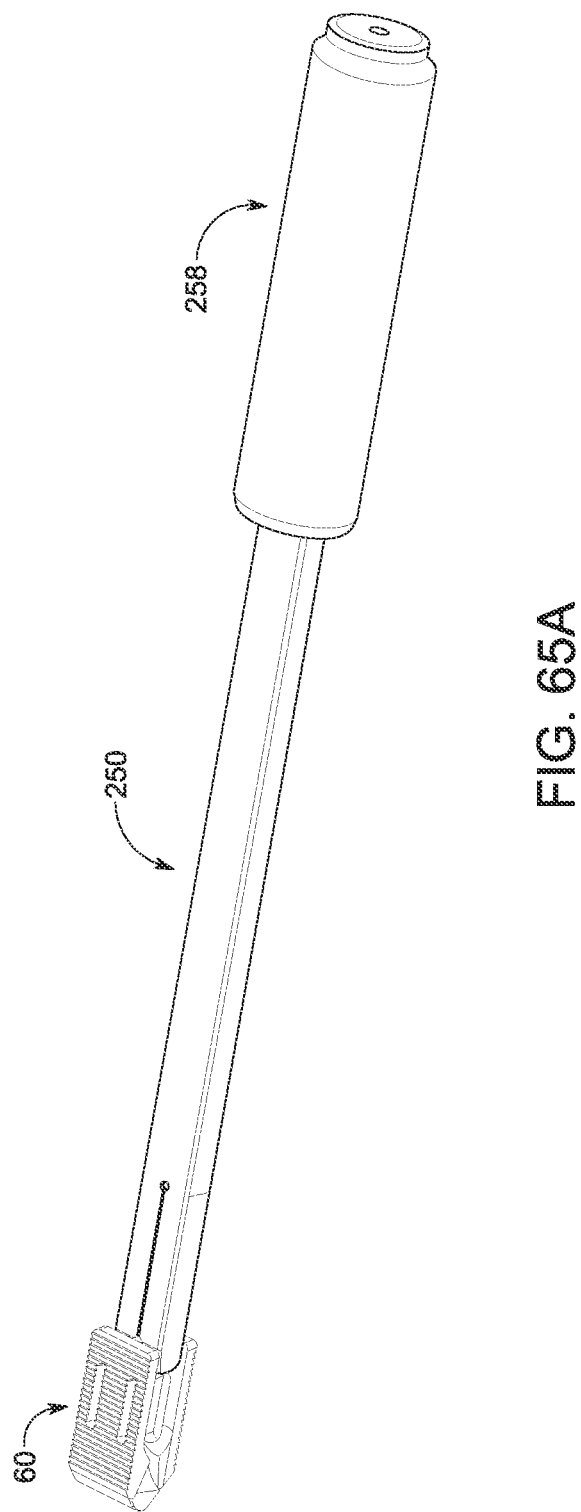
FIG. 65A is a left rear perspective view of the devices of FIG. 63A, shown with the fusion cage and installer/impactor components in an engaged state, and the installer/impactor comprising an installer/impactor handle.
Figure 65B:
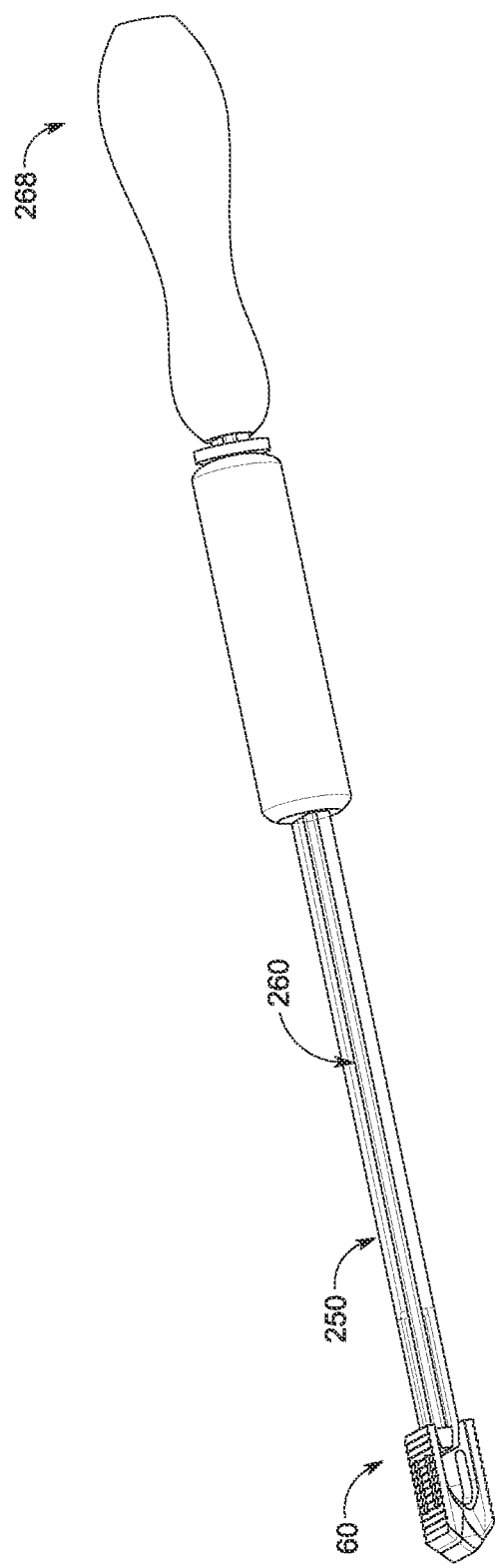
FIG. 65B is a left front perspective partial cross-sectional view of the devices of FIG. 63A in the state of FIG. 65A, shown with the fusion cage and installer/impactor components in an engaged state, the devices engaged with an expansion driver component, the installer/impactor component shown in partial cross-section to partially show the expansion driver fitted within the interior of the installer/impactor.

FIG. 65A details the installer/impactor 250 engaged with the fusion cage 60, the fusion cage 60 in an unexpanded state. FIG. 65B details the same system and configuration of FIG. 65A, except that the expansion driver 260, with expansion driver handle 268, is engaged with the fusion cage 60. More specifically, the expansion driver 260, which fits within the installer/impactor 250, engages the expansion screw head 242 (e.g. the expansion screw head 242 is a male star or Torx™ screw head that engages with the female star or Torx™ screwdriver end of the expansion driver 260.) FIG. 66 details the installer/impactor 250 engaged with the fusion cage 60, the fusion cage 60 in an expanded state (as a result of the expansion driver 260 engaging the expansion screw head 242 and, through rotation of the expansion screw head 242, expanding the fusion cage 60), and the hollow tube 2 fitted over the installer/impactor 250.

Figure 67:
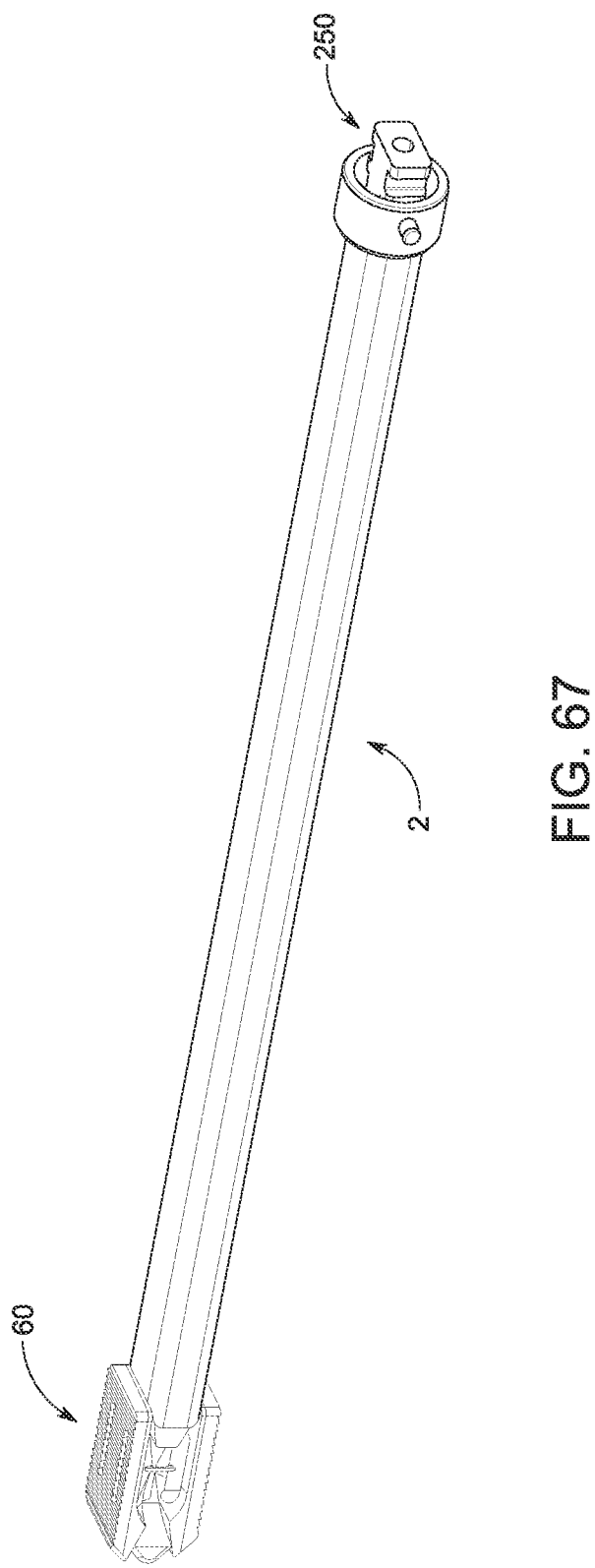
FIG. 67 is a left rear perspective view of the devices of FIG. 63A, shown with the fusion cage and installer/impactor components in an engaged state, and shown with the fusion cage and hollow tube in an engaged state.

After the fusion cage 60 is expanded to the desired degree, i.e. height, the expansion driver 260 disengages from the expansion screw head 242 and is removed. The hollow tube 2 is then slid downward or distally so as to engage the fusion cage 60, and the installer/impactor 250 must be removed (so as to allow bone graft material to be delivered via hollow tube 2 into the fusion cage 60 and the surrounding surgical site.) FIG. 67 details the installer/impactor 250 engaged with the fusion cage 60, the fusion cage 60 in an expanded state, and the hollow tube 2 fitted over the installer/impactor 250 and engaged with the fusion cage 60; this is the configuration of the integrated expandable fusion cage and bone graft delivery device when the installer/impactor 250 must be removed so as to enable bone graft delivery. In an alternate embodiment, the installer/impactor 250 is not used, and instead the hollow tube 2 is used to position the fusion cage 60 by way of the hollow tube external ramp 280 and/or hollow tube notch 282. The hollow tube external ramp 280 may form a press-fit with the fusion cage 60. The hollow tube may also engage the fusion cage 60 via the hollow tube notch 282, the hollow tube notch 282 configured to engage the rear block aft 238 portion above and below the rear block aperture 237.

Figure 68A:
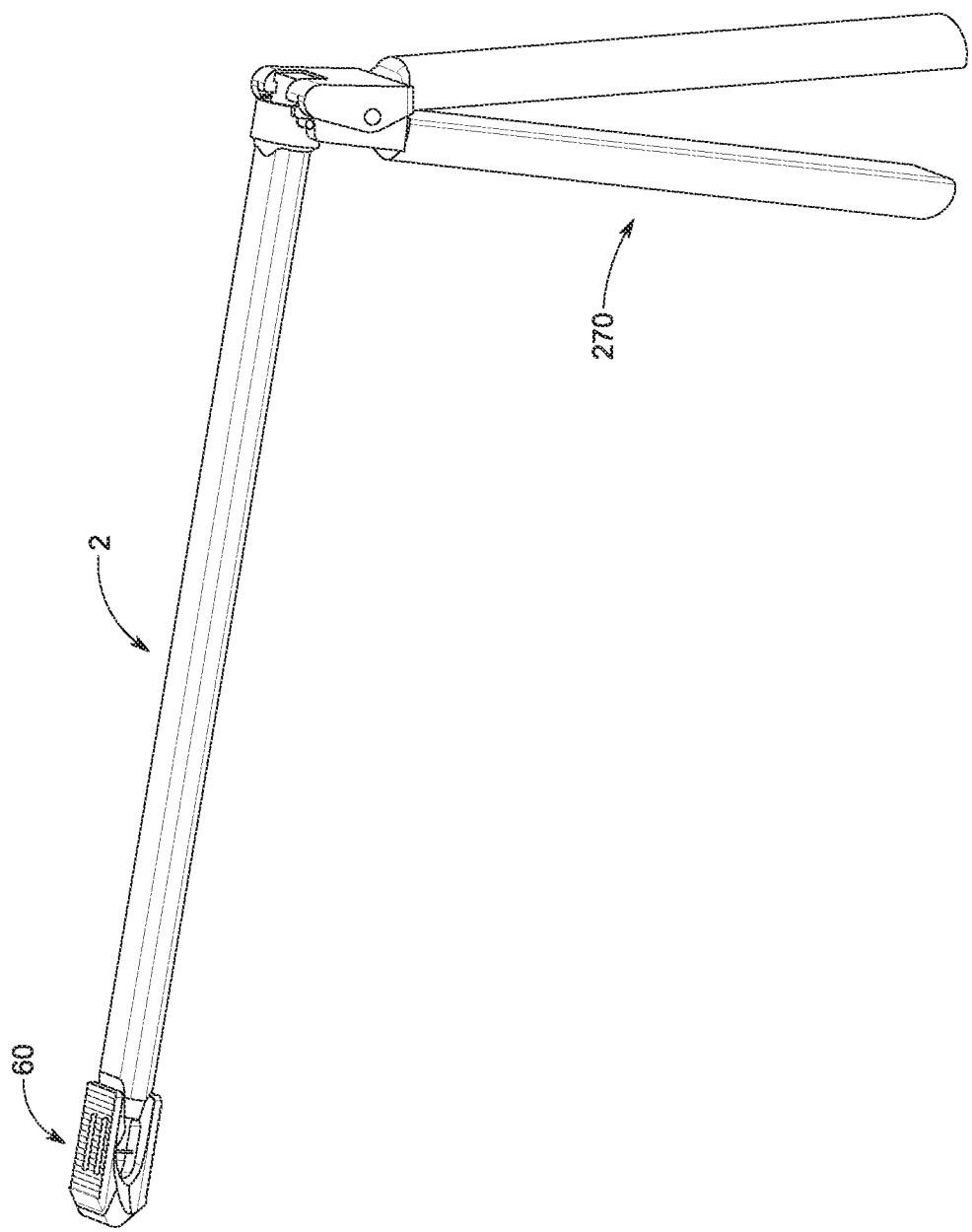
FIG. 68A is a left rear perspective view of the devices of FIG. 63A, shown in the configuration of FIG. 67, with a removal pliers component engaged with the hollow tube component.

FIGS. 68A-B detail a means with which the installer/impactor 250 may be removed by use of removal pliers 270. The removal pliers 270 are configured to engage the first end 6 of hollow tube and the proximal end of the installer/impactor 250, so as to pull the installer/impactor 250 from engagement with the fusion cage 60. Note that the installer/impactor 250 is configured to allow the installer/impactor tip 252 to spread apart over the rear block detent 239 groove, as facilitated by the installer/impactor channel 255.

Figure 69:
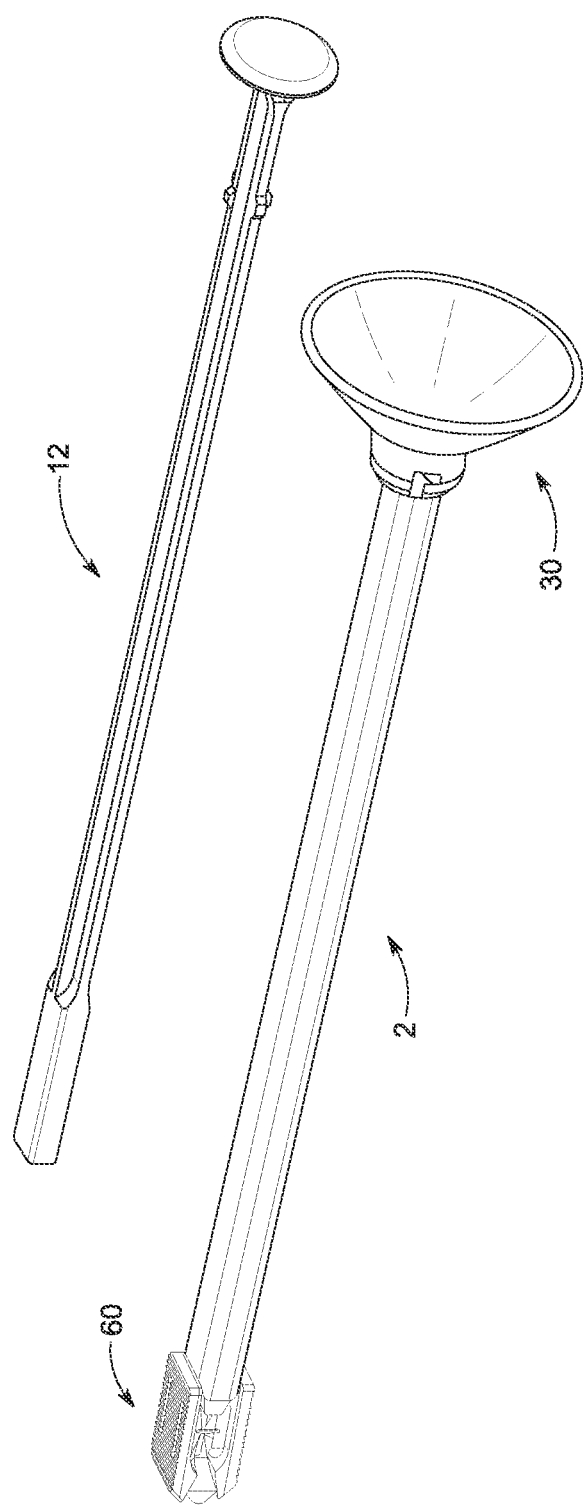
FIG. 69 is a left rear exploded perspective view of a fusion cage with expandable fusion cage feature engaged with a hollow tube component and a funnel component, as configured to engage with a plunger component.

After the fusion cage 60 has been positioned in the surgical site and expanded as required, bone graft material may be inserted into the fusion cage 60 and into the surrounding surgical site. FIG. 69 presents an exploded perspective view of the fusion cage 60 with expandable fusion cage feature engaged with the hollow tube 2 component and funnel 30 component, as configured to engage with the plunger 12 component. As described previously, bone graft material is placed into the funnel 30 and advanced down the hollow tube 2 by the plunger 12, whereby bone graft material flows into the fusion cage 60 and outward into the surgical site via one or more of the upper plate openings 203, lower plate openings 213, and lateral openings distal to the front block 230.

Figure 70:
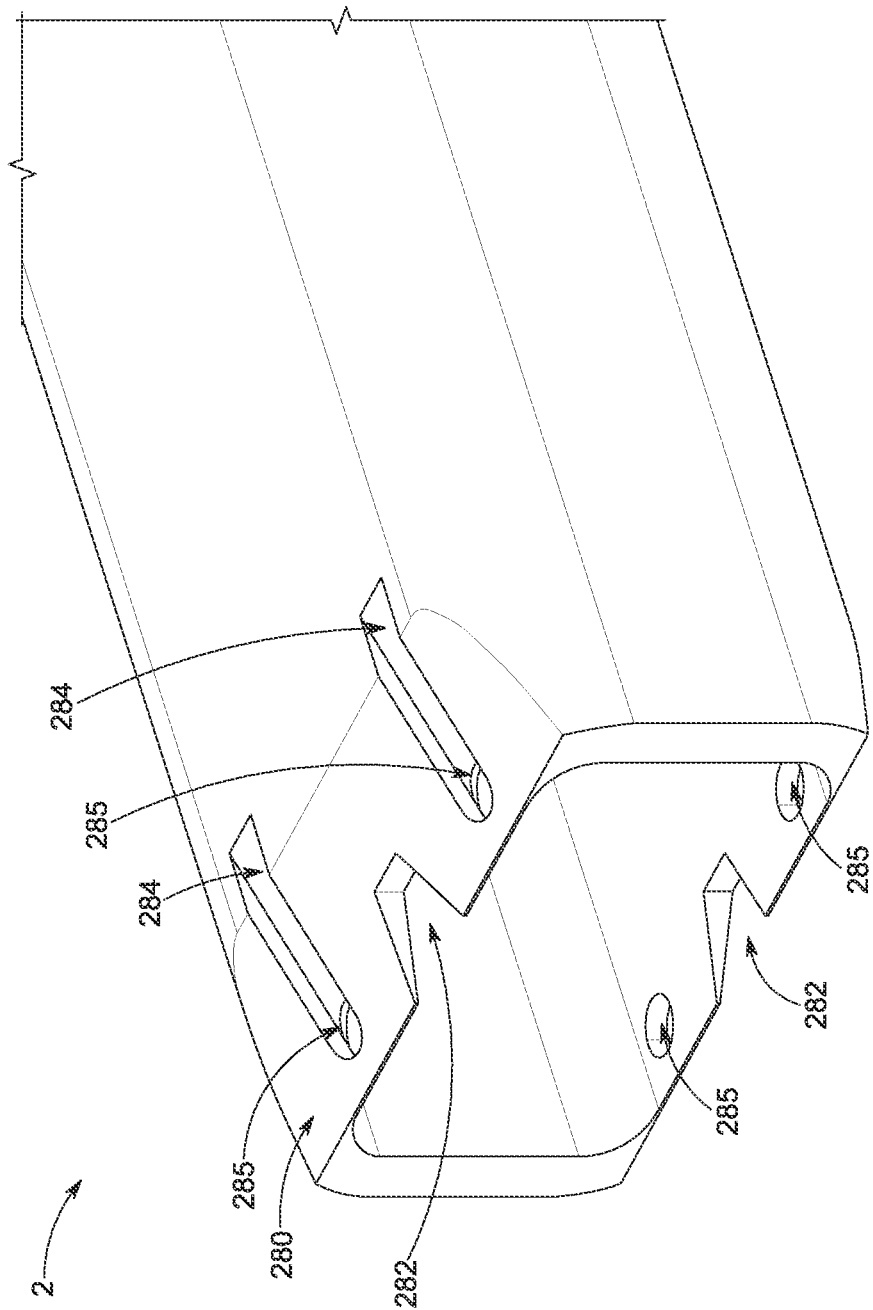
FIG. 70 is a left front partial perspective view of another embodiment of the hollow tube component configured to engage a fusion cage with expandable fusion cage feature, the hollow tube configured with hollow tube slot and hollow tube slot aperture features.
Figure 71:
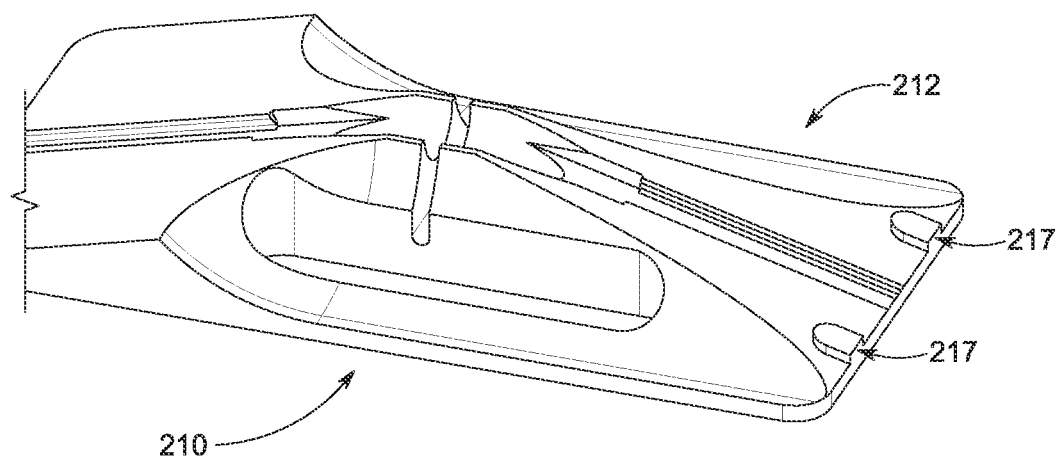
FIG. 71 is a left rear perspective view of another embodiment of the lower plate component of a fusion cage with expandable fusion cage feature, the lower plate configured with a plate tab feature configured to engage the hollow tube slot and hollow tube slot aperture features of FIG. 70.
Figure 72:
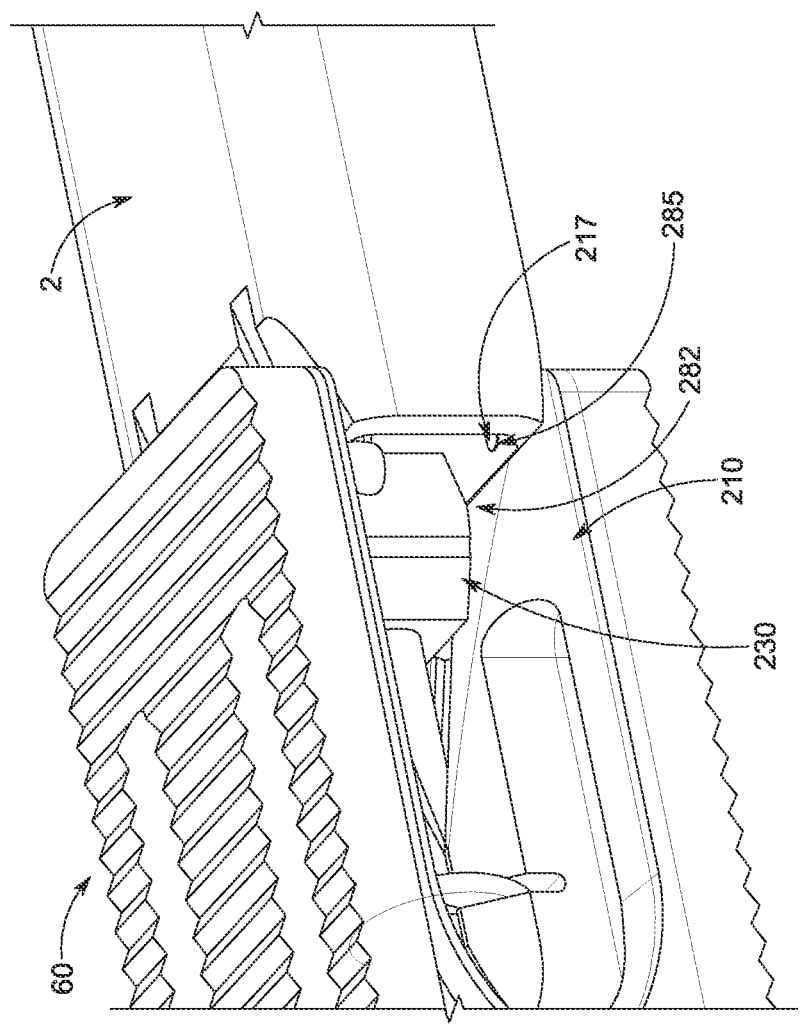
FIG. 72 is a left front partial cross-section perspective view of the devices of FIGS. 70 and 71, shown with the plate tab feature engaged with the hollow tube slot and hollow tube slot aperture features.

FIGS. 70-72 depict an alternate embodiment of hollow tube 2 and fusion cage 60 to enable the fusion cage 60 to be accurately and reliably positioned at a surgical site. The hollow tube 2 comprises two pairs of hollow tube slots 284, each with a hollow tube slot aperture 285 at the distal end. Each hollow tube slot 284 is disposed at least partially on the hollow tube external ramp 280. Each of the upper plate 200 and lower plate 210 comprise a pair of plate tabs 217, each of which engages one of the hollow tube slot apertures 285. When such an engagement occurs, the fusion cage 60 is slightly expanded as the hollow tube 2 is inserted into the fusion cage 60. In this arrangement, as the fusion cage 60 is expanded, the plate tabs 217 retreat or release from the hollow tube slot apertures 285; however, the hollow tube 2 still engages or registers with the fusion cage 60 via the hollow tube notches 282 which remain engaged with the rear block aft 238.

In one embodiment, the expansion screw 240 is configured to lock at defined expansion states of the fusion cage 60, to include at a maximum expansion state (as defined, e.g. as the maximum height dimension of which the fusion cage 60 may expand.)

Figure 73:
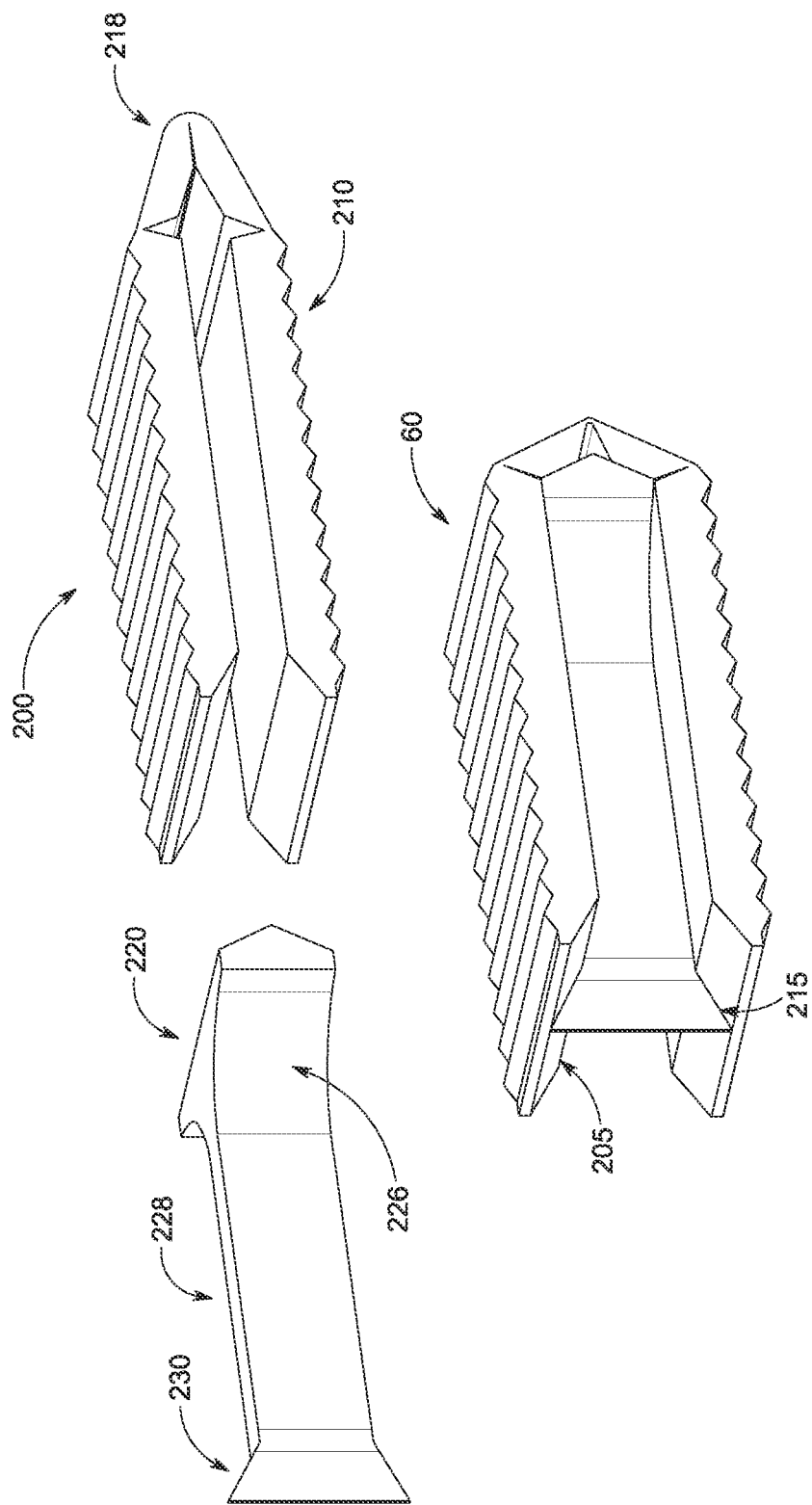
FIG. 73 is a right rear exploded view of another embodiment of the fusion cage with expandable cage feature.

In another embodiment, the fusion cage 60 with expandable cage feature is configured of modified and integrated embodiments of the afore-mentioned components. For example, FIG. 73 depicts a fusion cage 60 with expandable fusion cage feature wherein the upper plate 200 and lower plate 210 are joined through a plate nose element 218 ("plate/nose element"). These combined components are configured to form a first state wherein a minimal vertical height is provided and/or a flat profile is presented. Horizontal notches fitted between the upper plate 200 and plate nose element 218, and between the lower plate element 210 and plate nose element 218, enable the integrated upper plate 200, lower plate 210 and plate nose element to expand upon engagement with an integrated front block 220 and rear block 230 element. The integrated front block 220 and rear block 230 element comprises a block spine 228 ("block/spine element") such that, when inserted into the afore-mentioned plate/nose element, the fusion cage 60 expands. In one embodiment, each of the afore-mentioned integrated components would be held in a pistol grip type insertion tool (as known to those skilled in the art) which would allow placement of the unexpanded (i.e. the collapsed) plate/nose element into the surgical site (e.g. a disk space) with the block/spine element staged right behind. Upon pulling a lever on the pistol grip tool, the plate/nose element would be inserted into the block/spine element (in one embodiment, this insertion is facilitated by upper plate track 205 and lower plate track 215 engaging respective upper and lower rails of the block/spine element), thereby expanding the plate/nose element and forming an expanded fusion cage 60. In one embodiment, a locking feature is provided such that the plate/nose and block/spine elements are secured or locked together. In one embodiment, the insertion of this fusion cage 60 embodiment is by way of hollow tube 2 (e.g. the embodiment described in FIGS. 70-72). In one embodiment of the fusion cage 60 as provided in FIG. 73, one or more upper plate openings 203 and/or one or more lower plate openings 213 are provided.

In one embodiment, no springs, such as wire springs, are employed to expand the fusion cage 60. In one embodiment, other means, as known to those skilled in the art, are used to expand the fusion cage 60, to include springs, gears, cams, magnetic, electrical, electro-mechanical, electro-magnetic, and optical.

Figure 74:
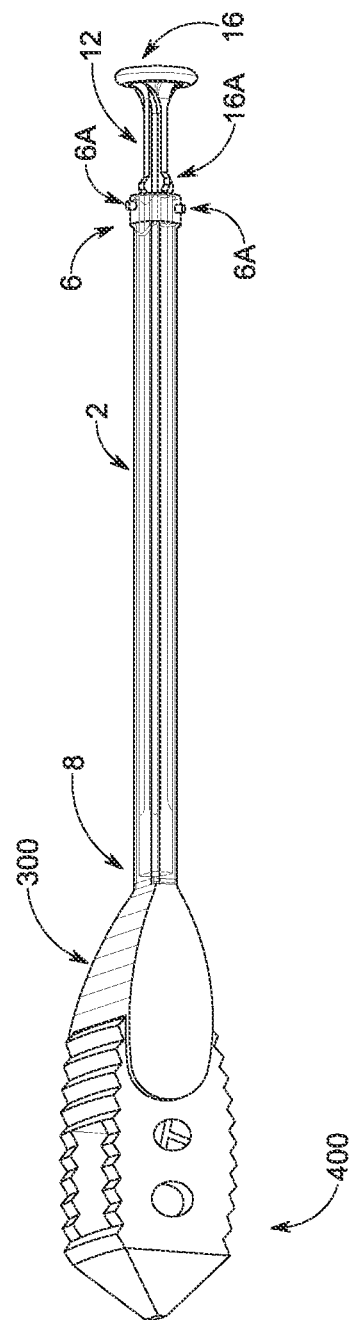
FIG. 74 depicts the fusion cage with expandable cage feature engaged with an angled insertion tool.

The means and components disclosed may engage, integrate and/or communicate with the fusion cage 60 embodiments of the disclosure as well as with traditional and conventional fusion cages. That is, the components of the disclosure may be readily adapted to engage conventional fusion cages, including expandable fusion cages, of the prior art. More specifically, the hollow tube 2, installer/impactor 250, expansion driver 260, and/or plunger 12 may be adapted to engage fusion cages of the prior art. FIG. 74 provides a representative depiction of adaptations of components of the disclosure so as to engage conventional fusion cages, both fixed or static fusion cages and expandable fusion cages.

In one embodiment, the bone graft delivery system of the disclosure may engage with an expandable fusion cage of the prior art. For example, the hollow tube 2 may be configured to engage the prior art (expandable) fusion cage 400 shown by, for example, geometric sizing of the hollow tube first distal opening 8, and/or fitting the hollow tube first distal opening 8 with a malleable portion that may be compressed and/or expanded so as to engage the prior art (expandable) fusion cage 400, and/or fitting to an adaptor 300 portion. Additionally, the installer/impactor 250 may be adapted (e.g. to use the same configuration of expansion end as that of the depicted fusion cage) to communicate with the end portion of the prior art (expandable) fusion cage 400 so as to enable the expansion of the prior art (expandable) fusion cage 400. The prior art (expandable) fusion cage 400 may also be engaged with one or more components of the disclosure, e.g. the hollow tube 2 and/or installer/impactor 250.

In one embodiment of the fusion cage 60, the fusion cage of the prior art is adapted wherein one or more of the upper plate 200 and/or lower plate 210 is adapted to fit on paired opposite sides of the fusion cage.

In another embodiment, the bone graft delivery system of the disclosure may engage with an unexpandable fusion cage of the prior art. The hollow tube 2 is configured to engage the prior art (unexpandable) fusion cage 400 shown by, for example, geometric sizing of the hollow tube first distal opening 8, and/or fitting the hollow tube first distal opening 8 with a malleable portion that may be compressed and/or expanded so as to engage the prior art (expandable) fusion cage 400, and/or fitting to an adaptor portion 300.

FIG. 74 depicts the bone graft delivery system of the disclosure, as engaged with an unexpandable fusion cage of the prior art, specifically an unexpandable fusion cage provided in US2012/0065613 and/or http://thompsonmis.com/node/23, incorporated by reference in entirety. The hollow tube 2 is configured to engage the prior art (unexpandable) fusion cage 400 shown by, for example, geometric sizing of the hollow tube first distal opening 8, and/or fitting the hollow tube first distal opening 8 with a malleable portion that may be compressed and/or expanded so as to engage the prior art (expandable) fusion cage 400, and/or fitting to an adaptor portion 300 (as shown).

In one embodiment, the adaptor 300 comprises at least two forked tines to engage, for example, exterior surfaces of a fusion cage. In one embodiment, the adaptor 300 forms an angled tool, that is, the adaptor 300 and the hollow tube 2 are not aligned or linear. In another embodiment, the adaptor 300 forms an angled tool relative to a fusion cage when engaged with a fusion cage, that is, the adaptor 300 and the hollow tube 2 are aligned or linear but are not in alignment with an engaged fusion cage.

In one embodiment, the fusion cage 60 is actuated, e.g. the expansion screw 240 is operated, remotely, e.g. through electrical means, magnetic means or other means known to those skilled in the art, during surgery or post-operative. The later situation, i.e. post-operative, enables adjustment of the height of the fusion cage 60 after surgery. In one embodiment, the fusion cage e.g. the expansion screw is operated or manipulated by way of additional devices to comprise a servo-motor.

In one embodiment, the fusion cage 60 is used in applications comprising L-LIF, A-LIF, Corpectomy adaptation, deformity correction and increasing lordosis.

In one embodiment, the expansion screw 240, comprising a left hand and a right hand threaded screw portion and a central disk, engages two opposing blocks at a 30 degree ramp angle with a dovetail joint. As the blocks are drawn in, the cage plates are forced outward (in the vertical direction). The narrow disk at the center of the screw registers in the slots of the cage plates to keep the plates from shifting fore/aft, reducing if not eliminating binding of the mechanism.

In one embodiment, at least some of the fusion cage is manufactured using 3-D printing technologies, metal additive manufacturing (AM), subtractive machining and/or direct metal laser sintering (DMLS) and may be provided a porous coating. In one embodiment, the fusion cage 60 comprises one or more surfaces, especially exterior surfaces, with pores so as to, for example, promote osseointegration. The article "EOS Teams with Medical Implant Designer to Advance 3D Printing in Medicine" published Oct. 17, 2012 in Graphic Speak is incorporated by reference in entirety.

In one configuration, the fusion cage comprises a titanium alloy, such as Ti6AL4V and/or lattice structures, the lattice structures covering all or at least part of one or more apertures of the fusion cage 60. In one configuration, the lattice structures in FIG. 82, herein incorporated by reference in entirety.

In one configuration, the hollow tube 2 is configured such that its distal upper and lower interior surfaces have grooves to engage the upper and lower portions of the rear cage actuating wedge. The screw tool, fitting inside the cannula, is still used to expand the cage. Once expanded, the screw tool is removed. Then BG material is inserted using the cannula/plunger scheme. The screw tool is put back in to engage the expandable screw and hold the fusion cage in place. The modified (interior grooved) cannula is pulled away from the cage with the screw tool providing an opposing force to the cage. The screw tool is then removed. Furthermore, the distal end of the modified cannula may be made of an elastic material so that, if initially engaged with the cage in compression, it expands as the cage expands to provide a sealed fit with the cage as the cage expands, thereby allowing a clean flow of BG material into the cage i.e. no back-flow.

In one embodiment, one or more alignment markers are placed on the funnel, e.g. lines at 0 degree and 180 degree. In one embodiment, one or more clamps are applied to the hollow tube for additional support and/or stability. The clamps may be, e.g. scissor-type clamps. In one embodiment, all or a portion of the plunger, hollow tube, fusion cage and ejection tool comprise a thermoplastic polycarbonate such as Lexan™. In one embodiment, the fusion cage comprises a different material than one or more of the hollow tube, plunger and ejection device. In one embodiment, the plunger comprises an elastic portion and elastic seal which functions, among other things, to restrict wiggle of the plunger when moving through the hollow tube. In one embodiment, one or more portions of the device are manufactured via sonic welding, and/or comprise a sonic weld. For example, the tip of the hollow tube and/or fusion cage may be sonic welded or comprise a sonic weld.

In one embodiment of the device, the width of the hollow tube second exterior surface 5 is between 10 and 14 mm. In a preferred embodiment, the width of the hollow tube second exterior surface 5 is between 11 and 13 mm. In a most preferred embodiment, the width of the hollow tube second exterior surface 5 is between 11.5 mm and 12.5 mm. In a preferred embodiment, the width of the hollow tube second exterior surface 5 is 12 mm.

In one embodiment of the device, the width of the hollow tube first exterior surface 3 is between 6 and 10 mm. In a preferred embodiment, the width of the hollow tube first exterior surface 3 is between 7 and 9 mm. In a most preferred embodiment, the width of the hollow tube first exterior surface 3 is between 7.5 mm and 8.5 mm. In a preferred embodiment, the width of the hollow tube first exterior surface 3 is 8 mm.

In one embodiment of the device, the ratio of the width of the hollow tube second exterior surface 5 and the width of the hollow tube first exterior surface 3 is between 1.7 and 1.3. In a preferred embodiment, the ratio of the width of the hollow tube second exterior surface 5 and the width of the hollow tube first exterior surface 3 is between 1.6 and 1.4. In a most preferred embodiment, the ratio of the width of the hollow tube second exterior surface 5 and the width of the hollow tube first exterior surface 3 is between 1.55 and 1.45. In one embodiment, the ratio of the width of the hollow tube second exterior surface 5 and the width of the hollow tube first exterior surface 3 is 1.5.

In one embodiment of the device, the width of the interior of the hollow tube major axis (located adjacent the second exterior surface 5) is between 9 and 13 mm. In a preferred embodiment, the width of the interior of the hollow tube major axis is between 10 and 12 mm. In a most preferred embodiment, the width of the interior of the hollow tube major axis is between 10.5 mm and 11.5 mm. In a preferred embodiment, the width of the interior of the hollow tube major axis is 11 mm.

In one embodiment of the device, the width of the interior of the hollow tube minor axis (located adjacent the first exterior surface 3) is between 5 and 9 mm. In a preferred embodiment, the width of the interior of the hollow tube minor axis is between 6 and 8 mm. In a most preferred embodiment, the width of the interior of the hollow tube minor axis is between 6.5 mm and 7.5 mm. In a preferred embodiment, the width of the interior of the hollow tube minor axis is 7 mm.

In one embodiment of the device, the ratio of the width of the interior of the hollow tube major axis and the width of the interior of the hollow tube minor axis is between 1.7 and 1.3. In a preferred embodiment, the ratio of the width of the interior of the hollow tube major axis and the width of the interior of the hollow tube minor axis is between 1.6 and 1.4. In a most preferred embodiment, the ratio of the width of the interior of the hollow tube major axis and the width of the interior of the hollow tube minor axis is between 1.55 and 1.45. In one embodiment, the ratio of the width of the interior of the hollow tube major axis and the width of the interior of the hollow tube minor axis is 1.5.

It should be noted that the rectangular configuration of the hollow tube affords several advantages over conventional circular configuration. For example, for a surgical area with smallest dimension set at a width of 8 mm with thickness dimension 0.5 mm, a conventional circular device (with resulting interior diameter of 7 mm or a radius of 3.5 mm) would realize a surface area of 38.48 mm.sup.2. Applicants' device would carry interior dimension of 7 mm by 11 mm for a surface area of 77 mm, an increased surface area factor of 2.0, thereby resulting in more bone graft material delivery, because, among other things, a given volume of bone graft encounters less surface area of the interior of a particular device which results in, among other things, reduced chance of jamming of bone graft material within the device.

In one embodiment, a one or more edges of the device are rounded. For example, the exterior edges of the hollow tube are rounded, and/or the interior edges of the hollow tube are rounded (in which case the edges of the plunger, at least at the plunger distal end, are identically rounded to ensure a congruous or conformal fit between the edges of the plunger and the interior of the hollow tube so as to, among other things, urge the majority of bone graft material to move through the hollow tube).

In one embodiment, the handle 16 of plunger is a planar disk shape, as depicted in FIG. 23. In another embodiment, handle 16 is not planar. For example, handle 16 is angled so as to conform to interior of funnel 30 when the plunger 12 is fully inserted into hollow tube 2.

In one embodiment, the hollow tube distal interior ramp surfaces 9A are linear in shape, that is, forming a triangle in cross-section. In another configuration, the hollow tube distal interior ramp surfaces 9A are of any shape that urges egress of bone graft material contained in the hollow tube to exit the interior of the hollow tube through the pair of first distal openings 7 of the device 1.

A bone graft tamping device may also be provided, which is adapted to be telescopically inserted into the hollow tube after the plunger is removed from the hollow tube. The bone graft tamping device, according to this embodiment, may include one or more longitudinal channels along the outer circumference of the bone graft packer for permitting any trapped air to flow from the bone graft receiving area to the graspable end of the hollow tube during packing of bone graft. The bone graft packer may further include a handle at one end designed ergonomically for improving ease of use. The bone graft packer in this embodiment thereby facilitates packing of bone graft within the hollow tube.

The hollow tube may also be fitted with a passageway wherein a surgical tube or other device may be inserted, such as to deliver a liquid to the surgical area or to extract liquid from the surgical area. In such an embodiment, the plunger is adapted in cross-section to conform to the hollow tube's cross-section.

In another embodiment of the present invention, a kit of surgical instruments comprises a plurality of differently sized and/or shaped hollow tubes and a plurality of differently sized and/or shaped plungers. Each of the plungers correspond to at least one of the hollow tubes, whereby a surgeon may select a hollow tube and a plunger which correspond with one another depending upon the size and shape of the graft receiving area and the amount or type of bone graft to be implanted at such area. The corresponding hollow tubes and plungers are constructed and arranged such that bone graft can be placed within the hollow tubes with the plungers, and inserted nearly completely into the hollow tubes for removing substantially all of the bone graft material from the hollow tubes, such as in the preferred embodiments for the plunger described above. The use of more than one hollow tube/plunger combination permits at least two different columns of material to be selectably delivered to the targeted site, e.g. one of bone graft material from the patient and another of Bone Morphogenetic Protein (BMP), or e.g. two different types of bone graft material or one delivering sealant or liquid. Also, one or both hollow tubes could be preloaded with bone graft material.

The kit of surgical instruments may comprise a plurality of differently sized and/or shaped graft retaining structures, each corresponding to at least one hollow tube and at least one plunger.

The bone graft receiving area can be any area of a patient that requires delivery of bone graft. In the preferred embodiment, the bone graft is delivered in a partially formed manner, and in accordance with another aspect of the present invention, requires further formation after initial delivery of the bone graft.

Another embodiment of the present invention provides a method by which a hollow tube and a plunger associated with the hollow tube are provided to facilitate delivery of the bone graft to a bone graft receiving area.

According to one embodiment, the present invention provides a bone graft delivery system, by which a hollow tube and/or plunger assembly may be prepared prior to opening a patient, thus minimizing the overall impact of the grafting aspect of a surgical implantation or other procedure. Moreover, the hollow tube may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

Thus, the integrated fusion cage and graft delivery device may either come with a pre-filled hollow tube, or a non-filled hollow tube, in which the surgeon will insert bone graft received from the patient (autograft), or from another source (allograft). In either case, the surgeon may first remove any wrapping or seals about the hollow tube, and/or the pre-filled bone graft, and insert the hollow tube into the patient such that the second end of the hollow tube is adjacent the bone graft receiving area. Once the hollow tube is in place, and the opening at the second end of the hollow tube is oriented in the direction of the desired placement of bone graft, the surgeon may then insert the second end of the plunger into the opening at the first end of the hollow tube, and begin pressing the second end of the plunger against the bone graft material in the hollow tube. In this fashion, the plunger and hollow tube cooperate similar to that of a syringe, allowing the surgeon to steadily and controllably release or eject bone graft from the second end of the hollow tube as the plunger is placed farther and farther into the opening in the hollow tube. Once the desired amount of bone graft has been ejected from the hollow tube (for in some instances all of the bone graft has been ejected from the hollow tube) the surgeon may remove the plunger from the hollow tube, and complete the surgery. In certain operations, the surgeon may elect to place additional bone graft into the hollow tube, and repeat the steps described above. Furthermore, the pre-filled bone graft elements may be color-coded to readily identify the type of bone graft material contained therein.

According to the embodiment described in the preceding paragraph, the present invention may be carried out by a method in which access is provided to a graft receiving area in a body, bone graft is placed into a hollow tube having a first end and a second end, the hollow tube, together with the bone graft, is arranged so that the first end of the hollow tube is at least adjacent to the graft receiving area and permits lateral or nearly lateral (in relation to the longitudinal axis of the hollow tube and plunger assembly) introduction of bone graft to the graft receiving area. This method prevents loss of bone graft due to improper or limited orientation of the integrated fusion cage and graft delivery device, and further allows a user to achieve insertion of a desired quantity of bone graft by way of the contoured plunger and hollow tube configuration described according to preferred embodiments herein.

The method of the present invention may also be carried out by providing a hollow tube having a first end and a second end, constructed so that it may receive a measurable quantity of bone graft, and so that the first end may be arranged at least adjacent to a bone graft receiving area, and so that bone graft can be delivered from the first end of the hollow tube through the second end of the hollow tube and eventually to the bone graft receiving area upon movement of the plunger in a generally downward direction through the hollow tube (i.e., in a direction from the first end to the second end). According to this embodiment, a graft retaining structure may also be provided for use in connection with the contoured edge of the plunger, such that the graft retaining structure is positioned between the contoured edge of the plunger and the bone graft, but which is adhered to the bone graft and remains at the graft receiving area following removal from the hollow tube. In one embodiment, the bone graft is provided in discrete packages or containers. Furthermore, this graft retaining structure may also be employed with another tool, such as a graft packer, which is employed either before or after the hollow tube is removed from the graft receiving area.

In another embodiment, the one or more plungers corresponding to the one or more hollow tubes are positioned with distal ends near the proximate end of the horizontal tube before use, said plungers having a detent to retain plunger in ready position without undesired movement before surgeon chooses which one or more plungers to extend through hollow horizontal tube and deliver bone graft material and/or desired material to the surgical area.

According to another embodiment of the present invention, a hollow tube and plunger assembly is provided in which the hollow tube and/or the plunger assembly is disposable. Alternatively, the tube may be made of a biocompatible material which remains at least partially in the patient without impairing the final implantation. Thus, the hollow tube may be formed from a material that is resorbable, such as a resorbable polymer, and remain in the patient after implantation, so as not to interfere with the growth of the bone or stability of any bone graft or implant.

The current design preferably comprises a hollow tubular member comprising a rounded edge rectangular shaft, which may be filled or is pre-filled with grafting material. The loading is carried out by the plunger. The rectangular design is preferable as it allows the largest surface area device to be placed into the annulotomy site of a disk, but in other embodiments may be formed similar to conventional round shafts. The other preferred feature includes a laterally-mounted exit site for the graft material. The combination of this design feature allows direction-oriented dispersion of the graft material. This allows ejection of the graft material into an empty disk space as opposed to below the hollow tube, which would tend to impact the material and not allow its spread through a disk space.

Another feature of this design is that a rectangular design allows the user to readily determine the orientation of the device and thereby the direction of entry of the bone graft material into the surgical area. However, such a feature may be obtained alternatively through exterior markings or grooves on the exterior on the hollow tube. Such exterior grooves or markings would allow use of a range of cross-sections for the device, to include a square, circle, or oval while allowing the user to readily determine the orientation of the device relative to the direction of entry of the bone graft material into the surgical area.

A further feature of this design is that an anti-perforation footing or shelf is paced on the bottom of the hollow tube to prevent annular penetration and/or injury to the patient's abdomen or other anatomy adjacent the bone graft receiving area.

Another alternative embodiment to the design described herein includes a removable funnel attachment. This allows easy loading of the cannula with the funnel and with its removal easy visualization of the operating site without visual blockage through the microscope.

In another embodiment of the invention, all or some of the elements of the device or sections of all or some of the device may be disposable. Disposable medical devices are advantageous as they typically have reduced recurring and initial costs of manufacture.

In another embodiment of the device, the distal tip or end of the plunger device is composed of a different material to the rest of the plunger, so as the material at the distal end of the plunger is sponge-like or softer-than or more malleable than the rest of the plunger so as upon engagement with the interior distal end of the hollow tube, the distal end of the plunger substantially conforms to the interior configuration of the hollow tube. Similarly, the plunger distal end may be made of a material that is adaptable to substantially conform to the interior shape of the distal end of the hollow tube. Such configurations enable substantially all of the material contained within the plunger to be delivered to the targeted site.

Another alternative embodiment to the design described herein includes a navigation aid on one or more surfaces of the tubular body to permit surgeon to know how far the device has been inserted or to ensure proper alignment relative to a transverse bone graft delivery site (i.e. disc space). Such capability is particularly important when the patient or surgical area is not positioned immediately below the surgeon, or multiple procedures are being performed. A navigation aid allows more immediate and reliable locating of the surgical area for receiving of bone graft material. In one embodiment, the hollow tube is scored or marked or provides some affirmative indication, actively or passively, to the surgeon to indicate degree of delivery of the material, e.g. bone graft material, to the delivery site, and/or position of the plunger element. For example, the exterior of the hollow tube could be color-coded and/or provided with bars. In another embodiment, a computer and/or electro-mechanical sensor or device is used to provide feedback to the surgeon to indicate degree of delivery of the material, e.g. amount of cc's of bone graft material, to the delivery site, and/or position of the plunger element.

In another alternative embodiment to the design described herein, the plunger could include an activation device, which is often in a liquid or semi-liquid state, and that may be injected once the semi-solid portion of the morphogenic protein has been displaced by the movement of the plunger through the tubular body. That is, the plunger pushes the dry material, and once completed has a bulb or other device on the usable end to insert the liquid portion of the activating agent through the inner lumen within the plunger to evacuate the liquid from the plunger and out an opening at the non-usable end of the plunger so as to contact the dry material already inserted into the disc space).

In one embodiment of the device, all or portions of the device are manufactured using 3-D printing techniques. In another embodiment, all or portions of the device are made by injection molding techniques.

In one embodiment, the ratio of the surface area of the bottom tip of the plunger is approximately half the surface area of the two lateral openings at the distal portion of the hollow tube.

In one embodiment, the device includes a supplemental means of gripping the device, such as a laterally extending cylindrically-shaped handle that engages the hollow tube.

In one embodiment, the material inserted into the hollow tube is a non-Newtonian fluid. In one embodiment, the device is adapted to accept and deliver compressible fluids. In another embodiment, the device is adapted to accept and deliver non-compressible fluids.

In one embodiment, the upper portion of plunger is fitted with one or more protrusions, which extends from the surface of the plunger so as to engage the upper surface of the hollow tube, to prevent the plunger from engaging the distal interior portion of the hollow tube. In one embodiment, the upper portion of plunger is fitted with one or more protrusions to prevent the plunger from engaging the apex of the hollow tube distal interior ramp surface.

In one embodiment, the funnel attaches to the upper portion of the hollow tube by a bayonet connection. In one embodiment, the funnel attaches to the upper portion of the hollow tube by an interference fit. In one embodiment, the funnel attaches to the upper portion of the hollow tube by a threaded connection. In one embodiment, the funnel attaches to the upper portion of the hollow tube by a slot/groove connection.

In one embodiment, the second end of hollow tube has one hollow tube distal opening. In one embodiment, the second end of hollow tube has two hollow tube distal openings located on opposite sides. In one embodiment, the second end of hollow tube has no more than two openings, the openings located on opposite sides.

In one embodiment, after bone graft material is delivered to a surgical site, a cavity approximately defined by the volume engaged by the device when inserted into the surgical site is left in the surgical site upon removal of the device from the surgical site. In one embodiment, the aforementioned cavity is then used as the site for insertion of a fusion cage.

The integrated fusion cage 60 with expandable cage feature provides a number of unique and innovative features not provided by conventional or traditional integrated fusion cages. For example, the integrated fusion cage with expandable cage feature of the disclosure is intentionally and deliberately designed to receive bone graft material (or any material suitable for use in surgical applications, as known to those skilled in the art) at its proximal end (i.e. the end generally facing the surgeon and/or the end opposite the end initially directed into a surgical site), such that the bone graft material flows into the fusion cage and also flows out from the fusion cage into the surgical site. Such features as the interior ramps of the fusion cage (e.g. located within the interior of the hollow tube, and/or on the front and/or rear blocks of the fusion cage) function to direct received bone graft material into the surgical site. Additionally, the features of the hollow tube and plunger wherein a greater volume of bone graft material may be reliably (e.g. not prone to blockage as is typical with most convention e.g. round hollow tubes or cannula systems) and readily delivered to a surgical site and/or a fusion cage are unique and not found in the prior art. Among other things, such features encourage improved surgical results by delivering more volume and coverage of bone graft material to the surgical site. Also, such features minimize gaps in bone graft coverage to include gaps between the fusion cage area and the surrounding surgical site. Also, the features of the one or more apertures of the fusion cage of the disclosure enable and encourage delivery of bone graft material, as received by the fusion cage, into the surrounding surgical site.

In contrast, conventional fusion cages, to include expandable fusion cages, do not provide such features and/or functions. For example, U.S. Pat. No. 8,852,242 to Morgenstern Lopez ("Lopez"), discloses a dilation introducer for orthopedic surgery for insertion of an intervertebral expandable fusion cage implant. The Lopez device does not allow receipt of bone graft material from its proximal end, or any end, in contrast to the disclosed fusion cage and fusion cage/bone graft delivery system. That is, the Lopez proximal end includes an array of components, all of which do not allow receipt of bone graft material. Furthermore, the Lopez device requires an elaborate array of components, e.g. upper side portion 240 of the upper body portion 202 and lower side portion 242 of the lower body portion 204, which also block any egress of bone graft from the inside of the Lopez fusion cage once deployed. Also, the Lopez wedges occupy the entire interior of the cage; there are no ramps to direct graft from the interior to the disk space. In short, the Lopez design is not made with bone graft delivery in mind, and indeed, cannot function to accept let alone deliver bone graft. Additionally, suggestions provided in the Lopez disclosure to deliver bone graft to the surgical site would not provide the integrated and complete fusion cage and surgical site bone graft delivery of the invention, e.g. the Lopez slot 918 of the Lopez lumen 916 and funnel assembly 910 at best provides limited delivery of bone graft material only before and after insertion of the Lopez fusion cage, and then only peripheral to the fusion cage. Also, it appears the Lopez device provides wedges 206 and 208 of similar if not identical interior ramp angles. In contrast, in certain embodiments of the present invention the interior wedged surfaces of the invention, i.e., front block ramp 226 and rear block ramp 236, are not of the same configuration and/or shape, e.g. front block ramp 226 is of a curved profile and rear block ramp 236 is of a linear or straight-line profile. Among other things, the curved profile of the front block ramp 226 urges egress of bone graft as received by the fusion cage 60.

In one embodiment of the fusion cage 60, no anti-torque structures or components are employed. In one embodiment of the invention, the lateral sides of the fusion cage 60 are substantially open to, among other things, allow egress of bone graft material as received to the fusion cage. In one embodiment, the expansion screw 240 is configured with a locking mechanism, such that the fusion cage 60 may be locked at a set expansion state. In one embodiment, such a locking mechanism is provided through a toggle device operated at or on the installer/impactor handle 258.

In one embodiment, the front block ramp 226 and rear block ramp 236 are identical and/or symmetrical.

In addition, it is contemplated that some embodiments of the fusion cage 60 can be configured to include side portions that project therefrom and facilitate the alignment, interconnection, and stability of the components of the fusion cage 60.

Furthermore, complementary structures can also include motion limiting portions that prevent expansion of the fusion cage beyond a certain height. This feature can also tend to ensure that the fusion cage is stable and does not disassemble during use.

In some embodiments, the expansion screw 240 can facilitate expansion of the fusion cage 60 through rotation, longitudinal contract of a pin, or other mechanisms. The expansion screw 240 can also facilitate expansion through longitudinal contraction of an actuator shaft as proximal and distal collars disposed on inner and outer sleeves move closer to each other to in turn move the proximal and distal wedged block members closer together. It is contemplated that in other embodiments, at least a portion of the actuator shaft can be axially fixed relative to one of the proximal and distal wedge block members with the actuator shaft being operative to move the other one of the proximal and distal wedge members via rotational movement or longitudinal contraction of the pin.

Further, in embodiments wherein the engagement screw 240 is threaded, it is contemplated that the actuator shaft can be configured to bring the proximal and distal wedged block members closer together at different rates. In such embodiments, the fusion cage 60 could be expanded to a V-configuration or wedged shape. For example, the actuator shaft can comprise a variable pitch thread that causes longitudinal advancement of the distal and proximal wedged block members at different rates. The advancement of one of the wedge members at a faster rate than the other could cause one end of the implant to expand more rapidly and therefore have a different height that the other end. Such a configuration can be advantageous depending on the intervertebral geometry and circumstantial needs.

In other embodiments, the implant 200 can be configured to include anti-torque structures. The anti-torque structures can interact with at least a portion of a deployment tool during deployment of the fusion cage 60 implant to ensure that the implant maintains its desired orientation. For example, when the implant is being deployed and a rotational force is exerted on the actuator shaft, the anti-torque structures can be engaged by a non-rotating structure of the deployment tool to maintain the rotational orientation of the implant while the actuator shaft is rotated. The anti-torque structures can comprise one or more inwardly extending holes or indentations on the rear wedged block member. However, the anti-torque structures can also comprise one or more outwardly extending structures.

According to yet other embodiments, the fusion cage 60 can be configured to include one or more additional apertures to facilitate osseointegration of the fusion cage 60 within the intervertebral space. The fusion cage 60 may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Indeed, various biologics can be used with the fusion cage 60 and can be inserted into the disc space or inserted along with the fusion cage 60 The apertures can facilitate circulation and bone growth throughout the intervertebral space and through the implant. In such implementations, the apertures can thereby allow bone growth through the implant and integration of the implant with the surrounding materials.

In one embodiment, the fusion cage 60 comprises an expandable cage configured to move a first surface vertically from a second surface by rotation of at least one screw that rotates without moving transversely with respect to either said first or second surface, said first plate and second plate having perimeters that overlap with each other in a vertical direction and that move along a parallel line upon rotation of the screw.

In one embodiment, the fusion cage 60 is stackable by any means known to those skilled in the art. For example, each upper plate 200 may be fitted with one or more notches on the lateral edges configured to fit with one or more protrusions on each lower plate 210.

Surprisingly, while conventional practice assumed that the amount of material that would be required, let alone desired, to fill a prepared disc space with bone paste (or BMP, etc.) would be roughly equivalent to the amount of material removed from such space prior to inserting a cage, a present inventor discovered that far more bone graft material can be—and should preferably be—inserted into such space to achieve desired fusion results. The reasons why this basic under appreciation for the volume of bone graft necessary to achieve optimal fusion results vary, but the clinical evidence arrived at via practice of the present invention compellingly demonstrates that more than doubling of the amount of bone graft material (and in some cases increasing the amount by 200%, 300% or 400% or more) than traditionally thought necessary or sufficient, is extremely beneficial to achieving desired results from fusion procedures.

The ramifications of this simple yet dramatic discovery (documented in part below) is part of the overall inventive aspect of the present invention, as it has been—to date—simply missed entirely by the practicing spine surgeons in the field. The prospect of reduced return surgeries, the reduction in costs, time, and physical suffering by patients, as well as the volume of legal complaints against surgeons and hospitals due to failed fusion results, is believed to be significant, as the evidence provided via use of the present invention indicates a vast reduction in the overall costs involved in both economic resources, as well as emotional capital, upon acceptance and wide-spread use of the present invention. Insurance costs should thus decrease as the present invention is adopted by the industry. While the costs of infusing increased amount of bone graft materials into the space of a patient's disc may at first appear to increase the costs of an individual operation, the benefits achieved thereby will be considerable, including the reduction of repeat surgeries to fix non-fused spines. Thus, regardless of the actual tools and devices employed to achieve the end result of attaining up to 100% more bone graft material being utilized in fusion operations, (as well as other surgeries where previously under-appreciated bone graft material delivery volumes have occurred) one important aspect of the present invention is directed to the appreciation of a previously unrecognized problem and the solution thereto, which forms part of the inventive aspects of the present invention described and claimed herein.

In one embodiment, at least twice the amount of disk material removed from a surgical site is replaced with bone graft material. In a preferred embodiment, at least three times the amount of disk material removed from a surgical site is replaced with bone graft material. In a most preferred embodiment, at least three and a half times the amount of disk material removed from a surgical site is replaced with bone graft material.

Experimental Results

The following experimental results are with respect to an apparatus and method for integrated delivery of bone graft material in a patient's spine. These results are sample results and are not intended to limit the invention.

Materials and Methods

During the time period from July 2010 through December 2012, a set of patients undergoing minimally invasive (MIS) transverse lumbar interbody fusion (T-LIF) at the L4-5 and/or L5-S1 levels were studied for disk material removed and BG delivered at each disk space during the surgical procedure. The diagnosis was spondylosis or spondylolisthesis in all patients. A total of 63 patients with an average age of 56 years were studied. There were 29 male and 34 female patients. Ninety-one disk spaces were analyzed. A single surgeon with the same surgical team performed all surgeries. The operations were carried out through a 22 mm cannula with microscopic control. The midline structures and spinous process attachments were left undisturbed. The disk space was debrided exhaustively using non-motorized, hand tools to bleeding subchondral bone. The debrided disk material was measured in a volumetric syringe. Bone Graft (BG) material consisting of silicated tricalcium phosphate granules and hyaluronic acid powder were mixed in a 1:1 ratio and local bone graft and bone marrow aspirate concentrate were added together to form a slurry. The slurry was measured volumetrically. Disk space mobilization and distraction was carried out with serial impaction of distractor tools until appropriate disk height was achieved. Distraction ranged from 8 mm to 14 mm, with the 10 mm or 12 mm height being most commonly observed.

The BG delivery tool of this disclosure was used to apply the BG slurry to the disk space. The embodiment had a rectangular cross section with the same footprint as a small fusion cage (8 mm×12 mm). The tapered tip was placed into the debrided disk space under microscopic control to allow for direct visualization, followed by the application of a snap-on funnel for loading the BG. The BG slurry was then placed in the funnel and the slurry was pushed into the disk space with the plunger. The biportal design of the delivery tool directed the slurry into the lateral areas of the prepared disk space, leaving a natural void for the fusion cage once the tool was removed. Once the disk space was filled entirely, the site of insertion was inspected for any BG material, which might have escaped the confines of the disk space. This material was excluded in the final measurement to ensure an accurate calculation of BG delivery. Removal of the delivery tool provided an unobscured path for the fusion cage to be applied.

A polyether ether ketone, hollow interbody fusion cage of the appropriate size was then placed into the disk space. A minimally invasive, bilateral pedicle screw/rod system was applied prior to wound closure. Average blood loss for the procedures was 127 ml+/−75 ml.

A two-tailed student's t-test was used to determine if any significant difference existed between the volumes of disk material removed at L4-5 versus L5-S1. The null hypothesis was that no significant difference existed between samples. Significance was set at p<0.05. The two-tailed t test was also used to determine whether a significant difference existed between volumes of BG delivery and disk material removed. The formula [(BG delivered+graft volume of the fusion cage)/disk material removed] was used to generate the ratio of BG delivery versus disk material removed.

In order to compare the volume of disk material removed during a T-LIF procedure with a complete, surgical diskectomy, the volume of disk material removed during L5-S1 anterior lumbar diskectomy was measured volumetrically. The L5-S1 disk was harvested and measured for patients undergoing either anterior fusion or total disk replacement. The material removed consisted of anterior and posterior annulus as well as complete nuclectomy, and represented more tissue (in terms of the annuli) than would be typically removed in a T-LIF procedure. There were 29 anterior L5-S1 diskectomy patients. The age range, gender distribution and diagnosis were the same as the T-LIF patients.

All study patients were followed up with anterior/posterior radiographs and a physical examination at 4 weeks, 12 weeks, 26 weeks and 52 weeks post surgery. A visual analog scale (VAS) for pain was obtained at each visit and an Oswestry Disability Index (ODI) was completed preoperatively and at 26 weeks postoperatively.

Results

There were 58 L4-5 disk spaces and 33 L5-S1 disk spaces evaluated. The average volumes of disk material harvested from L4-5 and L5-S1 were 4.1 ml+/−2.2 ml and 2.8 ml+/−1.9 ml, respectively. The p-value for the student's two-tailed t-test was equal to 0.01, revealing a significant difference in terms of disk material removed between L4-5 and L5-S1. The range of volume was less than 1 ml to 14.5 ml. The comparison between disk material removed and BG material inserted at L4-5 or at L5-S1 demonstrated a significant difference (p<<0.001).

Figure 34A:
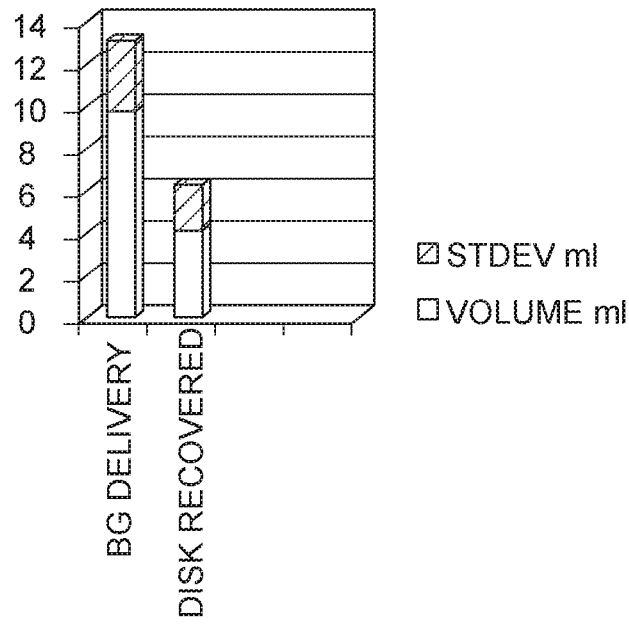
FIG. 34A is a bar graph describing experimental results of bone graft delivery and disk material removed for L4-5.
Figure 34B:
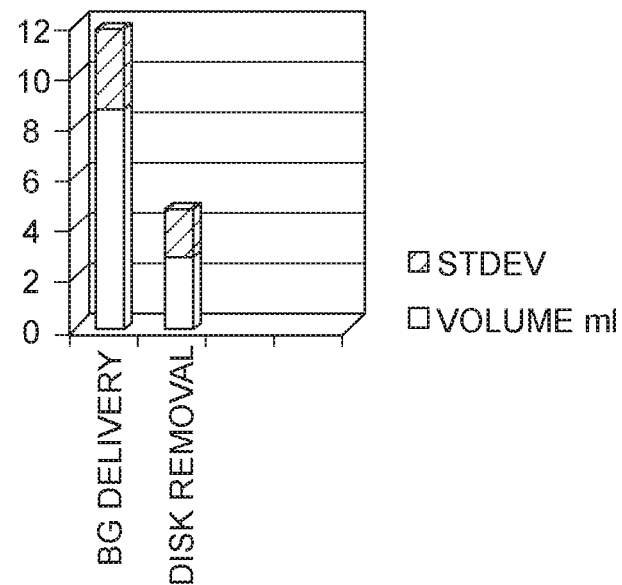
FIG. 34B is a bar graph describing experimental results of bone graft delivery and disk material removed for L5-S1.
Figures 35A, 35B:
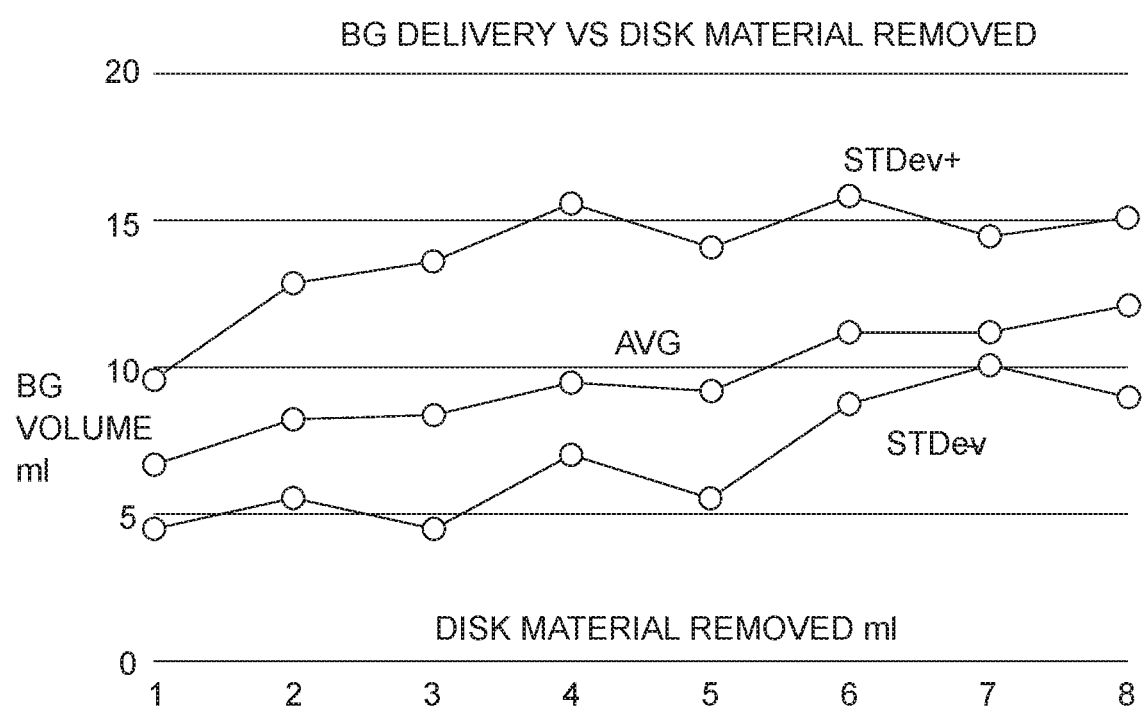
FIG. 35A is a table describing experimental results of bone graft delivery and disk material removed.
FIG. 35B is a graph of the table of FIG. 35A describing experimental results of bone graft delivery and disk material removed.
Figure 36:
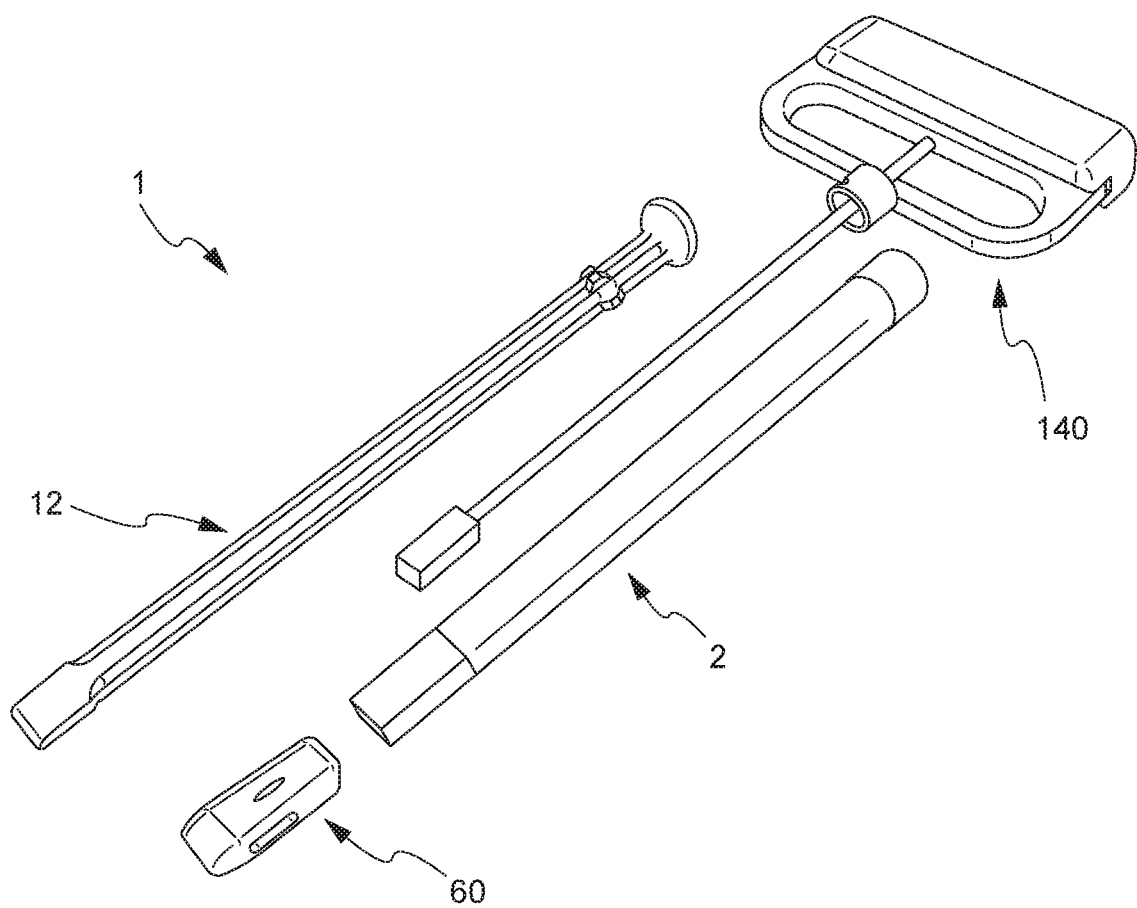
FIG. 36 is a front perspective exploded view of an integrated fusion cage and graft delivery device according to another embodiment.
Figure 37:
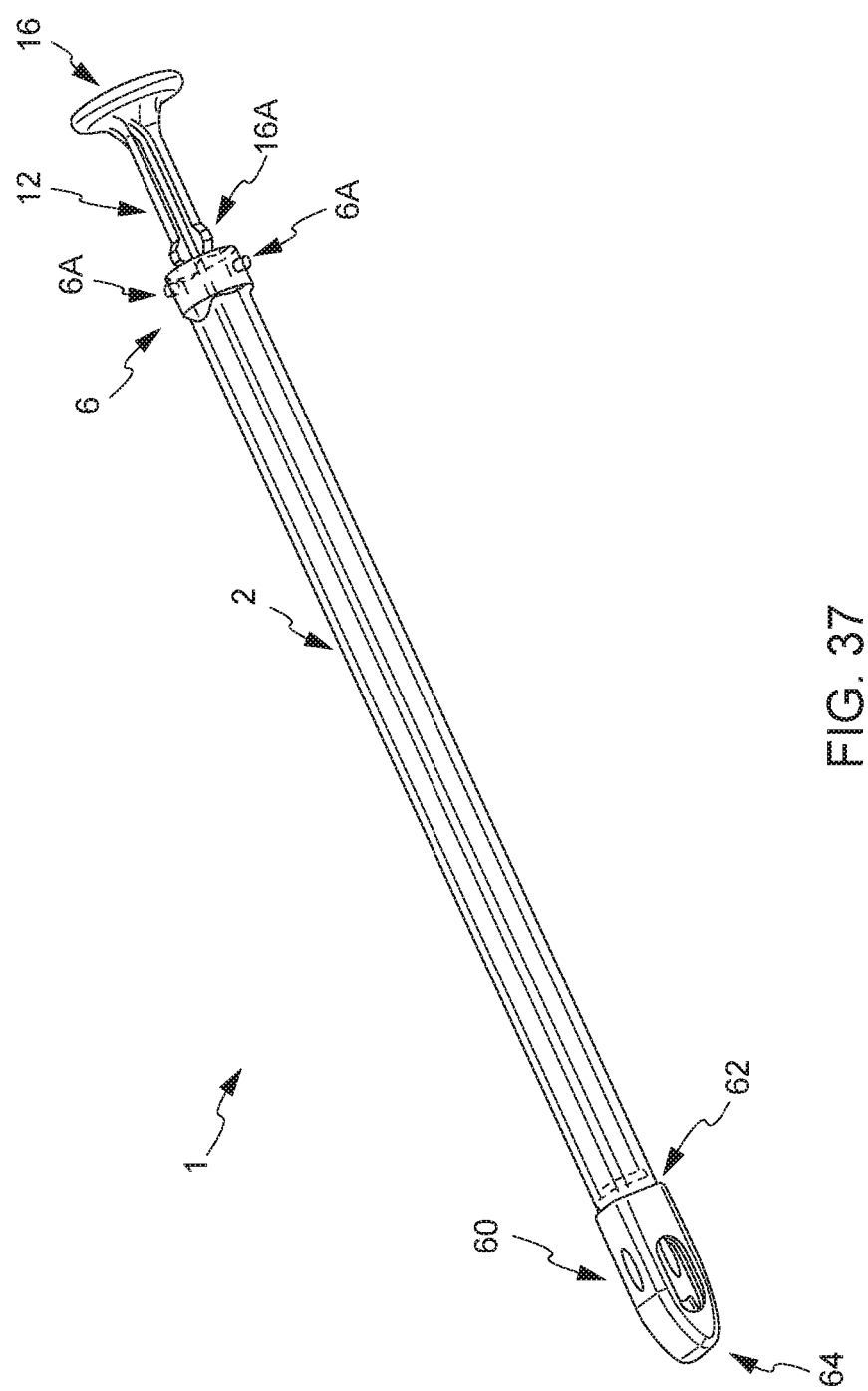
FIG. 37 is a front perspective view of the device of FIG. 36.
Figure 38:
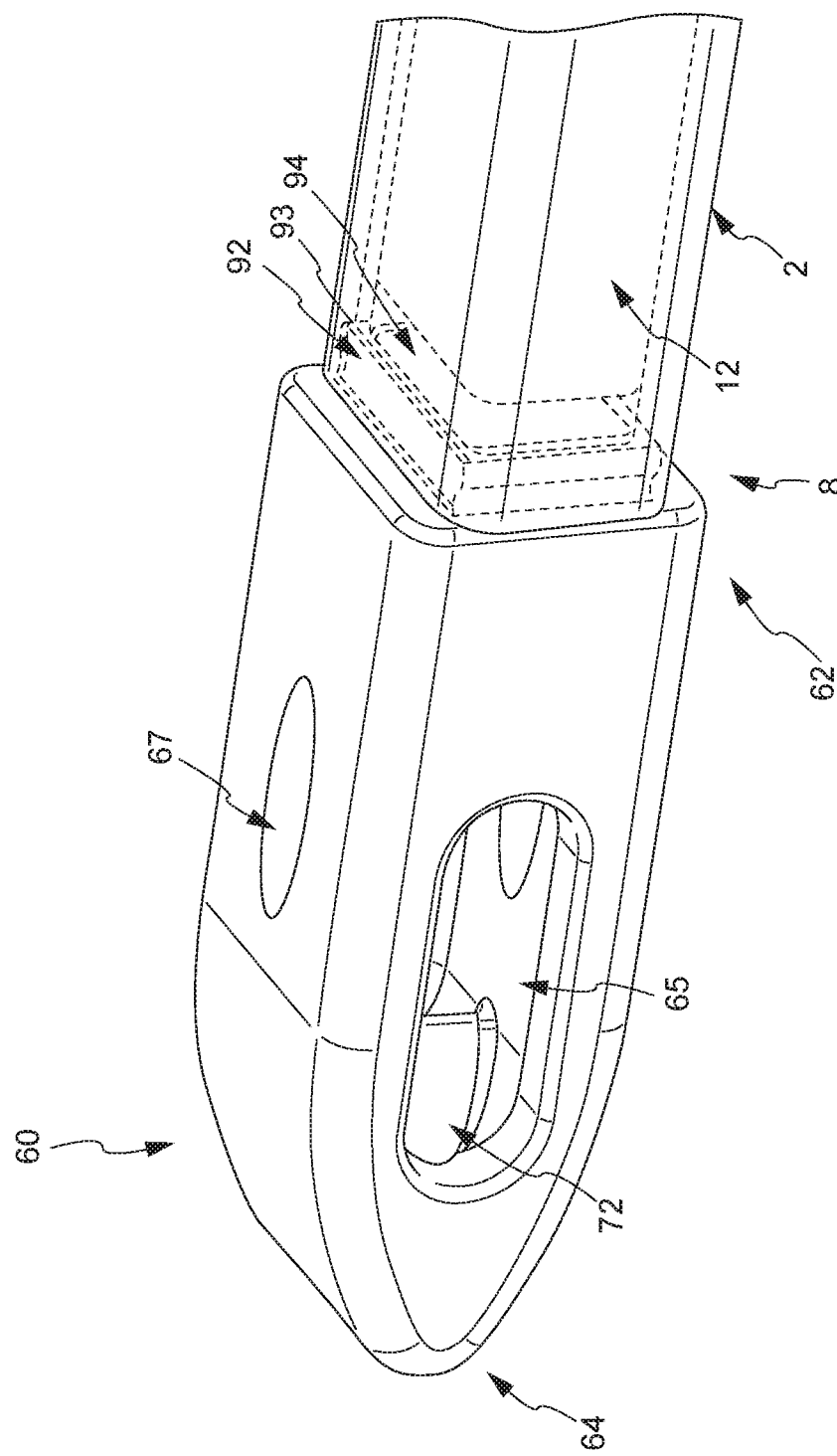
FIG. 38 is a closed-up front perspective view of the device of FIG. 36.
Figure 39:
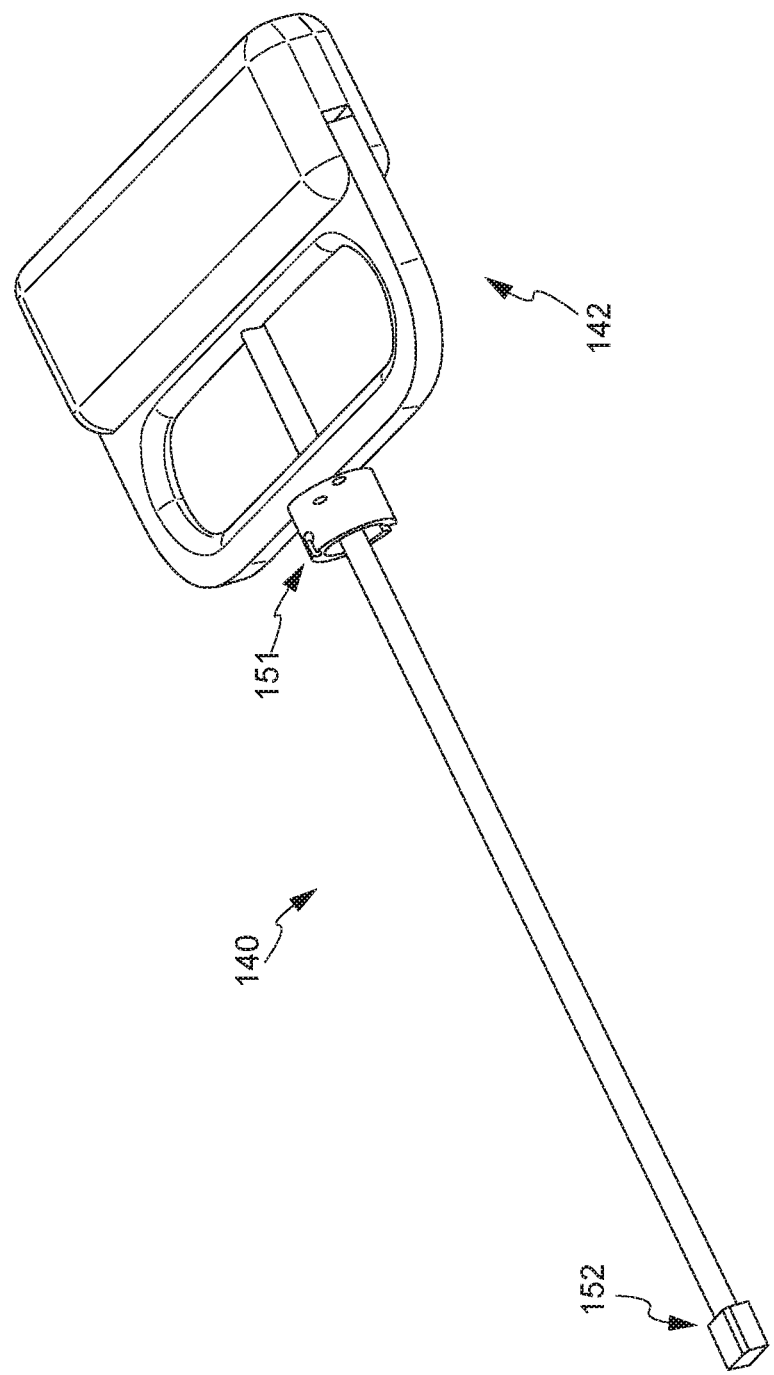
FIG. 39 is a front perspective view of the ejection tool element of the device of FIG. 36.

BG volume applied to L4-5 was 9.8 ml+/−3.3 ml. At L5-S1 it was 8.6 ml+/−3.2 ml. The p-value for the student's two-tailed t-test was equal to 0.07, trending to a significant difference in bone graft applied between L4-5 and L5-S1. The combined average was 9.2 ml+/−3.0 ml. The volume of BG applied ranged from 4.5 ml to 19 ml. The formula of [(BG delivered+graft volume of the fusion cage)/disk material removed] generated a surprising result: The amount of disk material removed compared to the amount of BG placed in the disk space was not a 1:1 ratio, as would have been empirically expected. At L4-5 the ratio was 3.4+/−2.2 and at L5-S1 it was 4.7+/−2.7, as shown in FIGS. 34A-B, respectively. This was statistically significant with a p-value of 0.02. With respect to the entire study, the ratio of BG inserted relative to disk material removed revealed that on average 3.7+/−2.3 times as much BG was inserted into the disk space as disk material removed. This finding was even more dramatic with collapsed disk spaces where 1 ml of disk material harvest led to an average of 6.6 ml+/−0.9 ml of BG delivery, as shown in FIGS. 35A-B. The volume of BG delivery was asymptotically related to the volume of disk material removed with 12.3 ml of disk material being delivered to a disk where 8.0 ml of disk was removed, as shown in FIGS. 35A-B.

The average volume of disk material removed during a T-LIF diskectomy at L5-S1 was 3.2 ml and the average volume of disk material from the anterior L5-S1 diskectomy was 8.1 ml. Dividing the average T-LIF volume by the average anterior diskectomy (including annuli) volume revealed that on average 34% of the disk material was removed at the time of T-LIF at the L5-S1 disk space.

Because of the tapered tip of the BG delivery tool, it was possible to enter the most collapsed disk space without endplate injury. The delivery device did not jam with the application of the BG slurry. The removable funnel allowed direct visualization of the tool under the microscope without obscuring its tip during insertion. Because the delivery device applied BG out of its side portals, it provided a natural void for fusion cage insertion, and no cage jamming resulted during impaction. BG delivery using the described tool took a fraction of the time (less than 2 minutes) usually devoted to depositing BG to the disk space. There were no complications associated with the use of the BG delivery tool.

The average preoperative ODI measured 29+/−9 and the postoperative value was 21+/−8. A significant difference was not detected with p=0.06. The VAS similarly improved with pre-operative score measuring 7.5+/−1.5 and postoperative score 4.0+/−2.5. The postoperative VAS was statistically significant relative to the corresponding preoperative value with p<0.05.

Pseudoarthrosis developed in 7 disks in 4 patients (7.6%). The patients with 2-level pseudoarthrosis had a diagnosis of hypothyroidism. This diagnosis was also present in one of the single level pseudoarthosis patients. The remaining pseudoarthrosis patients did not have discernable risk factors (diabetes, tobacco consumption or obesity).

Discussion

There is substantial variation in fusion rates after T-LIF surgery with pseudoarthrosis rates varying from 23.1% to 2.9%. The reasons for the range of successful arthrodesis vary from surgical technique, including BG preparation and application, to the way in which a pseudoarthrosis is diagnosed—direct surgical exploration or by radiographic means. Reason would dictate that the volume of BG delivered to a prepared disk space would contribute positively to successful arthrodesis with inadequate grafting leading to pseudoarthrosis. Using hand tools and the goal of disk space debridement, a conservative estimate of 34% of disk removal was observed in this study at the L5-S1 level. This substantial difference represents the different goals of the procedures and provides a baseline for general disk space debridement for T-LIF procedures.

The statistically significant difference between the amount of disk material removed from L4-5 versus L5-S1 correlates with the commonly observed radiographic finding of disk height at L4-5 being greater than that of L5-S1. Likewise, BG delivery to L4-5 was greater relative to the L5-S1 disk space. Although direct volume of BG insertion was greater in L4-5 relative to L5-S1, the ratio (BG delivered/disk material removed) was higher at L5-S1 (4.7+/−2.7) than at L4-5 (3.4+/−2.2). This was a statistically significant difference (p<0.02) and corresponds with the more collapsed disk spaces demonstrating a higher percentage of BG delivery (see FIGS. 34A-B).

On average, 3.7 times as much bone graft was applied to the debrided disk space relative to disk material removed. This is explained by the fact that the disk space was collapsed at the time of diskectomy, and then distracted and mobilized during the preparation process to a distracted height. This suggests that relying on an empiric 1:1 ratio of disk removal to BG insertion grossly under-fills the disk space and would be an important contributor to pseudoarthrosis. This is an especially important consideration in the most collapsed disk spaces since distraction to appropriate height in a non-collapsed disk reduces the ratio to 8:12.3 (see FIG. 35A) or a 1:1.4 ratio.

The BG slurry used in this study consisted of a mixture of granular material and liquid. This combination of materials does not behave as a typical, Newtonian (non-compressible) fluid. A non-Newtonian fluid will exude its fluid component as it is compressed, and the residual granular BG material occludes a conventional, cylindrical BG delivery device.

The BG delivery tool in this study revealed a number of advantages in that it allowed for BG application in collapsed disc spaces due to its wedged tip, a process which is not possible with round-ended injection cannulas. The increased cross sectional footprint relative to a round cannula allowed considerably less friction of non-Newtonian fluid material through the cannula, resulting in an increase in the BG flow dynamics, and eliminating jamming due to BG impaction. It is estimated that changing the cross-sectional area from 8 mm×8 mm to 8 mm×12 mm improves the flow dynamics of a non-Newtonian fluid by 40%. The two sites for BG extrusion at the sides of the cannula tip double the exit zone surface area, further decreasing the resistance to flow of the granular mixture. The removable funnel allowed direct visualization of the cannula as it was applied to the disk space without being obscured by the funnel. The biportal expression of the BG material allowed graft inoculation of all prepared areas of the disk space and left a void for the fusion cage. The applied BG delivery tool allowed refilling of the cannula without having to remove the device, resulting in decreased potential trauma to the adjacent nerve tissue.

The fusion rate in this study was 92.4% with three of the pseudoarthrosis patients having a diagnosis of hypothyroidism. This may be related to abnormalities in bone metabolism associated in patients with endocrinopathy. The other pseudoarthrosis patients did not have apparent risk factors. Postoperative pain scores and functional improvement correlated with progression to arthrodesis.

In summary, preparation of the disk spaces at L4-S1 can deliver 34% of the disk volume during debridement. BG delivery was on average 3.7 times the volume of disk removal with a relatively higher ratio of BG being delivered to the more collapsed disk spaces. A novel BG delivery device can be used to dispense a volume of BG to the disk space that is capable of filling the entire debrided area in an efficient and safe fashion. This should allow for maximization of arthrodesis potential, increase patient safety, and decrease operative time.

Referring now to FIGS. 75A to 75F, an embodiment of an integrated fusion cage and graft delivery device 1 of the present disclosure is illustrated. The graft delivery device generally includes a cannular or hollow tube 2, a plunger 12, and a detachable funnel 30.

The hollow tube 2 is the same as, or similar to, other embodiments of hollow tubes described herein. Accordingly, the hollow tube 2 generally includes an opening 4 at a proximal end 6. At least one discharge opening 7 is associated with a distal end 8 of the hollow tube. In one embodiment, the discharge opening 7 is positioned transverse to a longitudinal axis of the hollow tube 2. Accordingly, in one embodiment, the distal end 8 is at least partially closed opposite to the proximal opening 4. Alternatively, the distal end 8 may be completely closed. Optionally, a discharge opening 7 may be formed through at least a portion of the distal end. Specifically, in one embodiment, the hollow tube 2 can include a discharge opening 7 aligned with a longitudinal axis of the hollow tube.

In one embodiment, the distal end 8 is rounded or smooth with a wedge-shape 50. Specifically, the distal end can have a shape configured to facilitate easy entry into a disc space. In this manner, the shape of the distal end minimizes soft tissue damage or irritation. The wedge-shape 50 enables insertion of the distal end 8 into a collapsed disc space without damaging the endplates or skating off to an unintended location. In contrast, some prior art devices with an open distal end can injure bony end plates of the disc space of a patient.

Optionally, the hollow tube includes two discharge openings 7A, 7B. The two discharge openings 7 can be arranged on opposite sides of the hollow tube to eject graft material. Accordingly, in one embodiment, the hollow tube 2 is operable to dispense bone graft material laterally away from a longitudinal axis of the graft delivery device 1. In one embodiment, the two discharge openings 7 are of substantially the same size and shape. The discharge openings 7 may have a generally oval shape.

In another embodiment, at least one opening 7C (illustrated in FIG. 75D) is formed in the distal end 8. Thus, the graft delivery device 1 may discharge bone graft material through the distal end 8 in line with the longitudinal axis of the graft delivery device 1. The opening 7C may have any predetermined shape. Optionally, the opening 7C has a rectangular, round, or ovoid shape. The distal end 8 may optionally include a taper or wedge shape 50 with an end opening 7C formed therethrough.

The hollow tube 2 is substantial hollow between the proximal end and the distal end. Specifically, a lumen 28 extends through the hollow tube 2. The lumen 28 has a predetermined cross-sectional shape. In one embodiment, the cross-sectional shape of the lumen is one of round, ovoid, square, rectangular, and approximately rectangular with rounded corners or edges. In another embodiment, the interior of the lumen is not round and is, for example, rectangular. Optionally, the cross-sectional shape of the lumen 28 is substantially uniform along the length of the hollow tube 2. In one embodiment, the lumen 28 has a uniform cross-sectional size along its length. The exterior of the hollow tube 2 may have a shape that is one of round, ovoid, square, and rectangular.

A ramp 9 may be formed within the hollow tube proximate to the opening 7. As described herein, the ramp 9 includes surfaces configured to direct the bone graft material away from the opening 7 into a surgical site, such as a disc space. More specifically, the ramp 9 functions as a reverse funnel to disperse bone graft material ejected from the opening 7 as generally illustrated in FIG. 77A.

In one embodiment, surfaces of the ramp 9 are linear in shape, that is, forming a triangle in cross-section. In another configuration, surfaces of the ramp 9 are of any shape that urges egress of bone graft material contained in the hollow tube to exit the lumen 28 of the hollow tube 2 through the at least one opening 7 of the device 1.

The hollow tube 2 is configured to receive the plunger 12 of the present disclosure within the lumen 28. Any plunger 12 of the present disclosure may be used with the hollow tube 2. The plunger 12 can be used to push bone graft material positioned in the lumen 28 out of the opening 7 at the distal end 8. Optionally, a stop 16A can be formed on the plunger 12 to engage the proximal end 6 of the hollow tube. In this manner, the stop 16A prevents over insertion of the plunger within the lumen.

Optionally, the plunger 12 may include a plurality of teeth separated by notches 27. The notches 27 can be engaged by a means for advancing bone graft material described herein. In one embodiment, the means for advancing comprises a ratchet configured to engage the notches 27. In operation, the ratchet can engage successive notches to advance or withdraw the plunger within the hollow tube.

Additionally, or alternatively, the means for advancing can include a gear with teeth. The gear is aligned with the plunger and operable to convert rotational movement of the rear to linear movement of the plunger. As the gear rotates, the gear teeth engage the plunger notches 27 to move the plunger toward or away from the hollow tube distal end.

In still another embodiment, the means for advancing comprises a worm gear with at least one helical thread. As the worm gear rotates, the helical thread engages the plunger notches 27. In this manner, the worm gear can advance or retract the plunger within the hollow tube.

The plunger 12 includes a distal end 18. The distal end 18 substantially conforms to inner walls of the lumen 28. Specifically, in one embodiment, the distal end 18 has a cross-sectional shape which corresponds to the interior shape of the lumen 28. Optionally, the plunger distal end 18 is round, ovoid, square, or rectangular. In one embodiment, the distal end 18 is not round. In another embodiment, the plunger distal end is configured to contact the inner walls of the lumen 28 about an entire outer periphery of the plunger distal end. Additionally, or alternatively, the plunger 12 (or a portion of the plunger 12) may be made of rubber silicone to improve the seal with interior surfaces of the lumen 28. In some embodiments, at least the distal end 18 is made of a plastic or an elastomeric rubber.

In one embodiment, the plunger has a length sufficient for the distal end 18 of the plunger to extend beyond the opening 7 as generally illustrated in FIG. 75C. In one embodiment, the handle 16 of plunger is a planar disk shape, as depicted in FIG. 75C. In another embodiment, handle 16 is not planar. For example, handle 16 is angled so as to conform to interior of funnel 30 when the plunger 12 is fully inserted into hollow tube 2.

Notably at least one vent port 21 may be formed through the hollow tube 2 to the lumen 28. The vent port 21 is configured to release air from the interior of the hollow tube 2 as bone graft material is delivered to the distal end 8 for discharge out of the opening 7. As one of skill in the art will appreciate, air trapped within the lumen 28 of the hollow tube 2 between the distal end 8 and bone graft material may increase the amount of axial force required by the plunger 12 to move the bone graft material to the discharge opening 7 or may cause the plunger to jam or bind in the lumen. Applying excessive force to the plunger to eject the bone graft material can cause soft tissue inflammation or damage. By allowing air to escape from within the lumen 28 of the hollow tube 2 as the plunger 12 is pressed toward the distal end 8, the vent port 21 may decrease the amount of force required to deliver the bone graft material to the discharge opening 7. The possibility of the plunger 12 jamming within the hollow tube 2 is also reduced. Specifically, the vent port 21 eliminates or reduces the risk of jamming the plunger and also reduces the possibility of trapped air being forced into the disc space and into the patient's vascular system causing an air embolism.

The vent ports 21 also prevent introduction of air or other fluids into the surgical site. For example, air may be introduced into, and trapped within, bone graft material as the bone graft material is loaded into the hollow tube. As the plunger presses against the bone graft material, the air may be released from the bone graft material. The air can escape from the lumen 28 through the vent ports 21.

Vent ports 21 can be formed through the hollow tubes 2 of all embodiments of the present disclosure. Vent ports 21 may be formed at any location of the hollow tube 2 along the length of the hollow tube between to proximal end 6 and the distal end 8. Optionally, a vent port 21 is formed on at least one of the first surface 3 and the second surface 5. In one embodiment, vent ports 21 can be formed on more than one surface 3, 5 of the hollow tube.

The at least one vent port 21 is configured to prevent discharge of bone graft material from the lumen 28. Accordingly, the vent port 21 has one or more of a size and a shape selected to prevent passage of bone graft material therethrough. In one embodiment, a width or a diameter of the vent port is less than approximately 2 mm. Optionally, the vent port 21 includes a mesh or screen with apertures which allow passage of air therethrough.

As illustrated in FIG. 75B, the vent port 21 can optionally have a generally circular shape, such as a bore. Although the vent port 21 illustrated in FIG. 75B is generally circular, other shapes are contemplated. In one embodiment, the vent port is a slit or slot. The slot may be generally linear. In another embodiment, the vent port 21 has a shape that is generally triangular or rectangular. Specifically, the vent port 21 may have any size or shape which allows the passage of air but prevents passage of bone graft material therethrough.

Any number of vent ports 21 may be formed through the hollow tube 2. In one embodiment, the hollow tube 2 includes at least three vent ports 21. A first vent port 21A can be proximate to the proximal end 6 of the hollow tube 2. A second vent port 21B can be proximate to the distal end 8. A third vent port 21C can be formed between the first and second vent ports 21A, 21B.

Figure 75A:
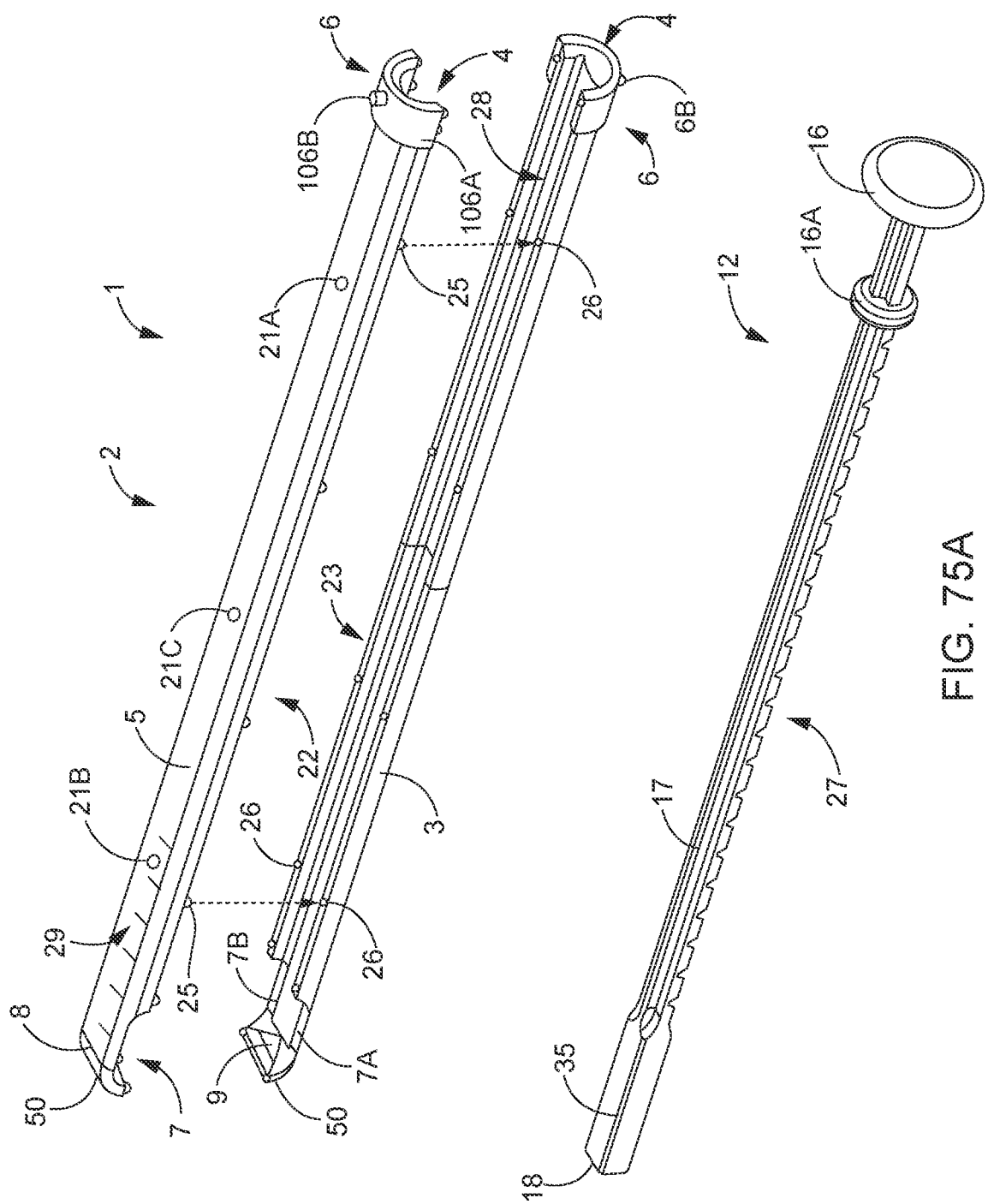
FIG. 75A is a perspective view of a device for delivering bone graft of another embodiment illustrating a hollow tubular member including a plurality of vent ports and a plunger of an embodiment of the present disclosure.

Additionally, or alternatively, in another embodiment, the plunger 17 includes a channel 35 (such as generally illustrated in FIG. 75A) configured to release air from the distal end 8 of the lumen 28 to the proximal end of the lumen. In this manner, as the plunger is advanced to eject bone graft material from the discharge opening 7, air trapped in the bone graft material and/or the lumen distal end 8 (the portion of the lumen distal to the distal end 18 of the plunger 12) can pass through the channel 35 into the proximal portion of the lumen.

Optionally, indicia 29 may be formed on one or more surface of the hollow tube 2. The indicia are configured to indicate a depth of insertion of the distal end 8 of the hollow tube into a surgical site. The indicia 29 can include marking and numerals. Optionally, one or more of the indicia 29 may be radiopaque. The indicia 29 may extend along the length of the hollow tube, or a predetermined portion of the length.

In one embodiment, the hollow tube 2 may comprise a first portion 22 and a second portion 23 which are configured to be interconnected. The hollow tube 2 thus includes a joint 24, illustrated in FIG. 75C, along which the first and second portions 22, 23 are connected. The joint 24 may substantially bisect the hollow tube 2.

The first and second portions 22, 23 can be interconnected by any suitable means. In one preferred embodiment, an ultraviolet activated adhesive is used to interconnect the first and second portions 22, 23. This forms a particularly strong bond in combination with optional alignment features 25, 26 (best seen in FIG. 75E) and the material of the hollow tube 2.

In another embodiment, the first and second portions 22, 23 are sonically welded together. Additionally, or alternatively, other glues or adhesives can be used to join the first and second portions 22, 23.

Optionally, the first and second portions can include the alignment features 25, 26. In addition to ensuring alignment of the first portion 22 with respect to the second portion 23 when the hollow tube 2 is assembled, the alignment features 25, 26 can also provide support to the hollow tube 2. In one embodiment, the alignment features 25, 26 have a shape selected to increase rigidity of the hollow tube 2, such as to prevent unintended or inadvertent bending or movement.

The alignment features 25, 26 may comprise a projection 25 formed on one of the first and second portions 22, 23 that is at least partially received in a bore or aperture 26 of another of the first and second portions 22, 23. In one embodiment, the alignment feature 25 comprises a peg or pin. Optionally, alignment feature 26 comprises a recess configured to receive the peg 25. In one embodiment, one of the alignment features 25, 26 comprises a flange. The flange may extend along some or all of the joint 24. The other one of the alignment features 26, 25 may comprise a groove configured to receive the flange. Similar to the flange, the groove may extend along some or all of the joint 24. Other shapes and features of the alignment features 25, 26 are contemplated.

The alignment features 25, 26 can also be configured to lock the first and second portion 22, 23 together. Specifically, in one embodiment, alignment feature 25 comprises a projection configured to engage a corresponding recess in alignment feature 26. Feature 26 can frictionally engage feature 25.

The hollow tube 2 may be made of a flexible, semi-rigid, or rigid material including one or more of a plastic, a composite, a metal. In one embodiment, the hollow tube 2 is formed of polycarbonate resin thermoplastic. Optionally, at least a portion of the hollow tube 2 is radiopaque. In one embodiment, at least the distal end 8 is radiopaque or includes radiopaque markers, such as indicia 29.

In one embodiment, the hollow tube 2 is substantially rigid. Optionally, at least a portion of the hollow tube 2 may be flexible. For example, in one embodiment, at least about one-half of the hollow tube 2 comprising the distal end 8 is flexible.

In one embodiment, the hollow tube 2 is generally linear. Alternatively, the hollow tube 2 can include a portion that is not linear. More specifically, in one embodiment, the hollow tube 2 can have a permanent (or temporary) curve or bend.

Alternatively, in another embodiment, the proximal end 6 of the hollow tube can extend along a first longitudinal axis. At least the distal end 8 of the hollow tube 2 may extend along a second longitudinal axis that is transverse to the first longitudinal axis of the proximal end. The distal end 8 can extend at a predetermined angle from the proximal end 6. Optionally, the angle can be between about 0° and about 75°. In one embodiment, the distal end 8 intersects the proximal end 6 at a joint. The joint may be adjustable such that a user can alter the angle between the proximal end and the distal end. Alternatively, the joint is not adjustable. The proximal end and the distal end may each extend generally linearly to the joint. Alternatively, the hollow tube 2 may include a transition portion between the proximal end and the distal end. The transition portion can have a shape that is curved, such as an elbow joint.

The hollow tube 2 may be made of a substantially transparent or translucent material. Accordingly, in one embodiment, the hollow tube is not opaque. Optionally, at least a portion of the hollow tube 2 is transparent or translucent. In one embodiment, the hollow tube 2 is comprised of a transparent or translucent material, or includes windows of a transparent or translucent material. Accordingly, in embodiments, the plunger 12 is at least partially visible within the lumen 28.

Referring now to FIG. 75D, one or more of an endoscope, camera, and image sensing device 36 can optionally be associated with the hollow tube 2. More specifically, in one embodiment, one or more of an endoscope and a camera or image sensor can be coupled to the hollow tube. The endoscope, camera, or image sensor 36 can be removably or permanently coupled to the hollow tube. In one embodiment, the endoscope, camera, or image sensor 36 can extend through a portion of the hollow tube 2. In another embodiment, the endoscope, camera, or image sensor are interconnected to an exterior surface of the hollow tube 2. Additionally, or alternatively, the endoscope, camera, or image sensor may extend within at least a portion of the lumen 28.

The endoscope, camera, or image sensing device 36 may be oriented to view at least the distal end 8. Optionally, the endoscope, camera, or image sensing device 36 is repositionable with respect to this distal end. In this manner, the endoscope, camera, or image sensing device 36 can be manipulated to view one or more openings 7 of the hollow tube 2, or view the internal aspect of the disc space 172A, or a debrided portion of the disc space 172A, prior to administration of bone graft.

Also, in another embodiment, the hollow tube 2 can include lighting elements 37. The lighting elements may be associated with the optional endoscope, camera, or image sensor 36. Additionally, or alternatively, one or more lighting elements 37 can be fixed to, or integrally formed with, the hollow tube 2. Suitable lighting elements, cameras, and displays that may be used with the integrated fusion cage and graft delivery device 1 of the present disclosure are described in U.S. Pat. Nos. 8,864,654, 9,717,403, and PCT Pub. WO 2012/145048 which are each incorporated herein by reference in their entirety.

As illustrated in FIGS. 75B and 75C, the funnel 30 can be releasably interconnected to the hollow tube. The funnel facilitates loading of bone graft material into the opening 4 at the proximal end 6 of the hollow tube 2. Once the lumen 28 is loaded with bone graft material, the funnel may be removed to improve visualization of the distal end 8 and opening 7 in a surgical site, such as a disc space. In contrast to prior devices which include a fixed funnel which cannot be removed, the releasable funnel 30 of the present disclosure does not obstruct visualizing the distal end 8 of the hollow tube 2 as it is placed in a disc space or other surgical site. Optionally, if additional bone graft material is required, the funnel 30 may be interconnected to the hollow tube during the surgical procedure without having to remove the hollow tube 2 from the surgical site, resulting in decreased potential trauma to adjacent nerve tissue.

In one embodiment, the funnel 30 is retained on the hollow tube 2 by a friction fit. Alternatively, the funnel can snap onto the hollow tube. Optionally, in one embodiment, the hollow tube 2 include a collar 106A with one or more projection 106B. The funnel 30 has a sleeve 32 that fits over the collar 106A and engages the projection 106B. Optionally, the sleeve 32 includes a slot 33 to engage the projection 106B. The slot 33 and projection 106B form a bayonet mount. In this manner, funnel can be releasably interconnected to the hollow tube.

Optionally, the hollow tube 2 can be configured to receive a fusion cage 60 of one or more of the embodiments described herein. Optionally, the fusion cage 60 may have a fixed height. Alternatively, the fusion cage may be expandable after placement in a disc space.

In one embodiment, the fusion cage includes an opening 65 to discharge bone graft material therethrough. The opening 65 is alignable with the opening 7 of the hollow tube. Optionally, the fusion cage 60 may include two or more openings 65 which each correspond to openings 7A, 7B of the hollow tube. Accordingly, as bone graft material is advanced through the lumen and through the opening 7 of the hollow tube, the bone graft material will be discharged through opening 65 of the fusion cage into a surgical site, such as a disc space.

In one embodiment, a distal end 64 of the fusion cage is closed. The distal end 64 may have a blunt or tapered shape similar to the wedge shaped end 50 of the hollow tube.

In one embodiment of the device 1, the width of the hollow tube second exterior surface 5 is between 9 and 15 mm. In a preferred embodiment, the width of the hollow tube second exterior surface 5 is between 11 and 13 mm. In another embodiment, the width of the hollow tube second exterior surface 5 is between 11.5 mm and 12.5 mm. In yet another embodiment, the width of the hollow tube second exterior surface 5 is 12 mm.

In one embodiment of the device 1, the width of the hollow tube first exterior surface 3 is between 5 and 11 mm. In another embodiment, the width of the hollow tube first exterior surface 3 is between 7 and 9 mm. Optionally, the width of the hollow tube first exterior surface 3 is between 7.5 mm and 8.5 mm. In one embodiment, the width of the hollow tube first exterior surface 3 is 8 mm.

In one embodiment of the device, the ratio of the width of the hollow tube second exterior surface 5 and the width of the hollow tube first exterior surface 3 is between approximately 1.7 and 1.3. In another embodiment, the ratio of the width of the hollow tube second exterior surface 5 and the width of the hollow tube first exterior surface 3 is between 1.6 and 1.4. In still another embodiment, the ratio of the width of the hollow tube second exterior surface 5 and the width of the hollow tube first exterior surface 3 is between 1.55 and 1.45. In one embodiment, the ratio of the width of the hollow tube second exterior surface 5 and the width of the hollow tube first exterior surface 3 is 1.5.

In one embodiment of the device, the width of the interior of the hollow tube major axis (located adjacent the second exterior surface 5) is between 9 and 13 mm. In another embodiment, the width of the interior of the hollow tube major axis is between 10 and 12 mm. Optionally, the width of the interior of the hollow tube major axis is between 10.5 mm and 11.5 mm. In one embodiment, the width of the interior of the hollow tube major axis is 11 mm.

In one embodiment of the device 1, the width of the interior of the hollow tube minor axis (located adjacent the first exterior surface 3) is between 5 and 9 mm. In another embodiment, the width of the interior of the hollow tube minor axis is between 6 and 8 mm. In yet another embodiment, the width of the interior of the hollow tube minor axis is between 6.5 mm and 7.5 mm. In one embodiment, the width of the interior of the hollow tube minor axis is 7 mm.

In one embodiment of the device 1, the ratio of the width of the interior of the hollow tube major axis and the width of the interior of the hollow tube minor axis is between approximately 1.7 and 1.3. In another embodiment, the ratio of the width of the interior of the hollow tube major axis and the width of the interior of the hollow tube minor axis is between 1.6 and 1.4. Optionally, the ratio of the width of the interior of the hollow tube major axis and the width of the interior of the hollow tube minor axis is between 1.55 and 1.45. In one embodiment, the ratio of the width of the interior of the hollow tube major axis and the width of the interior of the hollow tube minor axis is 1.5.

In one embodiment, one or more edges of the device are rounded. For example, the exterior edges of the hollow tube are rounded, and/or the interior edges of the hollow tube are rounded (in which case the edges of the plunger, at least at the plunger distal end, are identically rounded to ensure a congruous or conformal fit between the edges of the plunger and the interior of the hollow tube so as to, among other things, urge the majority of bone graft material to move through the hollow tube).

The device 1 may optionally be printed using a three-dimensional printing process. More specifically, one or more of the hollow tube 2, the plunger 12, the funnel 30, and the fusion cage 60 may be manufactured by one or more three-dimensional printing processes. A variety of materials, including a metal, PEEK, and other plastics may be used in a three-dimensional printer to form the device 1.

Figure 75F:
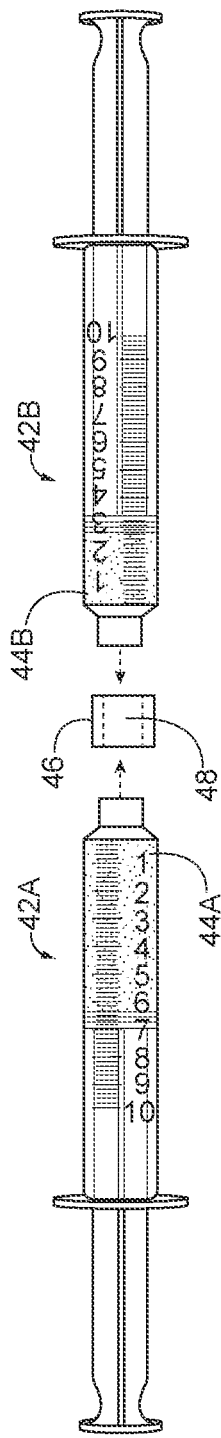
FIG. 75B is a top plan view of the hollow tubular member of FIG. 75A and detachable funnel.
FIG. 75C is a side elevation view of the hollow tubular member of FIG. 75A interconnected to the funnel and including a plunger inserted into a lumen of the hollow tubular member.
Figure 75G:
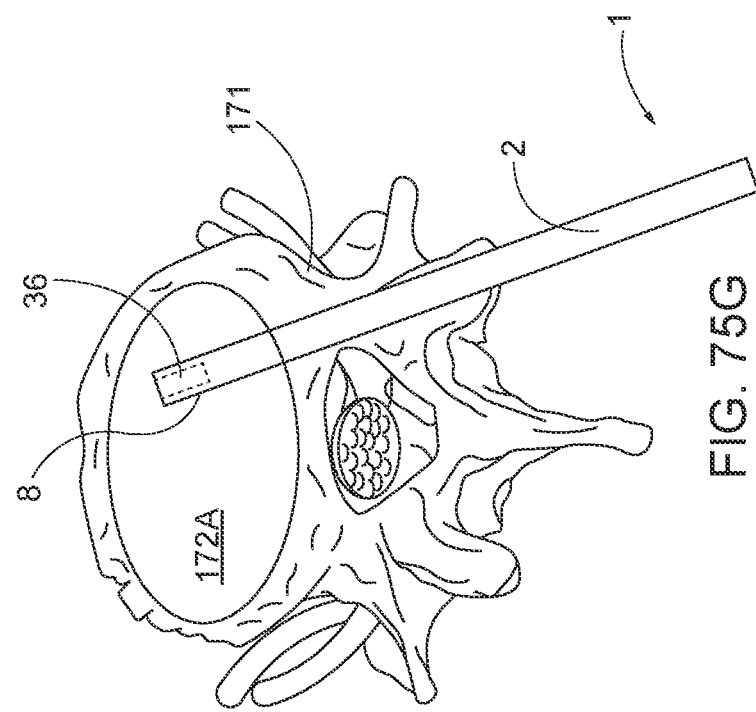

Referring now to FIG. 75F, devices 42 for preparing a bone graft material 44 according to one embodiment of the present disclosure are illustrated. Specifically, in one embodiment, bone graft material 44 is prepared within one or more devices 42, such as graduated syringes. The bone graft material 44 is compressed or compacted to form a desired and measured amount of bone graft material. Optionally, the bone graft material comprises two or more components 44A, 44B. A first one of the components 44A, 44B may be an activating agent or a liquid. A second one of the components 44A, 44B may be a dry material or a granular material.

The bone graft components 44A, 44B may be mixed together by interconnecting the devices 42A, 42B. Optionally, the devices 42A, 42B may be interconnected with a bayonet mount. In one embodiment, a connecting device 46 is provided to interconnect device 42B to device 42A. Connecting device 46 may include luer locks. The luer locks may include a locking or slip style connector. A bore 48 through the connecting device 46 enables bone graft material to be injected from one syringe to the other syringe 42. In one embodiment, component 44B is injected from device 42B into device 42A to be mixed with bone graft component 44A.

The mixed bone graft material 44A, 44B can subsequently be discharged from device 42A into the hollow tube 2. In one embodiment, the device 42A can be interconnected to the proximal end 6 of the hollow tube 2. Additionally, or alternatively, the bone graft material 44 can be ejected from the device 42A into the funnel 30. Suitable devices 42 that can be used to prepare bone graft material for use with the integrated fusion cage and graft deliver device 1 of the present disclosure are known and described in U.S. Pat. Pub. 2009/0124980, U.S. Pat. Pub. 2014/0088712, U.S. Pat. Pub. 2014/0276581, U.S. Pat. Pub. 2014/0371721, U.S. Pat. Nos. 8,439,929, and 9,174,147 which are each incorporated herein by reference in their entirety.

The integrated fusion cage and graft deliver device 1 of the present invention provides many benefits over other devices. For example, the rectangular or approximately rectangular lumen 28 of embodiments of the hollow tube 2 affords several advantages over conventional circular configurations. For a surgical area with a smallest dimension set at a width of 8 mm and a thickness dimension 0.5 mm, a conventional circular device (with resulting interior diameter of 7 mm or a radius of 3.5 mm) would realize a surface area of 38.48 mm$^2$ Applicants' device would carry interior dimension of 7 mm by 11 mm for a surface area of 77 mm$^2$, an increased surface area factor of 2.0, thereby resulting in more bone graft material delivery, because, among other things, a given volume of bone graft encounters less surface area of the interior of a particular device which results in, among other things, reduced chance of jamming of bone graft material within the device.

Figure 76:
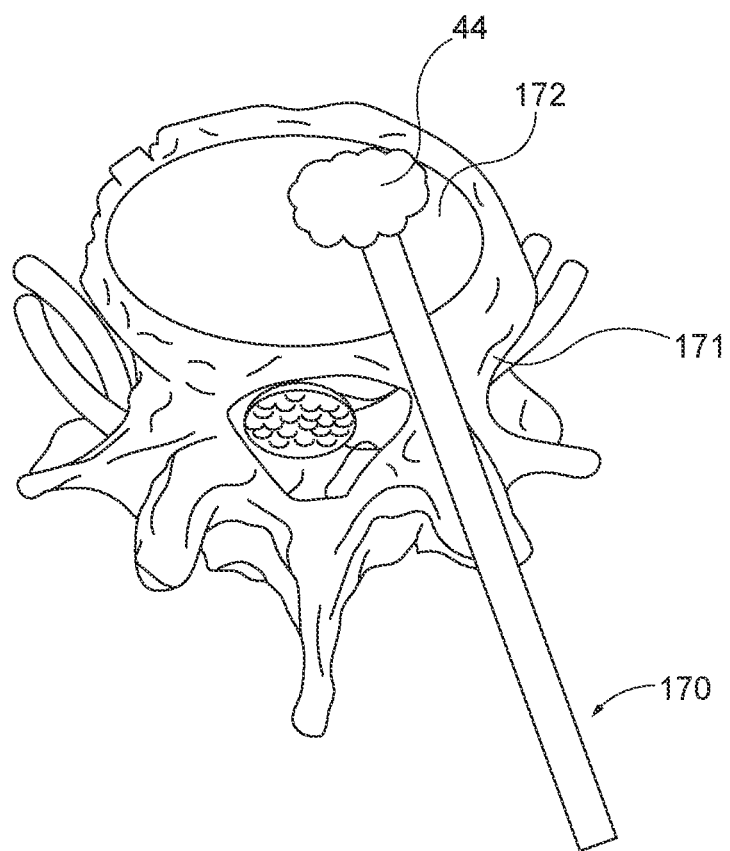

Referring now to FIG. 76, a cross-sectional view of a bone graft delivery device 170 provided in combination with a surgical work site 172 is illustrated. Specifically, a bone graft delivery device 170 is shown as providing a bone graft material 44 to an intervertebral space 172 within a human spine. The tool 170 is generally inserted into a patient from a transforaminal or lateral access site, and a second end of the delivery device 170 is provided within the intervertebral space to which bone graft material 44 is to be provided. The device 170 includes a conventional end-dispensing lumen that ejects and injects the bone graft material 44 directly into the intended path of a fusion cage. The device and method of FIG. 76 does not distribute bone graft delivery material into the periphery of the prepared disc space and generally fails to achieve appropriate distribution of bone graft delivery material within the disc space 172. Additionally, the small diameter tube necessitates injecting the bone graft material 44 in a more liquid (less viscous) state. In some cases, the pressure required to push bone graft material through the bore of device 170 is relatively high, increasing the risk of the device jamming. Generally, the risk of injury to the patient increases as the pressure required to eject the bone graft material from the delivery device 170 increases. Furthermore, if the device jams, then it needs to be removed, increasing the cumulative trauma to the surrounding nerve tissue as the device is removed and reinserted.

Referring now to FIG. 77A, an integrated fusion cage and graft deliver device 1 according to embodiments of the present disclosure is illustrated delivering bone graft material 44 to a disc space 172 within a patient's spine 171. As shown, the hollow tube 2 of the device 1 is provided with at least one opening 7. Bone graft material 44 is provided to the intervertebral space 172 by ejecting the material from the opening 7. In some embodiments, the hollow tube 2 has two openings such that bone graft material 44 is ejected on opposing sides of the device 1. In this manner, the device 1 provides enhanced distribution of bone graft material 44 and a greater quantity of bone graft material into a surgical site compared to the device 170 described in conjunction with FIG. 76. Further, the larger cross-sectional shape of the hollow tube 2 of the deliver tool 1 of the present invention allows injection of bone graft material in a thicker, more controllable viscous state and with less force than required by device 170.

An additional benefit of some embodiments of devices 1 of the present disclosure is that they avoid injection of bone graft material 44 directly into the path or intended path of a cage, such as illustrated in FIG. 76. For example, FIG. 77B provides a top view of the surgical workspace 172 according to FIG. 77A, after the integrated fusion cage and graft deliver device 1 has been removed after insertion or injection of the bone graft material 44. As shown in FIG. 77B, removal of the bone graft delivery tool provides an unobstructed path 174 and void space for subsequent insertion of a fusion cage (not shown in FIG. 77B). In this manner, devices 1 of the present disclosure provide for a sufficient amount of bone graft material within the surgical site 172 and provide an area 174 that is operable to receive a fusion cage.

Referring now to FIG. 78, another embodiment of an integrated fusion cage and graft delivery device 1 of the present disclosure is illustrated. The integrated device 1 generally includes a hollow tube 2, a fusion cage 60, and a means for advancing bone graft material through the hollow tube. The means for advancing may use manual force, mechanical force, electric force, pneumatic force, or any other force to advance bone graft material through the hollow tube. In one embodiment, a user can manipulate the integrated device 1 with a single hand. This beneficially frees the user's other hand for other action.

In one embodiment, the means for advancing includes a handle or grip 304. The grip 304 is operable to selectively move bone graft material through the lumen of the hollow tube 2 for discharge from an opening 7 at the tube distal end 8.

The hollow tube 2 includes a proximal end 6 configured to releasably interconnect to the grip 304. Bone graft material can be positioned within the lumen of the hollow tube 2, such as with a funnel 30 (illustrated in FIG. 75B). The funnel 30 may then be removed from the proximal end 6. The proximal end 6 can then be interconnected to the grip 304. Optionally, the hollow tube 2 can be used to eject bone graft material into a surgical site without being affixed to the grip.

The grip 304 can frictionally engage the tube proximal end 6. In one embodiment, the hollow tube 2 or the grip 304 include a lock or a latch to secure the hollow tube 2 to the grip. In another embodiment, a portion of the hollow tube 2 can threadably engage the grip 304. In another embodiment, the proximal end 6 and grip 304 are interconnected with a bayonet mount. Additionally, or alternatively, the grip 304 can optionally include a knob 310 such that the hollow tube 2 can be selectively interconnected to the grip 304. Other means of interconnecting the hollow tube 2 to the grip 304 are contemplated.

A channel 324 is formed through the grip 304. The channel 324 includes a proximal opening 326 and extends through the grip 304 and the knob 310. In one embodiment, the opening 326 is configured to receive a plunger 12. The plunger 12 can extend through the channel 324 into a hollow tube 2 interconnected to the grip 304.

The grip 304 includes a means for advancing bone graft material through the lumen of the hollow tube 2. In one embodiment, the means for advancing comprises a compressed fluid. Specifically, in one embodiment, the grip 304 is configured to advance the bone graft material using the compressed fluid, such as air. Manipulating the grip trigger 306 can release compressed fluid into the proximal end 6 of the lumen. In one embodiment, the hollow tube includes a single vent port 21B at the distal end. When a proximal end of bone graft material within the lumen reaches the vent port 21B, the compressed fluid is released from the lumen. In this manner, the fluid is not introduced into the surgical site.

Optionally, a pusher 18A may be positioned in the lumen of the hollow tube 2 after the lumen is loaded with bone graft material. The pusher 18A may be similar to the distal end 18 of a plunger 12, such as generally illustrated in FIG. 75A. Regardless, the pusher 18A is configured to substantially conform to interior surfaces of the lumen. In this manner, the pusher 18A prevents the fluid from being discharged from the opening 7 into the surgical site.

When a pressurized fluid is introduced into the lumen behind the pusher 18A, the pusher advances toward the distal end 8. The bone graft material is urged toward the distal end 8 and through the opening 7 by the pusher. In one embodiment, when a proximal end of the pusher 18A advances past the vent port 21B, the compressed fluid is released from the lumen and the pusher stops. Alternatively, the pusher may stop advancing by contact with an interior ramp 9 within the hollow tube 2.

In another embodiment, the means for advancing the bone graft material comprises a plunger 12. Accordingly, in one embodiment, the grip 304 is configured to selectively advance a plunger 12 through the lumen to advance the bone graft material. The grip 304 is configured to advance the plunger 12 axially with respect to the lumen of the hollow tube 2. Specifically, the grip can manipulate the plunger 12 such that a distal end of the plunger opposite the plunger handle 16 moves towards the distal end 8 of the hollow tube 2. The grip 304 is configured to manually or automatically apply a force to the plunger 12. The force can be generated by one or more of a user, a motor, a compressed fluid, or any other means of generating a force.

In one embodiment, the plunger 12 includes teeth, notches 27, or depressions which are engageable by the grip 304 to axially adjust the position of the plunger 12. The notches can be substantially evenly spaced along the plunger.

In one embodiment, a motor is positioned within the grip 304 to advance the plunger. Optionally, the motor is operable to rotate a shaft. The shaft may include a gear to translate the rotational movement into a linear movement of the plunger 12. In one embodiment, the gear includes teeth to engage the notches 27 or teeth of the plunger 12. A battery can provide power to the motor. In one embodiment, the battery is housed in the grip 304.

Optionally, the grip includes a gear or a ratchet configured to engage teeth, notches 27, or depressions on the plunger 12. Specifically, in one embodiment, the ratchet of the grip 304 is configured to engage the plurality of notches 27 formed in the plunger. In one embodiment, the channel 324 of the grip 304 includes an aperture or window through which a portion of the gear or ratchet can extend to engage the plunger 12.

In one embodiment, when activated, the ratchet engages a first notch and then a second notch to incrementally advance the plunger distally within the hollow tube 2. Bone graft material within the hollow tube 2 is then pushed by the plunger 12 toward the distal end 8 of the hollow tube. Ratcheting mechanisms that can be used with the grip 304 are known to those of skill in the art. Some examples of ratcheting mechanisms are described in U.S. Pat. App. Pub. 2002/0049448, U.S. Pat. App. Pub. 2004/0215201, U.S. Pat. App. Pub. 2009/0264892, U.S. Pat. Nos. 7,014,640, 8,932, 295, 9,655,748, and 9,668,881 which are each incorporated herein by reference in their entirety.

Optionally, the grip 304 can be configured to discharge a predetermined amount of bone graft material each time the plunger 12 is incrementally advanced within the hollow tube. In one embodiment, between about 0.25 and 1.0 cc of bone graft material is discharged from the distal end 8 of the hollow tube 2 each time the plunger is advanced. In another embodiment, between about 0.25 and 1.0 cc of bone graft material is discharged is discharged each time the trigger 306 is actuated by a user.

The grip 304 can optionally be configured to enable vision of a surgical sight by a user. Specifically, the grip 304 may be substantially even with one or more surfaces 3, 5 of the hollow tube. In this manner, in one embodiment, the grip 304 does not obstruction a line of sight along at least one surface 3, 5. In another embodiment, an exterior surface of the grip is about even with a plane defined by one of the side surfaces 3. Additionally, or alternatively, an upper portion of the grip does not extend beyond a plane defined by a top surface 5 of the hollow tube. Optionally, a window or view port is formed in the grip 304 to allow view of the distal end 8 of the hollow tube 2.

Additionally, or alternatively, a visualization system is associated with the hollow tube. In one embodiment, the visualization system includes (but is not limited to) one or more of a camera, a light, an endoscope, and a display. The visualization system may be permanently or removably affixed to the integrated fusion cage and graft delivery device 1.

In one embodiment, the grip 304 includes a motor or other actuator which can be manipulated by a user to advance or withdraw the plunger in the hollow tube 2. The motor or actuator can operate the ratchet.

Optionally, the grip 304 is manually manipulated by a user to move the plunger 12. In one embodiment, the grip 304 includes a trigger 306. The trigger 306 may be hinged or pivotally interconnected to the grip 304. When the trigger 306 is actuated by a user, the plunger 12 is advanced in the hollow tube 2.

Actuating the trigger 306 may include pulling the trigger toward a handle 308 of the grip. The trigger 306 can be biased away from the handle 308 as generally illustrated in FIG. 10. Pulling the trigger 306 toward the handle 308 causes the ratchet to engage the plunger 12. The ratchet engages a notch 27 of the plunger 12 and moves the plunger toward the distal end 8 of the hollow tube. Successively pulling the trigger 306 incrementally advances the plunger 12 forward in the hollow tube.

In one embodiment, the ratchet is associated with an upper end of the trigger 306. In this embodiment, pulling the trigger 306 causes the ratchet to move toward the hollow tube 2. Optionally, a lock pawl (not illustrated) can be associated with the grip 304. The lock pawl can engage a notch of the plunger 12 to prevent inadvertent movement of the plunger distally.

The grip 304 can be used to advance or withdraw the plunger 12. Optionally, the grip 304 includes a switch 312 operable to change the direction of movement of the plunger 12. By manipulating the switch 312, a user can cause the plunger 12 to advance into the hollow tube 2 or, alternatively, withdraw from the hollow tube. In one embodiment, to withdraw the plunger 12, the plunger handle 16 can be pulled away from the grip 304. The switch 312 may comprise a button.

The grip 304 can optionally include a loading port 314. The loading port 314 provides access to the lumen of the hollow tube 2. In one embodiment, the loading port 314 is in fluid communication with the channel 324 through the grip 304. Accordingly, bone graft material can be added to the hollow tube through the loading port 314. In one embodiment, the loading port 314 is configured to engage a funnel 30 of any embodiment of the present disclosure. Additionally, or alternatively, a syringe 42 may interconnect to the grip 304 to discharge bone graft material 42 into the lumen through the loading port.

Additionally, or alternatively, a capsule or package 316 of bone graft material can be loaded into the lumen through the loading port 314. The package 316 can include any type of bone graft material, including one or more of: autogenous (harvested from the patient's own body), allogeneic (harvested from another person), and synthetic. A predetermined amount of bone graft material can be included in the package 316. In one embodiment, each package includes between about 0.25 and 1.0 cc of bone graft material. One or more packages 316 may be loaded into the lumen to deliver a desired amount of bone graft material to a surgical site.

Referring now to FIG. 79, still another embodiment of an integrated fusion cage and graft delivery device 1 of the present disclosure is illustrated. The device 1 illustrated in FIG. 79 is similar to the device 1 described in conjunction with FIG. 78 and includes many of the same, or similar features. The integrated device 1 generally includes a hollow tube 2 configured to receive a fusion cage 60 and a means for advancing bone graft material through the hollow tube for discharge out of an opening 65 of the fusion cage.

In one embodiment, the means for advancing includes a grip 304. The grip 304 is configured to interconnect to a hollow tube 2 of any embodiment of the present disclosure. The grip 304 is operable to selectively move bone graft material through the lumen of the hollow tube 2 for discharge from the tube distal end 8. Bone graft material can be positioned within the lumen while the hollow tube 2 is interconnected to the grip 304.

The grip 304 can frictionally engage a predetermined portion of the hollow tube 2. In one embodiment, the hollow tube 2 or the grip 304 include a lock or a latch to secure the hollow tube 2 to the grip. Optionally, the grip 304 engages at least the two side surfaces 3 of the hollow tube 2. In one embodiment, the grip 304 includes opposing flanges 320. One or more of the flanges 320 can be moved inwardly toward the hollow tube similar to a clamp. In this manner, the flanges 320 can apply a compressive force to the side surfaces 3 to interconnect the hollow tube 2 to the grip. Other means of interconnecting the hollow tube 2 to the grip 304 are contemplated.

The grip 304 includes a means for advancing bone graft material through the lumen of the hollow tube 2. In one embodiment, the means for advancing comprises a compressed fluid. Specifically, in one embodiment, the grip 304 is configured to advance the bone graft material using the compressed fluid, such as air. Manipulating the grip trigger 306 can release compressed fluid into the proximal end 6 of the lumen. When a pressurized fluid is introduced into the lumen, the plunger advances toward the distal end 8. The bone graft material is urged toward the distal end 8 and through the opening 65 by the plunger 12. In one embodiment, the plunger may stop advancing by contact with an interior ramp within the hollow tube 2.

In another embodiment, the means for advancing the bone graft material is configured to selectively advance the plunger 12 through the lumen to advance the bone graft material. Specifically, the grip 304 is configured to manually or automatically apply a force to the plunger 12. The force can be generated by one or more of a user, a motor, a compressed fluid, or any other means of generating a force.

In one embodiment, a motor is positioned within the grip 304 to advance the plunger. Optionally, the motor is operable to rotate a shaft. The shaft may include a gear to translate the rotational movement of the shaft into a linear movement of the plunger 12. In one embodiment, the plunger includes notches to engage the gear of the shaft. A battery can provide power to the motor. In one embodiment, the battery is housed in the grip 304.

In one embodiment, the plunger 12 includes teeth, notches, or depressions which are engageable by the grip 304 to axially adjust the position of the plunger 12. Optionally, the grip includes a gear or a ratchet configured to engage teeth or notches on the plunger 12.

Specifically, in one embodiment, the ratchet of the grip 304 is configured to engage a plurality of notches formed in the plunger. The notches can be substantially evenly spaced along the plunger. The ratchet engages a first notch and then a second notch to incrementally advance the plunger distally within the hollow tube 2. Bone graft material within the hollow tube 2 is then pushed by the plunger 12 toward the distal end 8 of the hollow tube.

The grip 304 is configured to enable vision of a surgical sight by a user. Specifically, in one embodiment, the grip 304 does not extend above a top surface 5 of the hollow tube. In this manner, in one embodiment, the grip 304 does not obstruction a line of sight along at least the top surface 5. In another embodiment, lateral surfaces of the grip are about even with a plane defined by one of the side surfaces 3 of the hollow tube.

In one embodiment, the grip 304 includes a motor or other actuator which can be manipulated by a user to advance or withdraw the plunger in the hollow tube 2. The motor or actuator can operate the ratchet.

Optionally, the grip 304 is manually manipulated by a user to move the plunger 12. In one embodiment, the grip 304 includes a trigger 306. The trigger 306 may be hinged or pivotally interconnected to the grip 304. When the trigger 306 is actuated by a user, the plunger 12 advances in the hollow tube 2. Specifically, in one embodiment, the trigger 306 is functionally interconnected to the plunger 12.

In one embodiment, actuating the trigger 306 includes pulling the trigger toward a handle 308 of the grip. The trigger 306 can be biased away from the handle 308 as generally illustrated in FIG. 11. In one embodiment, pulling the trigger 306 toward the handle 308 causes the ratchet to engage the plunger 12. The ratchet engages a notch of the plunger 12 and moves the plunger toward the distal end 8 of the hollow tube. Successively pulling the trigger 306 incrementally advances the plunger 12 forward in the hollow tube.

In one embodiment, the ratchet is associated with an upper end of the trigger 306. In this embodiment, pulling the trigger 306 causes the ratchet to move toward the distal end of the hollow tube 2. Optionally, a lock pawl (not illustrated) can be associated with the grip 304. The lock pawl can engage a notch of the plunger 12 to prevent the plunger from moving distally.

The grip 304 can be used to advance or withdraw the plunger 12. Optionally, the grip 304 includes a switch operable to change the direction of movement of the plunger 12. By manipulating the switch, a user can cause the plunger 12 to advance into the hollow tube 2 or, alternatively, withdraw from the hollow tube. In one embodiment, to withdraw the plunger 12, the plunger handle 16 can be pulled away from the grip 304.

Additionally, or alternatively, the grip 304 can include a knob 318. In one embodiment, the knob 318 is configured to advance or withdraw the plunger 12 within the hollow tube 2. Specifically, rotating the knob in a first direction causes the plunger 12 to advance toward the distal end 8. Rotating the knob 318 in a second direction causes the plunger 12 to withdraw away from the distal end 8.

In one embodiment, the knob 318 includes a gear, such as a pinion. The gear includes teeth that engage notches or teeth extending linearly along the plunger 12, similar to a rack. Rotational movement of the knob 318 is converted into linear motion of the plunger by interaction between the knob pinion with the plunger rack.

Optionally, the hollow tube 2 may discharge a predetermined amount of bone graft material associated with each rotation, or partial rotation of the knob 318. Specifically, a calibrated amount of bone graft material may be discharged from the hollow tube 2 for each quarter, half, or full rotation of the knob 318. In one embodiment, the hollow tube 2 is configured to discharge approximately 1 cc of bone graft material for each half turn of the knob 318.

In one embodiment, the knob 318 is configured to provide tactile feedback to a user after a predetermined amount of rotation. For example, when the knob is rotated one or more of ⅛, ¼, ½, and 1 turn, the knob and/or the grip 304 may vibrate or provide other tactile feedback to the user.

The grip 304 is also operable to expand the fusion cage 60 and separate the fusion cage 60 from the hollow tube. In one embodiment, the knob 318 can slide within a slot 322 to release the fusion cage 60. In one embodiment, pulling the knob 318 away from the distal end 8 of the hollow tube detaches the fusion cage.

A bone graft tamping device may also be provided, which is adapted to be inserted into the hollow tube 2 after the plunger 12 is removed from the hollow tube. The bone graft tamping device, according to this embodiment, may include one or more longitudinal channels along the outer circumference of the bone graft packer for permitting any trapped air to flow from the bone graft receiving area to the graspable end of the hollow tube during packing of bone graft. The bone graft packer may further include a handle at one end designed ergonomically for improving ease of use. The bone graft packer in this embodiment thereby facilitates packing of bone graft within the hollow tube.

The hollow tube 2 may also be fitted with a passageway wherein a surgical tube or other device may be inserted, such as to deliver a liquid to the surgical area or to extract liquid from the surgical area. In such an embodiment, the plunger 12 is adapted in cross-section to conform to the hollow tube's cross-section.

In another embodiment of the present invention, a kit of surgical instruments comprises a plurality of differently sized and/or shaped hollow tubes 2 and a plurality of differently sized and/or shaped plungers 12. Each of the plungers correspond to at least one of the hollow tubes, whereby a surgeon may select a hollow tube and a plunger which correspond with one another depending upon the size and shape of the graft receiving area and the amount or type of bone graft to be implanted at such area. The corresponding hollow tubes and plungers are constructed and arranged such that bone graft can be placed within the hollow tubes with the plungers, and inserted nearly completely into the hollow tubes for removing substantially all of the bone graft material from the hollow tubes, such as in the preferred embodiments for the plunger described above. The use of more than one hollow tube/plunger combination permits at least two different columns of material to be selectively delivered to the targeted site, e.g. one of bone graft material from the patient and another of Bone Morphogenetic Protein (BMP), or e.g. two different types of bone graft material or one delivering sealant or liquid. Also, one or both hollow tubes could be preloaded with bone graft material.

The kit of surgical instruments may comprise a plurality of differently sized and/or shaped graft retaining structures, each corresponding to at least one hollow tube and at least one plunger.

The bone graft receiving area can be any area of a patient that requires delivery of bone graft. In the preferred embodiment, the bone graft is delivered in a partially formed manner, and in accordance with another aspect of the present invention, requires further formation after initial delivery of the bone graft.

Another embodiment of the present invention provides a method by which a hollow tube and a plunger associated with the hollow tube are provided to facilitate delivery of the bone graft to a bone graft receiving area.

According to one embodiment, the present invention provides a bone graft delivery system, by which a hollow tube and/or plunger assembly may be prepared prior to opening a patient, thus minimizing the overall impact of the grafting aspect of a surgical implantation or other procedure. Moreover, the hollow tube 2 may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

Thus, the integrated fusion cage and graft delivery device 1 may either come with a pre-filled hollow tube, or a non-filled hollow tube, in which the surgeon will insert bone graft received from the patient (autograft), or from another source (allograft). In either case, the surgeon may first remove any wrapping or seals about the hollow tube, and/or the pre-filled bone graft, and insert the hollow tube into the patient such that the second end of the hollow tube is adjacent the bone graft receiving area. Once the hollow tube is in place, and the opening at the second end of the hollow tube is oriented in the direction of the desired placement of bone graft, the surgeon may then insert the second end of the plunger into the opening at the first end of the hollow tube, and begin pressing the second end of the plunger against the bone graft material in the hollow tube. In this fashion, the plunger 12 and hollow tube 2 cooperate similar to that of a syringe, allowing the surgeon to steadily and controllably release or eject bone graft from the second end of the hollow tube as the plunger is placed farther and farther into the opening in the hollow tube. Once the desired amount of bone graft has been ejected from the hollow tube (for in some instances all of the bone graft has been ejected from the hollow tube) the surgeon may remove the plunger from the hollow tube, and complete the surgery. In certain operations, the surgeon may elect to place additional bone graft into the hollow tube, and repeat the steps described above. Furthermore, the pre-filled bone graft elements may be color-coded to readily identify the type of bone graft material contained therein.

According to the embodiment described in the preceding paragraph, the present invention may be carried out by a method in which access is provided to a graft receiving area in a body, bone graft is placed into a hollow tube having a first end and a second end, the hollow tube, together with the bone graft, is arranged so that the first end of the hollow tube is at least adjacent to the graft receiving area and permits lateral or nearly lateral (in relation to the longitudinal axis of the hollow tube and plunger assembly) introduction of bone graft to the graft receiving area. This method prevents loss of bone graft due to improper or limited orientation of the integrated fusion cage and graft delivery device, and further allows a user to achieve insertion of a desired quantity of bone graft by way of the contoured plunger and hollow tube configuration described according to preferred embodiments herein.

The method of the present invention may also be carried out by providing a hollow tube having a first end and a second end, constructed so that it may receive a measurable quantity of bone graft, and so that the first end may be arranged at least adjacent to a bone graft receiving area, and so that bone graft can be delivered from the first end of the hollow tube through the second end of the hollow tube and eventually to the bone graft receiving area upon movement of the plunger in a generally downward direction through the hollow tube (i.e., in a direction from the first end to the second end). According to this embodiment, a graft retaining structure may also be provided for use in connection with the contoured edge of the plunger, such that the graft retaining structure is positioned between the contoured edge of the plunger and the bone graft, but which is adhered to the bone graft and remains at the graft receiving area following removal from the hollow tube. In one embodiment, the bone graft is provided in discrete packages or containers. Furthermore, this graft retaining structure may also be employed with another tool, such as a graft packer, which is employed either before or after the hollow tube is removed from the graft receiving area.

In another embodiment, the one or more plungers corresponding to the one or more hollow tubes are positioned with distal ends near the proximate end of the horizontal tube before use, said plungers having a detent to retain plunger in ready position without undesired movement before surgeon chooses which one or more plungers to extend through hollow horizontal tube and deliver bone graft material and/or desired material to the surgical area.

According to another embodiment of the present invention, a hollow tube and plunger assembly is provided in which the hollow tube and/or the plunger assembly is disposable. Alternatively, the tube may be made of a biocompatible material which remains at least partially in the patient without impairing the final implantation. Thus, the hollow tube may be formed from a material that is resorbable, such as a resorbable polymer, and remain in the patient after implantation, so as not to interfere with the growth of the bone or stability of any bone graft or implant.

The current design preferably comprises a hollow tubular member comprising a rounded edge rectangular shaft, which may be filled or is pre-filled with grafting material. The loading is carried out by the plunger. The rounded edge rectangular design is preferable as it allows the largest surface area device to be placed into the annulotomy site of a disc, but in other embodiments may be formed similar to conventional round shafts. The other preferred feature includes a laterally-mounted exit site for the graft material. The combination of this design feature allows direction-oriented dispersion of the graft material. This allows ejection of the graft material into an empty disc space as opposed to below the hollow tube, which would tend to impact the material and not allow its spread through a disc space.

Another feature of this design is that a rectangular, approximately rectangular, or rounded edge rectangular design allows the user to readily determine the orientation of the device and thereby the direction of entry of the bone graft material into the surgical area. However, such a feature may be obtained alternatively through exterior markings or grooves on the exterior on the hollow tube. Such exterior grooves or markings would allow use of a range of cross-sections for the device, to include a square, circle, or oval while allowing the user to readily determine the orientation of the device relative to the direction of entry of the bone graft material into the surgical area.

A further feature of this design is that an anti-perforation footing or shelf is paced on the bottom of the hollow tube to prevent annular penetration and/or injury to the patient's abdomen or other anatomy adjacent the bone graft receiving area.

In another embodiment of the invention, all or some of the elements of the device or sections of all or some of the device may be disposable. Disposable medical devices are advantageous as they typically have reduced recurring and initial costs of manufacture.

In another embodiment of the device, the distal tip or end of the plunger device is composed of a different material to the rest of the plunger, so as the material at the distal end of the plunger is sponge-like or softer-than or more malleable than the rest of the plunger so as upon engagement with the interior distal end of the hollow tube, the distal end of the plunger substantially conforms to the interior configuration of the hollow tube. Similarly, the plunger distal end may be made of a material that is adaptable to substantially conform to the interior shape of the distal end of the hollow tube. Such configurations enable substantially all of the material contained within the plunger to be delivered to the targeted site.

Another alternative embodiment to the design described herein includes a navigation aid 29 on one or more surfaces of the hollow tube 2 to permit a surgeon to know how far the device 1 has been inserted or to ensure proper alignment relative to a transverse bone graft delivery site (i.e. disc space). Such capability is particularly important when the patient or surgical area is not positioned immediately below the surgeon, or multiple procedures are being performed. A navigation aid allows more immediate and reliable locating of the surgical area for receiving of bone graft material. In one embodiment, the hollow tube 2 is scored or marked 29 or provides some affirmative indication, actively or passively, to the surgeon to indicate degree of delivery of the material, e.g. bone graft material, to the delivery site, and/or position of the plunger 12. For example, the exterior of the hollow tube could be color-coded and/or provided with bars 29. In another embodiment, a computer and/or electromechanical sensor or device is used to provide feedback to the surgeon to indicate degree of delivery of the material, e.g. amount of cc's of bone graft material, to the delivery site, and/or position of the plunger element.

In another alternative embodiment to the design described herein, the plunger 12 could include an activation device, which is often in a liquid or semi-liquid state, and that may be injected once the semi-solid portion of the morphogenic protein has been displaced by the movement of the plunger through the hollow tube 2. That is, the plunger 12 pushes the dry material, and once completed has a bulb or other device on the usable end to insert the liquid portion of the activating agent through the inner lumen 28 within the plunger 12 to evacuate the liquid from the plunger and out an opening at the non-usable end of the plunger so as to contact the dry material already inserted into the disc space).

In one embodiment of the device, all or portions of the device 1 are manufactured using 3-D printing techniques. In another embodiment, all or portions of the device are made by injection molding techniques.

In one embodiment, the ratio of the surface area of the bottom tip of the plunger 12 is approximately half the surface area of the two lateral openings at the distal portion of the hollow tube.

In one embodiment, the device 1 includes a supplemental means of gripping the device, such as a laterally extending cylindrically-shaped handle that engages the hollow tube 2.

In one embodiment, the material inserted into the hollow tube 2 is a non-Newtonian fluid. In one embodiment, the device is adapted to accept and deliver compressible fluids. In another embodiment, the device is adapted to accept and deliver non-compressible fluids. The hollow tube 2 of one embodiment includes a rectangular or approximately rectangular lumen 28 which provides an increased cross-sectional footprint relative to a round lumen of other bone graft delivery devices. The increased cross-sectional footprint decreases friction of the non-Newtonian fluid material against the interior walls of the lumen, resulting in an improved flow of bone graft material through the lumen and eliminating (or reducing) jamming due compression of the bone graft material. The increased cross-section of hollow tube 2 of the present disclosure improves the flow dynamics of a non-Newtonian fluid by 40% compared to a prior art tool with a diameter equal to the height of the rectangular or approximately rectangular lumen of embodiments of the present invention.

In one embodiment, the upper portion of plunger is fitted with one or more protrusions, which extends from the surface of the plunger so as to engage the upper surface of the hollow tube, to prevent the plunger from engaging the distal interior portion of the hollow tube. In one embodiment, the upper portion of plunger is fitted with one or more protrusions to prevent the plunger from engaging the apex of the hollow tube distal interior ramp surface.

In one embodiment, the funnel 30 attaches to the hollow tube 2 by a bayonet connection. In one embodiment, the funnel attaches to the hollow tube by an interference fit. In one embodiment, the funnel attaches to the hollow tube by a threaded connection. In one embodiment, the funnel attaches to the hollow tube by a slot/groove connection.

In one embodiment, the distal end 8 of hollow tube has one opening 7. In one embodiment, the hollow tube 8 has two distal openings 7A, 7B located on opposite sides. In one embodiment, the hollow tube has no more than two openings 7, the openings located on opposite sides.

In one embodiment, after bone graft material 44 is delivered to a surgical site 172, a cavity 174 approximately defined by the volume engaged by the device 1 when inserted into the surgical site is left in the surgical site upon removal of the device from the surgical site. In one embodiment, the cavity 174 is then used as the site for insertion of a fusion cage 60.

The integrated fusion cage 60 with expandable cage feature provides a number of unique and innovative features not provided by conventional or traditional integrated fusion cages. For example, the integrated fusion cage with expandable cage feature of the disclosure is intentionally and deliberately designed to receive bone graft material (or any material suitable for use in surgical applications, as known to those skilled in the art) at its proximal end (i.e. the end generally facing the surgeon and/or the end opposite the end initially directed into a surgical site), such that the bone graft material flows into the fusion cage and also flows out from the fusion cage into the surgical site. Such features as the interior ramps of the fusion cage (e.g. located within the interior of the hollow tube, and/or on the front and/or rear blocks of the fusion cage) function to direct received bone graft material into the surgical site. Additionally, the features of the hollow tube and plunger wherein a greater volume of bone graft material may be reliably (e.g. not prone to blockage as is typical with most convention e.g. round hollow tubes or lumen systems) and readily delivered to a surgical site and/or a fusion cage are unique and not found in the prior art. Among other things, such features encourage improved surgical results by delivering more volume and coverage of bone graft material to the surgical site. Also, such features minimize gaps in bone graft coverage to include gaps between the fusion cage area and the surrounding surgical site. Also, the features of the one or more apertures of the fusion cage of the disclosure enable and encourage delivery of bone graft material, as received by the fusion cage, into the surrounding surgical site.

In contrast, conventional fusion cages, to include expandable fusion cages, do not provide such features and/or functions. For example, U.S. Pat. No. 8,852,242 to Morgenstern Lopez ("Lopez"), discloses a dilation introducer for orthopedic surgery for insertion of an intervertebral expandable fusion cage implant. The Lopez device does not allow receipt of bone graft material from its proximal end, or any end, in contrast to the disclosed fusion cage and fusion cage/bone graft delivery system. That is, the Lopez proximal end includes an array of components, all of which do not allow receipt of bone graft material. Furthermore, the Lopez device requires an elaborate array of components, e.g. upper side portion of the upper body portion and lower side portion of the lower body portion, which also block any egress of bone graft from the inside of the Lopez fusion cage once deployed. Also, the Lopez wedges occupy the entire interior of the cage; there are no ramps to direct graft from the interior to the disk space. In short, the Lopez design is not made with bone graft delivery in mind, and indeed, cannot function to accept let alone deliver bone graft. Additionally, suggestions provided in the Lopez disclosure to deliver bone graft to the surgical site would not provide the integrated and complete fusion cage and surgical site bone graft delivery of the invention, e.g. the Lopez slot of the Lopez lumen and funnel assembly at best provides limited delivery of bone graft material only before and after insertion of the Lopez fusion cage, and then only peripheral to the fusion cage. Also, it appears the Lopez device provides wedges and of similar if not identical interior ramp angles. In contrast, in certain embodiments of the present invention the interior wedged surfaces of the invention, i.e. front block ramp 226 and rear block ramp 236, are not of the same configuration and/or shape, e.g. front block ramp 226 is of a curved profile and rear block ramp 236 is of a linear or straight-line profile. Among other things, the curved profile of the front block ramp 226 urges egress of bone graft as received by the fusion cage 60.

In one embodiment of the fusion cage 60, no anti-torque structures or components are employed. In one embodiment of the invention, the lateral sides of the fusion cage 60 are substantially open to, among other things, allow egress of bone graft material as received to the fusion cage. In one embodiment, the expansion screw 240 is configured with a locking mechanism, such that the fusion cage 60 may be locked at a set expansion state. In one embodiment, such a locking mechanism is provided through a toggle device operated at or on the installer/impactor handle 258.

In one embodiment, the front block ramp 226 and rear block ramp 236 are identical and/or symmetrical.

In addition, it is contemplated that some embodiments of the fusion cage 60 can be configured to include side portions that project therefrom and facilitate the alignment, interconnection, and stability of the components of the fusion cage 60.

Furthermore, complementary structures can also include motion limiting portions that prevent expansion of the fusion cage beyond a certain height. This feature can also tend to ensure that the fusion cage is stable and does not disassemble during use.

In some embodiments, the expansion screw 240 can facilitate expansion of the fusion cage 60 through rotation, longitudinal contract of a pin, or other mechanisms. The expansion screw 240 can also facilitate expansion through longitudinal contraction of an actuator shaft as proximal and distal collars disposed on inner and outer sleeves move closer to each other to in turn move the proximal and distal wedged block members closer together. It is contemplated that in other embodiments, at least a portion of the actuator shaft can be axially fixed relative to one of the proximal and distal wedge block members with the actuator shaft being operative to move the other one of the proximal and distal wedge members via rotational movement or longitudinal contraction of the pin.

Further, in embodiments wherein the engagement screw 240 is threaded, it is contemplated that the actuator shaft can be configured to bring the proximal and distal wedged block members closer together at different rates. In such embodiments, the fusion cage 60 could be expanded to a V-configuration or wedged shape. For example, the actuator shaft can comprise a variable pitch thread that causes longitudinal advancement of the distal and proximal wedged block members at different rates. The advancement of one of the wedge members at a faster rate than the other could cause one end of the implant to expand more rapidly and therefore have a different height that the other end. Such a configuration can be advantageous depending on the intervertebral geometry and circumstantial needs.

In other embodiments, an upper plate 200 can be configured to include anti-torque structures. The anti-torque structures can interact with at least a portion of a deployment tool during deployment of the fusion cage 60 implant to ensure that the implant maintains its desired orientation. For example, when the implant is being deployed and a rotational force is exerted on the actuator shaft, the anti-torque structures can be engaged by a non-rotating structure of the deployment tool to maintain the rotational orientation of the implant while the actuator shaft is rotated. The anti-torque structures can comprise one or more inwardly extending holes or indentations on the rear wedged block member. However, the anti-torque structures can also comprise one or more outwardly extending structures.

According to yet other embodiments, the fusion cage 60 can be configured to include one or more additional apertures to facilitate osseointegration of the fusion cage 60 within the intervertebral space. The fusion cage 60 may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Indeed, various biologics can be used with the fusion cage 60 and can be inserted into the disc space or inserted along with the fusion cage 60 The apertures can facilitate circulation and bone growth throughout the intervertebral space and through the implant. In such implementations, the apertures can thereby allow bone growth through the implant and integration of the implant with the surrounding materials.

In one embodiment, the fusion cage 60 comprises an expandable cage configured to move a first surface vertically from a second surface by rotation of at least one screw that rotates without moving transversely with respect to either said first or second surface, said first plate and second plate having perimeters that overlap with each other in a vertical direction and that move along a parallel line upon rotation of the screw.

In one embodiment, the fusion cage 60 is stackable by any means known to those skilled in the art. For example, each upper plate 200 may be fitted with one or more notches on the lateral edges configured to fit with one or more protrusions on each lower plate 210.

Surprisingly, while conventional practice assumed that the amount of material that would be required, let alone desired, to fill a prepared disc space with bone paste (or BMP, etc.) would be roughly equivalent to the amount of material removed from such space prior to inserting a cage, a present inventor discovered that far more bone graft material can be—and should preferably be—inserted into such space to achieve desired fusion results. The reasons why this basic under appreciation for the volume of bone graft necessary to achieve optimal fusion results vary, but the clinical evidence arrived at via practice of the present invention compellingly demonstrates that more than doubling of the amount of bone graft material (and in some cases increasing the amount by 200%, 300% or 400% or more) than traditionally thought necessary or sufficient, is extremely beneficial to achieving desired results from fusion procedures.

The ramifications of this simple yet dramatic discovery (documented in part below) is part of the overall inventive aspect of the present invention, as it has been—to date—simply missed entirely by the practicing spine surgeons in the field. The prospect of reduced return surgeries, the reduction in costs, time, and physical suffering by patients, as well as the volume of legal complaints against surgeons and hospitals due to failed fusion results, is believed to be significant, as the evidence provided via use of the present invention indicates a vast reduction in the overall costs involved in both economic resources, as well as emotional capital, upon acceptance and wide-spread use of the present invention. Insurance costs should thus decrease as the present invention is adopted by the industry. While the costs of infusing increased amount of bone graft materials into the space of a patient's disc may at first appear to increase the costs of an individual operation, the benefits achieved thereby will be considerable, including the reduction of repeat surgeries to fix non-fused spines. Thus, regardless of the actual tools and devices employed to achieve the end result of attaining up to 100% more bone graft material being utilized in fusion operations, (as well as other surgeries where previously under-appreciated bone graft material delivery volumes have occurred) one important aspect of the present invention is directed to the appreciation of a previously unrecognized problem and the solution thereto, which forms part of the inventive aspects of the present invention described and claimed herein.

In one embodiment, at least twice the amount of disc material removed from a surgical site is replaced with bone graft material. In a preferred embodiment, at least three times the amount of disc material removed from a surgical site is replaced with bone graft material. In a most preferred embodiment, at least three and a half times the amount of disc material removed from a surgical site is replaced with bone graft material.

According to various embodiments of the present disclosure, and as illustrated at least by FIGS. 1 and 6-10D, one aspect of the invention is to provide a graft delivery device that comprises a tubular member, which is substantially hollow or contains at least one inner lumen and that has a generally rectangular cross-sectional shape. This generally rectangular cross-sectional shape offers a larger amount of surface area through which bone graft material may be inserted and ejected from the hollow tubular member. Furthermore, this generally rectangular shape is more congruent with the size or shape of the annulotomy of most disc spaces, which frequently are accessed by a bone graft delivery device for delivery of bone graft. However, as one skilled in the art would appreciate, the tool cross-section need not be limited to a generally rectangular shape. For example, cross-sections of an oval shape, or those that are approximately rectangular and have rounded corners or edges, or those with at least one defined angle to include obtuse, acute, and right angles can provide a shape in some situations that is more congruent with the size or shape of the annulotomy of a particular disc space. A substantially round shape may also be employed that provides the surgeon with an indication of directional orientation.

In embodiments, a distal end of the hollow tubular member may be at least partially closed, and/or may have a small aperture associated with the lumen. This partial closure and/or small aperture may help to create a consistent and clean break between bone graft material that has been ejected from the hollow tubular member and bone graft material held within the hollow tubular member.

In another embodiment of the present disclosure the distal end of the plunger is flexible to allow, for example, the user to maneuver the distal end and thereby any bone graft material in the hollow tube to the implantation site. One skilled in the art will appreciate that the flexible aspect of certain embodiments can be both passive and active in nature. Active flexibility and manipulation in the distal end of the plunger may incorporate, for example, the manipulative capabilities of an endoscope, including components for manipulation such as guidewires along the longitudinal axis of the shaft of the plunger.

The plunger 12 may be inserted into the hollow tube 2 such that the horizontal face 19 is substantially planar with the opening at the second end 8 of the hollow tube 2. As described above, the geometry of plunger 12 is such that it fits snugly or tightly in the interior of the hollow tube 2. This configuration is such that the sloped or curved surface 10 of the hollow tube 2 is substantially congruent to the sloped or curved surface 20, thereby allowing the plunger to be inserted into the hollow tube 2 and allowing substantially all of bone graft material which is placed into the hollow tube 2 to be ejected by the user.

Another embodiment for the bone graft insertion device comprises a hollow tube constructed to receive bone graft, where the hollow tube has a proximal and distal end, a plunger adapted for insertion at least partially within the hollow tube at the proximal end of the hollow tube, whereby the plunger is constructed and arranged with respect to the hollow tube so as to prevent rotation of the plunger during insertion into said hollow tube, whereby the plunger has a distal end that is contoured to an interior surface of the distal end of the hollow tube for removing substantially all of the bone graft received by the hollow tube and whereby the bone graft is delivered to the graft receiving area. Still another embodiment provides a rifling structure in the hollow tube interior that facilitates rotational movement of the plunger along a lengthwise axis of the hollow tube, therein delivering a substantially steady pressure and/or rate of delivery of the bone graft material as the plunger descends the hollow tube when the plunger is forced through the hollow tube. The rifling or screw-like movement may also translate to a predetermined delivery of material per full rotation, e.g. each 360 degree rotation of the plunger equates to 5 cc of bone graft material delivered to the bone graft site.

In embodiments, teeth may be formed along a longitudinal axis of the shaft of the plunger 12, which may be configured to engage with teeth of the grip 304 and/or knob 318 to facilitate advancement of the plunger 12 when the grip 304 and/or knob 318 is actuated. The engagement of the teeth of the plunger 12 with teeth of the grip 304 and/or knob 318 may thus, by way of non-limiting example, form a rack-and-pinion-type linear actuator that causes the plunger 12 to descend the hollow tube 2 and urge bone graft material through the hollow tube 2 to deliver bone graft material through an opening in a distal end of the hollow tube 2.

The indicia 29 may include one or more radiological or radiographic markers. Such radiological or radiographic markers may be made from known radiopaque materials, including platinum, gold, calcium, tantalum, and/or other heavy metals. At least one radiological or radiographic marker may be placed at or near the distal end of the hollow tube 2, to allow radiological visualization of the distal end within the targeted bone area.

In further embodiments, an actuating means may be provided for applying pressure to the plunger 12, and in particular to the shaft of the plunger 12. Upon actuation thereof, the actuating means may apply pressure against the plunger 12 to facilitate controlled movement of the plunger 12 and/or the hollow tube 2 relative to the plunger 12. The actuating means may, by way of non-limiting example, include a handle and a pivotally mounted trigger attached to a ratchet-type push bar (such as those commonly used with caulking guns) and/or a rack-and-pinion-type linear actuator.

According to a still further aspect of the present invention, the distal end of the spinal fusion implant may have a conical (bullet-shaped) shape including a pair of first tapered (angled) surfaces and a pair of second tapered (angled) surfaces. The first tapered surfaces extend between the lateral surfaces and the distal end of the implant, and function to distract the vertebrae adjacent to the target intervertebral space during insertion of the spinal fusion implant. The second tapered surfaces extend between the top and bottom surfaces and the distal end of the spinal fusion implant, and function to maximize contact with the anterior portion of the cortical ring of each adjacent vertebral body. Furthermore, the second tapered surfaces provide for a better fit with the contour of the vertebral body endplates, allowing for a more anterior positioning of the spinal fusion implant and thus advantageous utilization of the cortical rings of the vertebral bodies.

In embodiments of bone graft insertion devices and systems of the present invention, a spinal implant adapted for interconnection and use with the bone graft insertion device and/or included in the bone graft insertion system may comprise a covering or mesh, such as a biodegradable polymer mesh, and/or may be detachably interconnected to the bone graft insertion device by means of, e.g., a hook attachment mechanism, a screw attachment mechanism, a mechanical attachment mechanism, a suture attachment mechanism, a wrap attachment mechanism, and/or an adhesive attachment mechanism. Examples of spinal implants of this type, suitable for use in the present invention, include but are not limited to the spinal implants described in U.S. Pat. No. 10,028,837, issued Jul. 24, 2018 to Wei et al., the entirety of which is incorporated herein by reference.

In embodiments of bone graft insertion devices and systems of the present invention, a spinal implant adapted for interconnection and use with the bone graft insertion device and/or included in the bone graft insertion system may comprise an expandable portion adapted to expand or inflate when filled with bone graft or other material, and/or may be detachably interconnected to the bone graft insertion device by means of, e.g., an adhesive. Examples of spinal implants of this type, suitable for use in the present invention, include but are not limited to the spinal implants described in U.S. Pat. No. 9,925,060, issued Mar. 27, 2018 to DiMauro et al., the entirety of which is incorporated herein by reference.

In embodiments of bone graft insertion devices and systems of the present invention, a spinal implant adapted for interconnection and use with the bone graft insertion device and/or included in the bone graft insertion system may comprise any one or more of a nucleus replacement device, a nucleus augmentation device, an anulus augmentation device, an anulus replacement device, a drug carrier device, a carrier device seeded with living cells, a device that stimulates or supports fusion of the surrounding vertebra, and/or a membrane that prevents flow of a material through a defect in a disc of the patient; the implant may be wholly or partially rigid or wholly or partially flexible. Examples of spinal implants of this type, suitable for use in the present invention, include but are not limited to the spinal implants described in U.S. Pat. No. 9,333,087, issued May 10, 2016 to Lambrecht, the entirety of which is incorporated herein by reference.

In embodiments of bone graft insertion devices and systems of the present invention, a spinal implant adapted for interconnection and use with the bone graft insertion device and/or included in the bone graft insertion system may comprise any one or more of a plate, spacer, rod, or other stabilization device, and in particular may comprise an expandable or non-expandable spacer having an opening for receiving graft material therein, and/or may (but need not) be detachably interconnected to the bone graft insertion device by means of, e.g., a threaded attachment. Examples of spinal implants of this type, suitable for use in the present invention, include but are not limited to the spinal implants described in U.S. Pat. No. 9,827,113, issued Nov. 28, 2017 to Klimek et al., the entirety of which is incorporated herein by reference.

In embodiments of bone graft insertion devices and systems of the present invention, a spinal implant adapted for interconnection and use with the bone graft insertion device and/or included in the bone graft insertion system may comprise a body portion, a carriage portion, a deployment assembly, and an expandable portion, and/or may be detachably interconnected to the bone graft insertion device by means of, e.g., one or more detents and holes or apertures for receiving the detents. Examples of spinal implants of this type, suitable for use in the present invention, include but are not limited to the spinal implants described in U.S. Pat. No. 10,076,421, issued Sep. 18, 2018 to Dewey, the entirety of which is incorporated herein by reference.

In embodiments of bone graft insertion devices and systems of the present invention, a spinal implant adapted for interconnection and use with the bone graft insertion device and/or included in the bone graft insertion system may comprise a gear and a threaded shaft, whereby rotation of the gear engages the threaded shaft to expand the implant such that the implant can be inserted in a collapsed configuration and expanded in situ, and/or may (but need not) be detachably interconnected to the bone graft insertion device by means of, e.g., screws, clips, hooks, and/or clamps. Examples of spinal implants of this type, suitable for use in the present invention, include but are not limited to the spinal implants described in U.S. Pat. No. 10,226,358, issued Mar. 12, 2019 to Glerum, the entirety of which is incorporated herein by reference.

In embodiments of bone graft insertion devices and systems of the present invention, a spinal implant adapted for interconnection and use with the bone graft insertion device and/or included in the bone graft insertion system may comprise a plurality of chambers, each of the chambers being configured to receive bone graft material, and/or may include means allowing a surgeon or other user to select a chamber or portion of the interior of the implant into which bone graft material is delivered. Examples of spinal implants of this type, suitable for use in the present invention, include but are not limited to the spinal implants described in U.S. Pat. No. 9,545,282, issued Jan. 17, 2017 to Mathur et al., the entirety of which is incorporated herein by reference.

It is to be expressly understood that spinal implant suitable for use as part of, or in conjunction with, the devices, methods, and systems of the present invention are not limited to the examples described above, and that any type of spinal implant appropriate for a given application may be detachably interconnected to a bone graft delivery device and used in the methods and systems of the present invention. By way of non-limiting example, anterior and/or lateral interbody spinal implants, including but not limited to implants available under the SeaSpine Redondo™, Regatta®, and Vu a•POD™ product lines, may be detachably interconnected to a bone graft delivery device by any suitable means and used in the practice of the present invention. By way of further non-limiting example, posterior interbody spinal implants, including but not limited to implants available under the SeaSpine Hollywood™, Hollywood™ VI, Pacifica™, Steerable Interbody, Ventura®, and Vu a•POD™ product lines, may be detachably interconnected to a bone graft delivery device by any suitable means and used in the practice of the present invention. These and other spinal implants suitable for use in the present invention are described in U.S. Pat. Nos. 7,799,083, 7,976,549, 7,988,695, 8,100,972, 8,142,508, 8,292,958, 8,366,774, 8,409,290, 8,506,636, 8,545,562, 8,673,012, 8,864,829, and 9,522,069, the entirety of each of which is incorporated herein by reference.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A bone graft material delivery system, comprising:
   an elongate hollow tube constructed to receive bone graft material, said elongate hollow tube being generally linear and having an extended axis, a generally rectangular cross-section, a proximal end, a distal end with at least one opening, a hollow interior extending from said proximal end to said distal end, and indicia formed on an exterior surface of said elongate hollow tube; and
   a plunger adapted to extend in said elongate hollow tube, said plunger having a shaft and a distal portion with an exterior surface contoured to form a substantially congruent fit with said hollow interior of said elongate hollow tube such that said plunger is precluded from rotating within said elongate hollow tube, wherein teeth are formed along a longitudinal axis of said plunger shaft, and wherein said plunger is adapted to urge bone graft material through said elongate hollow tube to deliver bone graft material through said at least one opening of said distal end.

2. The system of claim 1, wherein said indicia are configured to indicate how far said elongate hollow tube has been inserted into a surgical site.

3. The system of claim 1, further comprising actuating means for applying pressure to said shaft of said plunger.

4. The system of claim 1, further comprising an actuator configured to engage said teeth of said plunger to advance said plunger toward said distal end of said elongate hollow tube.

5. The system of claim 4, further comprising a gear to engage said plunger teeth.

6. The system of claim 5, wherein rotational motion of said gear is translated into linear movement of said plunger.

7. The system of claim 1, wherein said distal end of said elongate hollow tube comprises a wedge or a bullet shaped distal tip.

8. The system of claim 1, wherein said elongate hollow tube is rigid.

9. The system of claim 1, further comprising a funnel configured to be coupled to said proximal end of said hollow tube.

10. A bone graft material delivery system, comprising:
    an elongate hollow tube constructed to receive bone graft material, said elongate hollow tube being generally linear and having an extended axis, a generally rectangular cross-section, a proximal end, a distal end, a hollow interior extending from said proximal end to said distal end, and indicia formed on an exterior surface of said elongate hollow tube, wherein said distal end of said elongate hollow tube is at least partially open; and
    a plunger adapted to extend in said elongate hollow tube, said plunger having a shaft and a distal portion with an exterior surface contoured to form a substantially congruent fit with said hollow interior of said elongate hollow tube such that said plunger is precluded from rotating within said elongate hollow tube, wherein teeth are formed along a longitudinal axis of said plunger shaft, and wherein said plunger is adapted to urge bone graft material through said elongate hollow tube to deliver bone graft material through said at least partially open distal end.

11. The system of claim 10, wherein said indicia are configured to indicate how far said elongate hollow tube has been inserted into a surgical site.

12. The system of claim 11, further comprising actuating means for applying pressure to said shaft of said plunger.

13. The system of claim 10, further comprising an actuator configured to engage said teeth of said plunger to advance said plunger toward said distal end of said elongate hollow tube.

14. The system of claim 13, further comprising a gear to engage said plunger teeth.

15. The system of claim 14, wherein rotational motion of said gear is translated into linear movement of said plunger.

16. The system of claim 10, wherein said distal end of said elongate hollow tube comprises a wedge or a bullet shaped distal tip.

17. A bone graft material delivery system, comprising:
an elongate hollow tube constructed to receive bone graft material, said elongate hollow tube being generally linear and having an extended axis, a generally rectangular cross-section, a proximal end, a distal end with at least one opening, a hollow interior extending from said proximal end to said distal end, and indicia formed on an exterior surface of said elongate hollow tube and configured to indicate how far said elongate hollow tube has been inserted into a surgical site, wherein said distal end of said elongate hollow tube comprises a wedge or a bullet shaped distal tip; and
a plunger adapted to extend in said elongate hollow tube, said plunger having a shaft and a distal portion with an exterior surface contoured to form a substantially congruent fit with said hollow interior of said elongate hollow tube such that said plunger is precluded from rotating within said elongate hollow tube, wherein teeth are formed along a longitudinal axis of said plunger shaft, and wherein said plunger is adapted to urge bone graft material through said elongate hollow tube to deliver bone graft material through said at least one opening of said distal end.

18. The system of claim 17, further comprising an actuator configured to engage said teeth of said plunger to advance said plunger toward said distal end of said elongate hollow tube.

19. The system of claim 18, further comprising a gear to engage said plunger teeth.

20. The system of claim 19, wherein rotational motion of said gear is translated into linear movement of said plunger.

\* \* \* \* \*